United States Patent
Parham et al.

(10) Patent No.: US 9,133,119 B2
(45) Date of Patent: *Sep. 15, 2015

(54) COMPOUNDS FOR ELECTRONIC DEVICES

(75) Inventors: Amir Hossain Parham, Frankfurt am Main (DE); Christof Pflumm, Frankfurt am Main (DE); Constanze Brocke, Gross-Gerau (DE)

(73) Assignee: Merck Patent GmbH (DE)

( * ) Notice: Subject to any disclaimer, the term of this patent is extended or adjusted under 35 U.S.C. 154(b) by 218 days.

This patent is subject to a terminal disclaimer.

(21) Appl. No.: 13/574,004

(22) PCT Filed: Dec. 17, 2010

(86) PCT No.: PCT/EP2010/007740
§ 371 (c)(1),
(2), (4) Date: Jul. 19, 2012

(87) PCT Pub. No.: WO2011/088877
PCT Pub. Date: Jul. 28, 2011

(65) Prior Publication Data
US 2012/0292576 A1  Nov. 22, 2012

(30) Foreign Application Priority Data
Jan. 25, 2010  (DE) .................. 10 2010 005 697

(51) Int. Cl.
| | | |
|---|---|---|
| C07D 209/86 | (2006.01) | |
| C07D 265/34 | (2006.01) | |
| C07D 401/14 | (2006.01) | |
| C07D 403/14 | (2006.01) | |
| C07D 413/14 | (2006.01) | |
| C09B 15/00 | (2006.01) | |
| C09B 17/00 | (2006.01) | |
| C09B 21/00 | (2006.01) | |
| C09B 57/00 | (2006.01) | |
| H01L 51/00 | (2006.01) | |
| H01L 51/50 | (2006.01) | |

(52) U.S. Cl.
CPC ............ *C07D 209/86* (2013.01); *C07D 265/34* (2013.01); *C07D 401/14* (2013.01); *C07D 403/14* (2013.01); *C07D 413/14* (2013.01); *C09B 15/00* (2013.01); *C09B 17/00* (2013.01); *C09B 21/00* (2013.01); *C09B 57/00* (2013.01); *C09B 57/008* (2013.01); *H01L 51/006* (2013.01); *H01L 51/0061* (2013.01); *H01L 51/0072* (2013.01); *H01L 51/0058* (2013.01); *H01L 51/5056* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

2012/0178928 A1   7/2012   Fukuzaki

FOREIGN PATENT DOCUMENTS

| EP | 21182040 | * | 5/2010 | ............. C09K 11/06 |
| JP | 2010-087496 A | | 4/2010 | |
| JP | 2012-507507 A | | 3/2012 | |
| WO | WO 2006033563 | * | 3/2006 | ............. C09K 11/06 |
| WO | WO-2010/050778 A1 | | 5/2010 | |

OTHER PUBLICATIONS

Jiang, Zuoquan, et al., "Diarylmethylene-Bridged 4,4'-(Bis(9-Carbazolyl))Biphenyl: Morphological Stable Host Material for Highly Efficient Electrophosphorescence", Journal of Materials Chemistry, vol. 19, (2009), pp. 7661-7665.
International Search Report for PCT/EP2010/007740 mailed Feb. 7, 2011.
Wharton et al., "The Production and Characterisation of Novel Conducting Redox-Active Oligomeric Thin Films From Electrooxidised Indolo[3,2,1-*jk*]carbazole", Chem. Eur. J., vol. 15, pp. 5482-5490 (2009).

* cited by examiner

*Primary Examiner* — Gregory Clark
(74) *Attorney, Agent, or Firm* — Drinker Biddle & Reath LLP

(57) ABSTRACT

The present invention relates to compounds of the formula (I) and to the use thereof in organic electronic devices, and to organic electronic devices which comprise compounds of the formula (I), preferably as hole-transport materials and/or as matrix materials, in particular in combination with a further matrix material.

17 Claims, No Drawings

COMPOUNDS FOR ELECTRONIC DEVICES

RELATED APPLICATIONS

This application is a national stage application (under 35 U.S.C. §371) of PCT/EP2010/007740, filed Dec. 17, 2010, which claims benefit of German Patent Application No. 10 2010 005 697.9, filed Jan. 25, 2010.

The present invention relates to compounds of the formula (I) and to the use thereof in electronic devices and to electronic devices which comprise these compounds.

Organic semiconductor materials, such as the compounds according to the invention, are being developed for a number of different applications in electronic devices.

The structure of organic electroluminescent devices (OLEDs) in which the compounds according to the invention can be employed as functional materials is described, for example, in U.S. Pat. No. 4,539,507, U.S. Pat. No. 5,151,629, EP 0676461 and WO 98/27136.

Regarding the performance data of the organic electroluminescent devices, further improvements are still necessary, in particular with respect to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices.

In addition, it is desirable for the compounds for use as organic semiconductor materials to have high thermal stability and a high glass-transition temperature and to be sublimable without decomposition.

Furthermore, the voltage in the case of hole-transport materials in accordance with the prior art generally increases with the layer thickness of the hole-transport layer. In practice, a greater layer thickness of the hole-transport layer would frequently be desirable, but this often has the consequence of a higher operating voltage and poorer performance data. In this connection, there is a demand for novel hole-transport materials which have high charge-carrier mobility, enabling thicker hole-transport layers to be achieved with only a slight increase in the operating voltage.

Arylamine derivatives are known from the prior art as hole-transport and hole-injection materials. Materials of this type based on indenofluorenes are disclosed, for example, in WO 06/100896 and WO 06/122630. The indenofluorenamines described above have disadvantages in processability: during the vapour-deposition or coating process, premature deposition and thus complication of the industrial process may occur. In addition, the known hole-transporting materials frequently have low electron stability, which results in short lifetimes of the electronic devices comprising the compounds. There is a further need for improvement here.

Furthermore, there is a demand for alternative matrix materials for use in electronic devices. In particular, there is a demand for matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis-(carbazolyl)biphenyl, are frequently used as matrix materials. There is still potential for improvement here, in particular with respect to the lifetime and glass-transition temperature of the materials. Furthermore, there is a need for improvement with respect to the operating voltage of the electronic devices comprising the materials in question.

Furthermore, ketones (WO 04/093207), phosphine oxides, sulfones (WO 05/003253) and triazine compounds, such as triazinylspirobifluorene (cf. the application WO 05/053055 and the applications WO 10/015,306 and WO 10/072,300), are used as matrix materials for phosphorescent emitters. Low operating voltages and long lifetimes are achieved, in particular, with ketones. There is still potential for improvement here, in particular with respect to the efficiency and compatibility with metal complexes which comprise ketoketonate ligands, for example acetylacetonate.

Furthermore, metal complexes, for example BAlq or bis[2-(2-benzothiazole)phenolate]zinc(II), are used as matrix materials for phosphorescent emitters. There is still a need for improvement here, in particular with respect to the operating voltage and chemical stability. Purely organic compounds are frequently more stable than these metal complexes. Thus, some of these metal complexes are sensitive to hydrolysis, which makes handling of the complexes more difficult.

Also of particular interest is the provision of alternative materials as matrix components of mixed-matrix systems. A mixed-matrix system in the sense of this application is taken to mean a system in which two or more different matrix compounds mixed together with one or more dopant compounds are used as the emitting layer. These systems are, in particular, of interest in the case of phosphorescent organic electroluminescent devices. For more detailed information, reference is made to the unpublished application DE 102009014513.3.

Compounds known from the prior art which may be mentioned as matrix components in mixed-matrix systems are, inter alia, CBP (biscarbazolylbiphenyl) and TCTA (triscarbazolyltriphenylamine) (cf. Example Part Table 4). However, there continues to be a demand for alternative compounds for use as matrix components in mixed-matrix systems. In particular, there is a demand for compounds which effect an improvement in the operating voltage and lifetime of the electronic devices.

For fluorescent OLEDs, the matrix materials used in accordance with the prior art, especially for blue-emitting electroluminescent devices, are especially condensed aromatic compounds, in particular anthracene derivatives, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 01/076323, WO 01/021729, WO 04/013073, WO 04/018588, WO 03/087023 or WO 04/018587. Matrix materials based on aryl-substituted pyrenes and chrysenes are disclosed in WO 04/016575. Matrix materials based on benzanthracene derivatives are disclosed in WO 08/145,239. For high-quality applications, it is desirable to have available further matrix materials, which preferably have improved properties.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high techni-complexity for OLED production and thus represents a technical disadvantage. For high-quality applications, it is therefore desirable to have available improved emitters, in particular with respect to device and sublimation stability and emission colour.

Overall, there is a demand in the area of functional materials for electronic devices for alternative materials which preferably have improved properties.

The applications WO 2006/033563 and US 2009/0136779, inter alia, disclose triarylamine derivatives in which the individual aryl groups are bridged to one another. The compounds are employed as hole-transport materials and/or as emitting materials in electronic devices.

The application WO 10/083,871 discloses compounds in which aryl groups are condensed onto a piperidine ring. The compounds are employed as hole-transport materials and/or as emitting materials in electronic devices. Furthermore, the unpublished application DE 102009048791.3 discloses bridged carbazole derivatives containing triazinyl groups. The compounds are preferably employed as matrix materials for phosphorescent dopants and as electron-transport materials.

However, there continues to be a need for improvement with respect to the lifetime, efficiency and operating voltage of the devices. In addition, it is advantageous for the compounds to have high thermal stability and a high glass-transition temperature and to be sublimable without decomposition.

The invention thus relates to a compound of the formula (I)

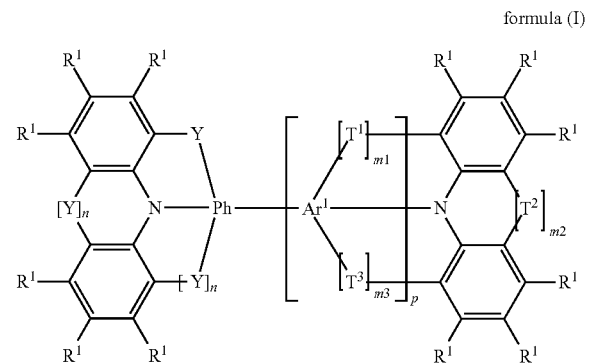

formula (I)

where the following applies to the symbols and indices occurring:

Y is on each occurrence, identically or differently, a single bond, $BR^2$, $C(R^2)_2$, $R^2C=CR^2$, $Si(R^2)_2$, $C=O$, $C=NR^2$, O, S, SO, $SO_2$, $PR^2$, $POR^2$ or $NR^2$, where at least one group Y which represents a single bond is present;

$T^1, T^2, T^3$ are on each occurrence, identically or differently, a single bond, $BR^2$, $C(R^2)_2$, $R^2C=CR^2$, $Si(R^2)_2$, $C=O$, $C=NR^2$, O, S, SO, $SO_2$, $PR^2$, $POR^2$ or $NR^2$;

Ph is a phenyl group, which may be substituted by one or more radicals $R^1$;

$Ar^1$ is an aromatic ring system having 6 to 30 aromatic ring atoms, which may be substituted by one or more radicals $R^1$;

$R^1, R^2$ are on each occurrence, identically or differently, H, D, F, Cl, Br, I, CHO, $N(R^3)_2$, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OSO_2R^3$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals $R^3$, or an aryloxy or heteroaryloxy group having 5 to 60 aromatic ring atoms, which may be substituted by one or more non-aromatic radicals $R^3$, or a combination of these systems, where two or more radicals $R^1$ and/or $R^2$ may be linked to one another and may form a mono- or polycyclic, aliphatic or aromatic ring system;

$R^3$ is on each occurrence, identically or differently, H, D, F, Cl, Br, I, CHO, $N(R^4)_2$, $C(=O)R^4$, $P(=O)(R^4)_2$, $S(=O)R^4$, $S(=O)_2R^4$, $CR^4=C(R^4)_2$, CN, $NO_2$, $Si(R^4)_3$, $B(OR^4)_2$, $OSO_2R^4$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^4$, where one or more non-adjacent $CH_2$ groups may be replaced by $R^4C=CR^4$, $C\equiv C$, $Si(R^4)_2$, $Ge(R^4)_2$, $Sn(R^4)_2$, $C=O$, $C=S$, $C=Se$, $C=NR^4$, $P(=O)(R^4)$, SO, $SO_2$, $NR^4$, O, S or $CONR^4$ and where one or more H atoms may be replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals $R^4$, or an aryloxy or heteroaryloxy group having 5 to 60 aromatic ring atoms, which may be substituted by one or more non-aromatic radicals $R^4$, or a combination of these systems, where two or more radicals $R^3$ may be linked to one another and may form a mono- or polycyclic, aliphatic or aromatic ring system;

$R^4$ is on each occurrence, identically or differently, H, D, F or an aliphatic, aromatic and/or heteroaromatic organic radical having 1 to 20 C atoms, in which, in addition, one or more H atoms may be replaced by D or F; two or more identical or different substituents $R^4$ here may also be linked to one another and may form a mono- or polycyclic, aliphatic or aromatic ring system;

n is on each occurrence, identically or differently, 0 or 1, where the sum of the values of n is equal to 1 or 2 and where, for n=0, a group $R^1$ is bonded instead of a group Y;

m1, m2, m3 are on each occurrence, identically or differently, 0 or 1, where, for m1, m2 or m3=0, a group $R^1$ is bonded instead of a group $T^1$, $T^2$ or $T^3$ respectively;

p is equal to 0 or 1;

where the following structures are excluded:

5
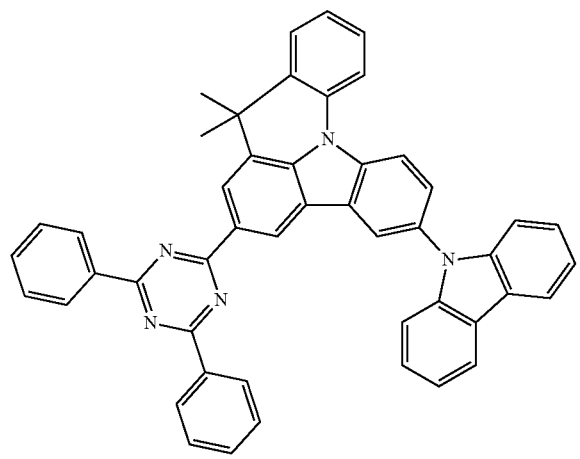
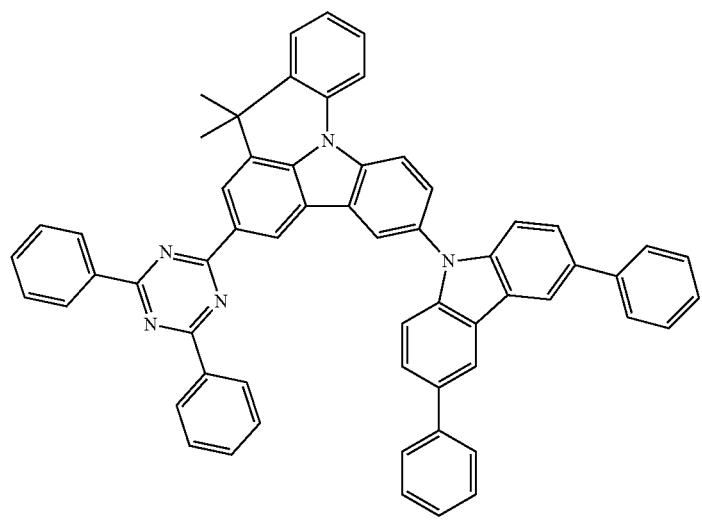
6
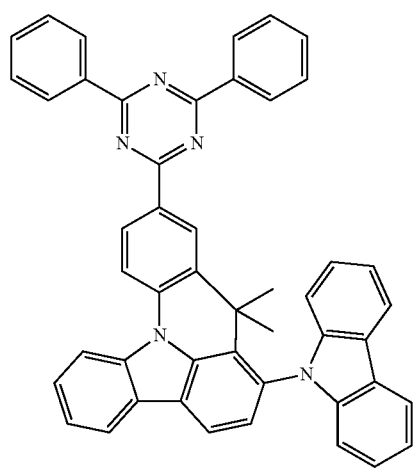
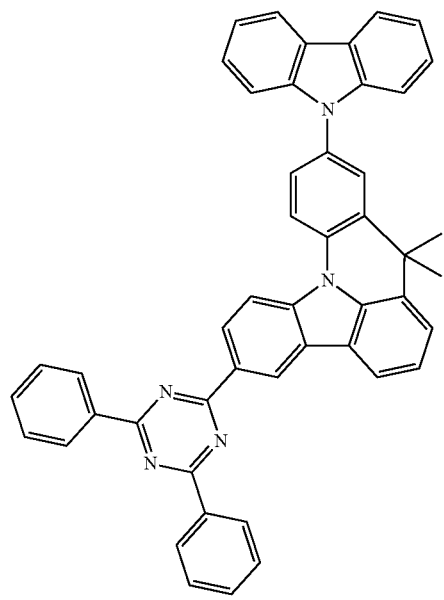

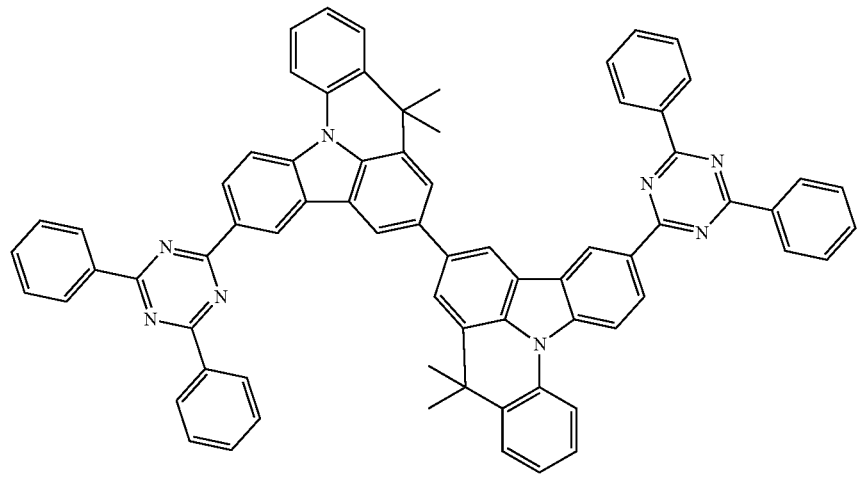
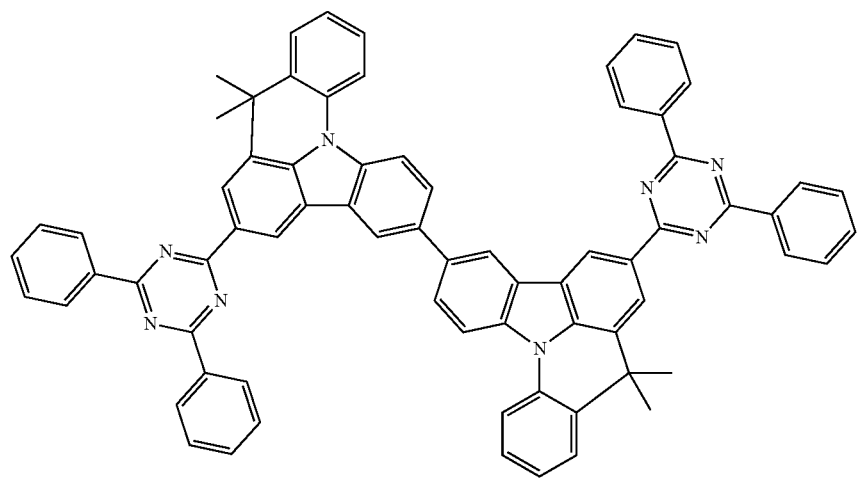
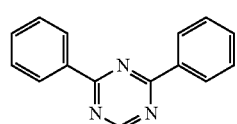
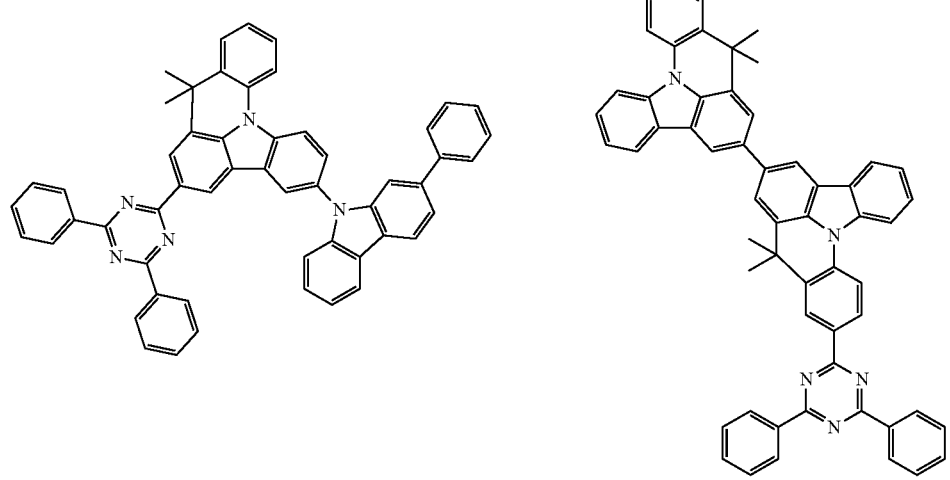

-continued

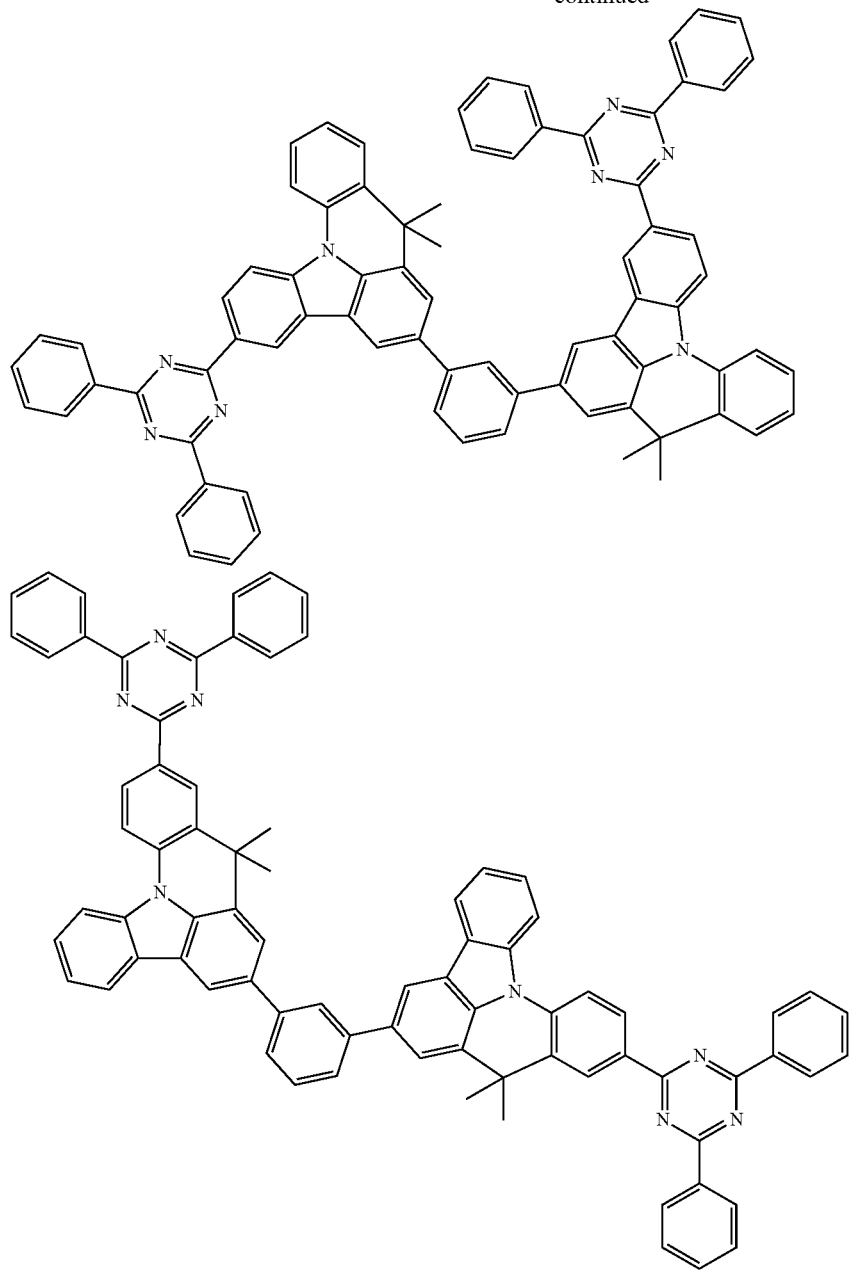

and where not more than one group $R^1$ which represents a group of the formula $N(R^3)_2$, where $R^3$ is an aryl group, may be bonded to a single triarylamine group in formula (I).

In a preferred embodiment of the invention, the group $T^2$ in compounds of the formula (I) cannot represent a single bond for p=1 and m1=m3=0. In a particularly preferred embodiment of the invention, $T^1$, $T^2$ and $T^3$ do represent a single bond in the case where p is equal to 1 and the sum of the values of the indices m1, m2 and m3 is equal to 1. In a further particularly preferred embodiment of the invention, the group $T^2$ in the compounds of the formula (I) cannot represent a single bond if m1=m3=0.

The condition that not more than one group $R^1$ which represents a group of the formula $N(R^3)_2$, where $R^3$ is an aryl group, may be bonded to a single triarylamino group in formula (I) will be explained in greater detail below.

Both the left-hand moiety (formula (Ia)) and the right-hand moiety (formula (Ib)) in the structural formulae of the compounds according to the invention represent a single triarylamino group in the sense of the above definition.

formula (Ia)

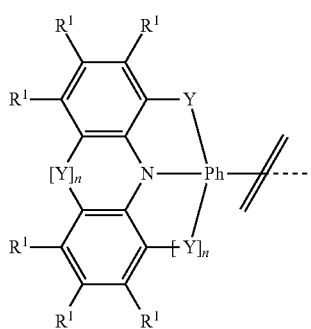

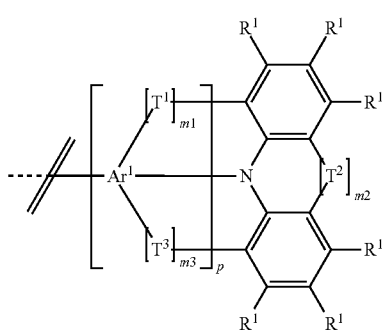

formula (Ib)

For example, the formula indicated below in which $R^3$ stands for an aryl group represents compounds which do not fall within the scope of the claims of the present application:

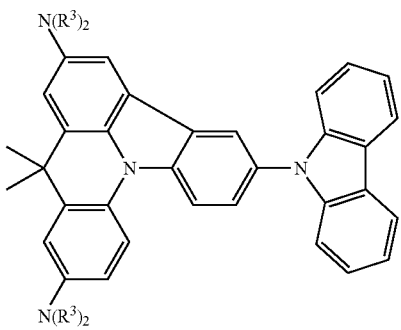

In the compounds represented by the generic formula shown above, two groups $N(R^3)_2$, where $R^3$ is an aryl group, are bonded to a single triarylamino group, as explained above.

The situation is the same with compounds of the following formula in which $R^3$ stands for an aryl group:

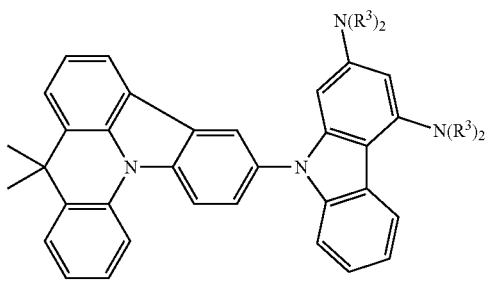

By contrast, compounds of the following formula in which $R^3$ stands for an aryl group are covered by the claims of the present application:

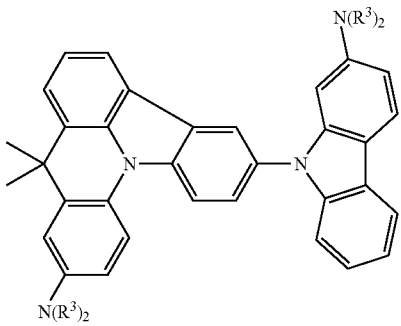

This is because in this case a single group $N(R^3)_2$, where $R^3$ stands for an aryl group, is bonded to a single triarylamino group, as explained above.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aromatic ring system in the sense of this invention contains 6 to 60 C atoms in the ring system. A heteroaromatic ring system in the sense of this invention contains 5 to 60 aromatic ring atoms and at least one heteroatom in the ring system, with the proviso that the sum of the C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl, group or by a silyl group.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, indolocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, ter-phenylene, fluorene, indenofluorene, indenocarbazole, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, a straight-chain alkyl group having 1 to 40 C atoms or a branched or cyclic alkyl group having 3 to 40 atoms or an alkenyl or alkynyl group having 2 to 40 C atoms, in which, in addition, individual H atoms or $CH_2$ groups may be substituted by the groups mentioned above under the definition of the radicals $R^1$ and $R^2$, is preferably taken to mean the radicals methyl, ethyl, n-propyl, i-propyl, n-butyl, i-butyl, s-butyl, t-butyl, 2-methylbutyl, n-pentyl, s-pentyl, cyclo-pentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoro-methoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoro-ethylthio, 2,2,2-trifluoroethylthio, ethenylthio, propenylthio, butenylthio, pentenylthio, cyclopentenylthio, hexenylthio, cyclohexenylthio, heptenyl-thio, cycloheptenylthio, octenylthio, cyclooctenylthio, ethynylthio, propynyl-thio, butynylthio, pentynylthio, hexynylthio, heptynylthio or octynylthio.

It is preferred for the groups Y, if present, each to be bonded to the group Ph in the ortho-position to the bond to the nitrogen atom.

It is furthermore preferred for the groups $T^1$, $T^2$ and $T^3$, if present, each to be bonded to $Ar^1$ in the ortho-position to the bond to the nitrogen atom.

In a preferred embodiment of the compounds according to the invention, a maximum of 2 groups Y which represent a single bond are present. Particularly preferably, precisely one group Y which represents a single bond is present.

In a further preferred embodiment of the invention, the sum of the values of n is equal to 1.

In a particularly preferred embodiment of the invention, precisely one group Y represents a single bond and precisely one further group Y is selected from $BR^2$, $C(R^2)_2$, $Si(R^2)_2$, $C=O$, $C=NR^2$, O, S, SO, $SO_2$, $PR^2$, $POR^2$ and $NR^2$.

It is furthermore preferred for $T^1$, $T^2$ and $T^3$ to be selected on each occurrence, identically or differently, from a single bond, $C(R^2)_2$, $C=O$, O, S and $NR^2$. In this case, $R^2$ is preferably selected from H, D, a straight-chain alkyl group having 1 to 8 carbon atoms, a branched alkyl group having 3 to 8 carbon atoms or an aryl group having 6 to 10 carbon atoms, where the said groups may each be substituted by one or more groups $R^3$. $T^1$, $T^2$ and $T^3$ are particularly preferably on each occurrence a single bond. It is furthermore preferred here, in combination with the two preferred embodiments of $T^1$, $T^2$ and $T^3$ mentioned above, for $T^2$ not to represent a single bond if p=1 and m1=m3=0.

It is furthermore preferred in accordance with the invention for

Y to be on each occurrence, identically or differently, a single bond, $C(R^2)_2$, $C=O$, O, S or $NR^2$, where at least one group Y which represents a single bond is present.

In this case, $R^2$ is preferably selected from H, D, a straight-chain alkyl group having 1 to 8 carbon atoms, a branched alkyl group having 3 to 8 carbon atoms or an aryl group having 6 to 10 carbon atoms, where the said groups may each be substituted by one or more groups $R^3$.

In a preferred embodiment of the invention, the sum of the values of the indices m1, m2 and m3 is equal to 2.

In this case, it is preferred in accordance with the invention for precisely one of the two groups $T^1$, $T^2$ and $T^3$ to represent a single bond and for the other of the two groups $T^1$, $T^2$ and $T^3$ present to represent a group selected from the group comprising $C(R^2)_2$, $C=O$, O, S or $NR^2$. In this case, it is furthermore preferred for the sum of the values n simultaneously to be equal to one.

In a further preferred embodiment of the invention, the sum of the values of the indices m1, m2 and m3 is equal to 1. In combination with the said preferred embodiment, it is preferred for the single group $T^1$, $T^2$ or $T^3$ present in this case not to represent a single bond.

In a further preferred embodiment of the invention, all indices m1, m2 and m3 are equal to zero.

$R^1$ is furthermore preferably not a group $N(R^3)_2$ where $R^3$ is an aryl group.

$R^1$ is again furthermore preferably selected on each occurrence, identically or differently, from H, D, F, CN, $Si(R^3)_3$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by $-C\equiv C-$, $R^3C=CR^3$, $Si(R^3)_2$, $C=O$, $C=NR^3$, $NR^3$, O, S, COO or $CONR^3$, or an aryl or heteroaryl group having 5 to 30 aromatic ring atoms, which may in each case be substituted by one or more radicals $R^3$.

The radical $R^2$ is preferably selected on each occurrence, identically or differently, from H, D, F, CN, $Si(R^3)_3$, $N(R^3)_2$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by $-C\equiv C-$, $R^3C=CR^3$, $Si(R^3)_2$, $C=O$, $C=NR^3$, $NR^3$, O, S, COO or $CONR^3$, or an aryl or heteroaryl group having 5 to 30 aromatic ring atoms, which may in each case be substituted by one or more radicals $R^3$.

$R^2$ is particularly preferably selected on each occurrence, identically or differently, from H, D, a straight-chain alkyl group having 1 to 8 carbon atoms, a branched alkyl group having 3 to 8 carbon atoms or an aryl group having 6 to 18 carbon atoms, where the said groups may each be substituted by one or more groups $R^3$. $R^2$ is very particularly preferably equal to H, D, methyl or phenyl.

It is furthermore preferred for the compounds according to the invention to have to contain at least one group $R^2$ which represents an aryl group having 6 to 10 carbon atoms which is substituted by one or more radicals $R^3$.

The compounds according to the invention particularly preferably contain least one group $R^2$ which represents a phenyl group which is substituted one or more radicals $R^3$.

It is furthermore preferred for two or more radicals $R^2$ to form a ring with one another. It is particularly preferred for the ring formation of two radicals $R^2$ to form a spiro compound. Furthermore, two radicals $R^2$ which are part of a group $C(R^2)_2$ which stands for Y, $T^1$, $T^2$, $T^3$ or L particularly preferably form a spiro compound. L here is as defined in one of the following sections.

It is preferred in accordance with the invention for the radicals $R^1$ and $R^2$ not to represent structures of the following formulae (A) to (G):

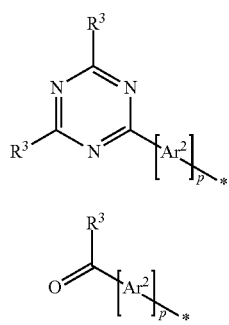

formula (A)

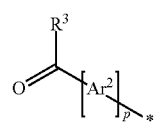

formula (B)

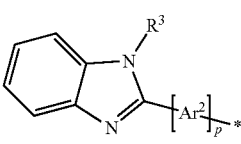

formula (C)

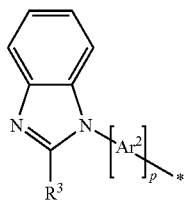

formula (D)

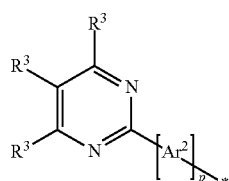

formula (E)

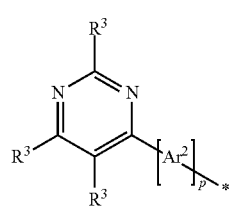

formula (F)

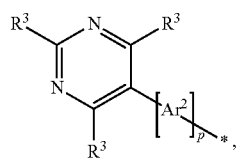

formula (G)

where the following applies to the symbols and indices occurring:
$Ar^2$ is on each occurrence, identically or differently, an aromatic or heteroaromatic ring system having 5-30 aromatic ring atoms, which may be substituted by one or more non-aromatic radicals $R^3$; two radicals $Ar^2$ here which are bonded to the same N atom or P atom may also be linked to one another by a single bond or a bridge selected from $N(R^3)$, $C(R^3)_2$ or O;
$R^3$ is as defined above;
p stands for 0 or 1;
and the symbol * indicates the position in which the group is bonded.

It is furthermore preferred in accordance with the invention for the radicals $R^1$ and $R^2$ not to be linked to one another.

The radical $R^3$ is preferably selected on each occurrence, identically or differently, from H, D, F, CN, $Si(R^4)_3$, $N(R^4)_2$ or a straight-chain alkyl or alkoxy group having 1 to 20 C atoms or a branched or cyclic alkyl or alkoxy group having 3 to 20 C atoms, each of which may be substituted by one or more radicals $R^4$, where one or more adjacent or non-adjacent $CH_2$ groups may be replaced by $—C{\equiv}C—$, $R^4C{=}CR^4$, $Si(R^4)_2$, $C{=}O$, $C{=}NR^4$, $NR^4$, O, S, COO or $CONR^4$, or an aryl or heteroaryl group having 5 to 30 aromatic ring atoms, which may in each case be substituted by one or more radicals $R^4$.

The compounds of the formula (I) according to the invention can also be represented by one of the two formulae (II) and (III):

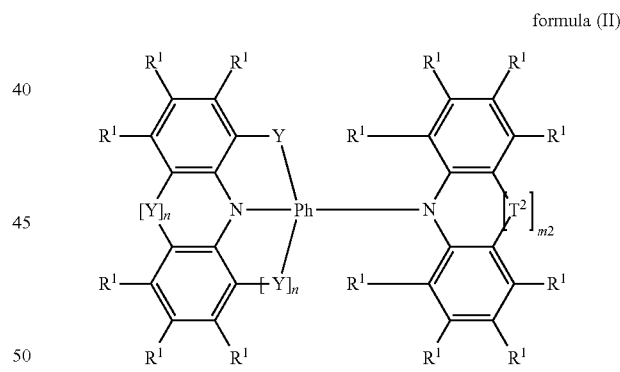

formula (II)

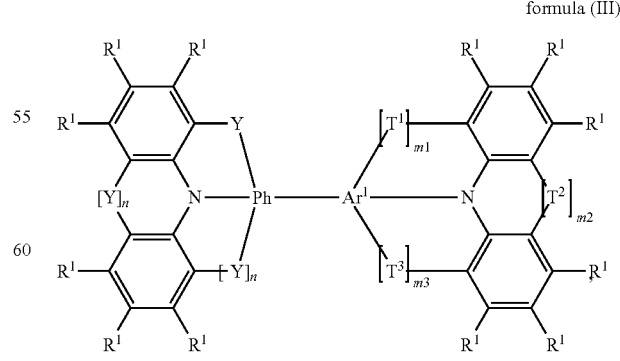

formula (III)

where the symbols and indices occurring are defined as indicated above.

For compounds of the formula (III), it is preferred for the group $T^2$ not to represent a single bond if m1=m3=0.

Preferred embodiments of the group Ph conform to the formulae (Ph-1) and (Ph-2):

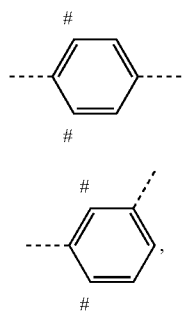

formula (Ph-1)

formula (Ph-2)

where the bonds to the two nitrogen atoms or to the nitrogen atom and to the group $Ar^1$ are represented by the dashed lines, and the symbols # mark the position of the bond to a group Y, if present, and where the structures may be substituted in all free positions by radicals $R^1$ as defined above.

Preferred embodiments of the group $Ar^1$ conform to the following formulae $(Ar^1-1)$ to $(Ar^1-7)$:

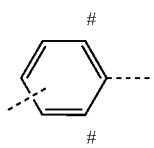

formula $(Ar^1-1)$

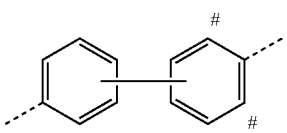

formula $(Ar^1-2)$

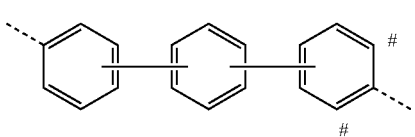

formula $(Ar^1-3)$

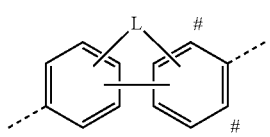

formula $(Ar^1-4)$

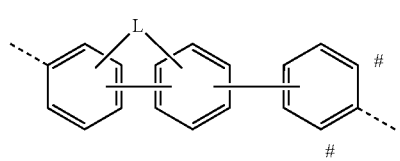

formula $(Ar^1-5)$

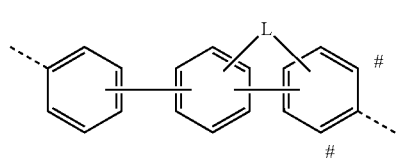

formula $(Ar^1-6)$

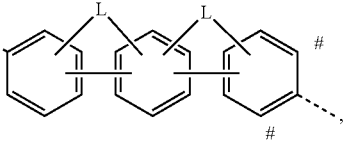

formula $(Ar^1-7)$ where

L is selected on each occurrence, identically or differently, from $BR^2$, $C(R^2)_2$, $R^2C=CR^2$, $Si(R^2)_2$, C=O, C=$NR^2$, O, S, SO, $SO_2$, $PR^2$, $POR^2$ and $NR^2$;

and where the bonds to the group Ph and to the nitrogen atom are represented by the dashed lines, and the symbols # mark the position of the bond to a group $T^1$, $T^2$ or $T^3$, if present, and where the groups may be substituted in all free positions by radicals $R^1$ as defined above.

In a preferred embodiment of the invention,

L is selected on each occurrence, identically or differently, from $C(R^2)_2$, C=O, O, S and $NR^2$.

In this case, $R^2$ is preferably selected from H, D, a straight-chain alkyl group having 1 to 8 carbon atoms, a branched alkyl group having 3 to 8 carbon atoms or an aryl group having 6 to 10 carbon atoms, where the said groups may each be substituted by one or more groups $R^3$.

L is very particularly preferably selected on each occurrence, identically or differently, from $C(R^2)_2$ and $NR^2$.

In this case, $R^2$ is preferably selected from H, D, a straight-chain alkyl group having 1 to 8 carbon atoms, a branched alkyl group having 3 to 8 carbon atoms or an aryl group having 6 to 10 carbon atoms, where the said groups may each be substituted by one or more groups $R^3$.

It is preferred in accordance with the invention for $Ar^1$ to represent an aromatic ring system having 6 to 20 aromatic ring atoms which is substituted by one or more radicals $R^1$. $Ar^1$ is particularly preferably an aromatic system having 6 to 18 aromatic ring atoms which comprises exclusively phenyl groups and which is substituted by one or more radicals $R^1$. In a particularly preferred embodiment of the invention, $Ar^1$ is a phenyl group which is substituted by one or more radicals $R^1$.

Particularly preferred embodiments of the group $Ar^1$ conform to the following formulae $(Ar^1-8)$ to $(Ar^1-35)$:

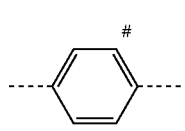

formula $(Ar^1-8)$

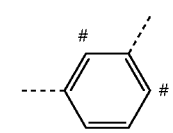

formula $(Ar^1-9)$

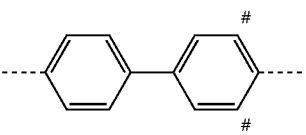

formula (Ar1-10)

-continued
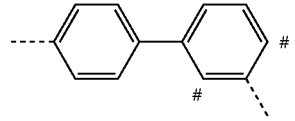
formula (Ar¹-11)
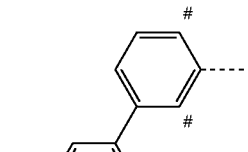
formula (Ar¹-12)
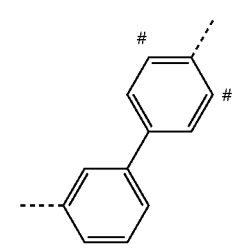
formula (Ar¹-13)
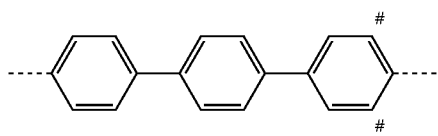
formula (Ar¹-14)
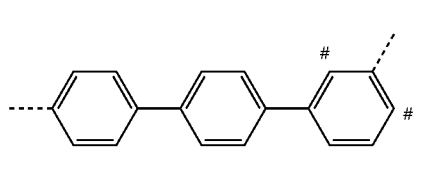
formula (Ar¹-15)
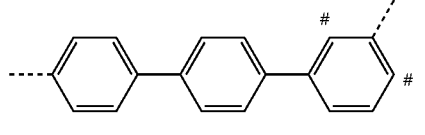
formula (Ar¹-16)
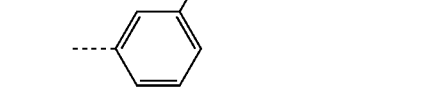
formula (Ar¹-17)
-continued
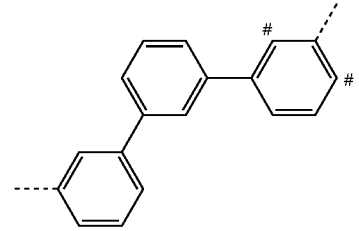
formula (Ar¹-18)
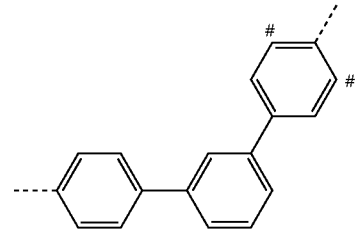
formula (Ar¹-19)
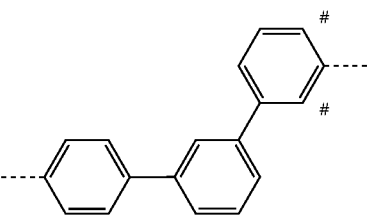
formula (Ar¹-20)
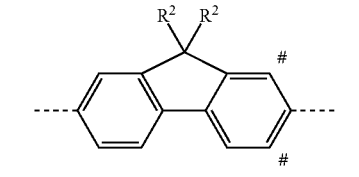
formula (Ar¹-21)
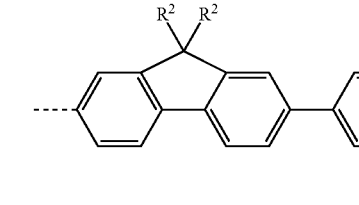
formula (Ar¹-22)
formula (Ar¹-23)
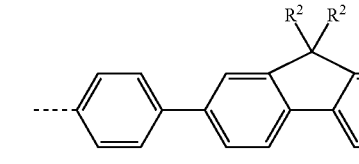
formula (Ar¹-24)

formula (Ar¹-25)
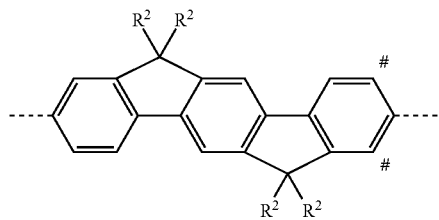

formula (Ar¹-26)
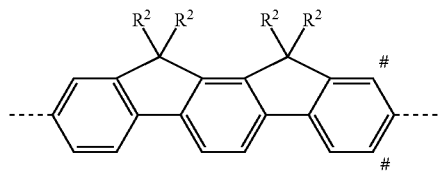

formula (Ar¹-27)
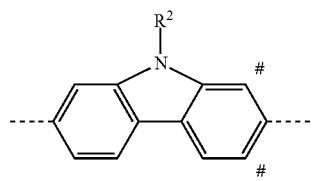

formula (Ar¹-28)
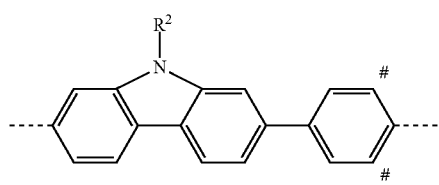

formula (Ar¹-29)
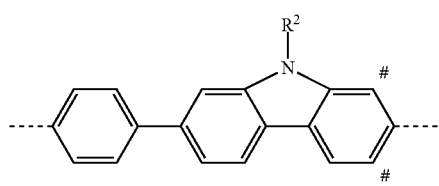

formula (Ar¹-30)
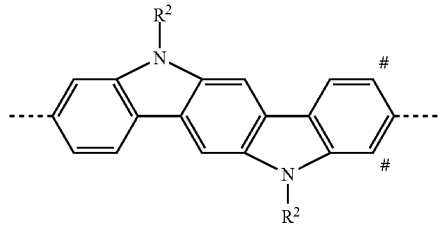

formula (Ar¹-31)
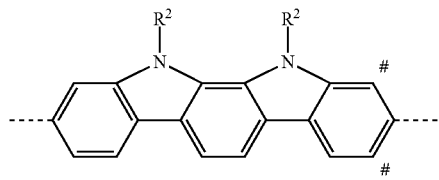

formula (Ar¹-32)
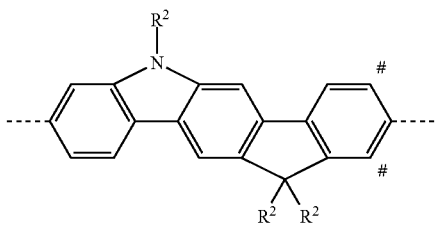

formula (Ar¹-33)
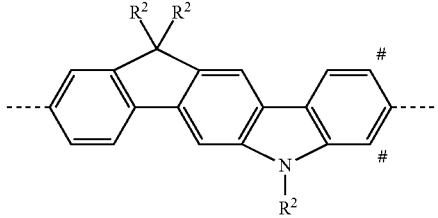

formula (Ar¹-34)
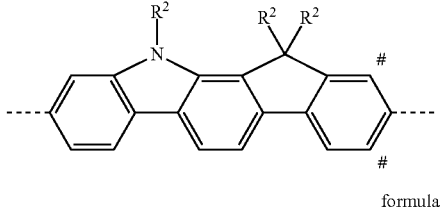

formula (Ar¹-35)
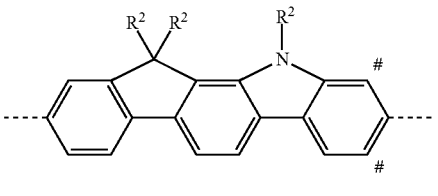

where the bonds to the group Ph and to the nitrogen atom are represented by the dashed lines, and the symbols # mark the position of the bond to a group $T^1$, $T^2$ or $T^3$, if present, and where the groups may be substituted in all free positions by radicals $R^1$, and the groups $R^1$ may be linked to one another and may thus form a further aliphatic or aromatic ring.

Particularly preferred embodiments of the compounds of the formula (I) according to the invention are represented by the following formulae (I-1) to (I-55):

formula (I-1)
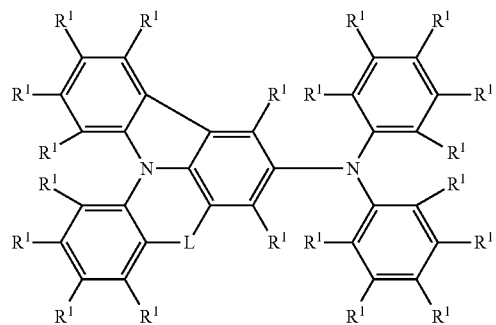

formula (I-2)
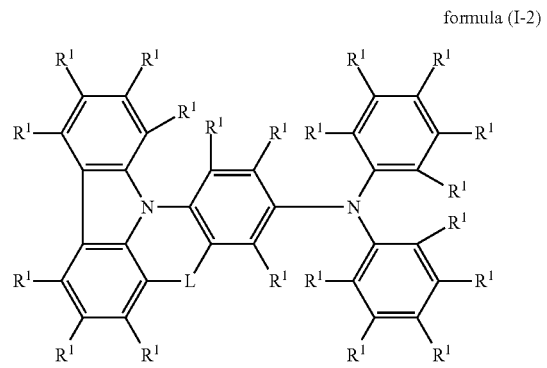
formula (I-3)
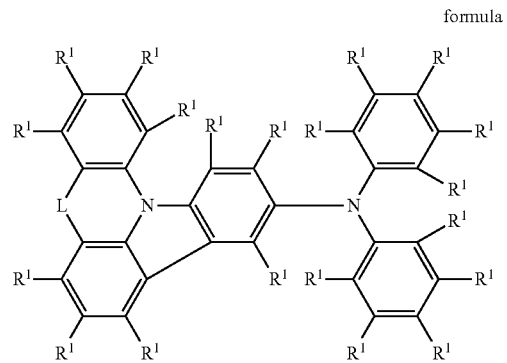
formula (I-4)
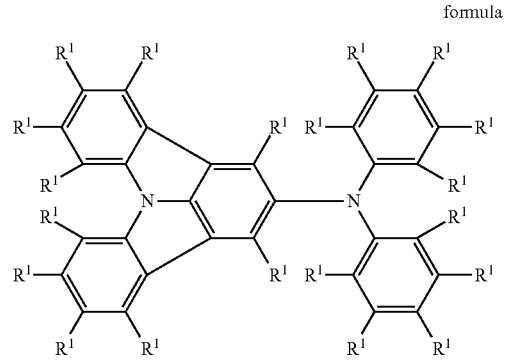
formula (I-5)
formula (I-6)
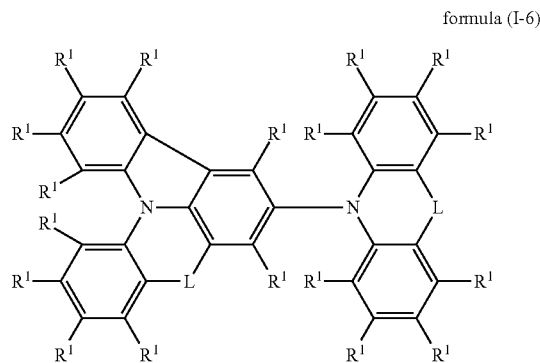
formula (I-7)
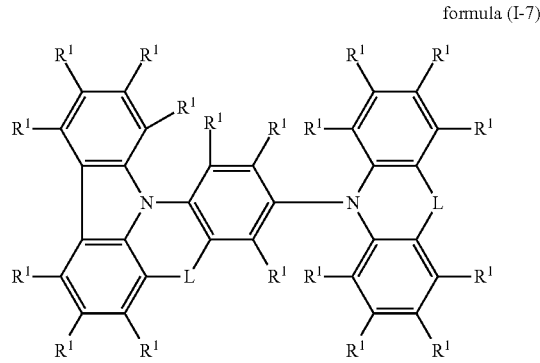
formula (I-8)
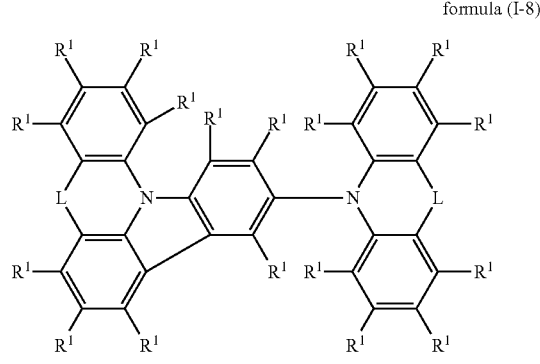
formula (I-9)
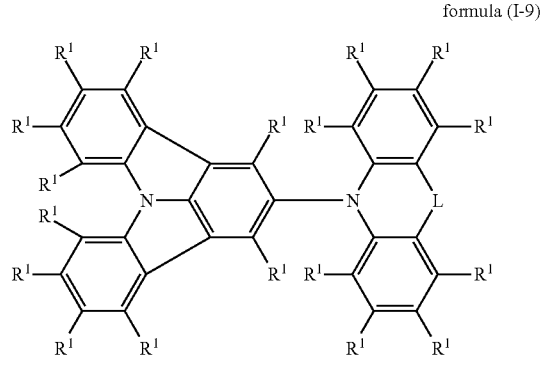

-continued
formula (I-10)
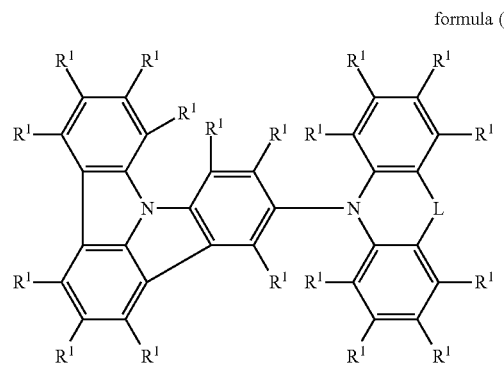
formula (I-11)
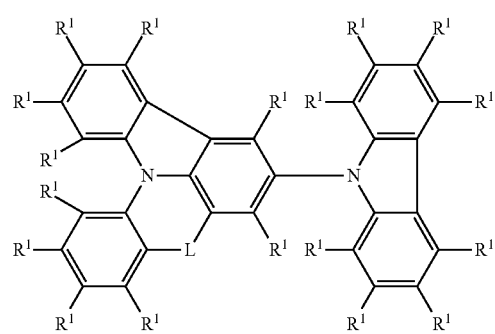
formula (I-12)
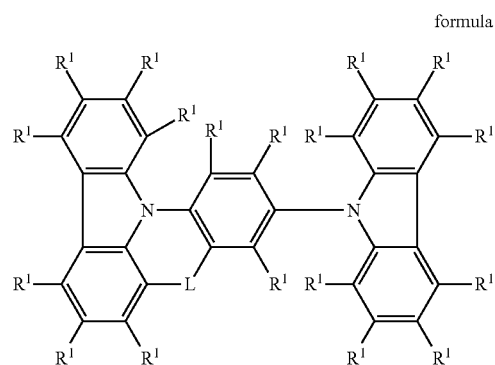
formula (I-13)
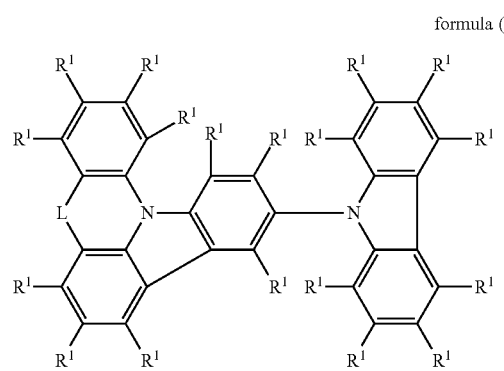
formula (I-14)
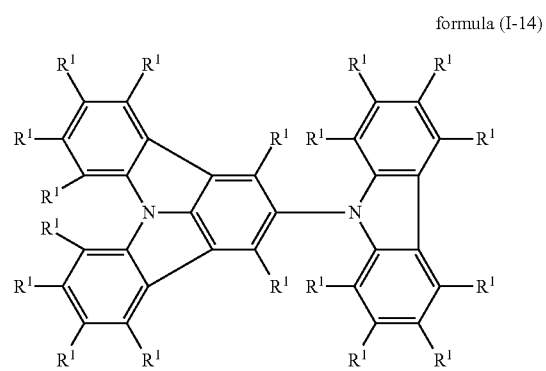
formula (I-15)
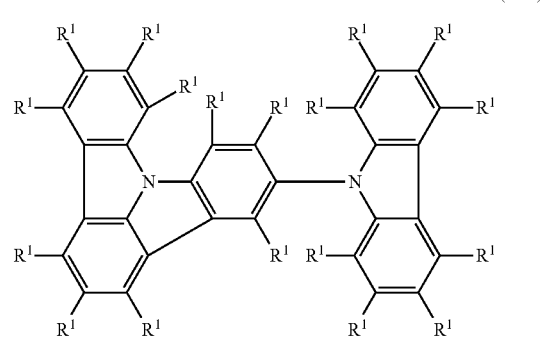
formula (I-16)
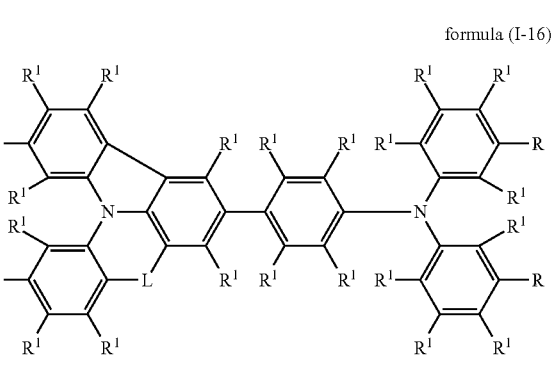
formula (I-17)
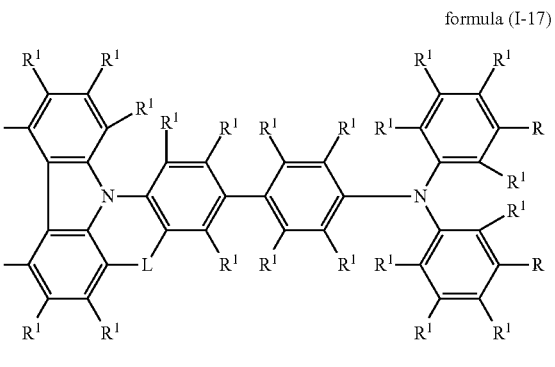

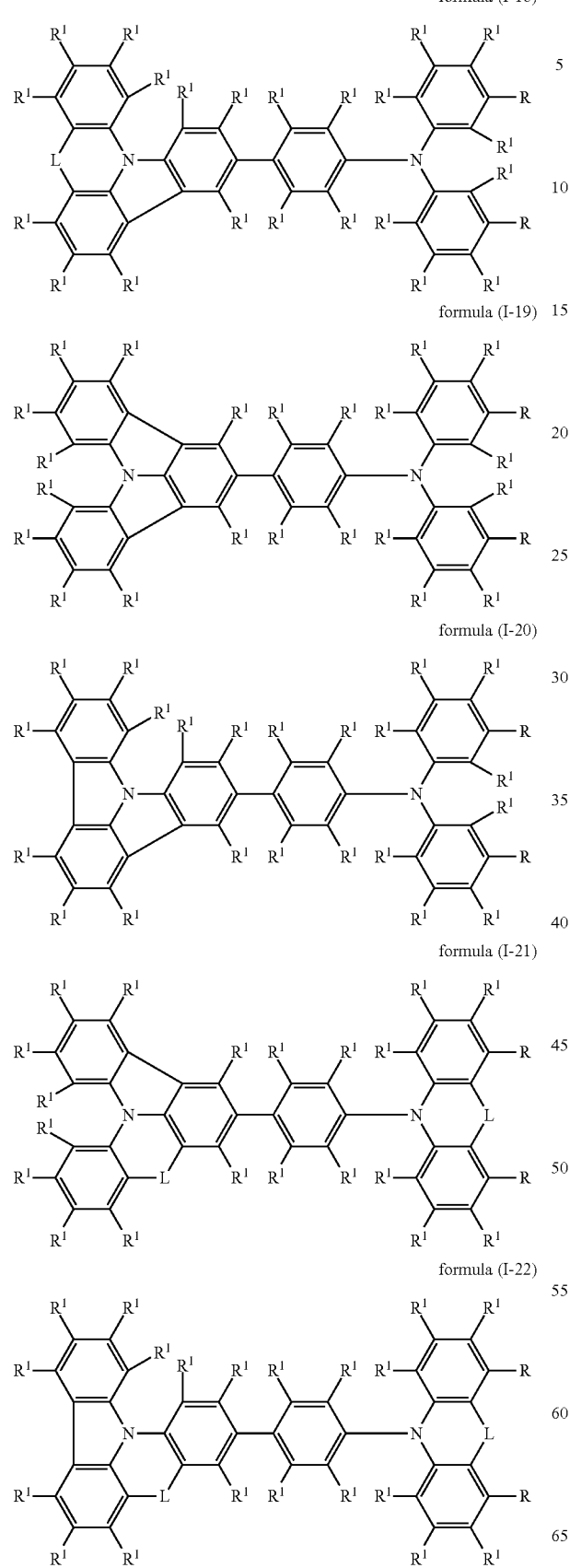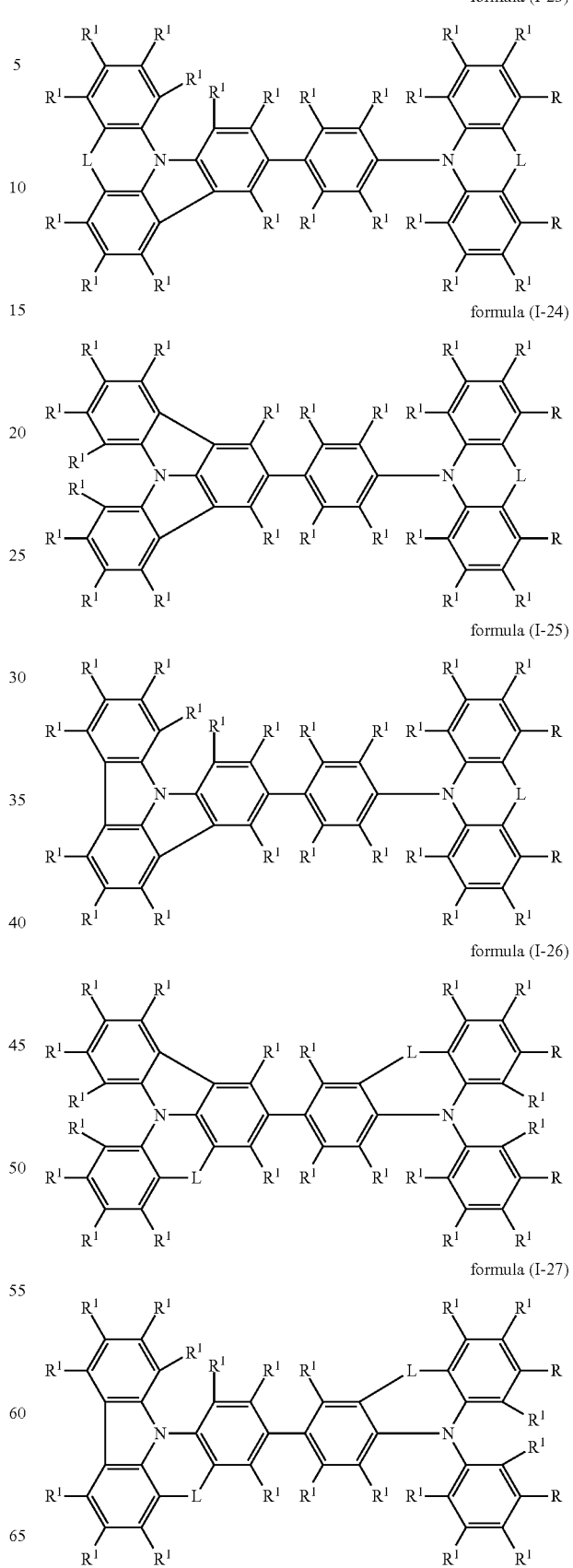

formula (I-28)
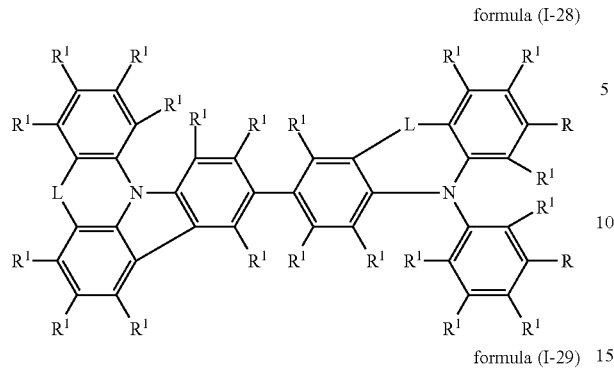
formula (I-29)
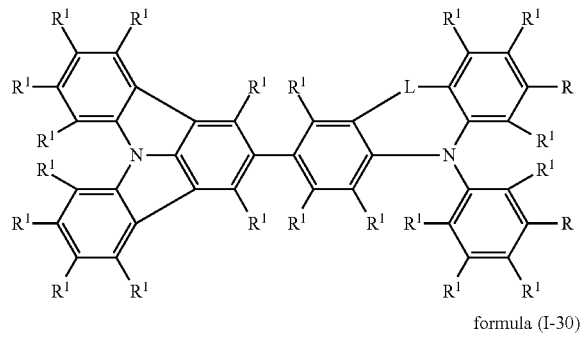
formula (I-30)
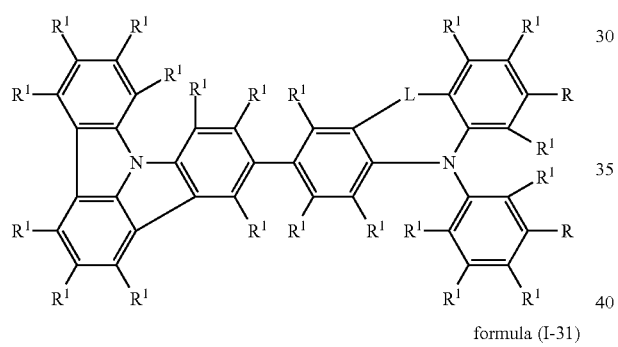
formula (I-31)
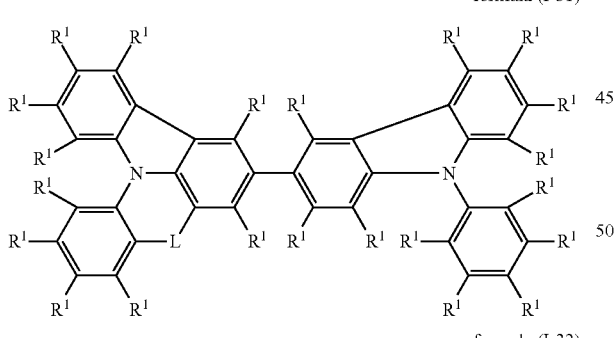
formula (I-32)
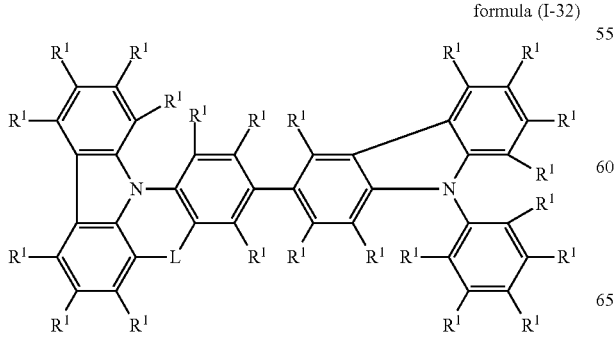
formula (I-33)
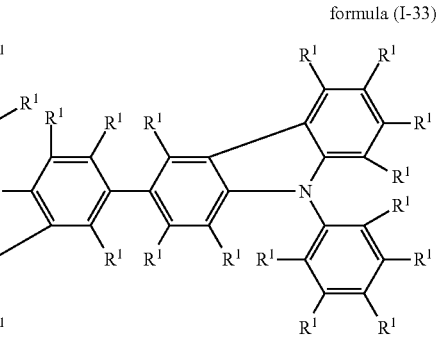
formula (I-34)
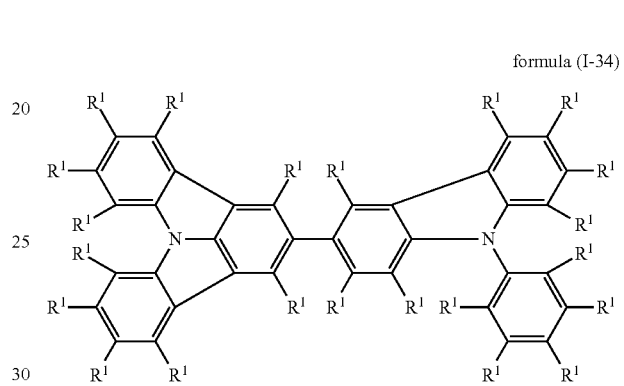
formula (I-35)
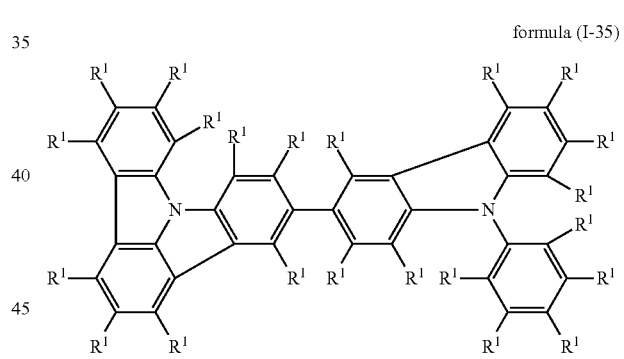
formula (I-36)
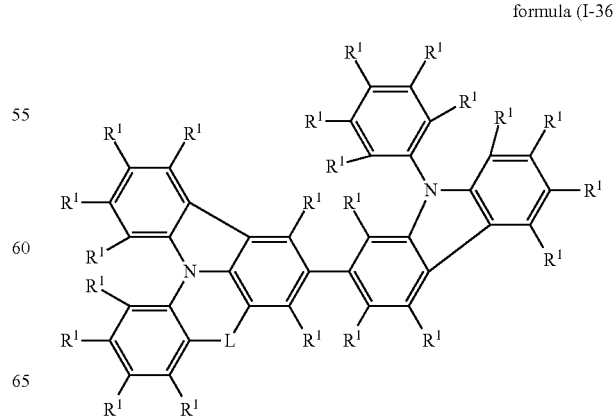

formula (I-37)
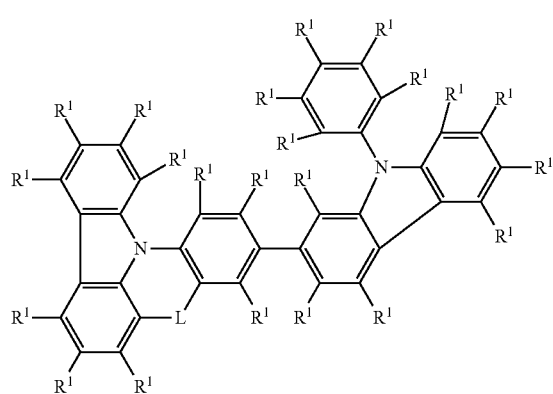
formula (I-41)
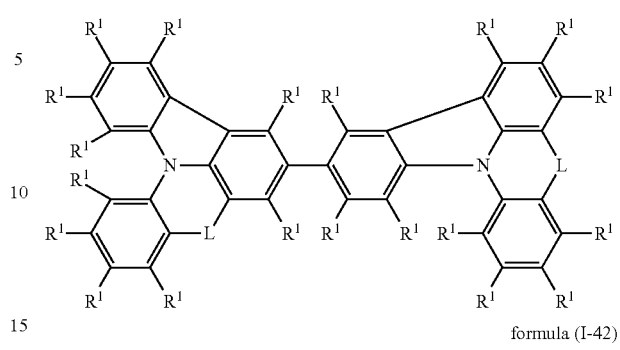
formula (I-38)
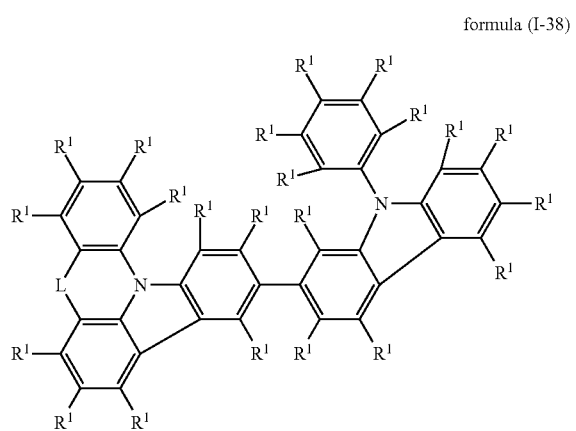
formula (I-42)
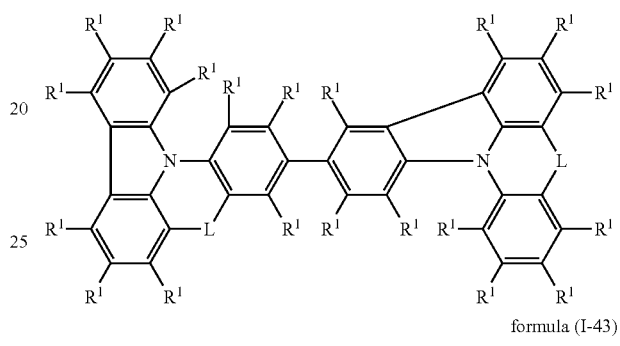
formula (I-39)
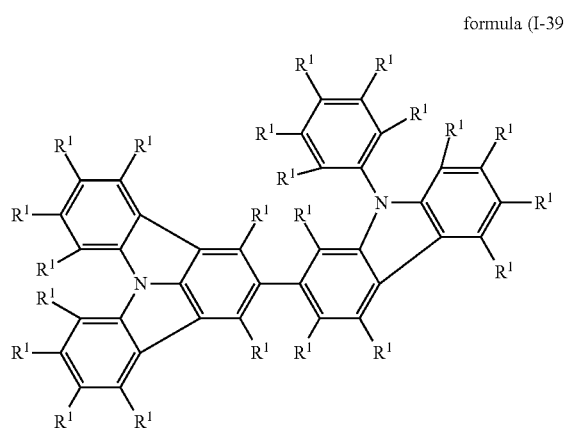
formula (I-43)
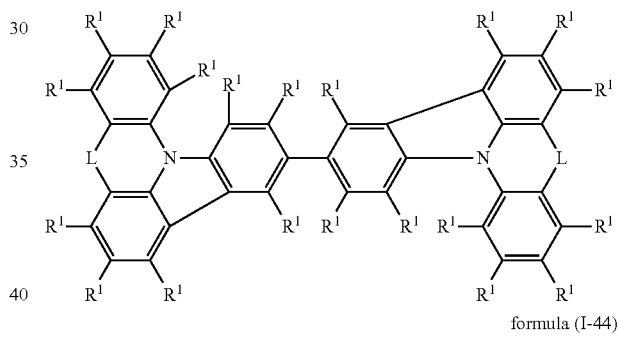
formula (I-40)
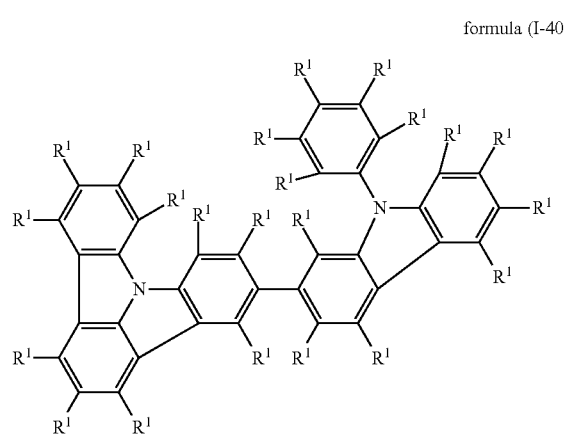
formula (I-44)
formula (I-45)
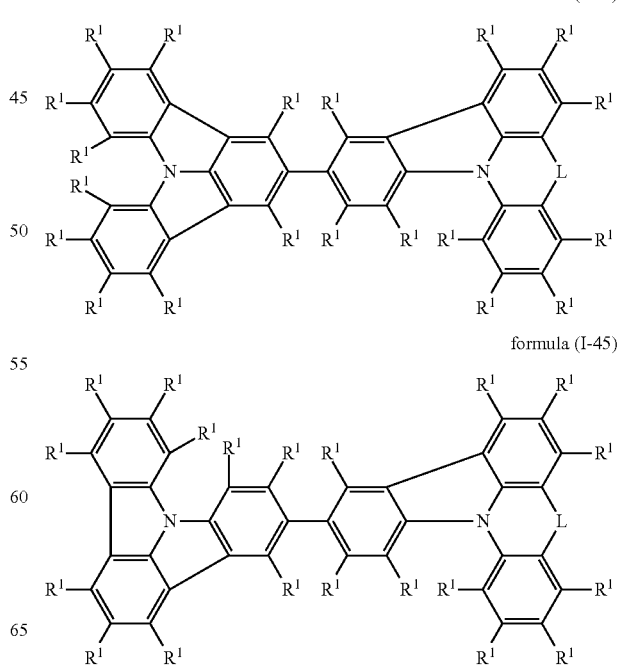

-continued
formula (I-46)
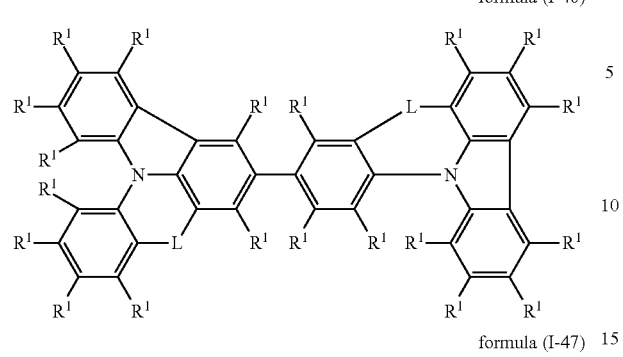
formula (I-47)
formula (I-48)
formula (I-49)
formula (I-50)
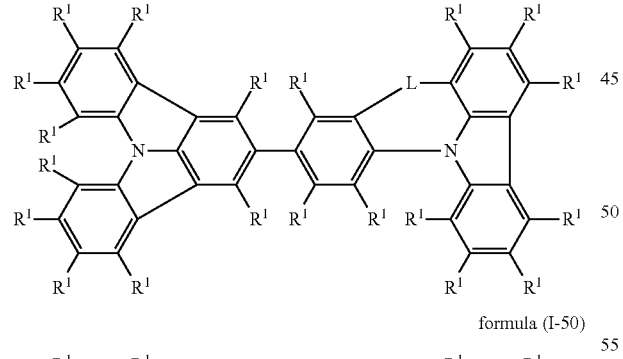
formula (I-51)
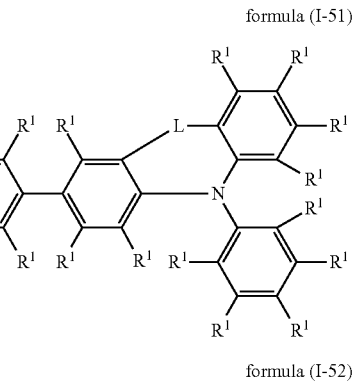
formula (I-52)
formula (I-53)
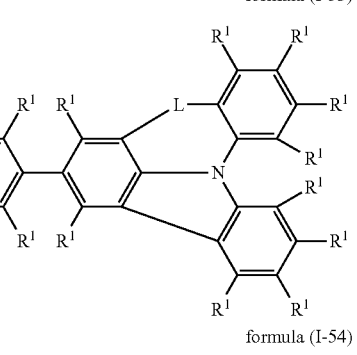
formula (I-54)
formula (I-55)
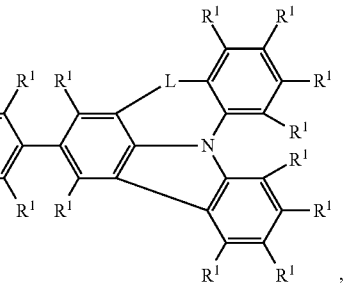
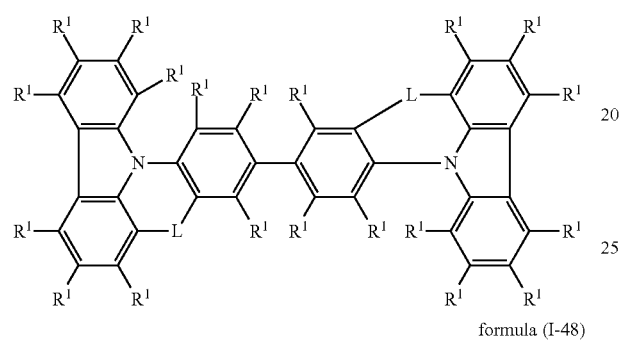
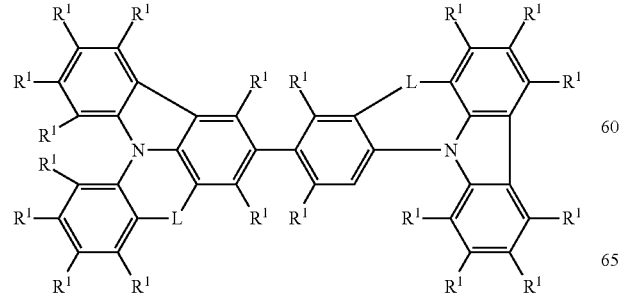

where the groups L and $R^1$ are defined as indicated above. L in the formulae indicated above is very particularly preferably selected on each occurrence, identically or differently, from $C(R^2)_2$ and $NR^2$.

In this case, $R^2$ is preferably selected from H, D, a straight-chain alkyl group having 1 to 8 carbon atoms, a branched alkyl group having 3 to 8 carbon atoms or an aryl group having 6 to 10 carbon atoms, where the said groups may each be substituted by one or more groups $R^3$.

In general, the preferred and particularly preferred embodiments mentioned in the present application can in accordance with the invention be combined with one another as desired.

In particular, it is preferred for the said preferred embodiments for $Ar^1$, $R^1$, Y, $T^1$, $T^2$, $T^3$ and L to occur in combination with one another.

Examples of preferred compounds of the formula (I) are the structures depicted below.

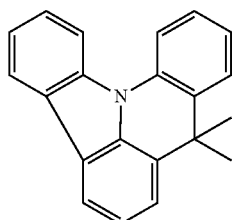

1

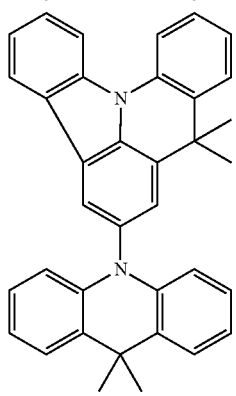 [SMILES: CC1(C)c2ccccc2N(c2cc3c4c(c2)c2ccccc2n4-c2ccccc2C3(C)C)c2ccccc21]

2

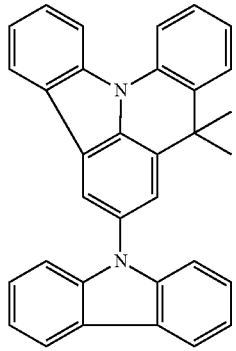 [SMILES: CC1(C)c2ccccc2-n2c3ccccc3c3cc(-n4c5ccccc5c5ccccc54)cc1c32]

3

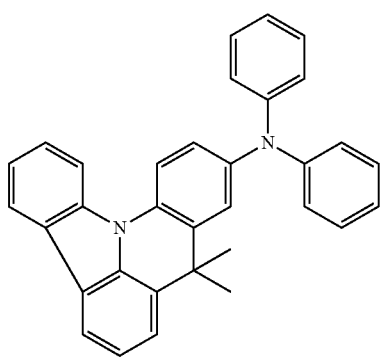 [SMILES: CC1(C)c2cc(N(c3ccccc3)c3ccccc3)ccc2-n2c3ccccc3c3cccc1c32]

4

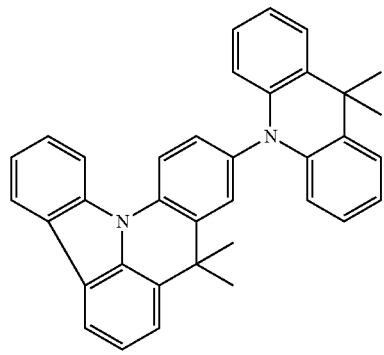 [SMILES: CC1(C)c2ccccc2N(c2ccc3c(c2)C(C)(C)c2cccc4c5ccccc5n-3c24)c2ccccc21]
5
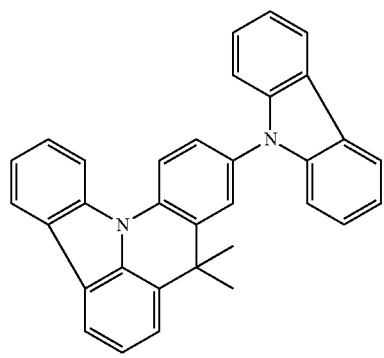 [SMILES: CC1(C)c2cc(-n3c4ccccc4c4ccccc43)ccc2-n2c3ccccc3c3cccc1c32]
6
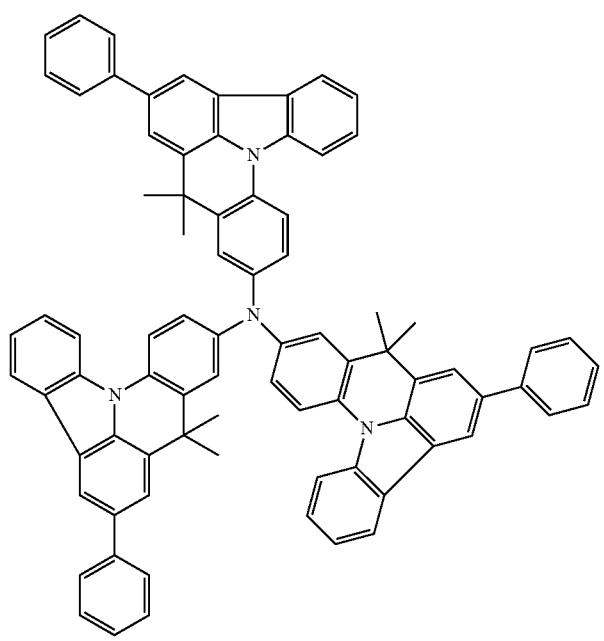 [SMILES: CC1(C)c2cc(N(c3ccc4c(c3)C(C)(C)c3cc(-c5ccccc5)cc5c6ccccc6n-4c35)c3ccc4c(c3)C(C)(C)c3cc(-c5ccccc5)cc5c6ccccc6n-4c35)ccc2-n2c3ccccc3c3cc(-c4ccccc4)cc1c32]
7

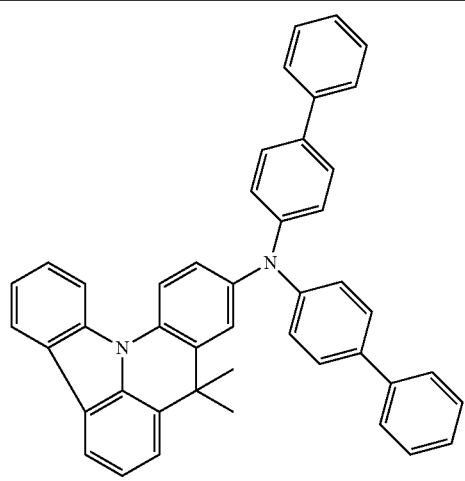
8
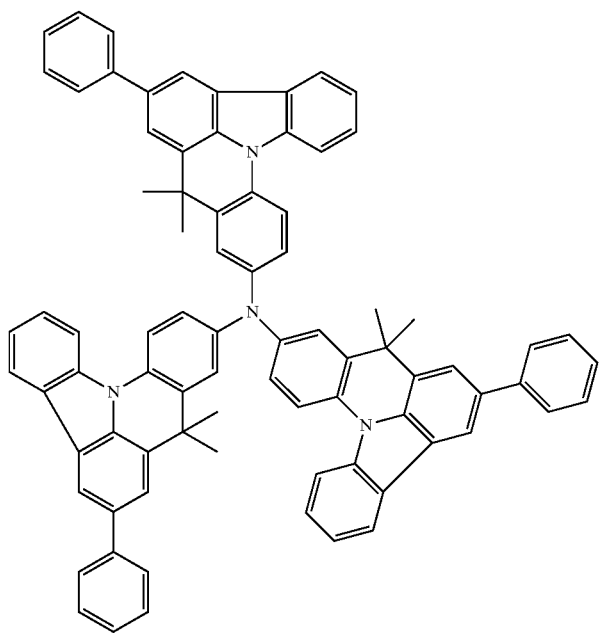 [SMILES: CC1(C)c2cc(N(c3ccc4c(c3)C(C)(C)c3cc(-c5ccccc5)cc5c6ccccc6n-4c35)c3ccc4c(c3)C(C)(C)c3cc(-c5ccccc5)cc5c6ccccc6n-4c35)ccc2-n2c3ccccc3c3cc(-c4ccccc4)cc1c32]
9
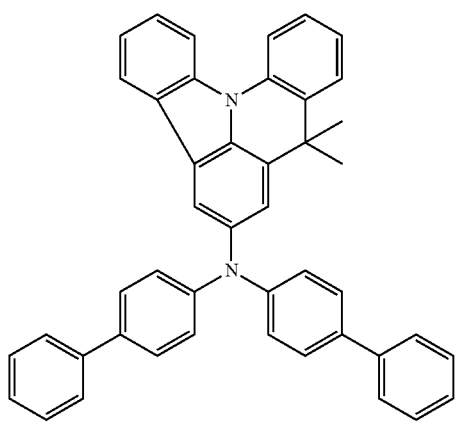 [SMILES: CC1(C)c2ccccc2-n2c3ccccc3c3cc(N(c4ccc(-c5ccccc5)cc4)c4ccc(-c5ccccc5)cc4)cc1c32]
10

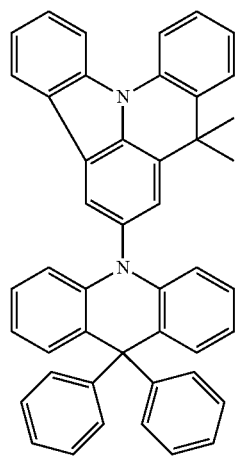 [SMILES: CC1(C)c2ccccc2-n2c3ccccc3c3cc(N4c5ccccc5C(c5ccccc5)(c5ccccc5)c5ccccc54)cc1c32]
11
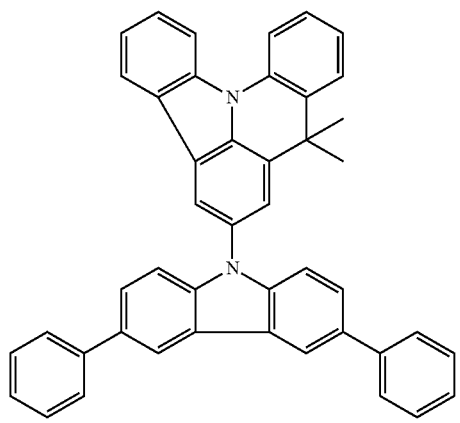 [SMILES: CC1(C)c2ccccc2-n2c3ccccc3c3cc(-n4c5ccc(-c6ccccc6)cc5c5cc(-c6ccccc6)ccc54)cc1c32]
12
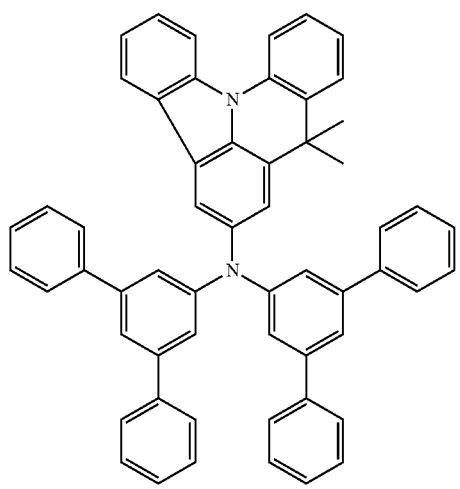 [SMILES: CC1(C)c2ccccc2-n2c3ccccc3c3cc(N(c4cc(-c5ccccc5)cc(-c5ccccc5)c4)c4cc(-c5ccccc5)cc(-c5ccccc5)c4)cc1c32]
13

-continued
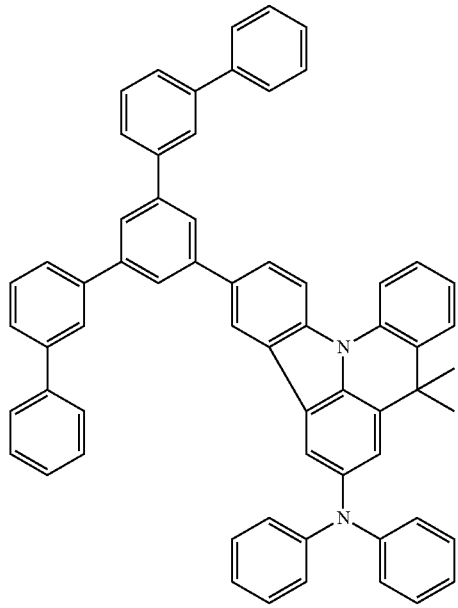 [SMILES: CC1(C)c2ccccc2-n2c3ccc(-c4cc(-c5cccc(-c6ccccc6)c5)cc(-c5cccc(-c6ccccc6)c5)c4)cc3c3cc(N(c4ccccc4)c4ccccc4)cc1c32]
14
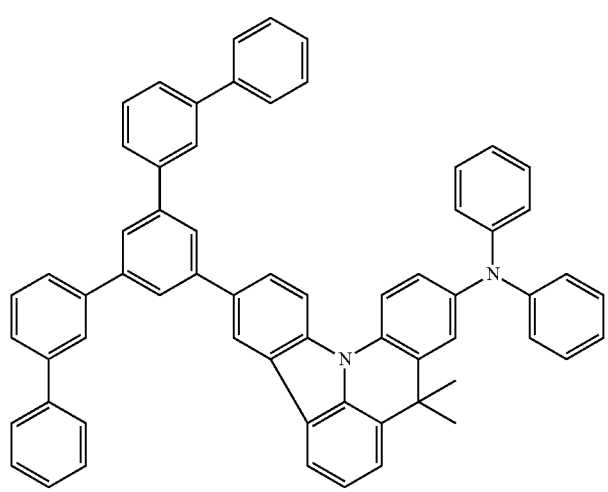 [SMILES: CC1(C)c2cc(N(c3ccccc3)c3ccccc3)ccc2-n2c3ccc(-c4cc(-c5cccc(-c6ccccc6)c5)cc(-c5cccc(-c6ccccc6)c5)c4)cc3c3cccc1c32]
15
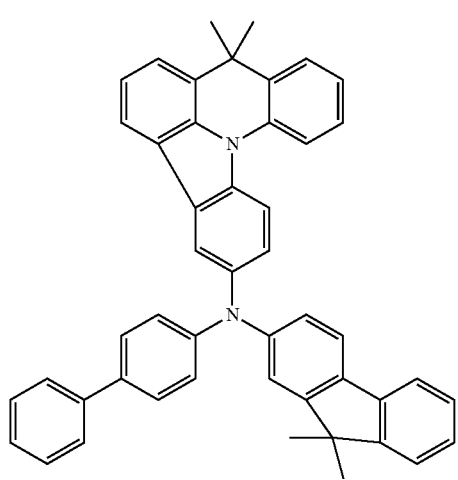 [SMILES: CC1(C)c2ccccc2-c2ccc(N(c3ccc(-c4ccccc4)cc3)c3ccc4c(c3)c3cccc5c3n4-c3ccccc3C5(C)C)cc21]
16

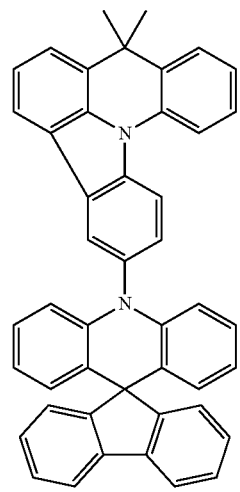 [SMILES: CC1(C)c2ccccc2-n2c3ccc(N4c5ccccc5C5(c6ccccc6-c6ccccc65)c5ccccc54)cc3c3cccc1c32]
17
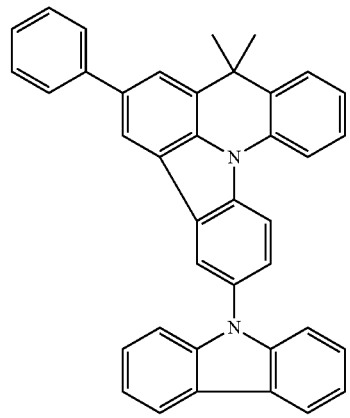 [SMILES: CC1(C)c2ccccc2-n2c3ccc(-n4c5ccccc5c5ccccc54)cc3c3cc(-c4ccccc4)cc1c32]
18
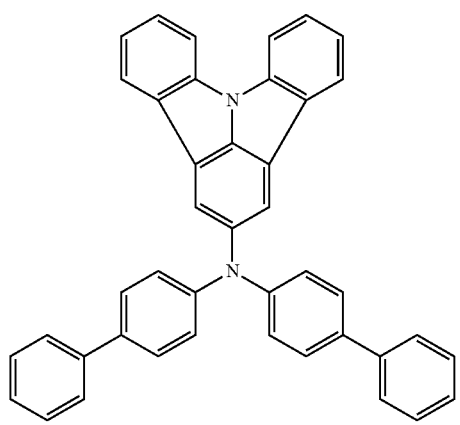 [SMILES: c1ccc(-c2ccc(N(c3ccc(-c4ccccc4)cc3)c3cc4c5ccccc5n5c6ccccc6c(c3)c45)cc2)cc1]
19

-continued
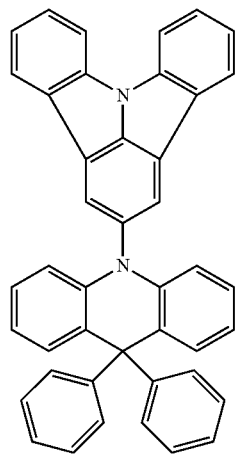 [SMILES: c1ccc(C2(c3ccccc3)c3ccccc3N(c3cc4c5ccccc5n5c6ccccc6c(c3)c45)c3ccccc32)cc1]
20
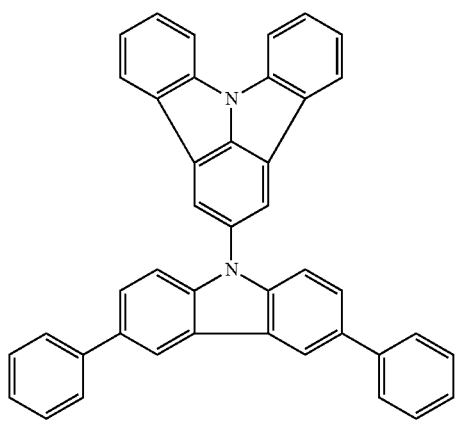 [SMILES: c1ccc(-c2ccc3c(c2)c2cc(-c4ccccc4)ccc2n3-c2cc3c4ccccc4n4c5ccccc5c(c2)c34)cc1]
21
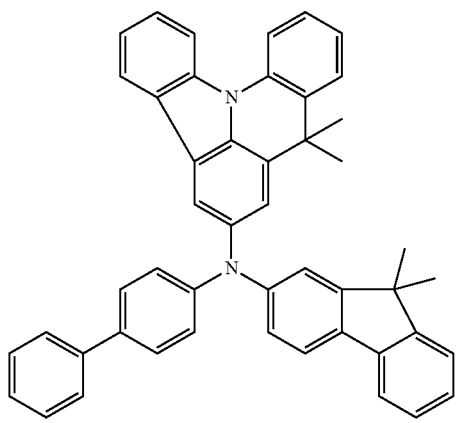 [SMILES: CC1(C)c2ccccc2-c2ccc(N(c3ccc(-c4ccccc4)cc3)c3cc4c5c(c3)c3ccccc3n5-c3ccccc3C4(C)C)cc21]
22

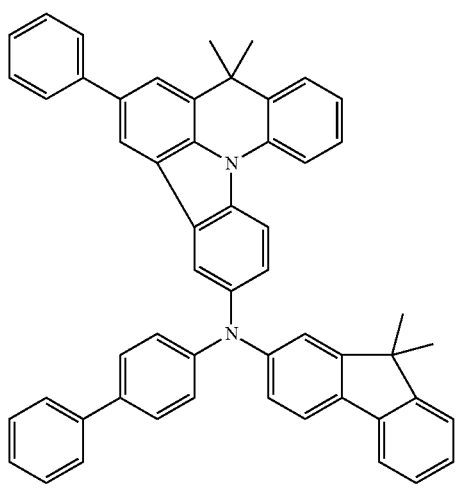 [SMILES: CC1(C)c2ccccc2-c2ccc(N(c3ccc(-c4ccccc4)cc3)c3ccc4c(c3)c3cc(-c5ccccc5)cc5c3n4-c3ccccc3C5(C)C)cc21]
23
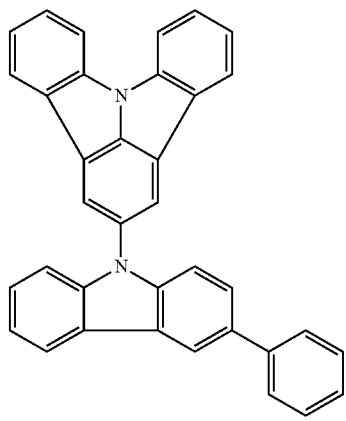 [SMILES: c1ccc(-c2ccc3c(c2)c2ccccc2n3-c2cc3c4ccccc4n4c5ccccc5c(c2)c34)cc1]
24
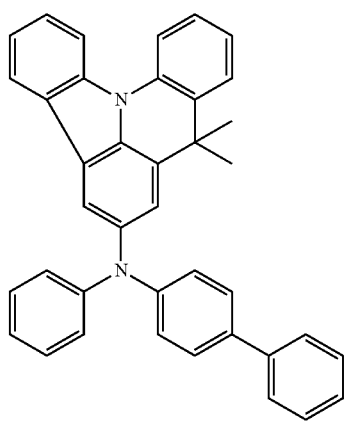 [SMILES: CC1(C)c2ccccc2-n2c3ccccc3c3cc(N(c4ccccc4)c4ccc(-c5ccccc5)cc4)cc1c32]
25

-continued
26
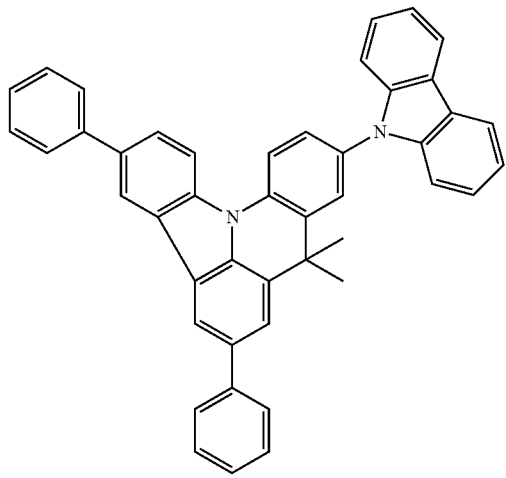 [SMILES: CC1(C)c2cc(-n3c4ccccc4c4ccccc43)ccc2-n2c3ccc(-c4ccccc4)cc3c3cc(-c4ccccc4)cc1c32]
27
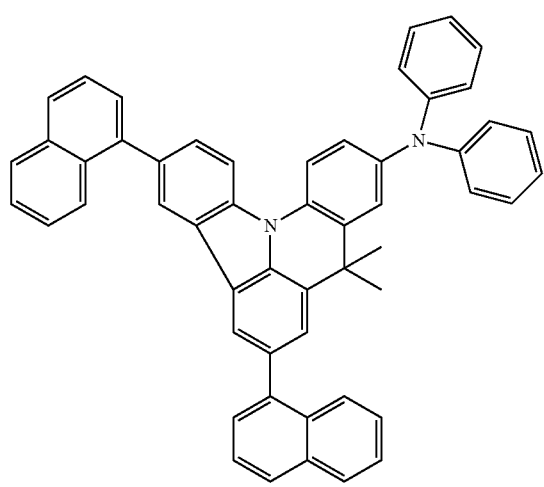 [SMILES: CC1(C)c2cc(N(c3ccccc3)c3ccccc3)ccc2-n2c3ccc(-c4cccc5ccccc45)cc3c3cc(-c4cccc5ccccc45)cc1c32]
28
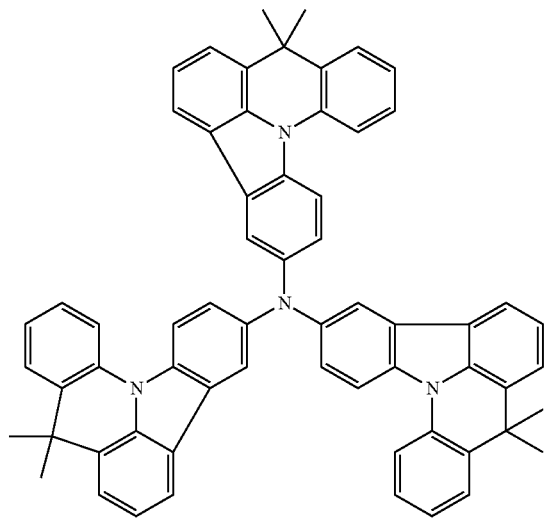

-continued
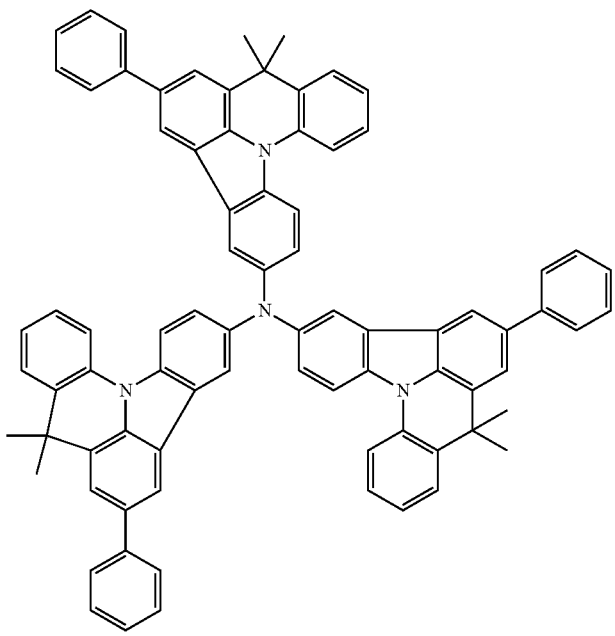 [SMILES: CC1(C)c2ccccc2-n2c3ccc(N(c4ccc5c(c4)c4cc(-c6ccccc6)cc6c4n5-c4ccccc4C6(C)C)c4ccc5c(c4)c4cc(-c6ccccc6)cc6c4n5-c4ccccc4C6(C)C)cc3c3cc(-c4ccccc4)cc1c32]
29
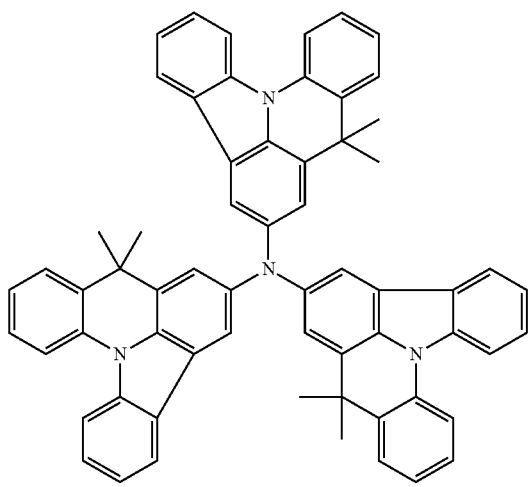 [SMILES: CC1(C)c2ccccc2-n2c3ccccc3c3cc(N(c4cc5c6c(c4)c4ccccc4n6-c4ccccc4C5(C)C)c4cc5c6c(c4)c4ccccc4n6-c4ccccc4C5(C)C)cc1c32]
30
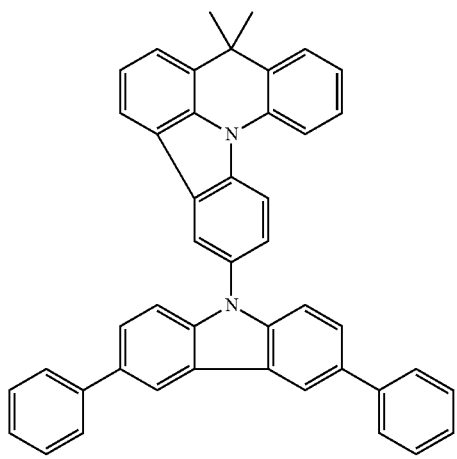 [SMILES: CC1(C)c2ccccc2-n2c3ccc(-n4c5ccc(-c6ccccc6)cc5c5cc(-c6ccccc6)ccc54)cc3c3cccc1c32]
31

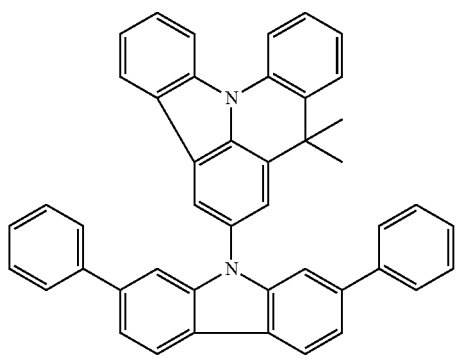 [SMILES: CC1(C)c2ccccc2-n2c3ccccc3c3cc(-n4c5cc(-c6ccccc6)ccc5c5ccc(-c6ccccc6)cc54)cc1c32]
32
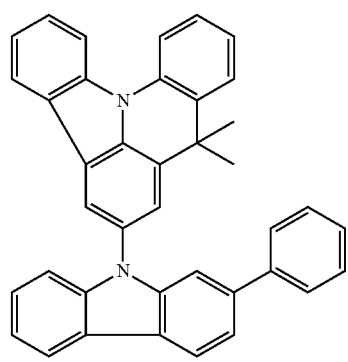 [SMILES: CC1(C)c2ccccc2-n2c3ccccc3c3cc(-n4c5ccccc5c5ccc(-c6ccccc6)cc54)cc1c32]
33
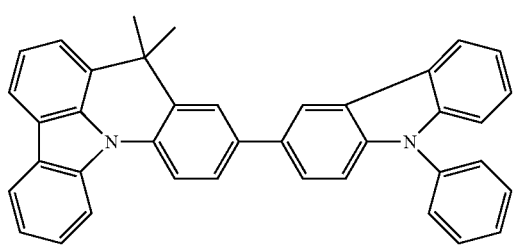 [SMILES: CC1(C)c2cc(-c3ccc4c(c3)c3ccccc3n4-c3ccccc3)ccc2-n2c3ccccc3c3cccc1c32]
34
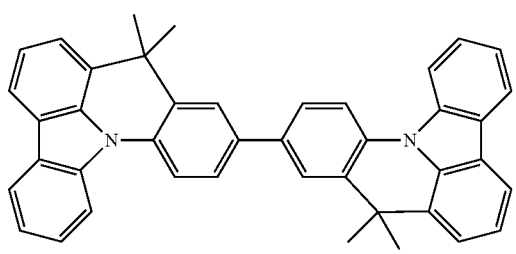 [SMILES: CC1(C)c2cc(-c3ccc4c(c3)C(C)(C)c3cccc5c6ccccc6n-4c35)ccc2-n2c3ccccc3c3cccc1c32]
35
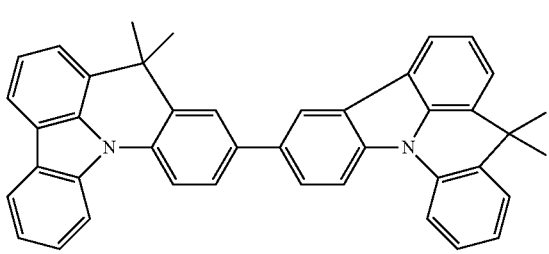 [SMILES: CC1(C)c2cc(-c3ccc4c(c3)c3cccc5c3n4-c3ccccc3C5(C)C)ccc2-n2c3ccccc3c3cccc1c32]
36

-continued
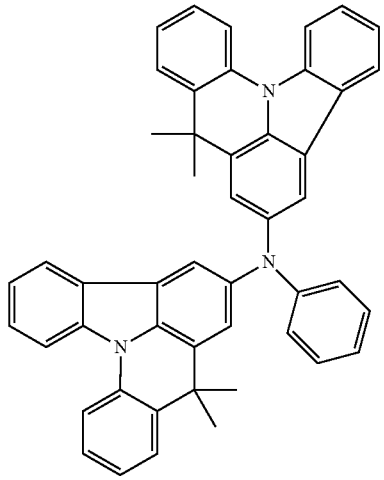 [SMILES: CC1(C)c2ccccc2-n2c3ccccc3c3cc(N(c4ccccc4)c4cc5c6c(c4)c4ccccc4n6-c4ccccc4C5(C)C)cc1c32]
37
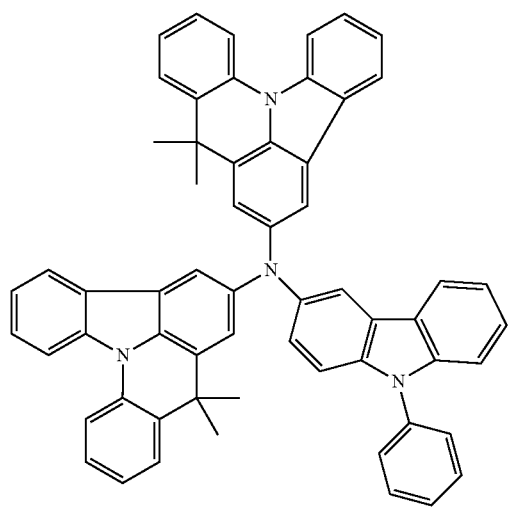 [SMILES: CC1(C)c2ccccc2-n2c3ccccc3c3cc(N(c4ccc5c(c4)c4ccccc4n5-c4ccccc4)c4cc5c6c(c4)c4ccccc4n6-c4ccccc4C5(C)C)cc1c32]
38
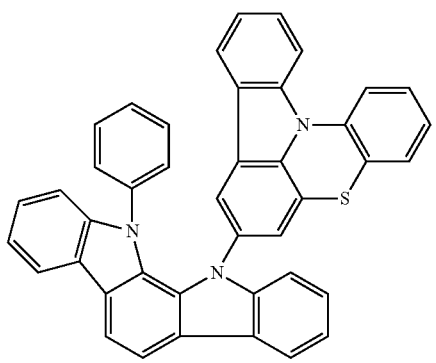 [SMILES: c1ccc(-n2c3ccccc3c3ccc4c5ccccc5n(-c5cc6c7c(c5)c5ccccc5n7-c5ccccc5S6)c4c32)cc1]
39

-continued
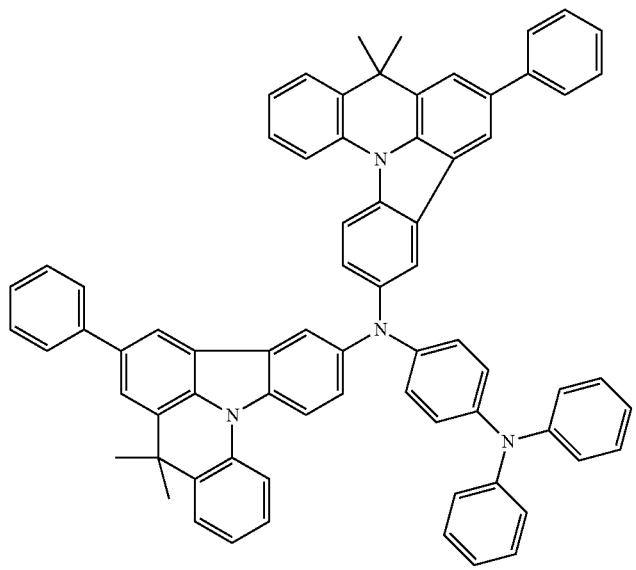 [SMILES: CC1(C)c2ccccc2-n2c3ccc(N(c4ccc(N(c5ccccc5)c5ccccc5)cc4)c4ccc5c(c4)c4cc(-c6ccccc6)cc6c4n5-c4ccccc4C6(C)C)cc3c3cc(-c4ccccc4)cc1c32]
40
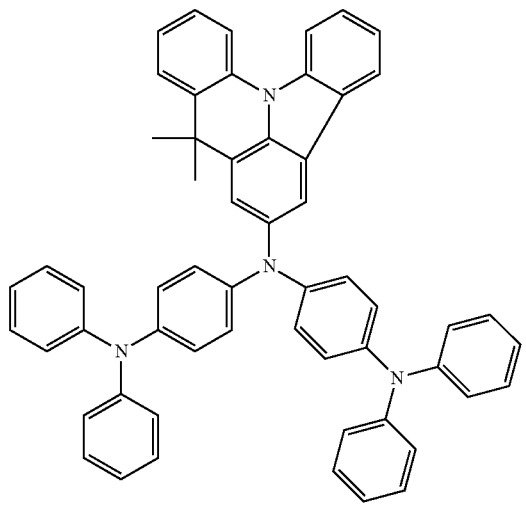 [SMILES: CC1(C)c2ccccc2-n2c3ccccc3c3cc(N(c4ccc(N(c5ccccc5)c5ccccc5)cc4)c4ccc(N(c5ccccc5)c5ccccc5)cc4)cc1c32]
41
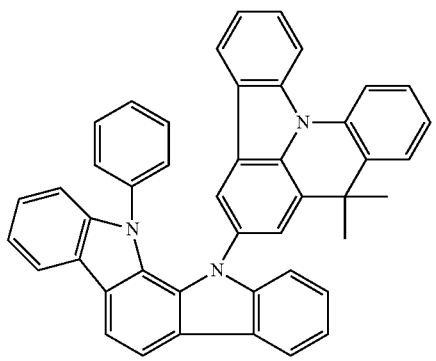 [SMILES: CC1(C)c2ccccc2-n2c3ccccc3c3cc(-n4c5ccccc5c5ccc6c7ccccc7n(-c7ccccc7)c6c54)cc1c32]
42

-continued
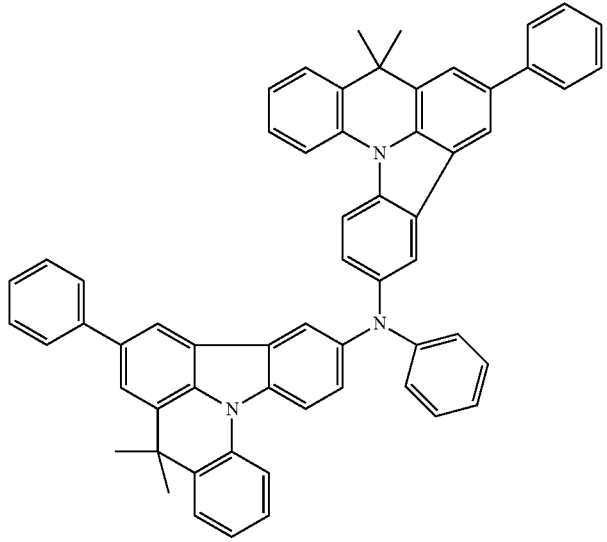 [SMILES: CC1(C)c2ccccc2-n2c3ccc(N(c4ccccc4)c4ccc5c(c4)c4cc(-c6ccccc6)cc6c4n5-c4ccccc4C6(C)C)cc3c3cc(-c4ccccc4)cc1c32]
43
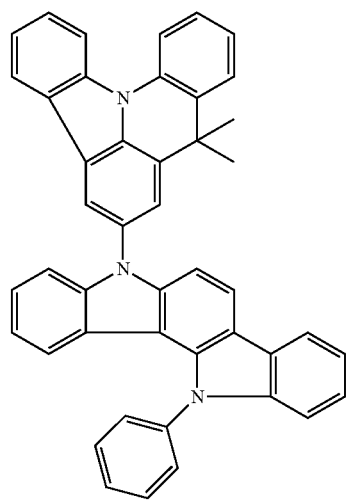 [SMILES: CC1(C)c2ccccc2-n2c3ccccc3c3cc(-n4c5ccccc5c5c4ccc4c6ccccc6n(-c6ccccc6)c45)cc1c32]
44
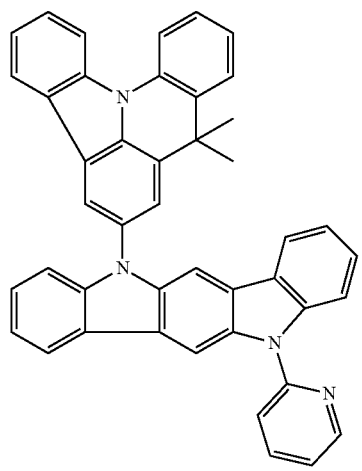 [SMILES: CC1(C)c2ccccc2-n2c3ccccc3c3cc(-n4c5ccccc5c5cc6c(cc54)c4ccccc4n6-c4ccccn4)cc1c32]
45

-continued
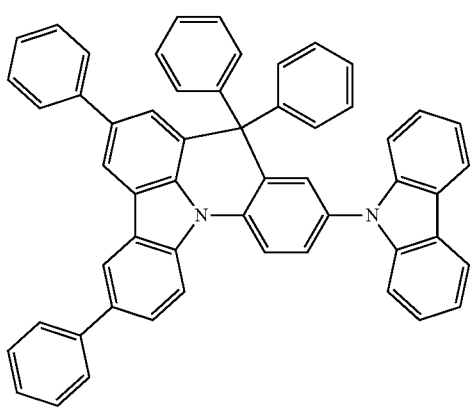 [SMILES: c1ccc(-c2ccc3c(c2)c2cc(-c4ccccc4)cc4c2n3-c2ccc(-n3c5ccccc5c5ccccc53)cc2C4(c2ccccc2)c2ccccc2)cc1]
46
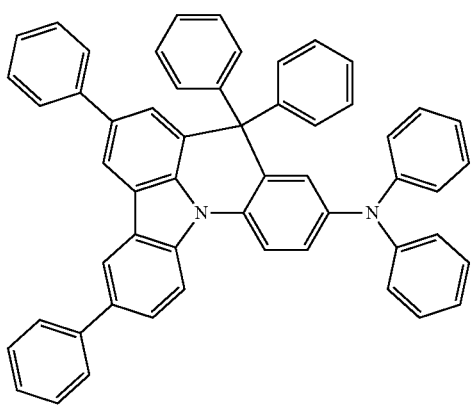 [SMILES: c1ccc(-c2ccc3c(c2)c2cc(-c4ccccc4)cc4c2n3-c2ccc(N(c3ccccc3)c3ccccc3)cc2C4(c2ccccc2)c2ccccc2)cc1]
47
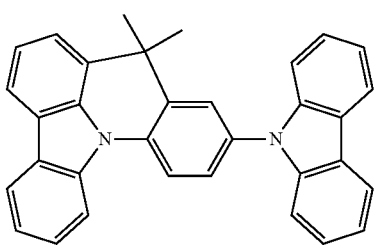 [SMILES: CC1(C)c2cc(-n3c4ccccc4c4ccccc43)ccc2-n2c3ccccc3c3cccc1c32]
48
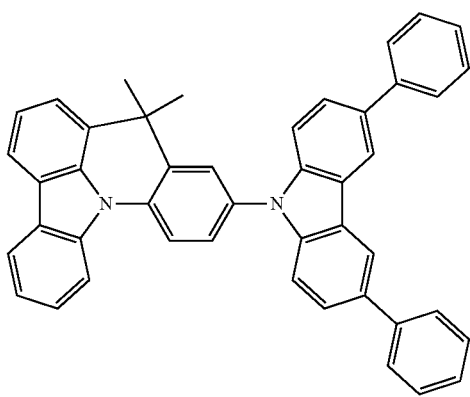 [SMILES: CC1(C)c2cc(-n3c4ccc(-c5ccccc5)cc4c4cc(-c5ccccc5)ccc43)ccc2-n2c3ccccc3c3cccc1c32]
49

-continued
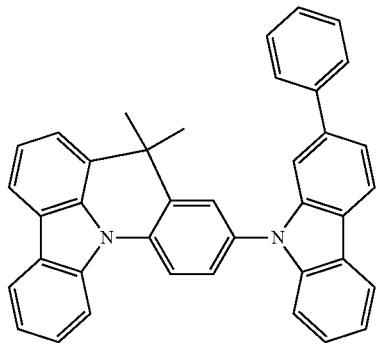 [SMILES: CC1(C)c2cc(-n3c4ccccc4c4ccc(-c5ccccc5)cc43)ccc2-n2c3ccccc3c3cccc1c32]
50
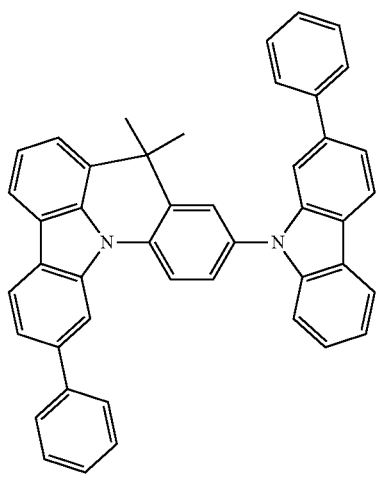 [SMILES: CC1(C)c2cc(-n3c4ccccc4c4ccc(-c5ccccc5)cc43)ccc2-n2c3cc(-c4ccccc4)ccc3c3cccc1c32]
51
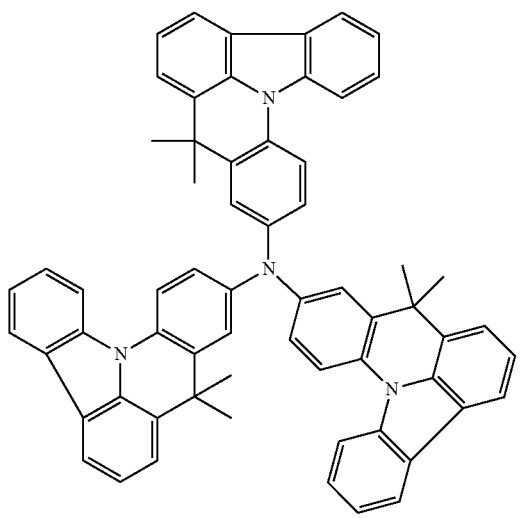 [SMILES: CC1(C)c2cc(N(c3ccc4c(c3)C(C)(C)c3cccc5c6ccccc6n-4c35)c3ccc4c(c3)C(C)(C)c3cccc5c6ccccc6n-4c35)ccc2-n2c3ccccc3c3cccc1c32]
52

-continued
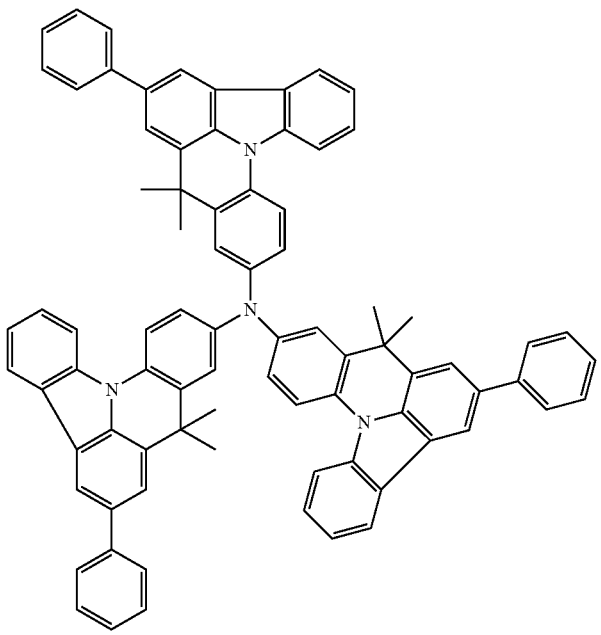 [SMILES: CC1(C)c2cc(N(c3ccc4c(c3)C(C)(C)c3cc(-c5ccccc5)cc5c6ccccc6n-4c35)c3ccc4c(c3)C(C)(C)c3cc(-c5ccccc5)cc5c6ccccc6n-4c35)ccc2-n2c3ccccc3c3cc(-c4ccccc4)cc1c32]
53
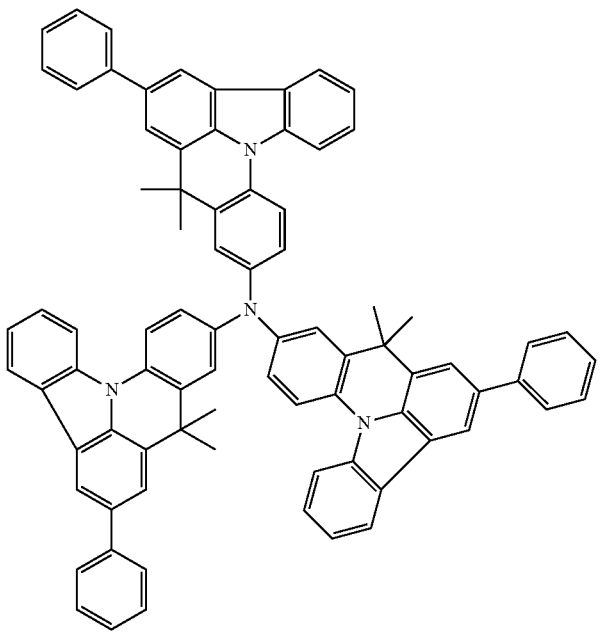 [SMILES: CC1(C)c2cc(N(c3ccc4c(c3)C(C)(C)c3cc(-c5ccccc5)cc5c6ccccc6n-4c35)c3ccc4c(c3)C(C)(C)c3cc(-c5ccccc5)cc5c6ccccc6n-4c35)ccc2-n2c3ccccc3c3cc(-c4ccccc4)cc1c32]
54
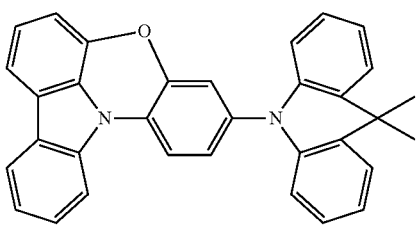 [SMILES: CC1(C)c2ccccc2N(c2ccc3c(c2)Oc2cccc4c5ccccc5n-3c24)c2ccccc21]
55

-continued
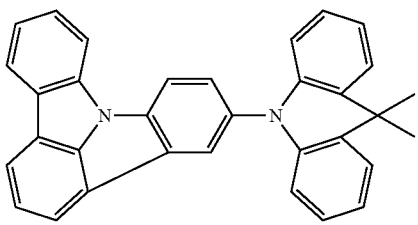 [SMILES: CC1(C)c2ccccc2N(c2ccc3c(c2)c2cccc4c5ccccc5n3c42)c2ccccc21]
56
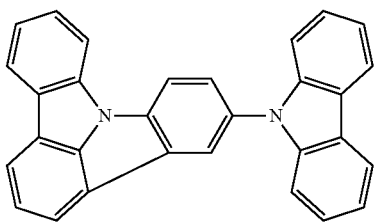 [SMILES: c1ccc2c(c1)c1ccccc1n2-c1ccc2c(c1)c1cccc3c4ccccc4n2c31]
57
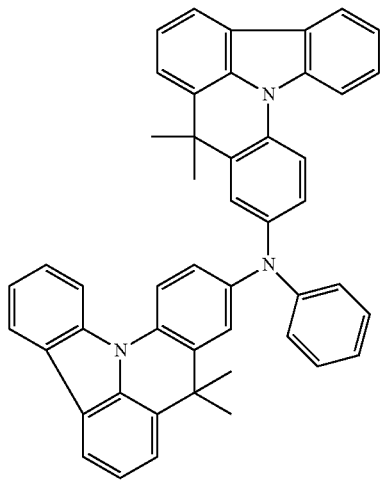 [SMILES: CC1(C)c2cc(N(c3ccccc3)c3ccc4c(c3)C(C)(C)c3cccc5c6ccccc6n-4c35)ccc2-n2c3ccccc3c3cccc1c32]
58
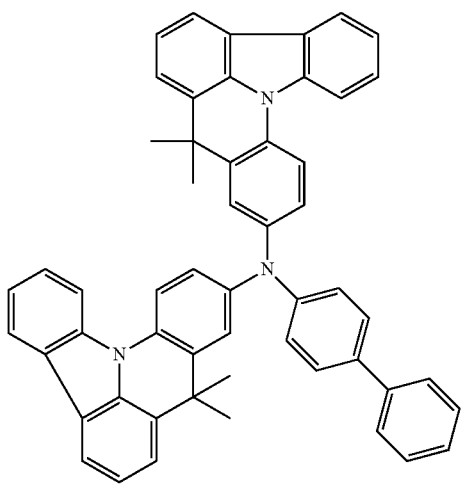 [SMILES: CC1(C)c2cc(N(c3ccc(-c4ccccc4)cc3)c3ccc4c(c3)C(C)(C)c3cccc5c6ccccc6n-4c35)ccc2-n2c3ccccc3c3cccc1c32]
59

-continued
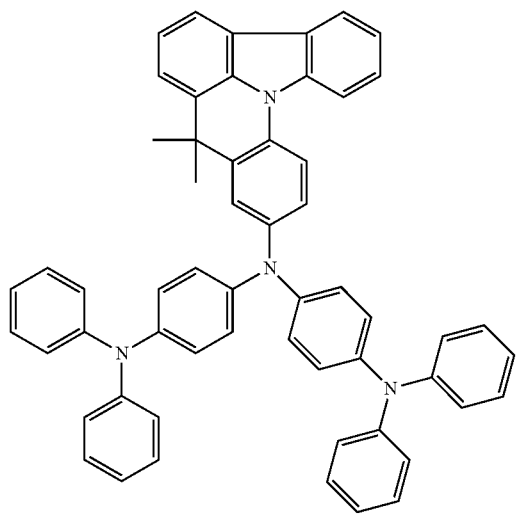 [SMILES: CC1(C)c2cc(N(c3ccc(N(c4ccccc4)c4ccccc4)cc3)c3ccc(N(c4ccccc4)c4ccccc4)cc3)ccc2-n2c3ccccc3c3cccc1c32]
60
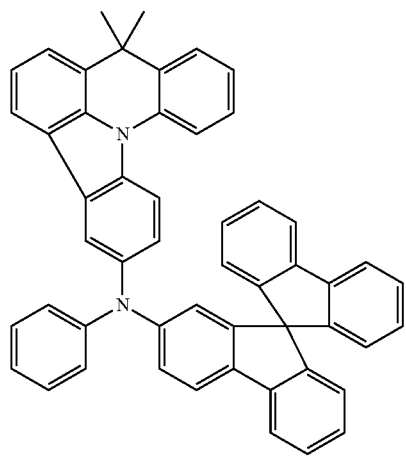 [SMILES: CC1(C)c2ccccc2-n2c3ccc(N(c4ccccc4)c4ccc5c(c4)C4(c6ccccc6-c6ccccc64)c4ccccc4-5)cc3c3cccc1c32]
61
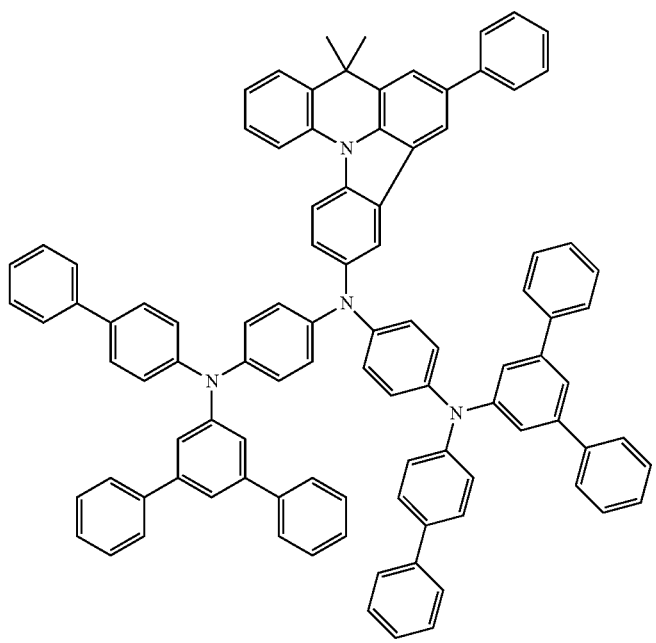 [SMILES: CC1(C)c2ccccc2-n2c3ccc(N(c4ccc(N(c5ccc(-c6ccccc6)cc5)c5cc(-c6ccccc6)cc(-c6ccccc6)c5)cc4)c4ccc(N(c5ccc(-c6ccccc6)cc5)c5cc(-c6ccccc6)cc(-c6ccccc6)c5)cc4)cc3c3cc(-c4ccccc4)cc1c32]
62

-continued
63
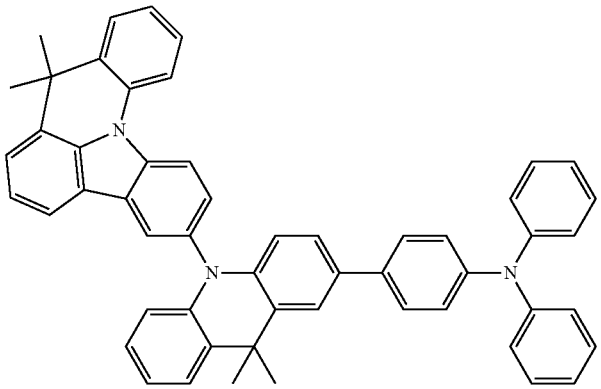 [SMILES: CC1(C)c2ccccc2N(c2ccc3c(c2)c2cccc4c2n3-c2ccccc2C4(C)C)c2ccc(-c3ccc(N(c4ccccc4)c4ccccc4)cc3)cc21]
64
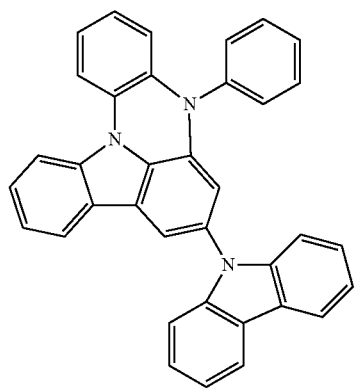 [SMILES: c1ccc(N2c3ccccc3-n3c4ccccc4c4cc(-n5c6ccccc6c6ccccc65)cc2c43)cc1]
65
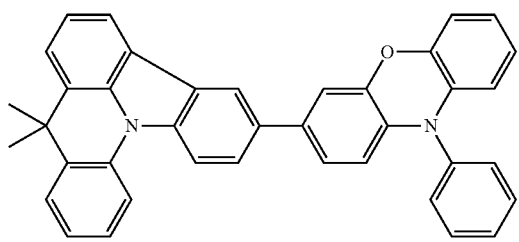 [SMILES: CC1(C)c2ccccc2-n2c3ccc(-c4ccc5c(c4)Oc4ccccc4N5c4ccccc4)cc3c3cccc1c32]
66
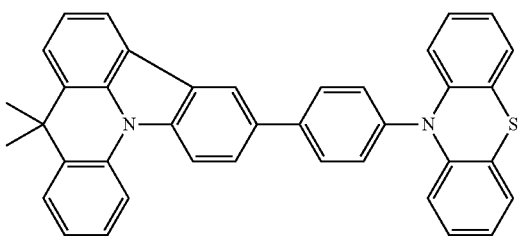 [SMILES: CC1(C)c2ccccc2-n2c3ccc(-c4ccc(N5c6ccccc6Sc6ccccc65)cc4)cc3c3cccc1c32]
67
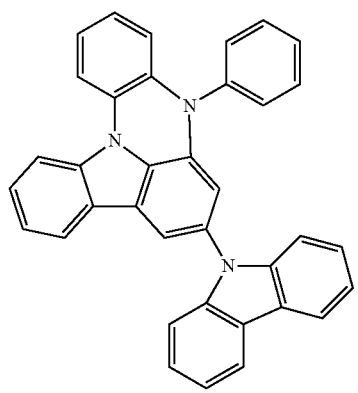 [SMILES: c1ccc(N2c3ccccc3-n3c4ccccc4c4cc(-n5c6ccccc6c6ccccc65)cc2c43)cc1]

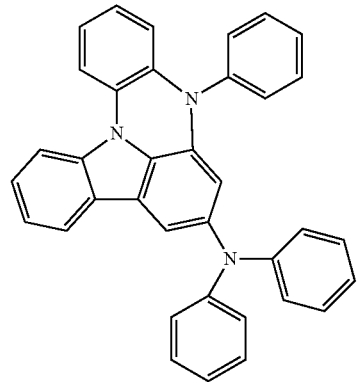 [SMILES: c1ccc(N(c2ccccc2)c2cc3c4c(c2)c2ccccc2n4-c2ccccc2N3c2ccccc2)cc1]
68
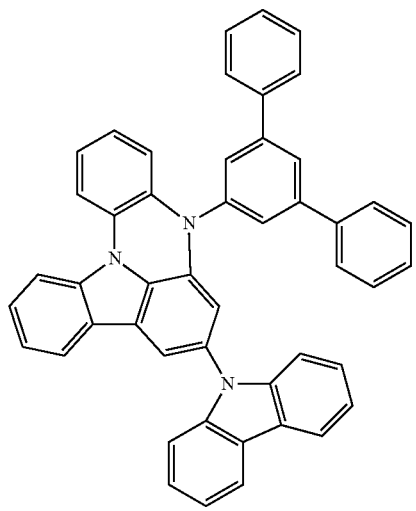 [SMILES: c1ccc(-c2cc(-c3ccccc3)cc(N3c4ccccc4-n4c5ccccc5c5cc(-n6c7ccccc7c7ccccc76)cc3c54)c2)cc1]
69
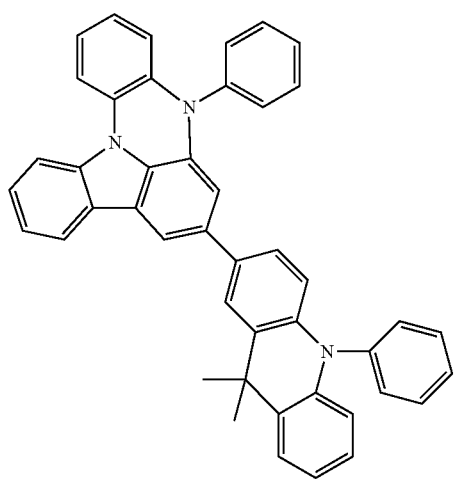 [SMILES: CC1(C)c2ccccc2N(c2ccccc2)c2ccc(-c3cc4c5c(c3)c3ccccc3n5-c3ccccc3N4c3ccccc3)cc21]
70

71
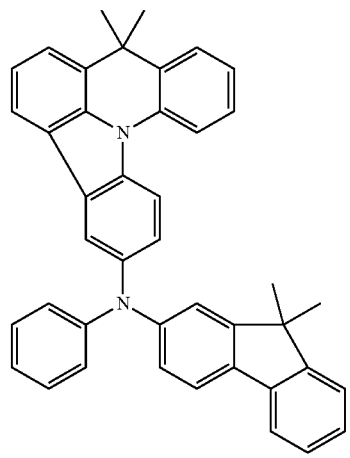 [SMILES: CC1(C)c2ccccc2-c2ccc(N(c3ccccc3)c3ccc4c(c3)c3cccc5c3n4-c3ccccc3C5(C)C)cc21]
72
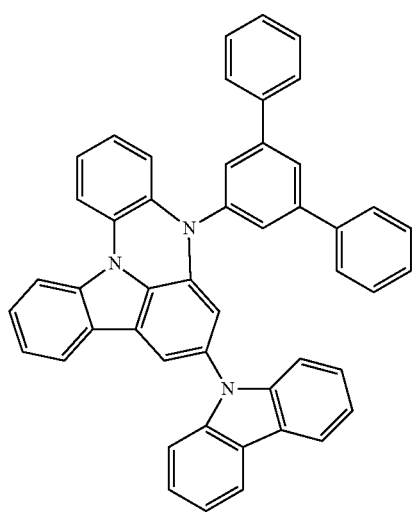 [SMILES: c1ccc(-c2cc(-c3ccccc3)cc(N3c4ccccc4-n4c5ccccc5c5cc(-n6c7ccccc7c7ccccc76)cc3c54)c2)cc1]
73
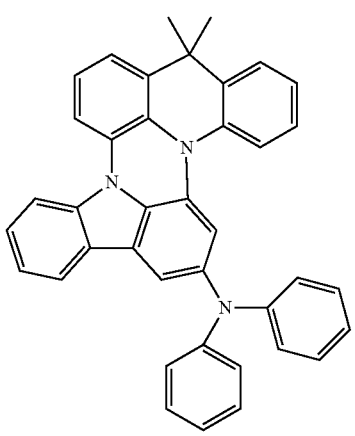 [SMILES: CC1(C)c2ccccc2N2c3c(cccc31)-n1c3ccccc3c3cc(N(c4ccccc4)c4ccccc4)cc2c31]

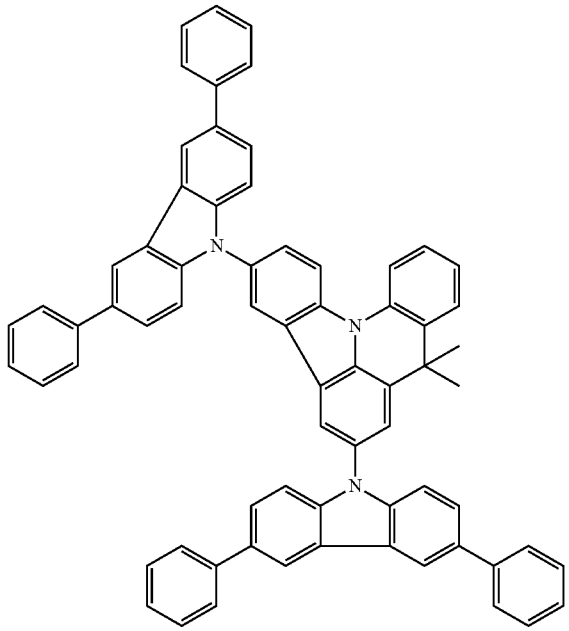 [SMILES: CC1(C)c2ccccc2-n2c3ccc(-n4c5ccc(-c6ccccc6)cc5c5cc(-c6ccccc6)ccc54)cc3c3cc(-n4c5ccc(-c6ccccc6)cc5c5cc(-c6ccccc6)ccc54)cc1c32]
74
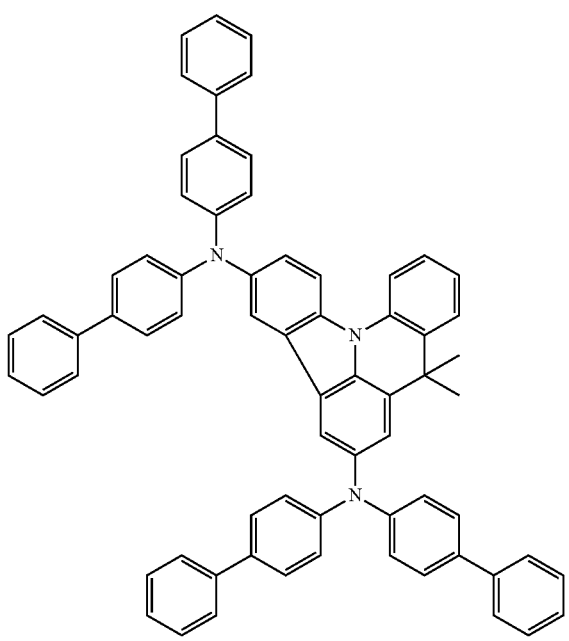 [SMILES: CC1(C)c2ccccc2-n2c3ccc(N(c4ccc(-c5ccccc5)cc4)c4ccc(-c5ccccc5)cc4)cc3c3cc(N(c4ccc(-c5ccccc5)cc4)c4ccc(-c5ccccc5)cc4)cc1c32]
75

-continued
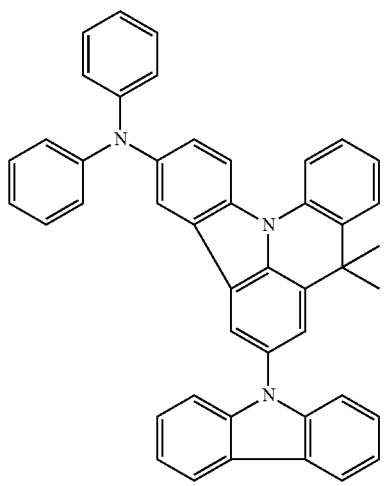 [SMILES: CC1(C)c2ccccc2-n2c3ccc(N(c4ccccc4)c4ccccc4)cc3c3cc(-n4c5ccccc5c5ccccc54)cc1c32]
76
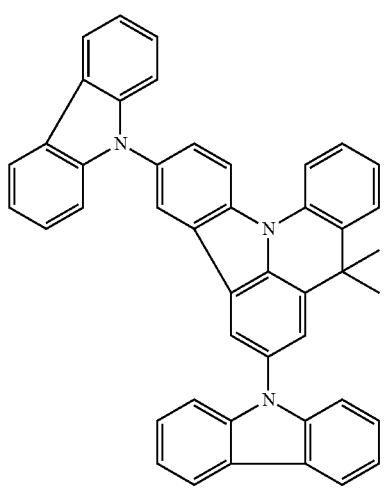 [SMILES: CC1(C)c2ccccc2-n2c3ccc(-n4c5ccccc5c5ccccc54)cc3c3cc(-n4c5ccccc5c5ccccc54)cc1c32]
77
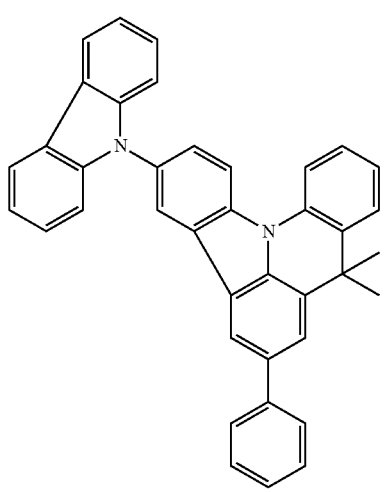 [SMILES: CC1(C)c2ccccc2-n2c3ccc(-n4c5ccccc5c5ccccc54)cc3c3cc(-c4ccccc4)cc1c32]
78

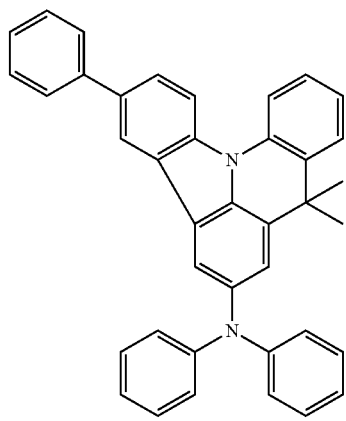 [SMILES: CC1(C)c2ccccc2-n2c3ccc(-c4ccccc4)cc3c3cc(N(c4ccccc4)c4ccccc4)cc1c32]
79
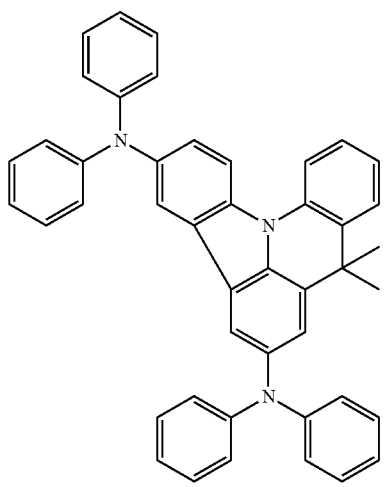 [SMILES: CC1(C)c2ccccc2-n2c3ccc(N(c4ccccc4)c4ccccc4)cc3c3cc(N(c4ccccc4)c4ccccc4)cc1c32]
80
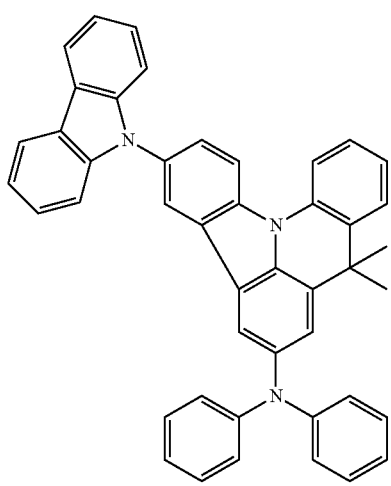 [SMILES: CC1(C)c2ccccc2-n2c3ccc(-n4c5ccccc5c5ccccc54)cc3c3cc(N(c4ccccc4)c4ccccc4)cc1c32]
81

-continued
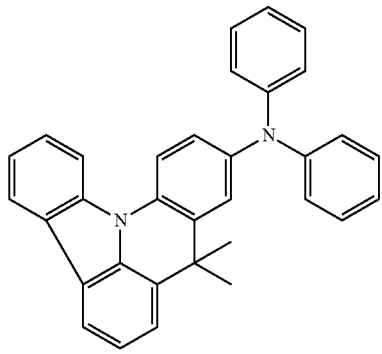 [SMILES: CC1(C)c2cc(N(c3ccccc3)c3ccccc3)ccc2-n2c3ccccc3c3cccc1c32]
82
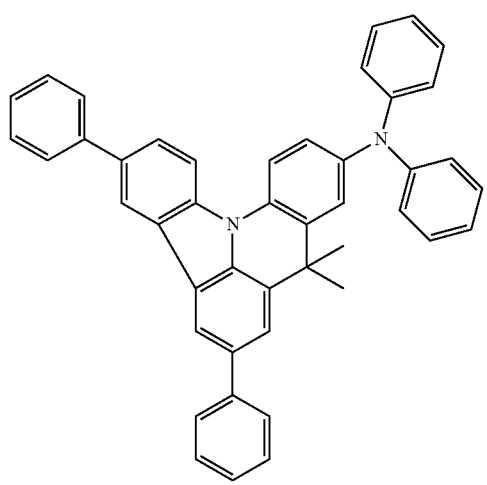 [SMILES: CC1(C)c2cc(N(c3ccccc3)c3ccccc3)ccc2-n2c3ccc(-c4ccccc4)cc3c3cc(-c4ccccc4)cc1c32]
83
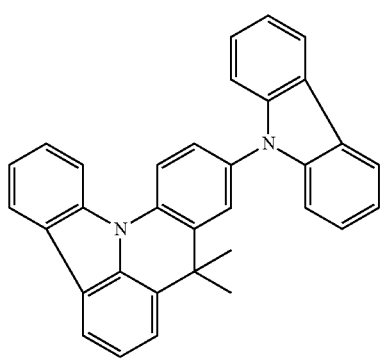 [SMILES: CC1(C)c2cc(-n3c4ccccc4c4ccccc43)ccc2-n2c3ccccc3c3cccc1c32]
84
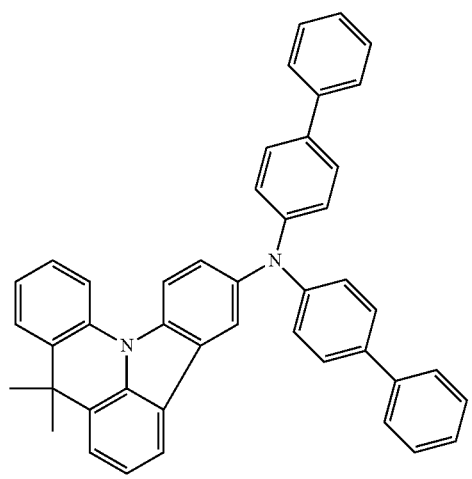 [SMILES: CC1(C)c2ccccc2-n2c3ccc(N(c4ccc(-c5ccccc5)cc4)c4ccc(-c5ccccc5)cc4)cc3c3cccc1c32]
85

86
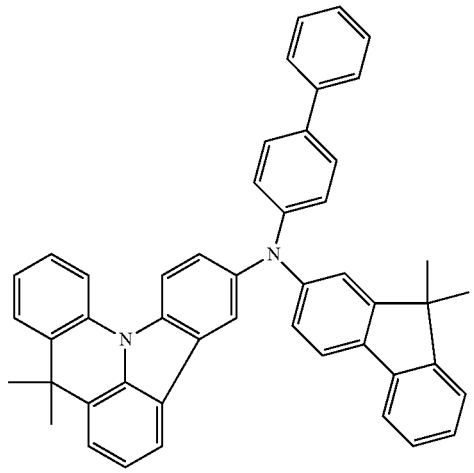
87
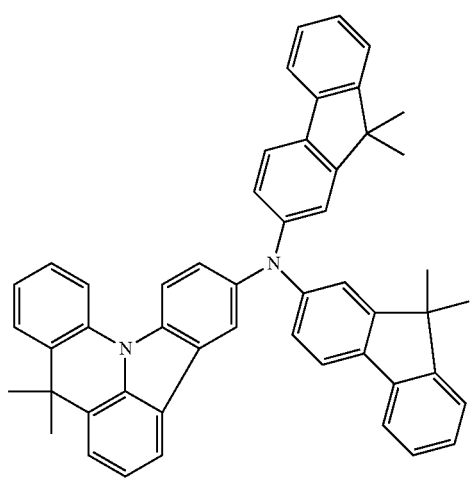
88
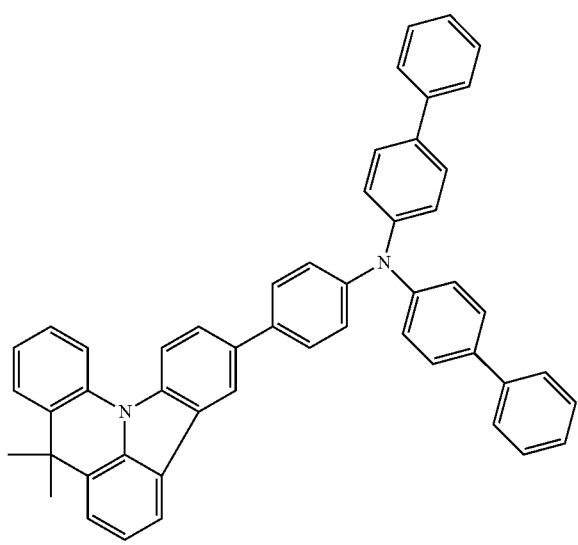 [SMILES: CC1(C)c2ccccc2-n2c3ccc(-c4ccc(N(c5ccc(-c6ccccc6)cc5)c5ccc(-c6ccccc6)cc5)cc4)cc3c3cccc1c32]

-continued
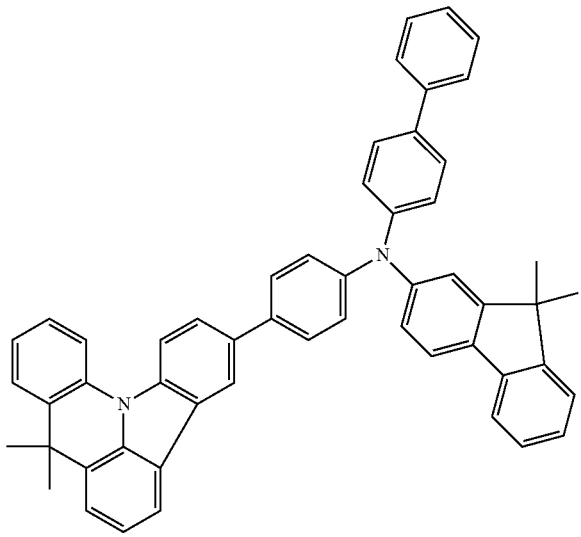
89
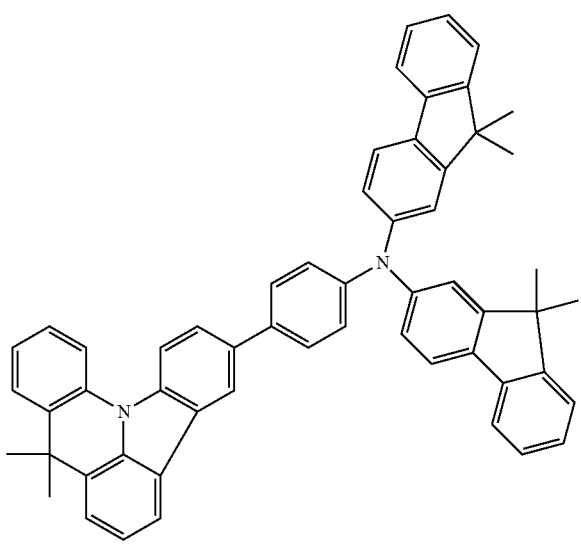
90
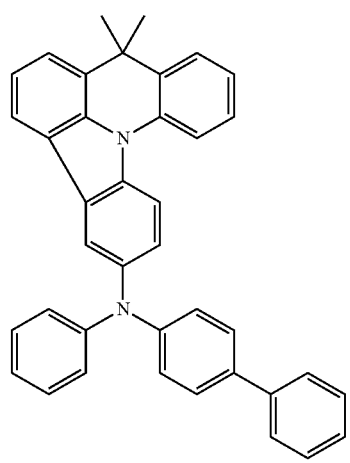 [SMILES: CC1(C)c2ccccc2-n2c3ccc(N(c4ccccc4)c4ccc(-c5ccccc5)cc4)cc3c3cccc1c32]
91

-continued
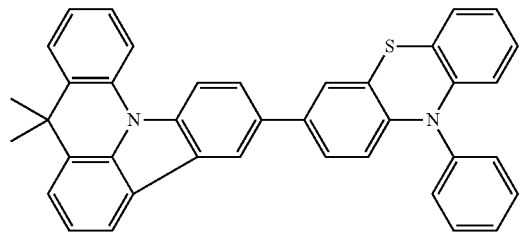
92
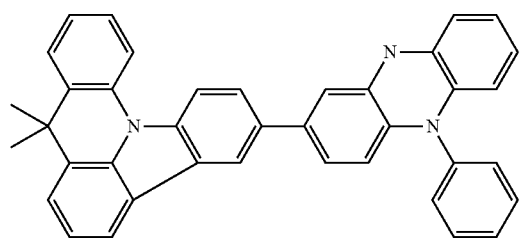 [SMILES: CC1(C)c2ccccc2-n2c3ccc(-c4ccc5c(c4)Sc4ccccc4N5c4ccccc4)cc3c3cccc1c32]
93
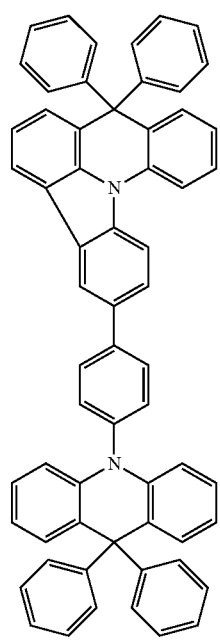 [SMILES: c1ccc(C2(c3ccccc3)c3ccccc3N(c3ccc(-c4ccc5c(c4)c4cccc6c4n5-c4ccccc4C6(c4ccccc4)c4ccccc4)cc3)c3ccccc32)cc1]
94

-continued
95
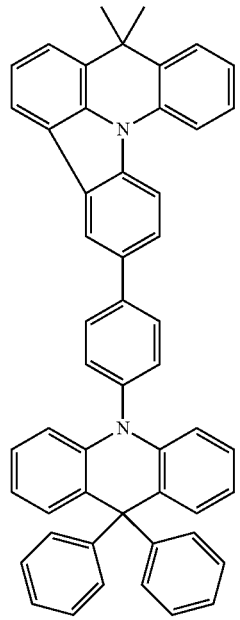 [SMILES: CC1(C)c2ccccc2-n2c3ccc(-c4ccc(N5c6ccccc6C(c6ccccc6)(c6ccccc6)c6ccccc65)cc4)cc3c3cccc1c32]
96
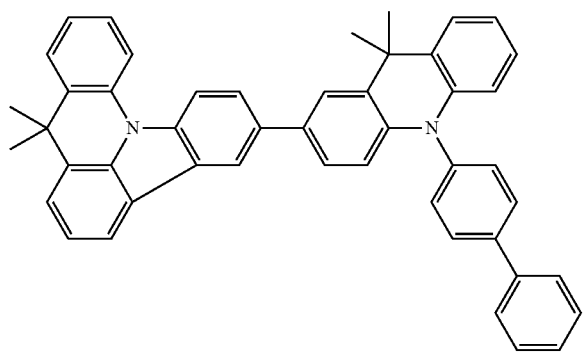 [SMILES: CC1(C)c2ccccc2N(c2ccc(-c3ccccc3)cc2)c2ccc(-c3ccc4c(c3)c3cccc5c3n4-c3ccccc3C5(C)C)cc21]
97
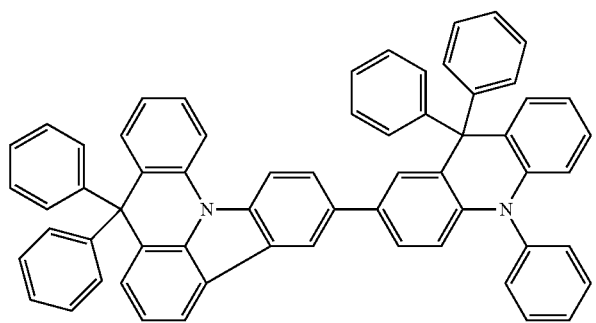 [SMILES: c1ccc(N2c3ccccc3C(c3ccccc3)(c3ccccc3)c3cc(-c4ccc5c(c4)c4cccc6c4n5-c4ccccc4C6(c4ccccc4)c4ccccc4)ccc32)cc1]
98
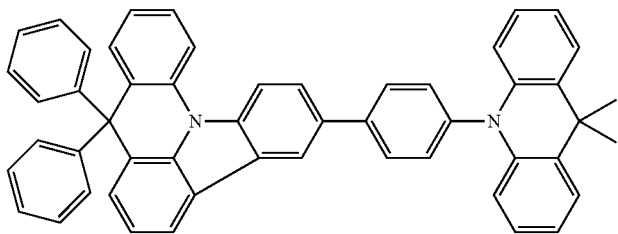 [SMILES: CC1(C)c2ccccc2N(c2ccc(-c3ccc4c(c3)c3cccc5c3n4-c3ccccc3C5(c3ccccc3)c3ccccc3)cc2)c2ccccc21]

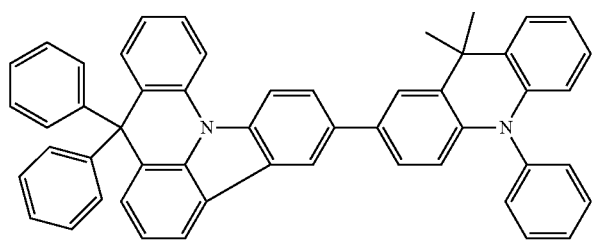 [SMILES: CC1(C)c2ccccc2N(c2ccccc2)c2ccc(-c3ccc4c(c3)c3cccc5c3n4-c3ccccc3C5(c3ccccc3)c3ccccc3)cc21]
99
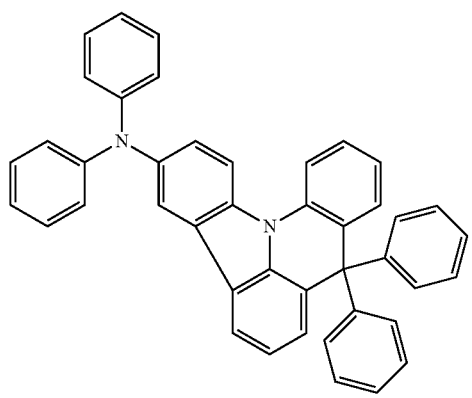 [SMILES: c1ccc(N(c2ccccc2)c2ccc3c(c2)c2cccc4c2n3-c2ccccc2C4(c2ccccc2)c2ccccc2)cc1]
100
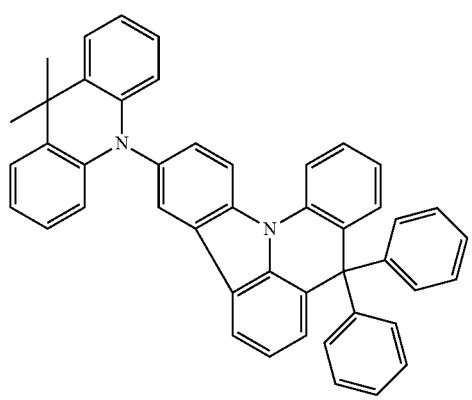 [SMILES: CC1(C)c2ccccc2N(c2ccc3c(c2)c2cccc4c2n3-c2ccccc2C4(c2ccccc2)c2ccccc2)c2ccccc21]
101
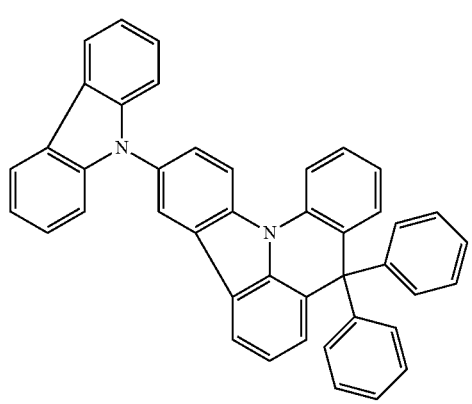 [SMILES: c1ccc(C2(c3ccccc3)c3ccccc3-n3c4ccc(-n5c6ccccc6c6ccccc65)cc4c4cccc2c43)cc1]
102

-continued
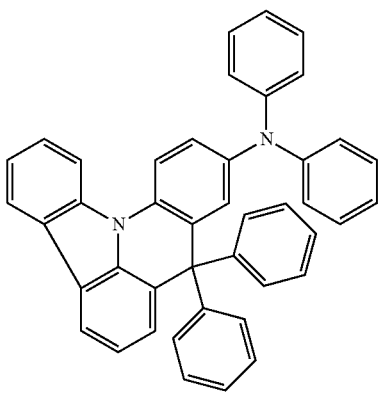 [SMILES: c1ccc(N(c2ccccc2)c2ccc3c(c2)C(c2ccccc2)(c2ccccc2)c2cccc4c5ccccc5n-3c24)cc1]
103
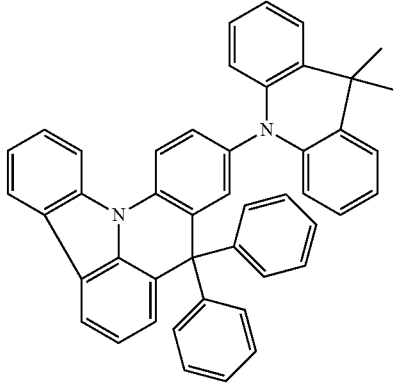 [SMILES: CC1(C)c2ccccc2N(c2ccc3c(c2)C(c2ccccc2)(c2ccccc2)c2cccc4c5ccccc5n-3c24)c2ccccc21]
104
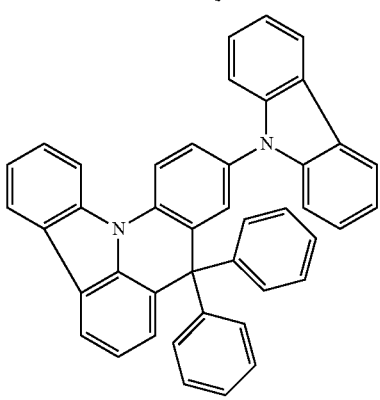
104
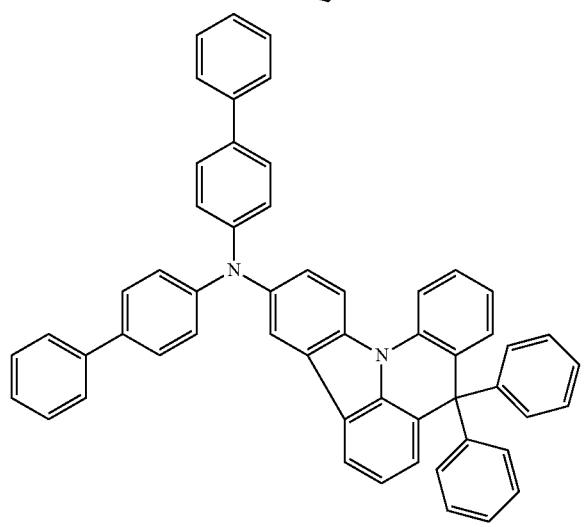
106

107
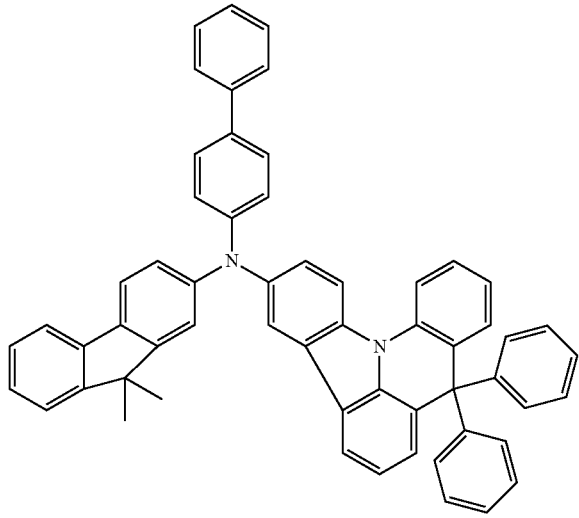 [SMILES: CC1(C)c2ccccc2-c2ccc(N(c3ccc(-c4ccccc4)cc3)c3ccc4c(c3)c3cccc5c3n4-c3ccccc3C5(c3ccccc3)c3ccccc3)cc21]
108
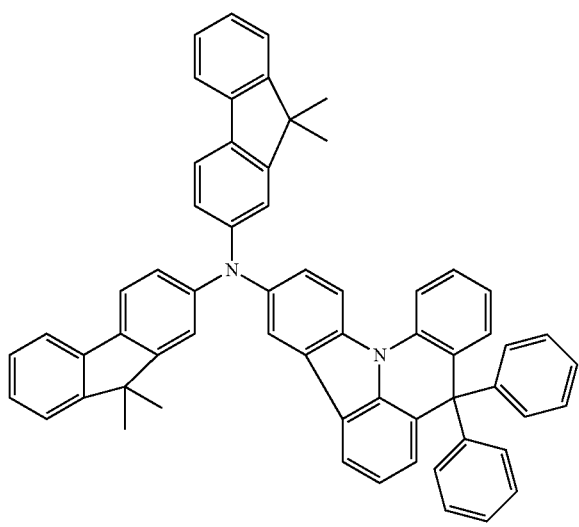 [SMILES: CC1(C)c2ccccc2-c2ccc(N(c3ccc4c(c3)C(C)(C)c3ccccc3-4)c3ccc4c(c3)c3cccc5c3n4-c3ccccc3C5(c3ccccc3)c3ccccc3)cc21]
109
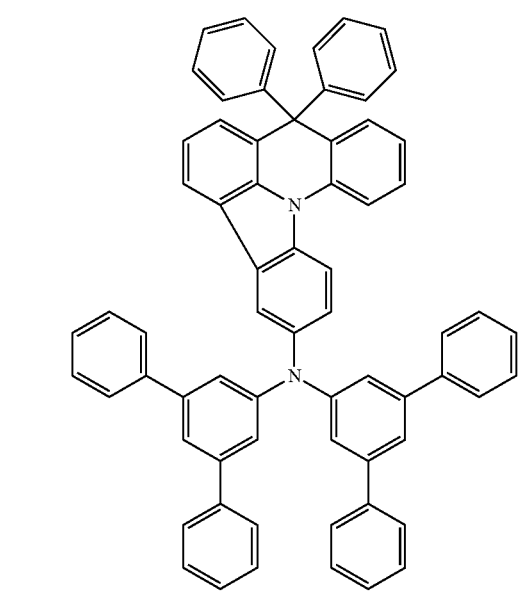 [SMILES: c1ccc(-c2cc(-c3ccccc3)cc(N(c3cc(-c4ccccc4)cc(-c4ccccc4)c3)c3ccc4c(c3)c3cccc5c3n4-c3ccccc3C5(c3ccccc3)c3ccccc3)c2)cc1]

-continued
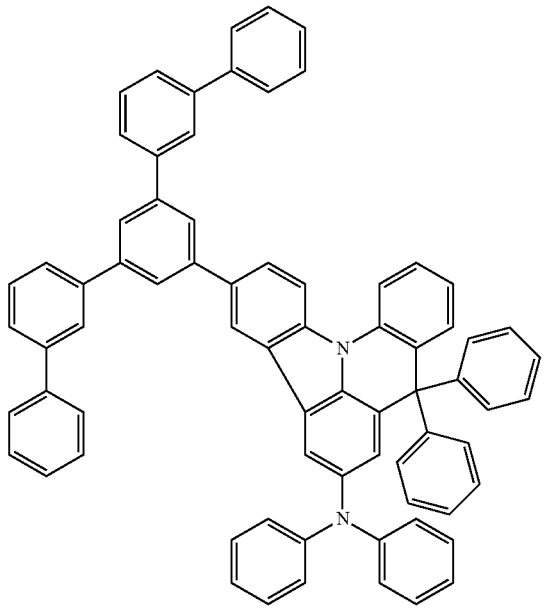 [SMILES: c1ccc(-c2cccc(-c3cc(-c4cccc(-c5ccccc5)c4)cc(-c4ccc5c(c4)c4cc(N(c6ccccc6)c6ccccc6)cc6c4n5-c4ccccc4C6(c4ccccc4)c4ccccc4)c3)c2)cc1]
110
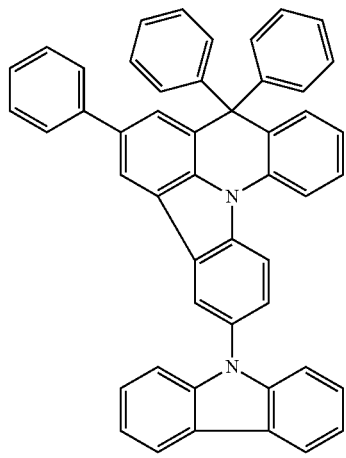 [SMILES: c1ccc(-c2cc3c4c(c2)c2cc(-n5c6ccccc6c6ccccc65)ccc2n4-c2ccccc2C3(c2ccccc2)c2ccccc2)cc1]
111
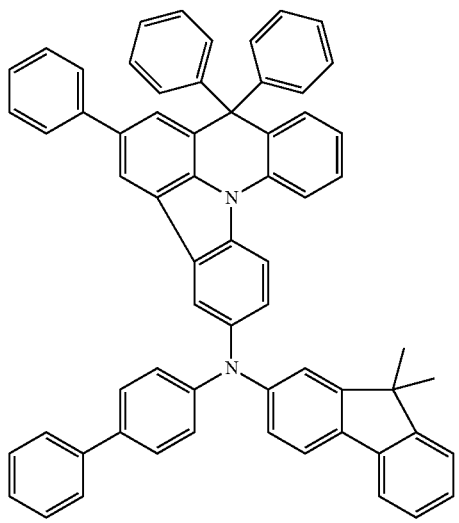 [SMILES: CC1(C)c2ccccc2-c2ccc(N(c3ccc(-c4ccccc4)cc3)c3ccc4c(c3)c3cc(-c5ccccc5)cc5c3n4-c3ccccc3C5(c3ccccc3)c3ccccc3)cc21]
112

-continued
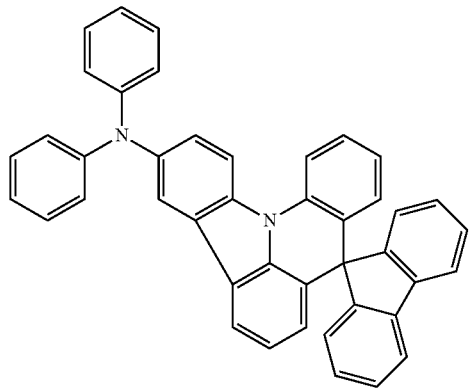 [SMILES: c1ccc(N(c2ccccc2)c2ccc3c(c2)c2cccc4c2n3-c2ccccc2C42c3ccccc3-c3ccccc32)cc1]
113
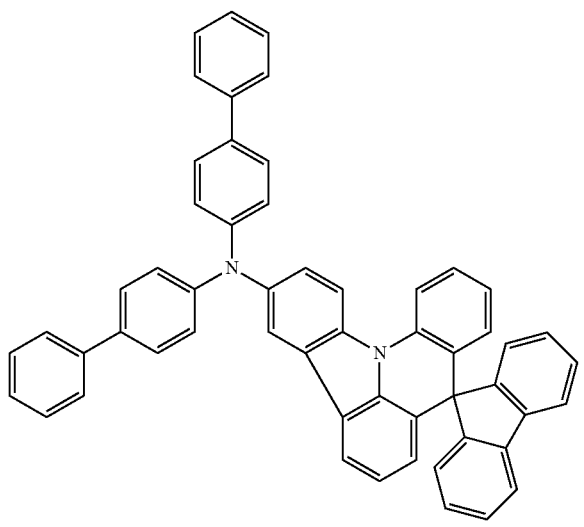 [SMILES: c1ccc(-c2ccc(N(c3ccc(-c4ccccc4)cc3)c3ccc4c(c3)c3cccc5c3n4-c3ccccc3C53c4ccccc4-c4ccccc43)cc2)cc1]
114
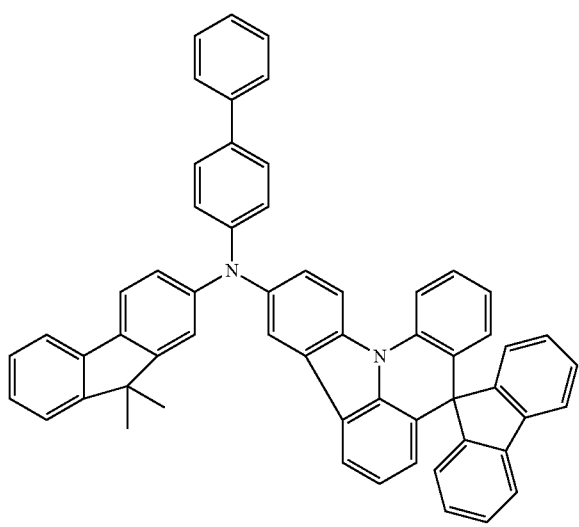 [SMILES: CC1(C)c2ccccc2-c2ccc(N(c3ccc(-c4ccccc4)cc3)c3ccc4c(c3)c3cccc5c3n4-c3ccccc3C53c4ccccc4-c4ccccc43)cc21]
115

-continued
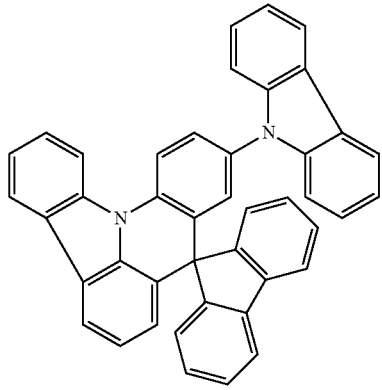 [SMILES: c1ccc2c(c1)-c1ccccc1C21c2cc(-n3c4ccccc4c4ccccc43)ccc2-n2c3ccccc3c3cccc1c32]
116
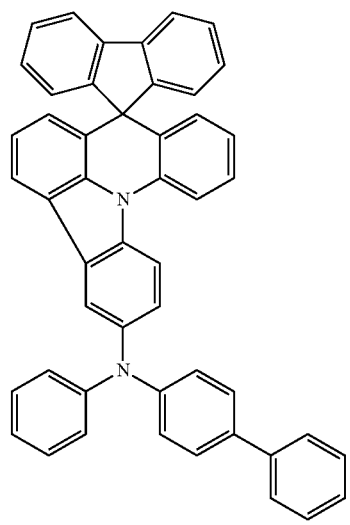 [SMILES: c1ccc(-c2ccc(N(c3ccccc3)c3ccc4c(c3)c3cccc5c3n4-c3ccccc3C53c4ccccc4-c4ccccc43)cc2)cc1]
117
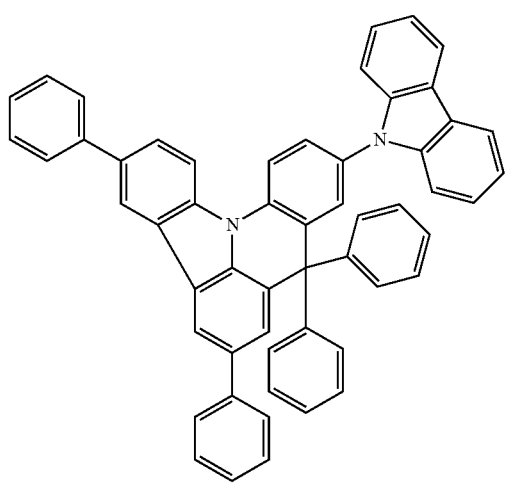 [SMILES: c1ccc(-c2ccc3c(c2)c2cc(-c4ccccc4)cc4c2n3-c2ccc(-n3c5ccccc5c5ccccc53)cc2C4(c2ccccc2)c2ccccc2)cc1]
118

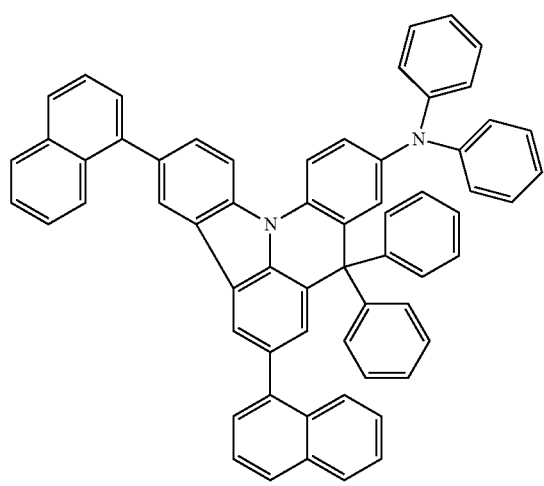 [SMILES: c1ccc(N(c2ccccc2)c2ccc3c(c2)C(c2ccccc2)(c2ccccc2)c2cc(-c4cccc5ccccc45)cc4c5cc(-c6cccc7ccccc67)ccc5n-3c24)cc1]
118
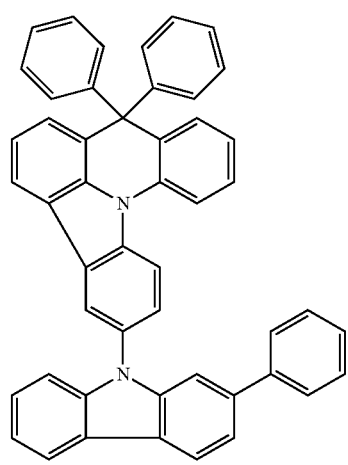 [SMILES: c1ccc(-c2ccc3c4ccccc4n(-c4ccc5c(c4)c4cccc6c4n5-c4ccccc4C6(c4ccccc4)c4ccccc4)c3c2)cc1]
120
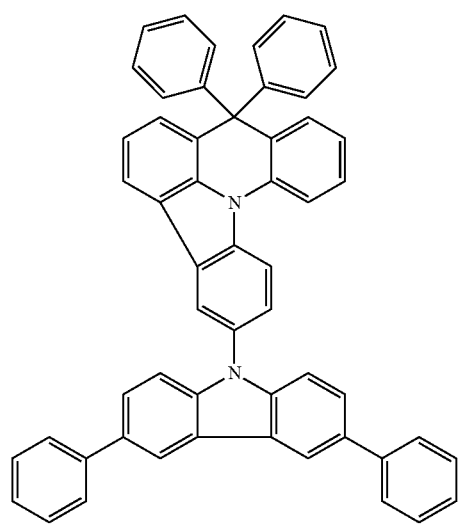 [SMILES: c1ccc(-c2ccc3c(c2)c2cc(-c4ccccc4)ccc2n3-c2ccc3c(c2)c2cccc4c2n3-c2ccccc2C4(c2ccccc2)c2ccccc2)cc1]
121

-continued
122
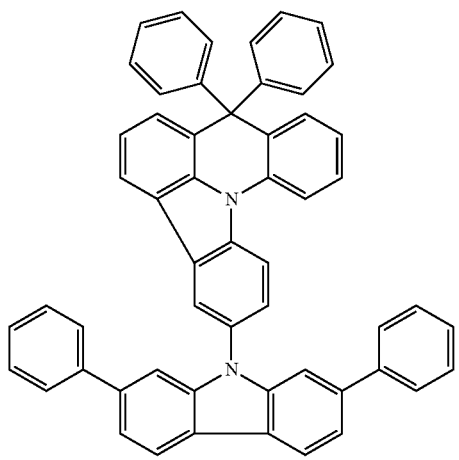 [SMILES: c1ccc(-c2ccc3c4ccc(-c5ccccc5)cc4n(-c4ccc5c(c4)c4cccc6c4n5-c4ccccc4C6(c4ccccc4)c4ccccc4)c3c2)cc1]
123
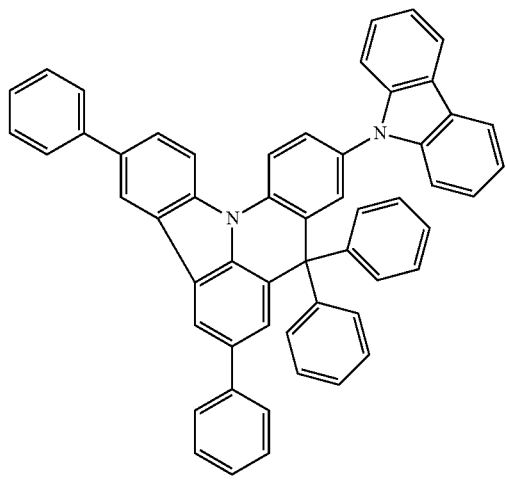 [SMILES: c1ccc(-c2ccc3c(c2)c2cc(-c4ccccc4)cc4c2n3-c2ccc(-n3c5ccccc5c5ccccc53)cc2C4(c2ccccc2)c2ccccc2)cc1]
124
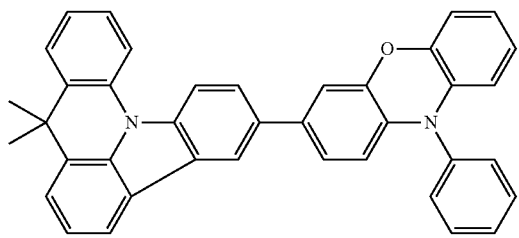
125
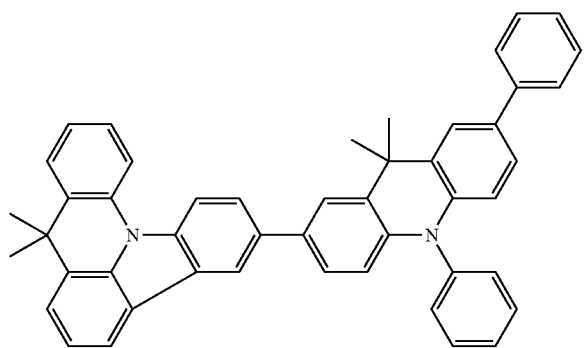 [SMILES: CC1(C)c2cc(-c3ccccc3)ccc2N(c2ccccc2)c2ccc(-c3ccc4c(c3)c3cccc5c3n4-c3ccccc3C5(C)C)cc21]

-continued
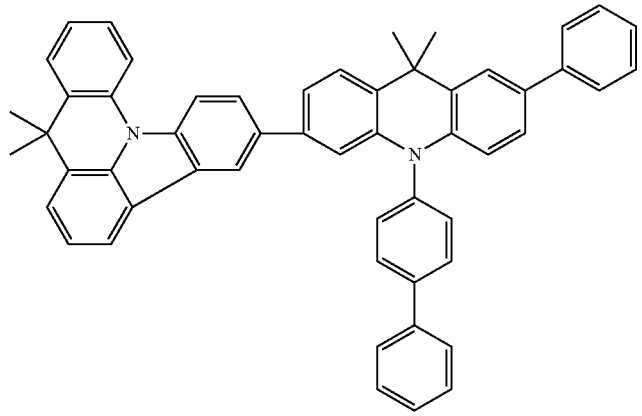 [SMILES: CC1(C)c2ccc(-c3ccc4c(c3)c3cccc5c3n4-c3ccccc3C5(C)C)cc2N(c2ccc(-c3ccccc3)cc2)c2ccc(-c3ccccc3)cc21]
126
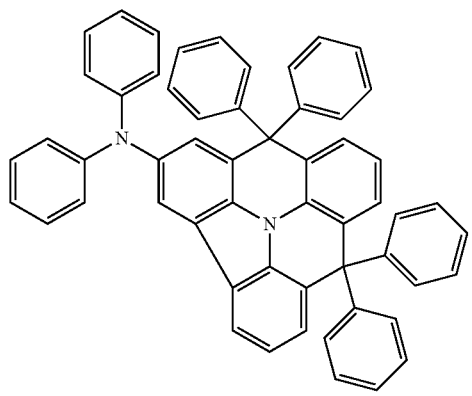 [SMILES: c1ccc(N(c2ccccc2)c2cc3c4c(c2)c2cccc5c2n4-c2c(cccc2C3(c2ccccc2)c2ccccc2)C5(c2ccccc2)c2ccccc2)cc1]
127
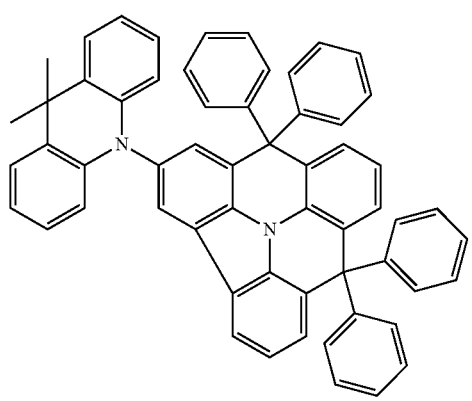 [SMILES: CC1(C)c2ccccc2N(c2cc3c4c(c2)c2cccc5c2n4-c2c(cccc2C3(c2ccccc2)c2ccccc2)C5(c2ccccc2)c2ccccc2)c2ccccc21]
128

-continued
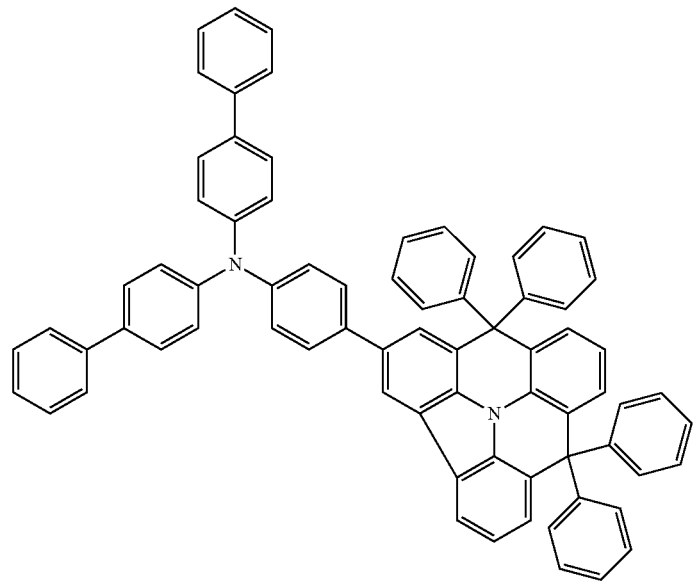 [SMILES: c1ccc(-c2ccc(N(c3ccc(-c4ccccc4)cc3)c3ccc(-c4cc5c6c(c4)c4cccc7c4n6-c4c(cccc4C5(c4ccccc4)c4ccccc4)C7(c4ccccc4)c4ccccc4)cc3)cc2)cc1]
129
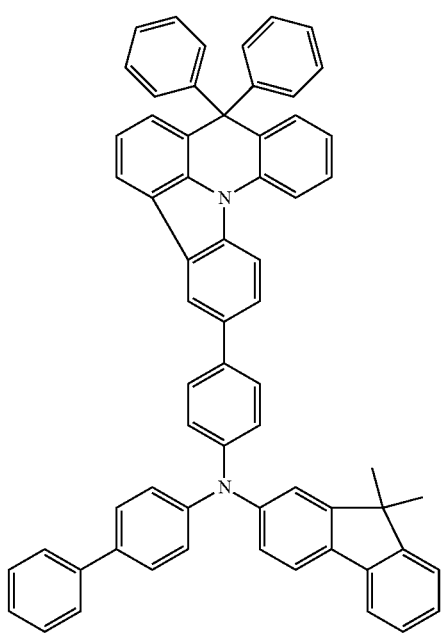 [SMILES: CC1(C)c2ccccc2-c2ccc(N(c3ccc(-c4ccccc4)cc3)c3ccc(-c4ccc5c(c4)c4cccc6c4n5-c4ccccc4C6(c4ccccc4)c4ccccc4)cc3)cc21]
130

-continued
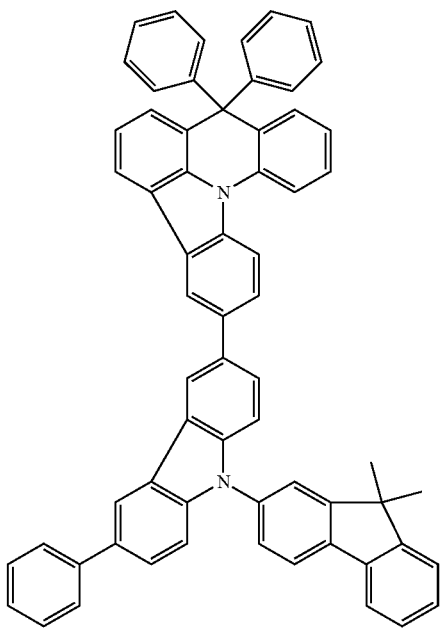 [SMILES: CC1(C)c2ccccc2-c2ccc(-n3c4ccc(-c5ccccc5)cc4c4cc(-c5ccc6c(c5)c5cccc7c5n6-c5ccccc5C7(c5ccccc5)c5ccccc5)ccc43)cc21]
131
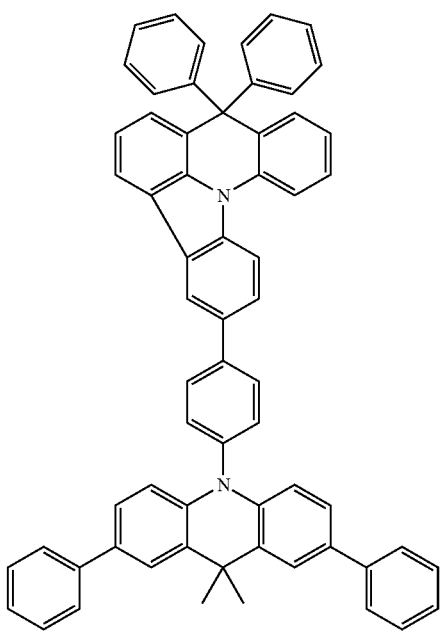 [SMILES: CC1(C)c2cc(-c3ccccc3)ccc2N(c2ccc(-c3ccc4c(c3)c3cccc5c3n4-c3ccccc3C5(c3ccccc3)c3ccccc3)cc2)c2ccc(-c3ccccc3)cc21]
132

-continued
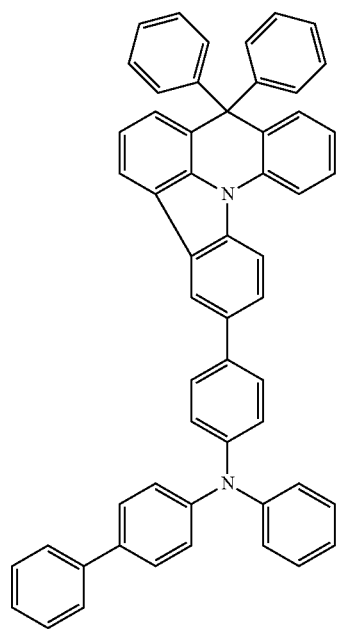 [SMILES: c1ccc(-c2ccc(N(c3ccccc3)c3ccc(-c4ccc5c(c4)c4cccc6c4n5-c4ccccc4C6(c4ccccc4)c4ccccc4)cc3)cc2)cc1]
133
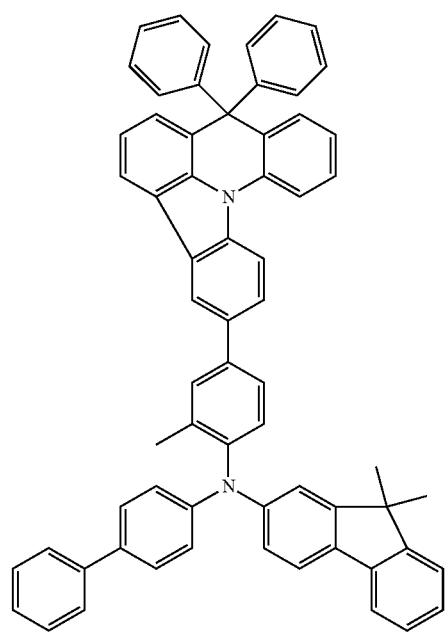 [SMILES: Cc1cc(-c2ccc3c(c2)c2cccc4c2n3-c2ccccc2C4(c2ccccc2)c2ccccc2)ccc1N(c1ccc(-c2ccccc2)cc1)c1ccc2c(c1)C(C)(C)c1ccccc1-2]
134

-continued
135
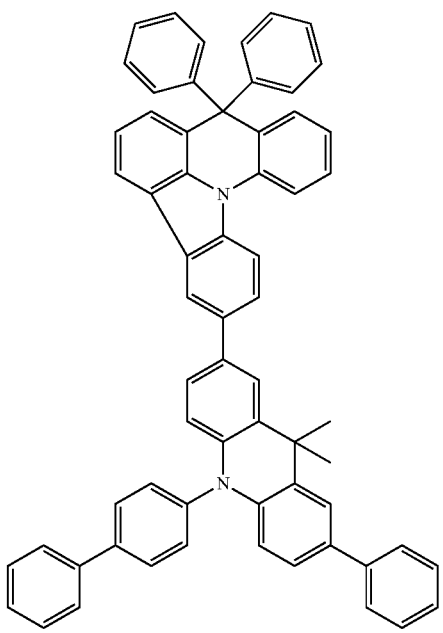 [SMILES: CC1(C)c2cc(-c3ccccc3)ccc2N(c2ccc(-c3ccccc3)cc2)c2ccc(-c3ccc4c(c3)c3cccc5c3n4-c3ccccc3C5(c3ccccc3)c3ccccc3)cc21]
136
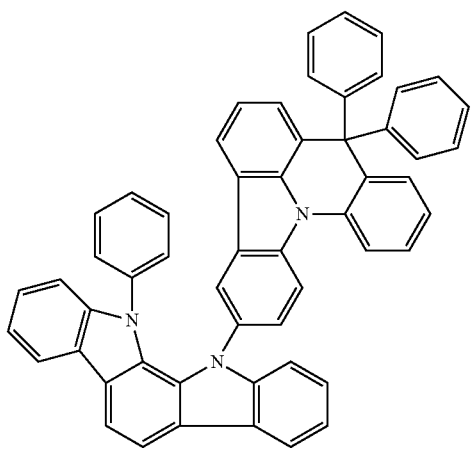 [SMILES: c1ccc(-n2c3ccccc3c3ccc4c5ccccc5n(-c5ccc6c(c5)c5cccc7c5n6-c5ccccc5C7(c5ccccc5)c5ccccc5)c4c32)cc1]
137
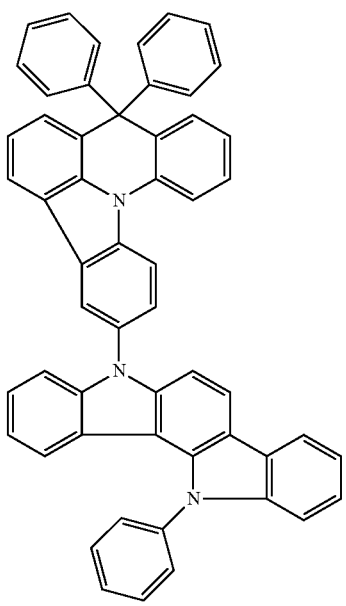 [SMILES: c1ccc(-n2c3ccccc3c3ccc4c(c5ccccc5n4-c4ccc5c(c4)c4cccc6c4n5-c4ccccc4C6(c4ccccc4)c4ccccc4)c32)cc1]

138
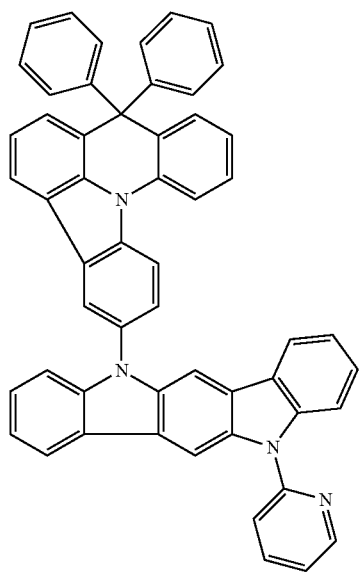 [SMILES: c1ccc(C2(c3ccccc3)c3ccccc3-n3c4ccc(-n5c6ccccc6c6cc7c(cc65)c5ccccc5n7-c5ccccn5)cc4c4cccc2c43)cc1]
139
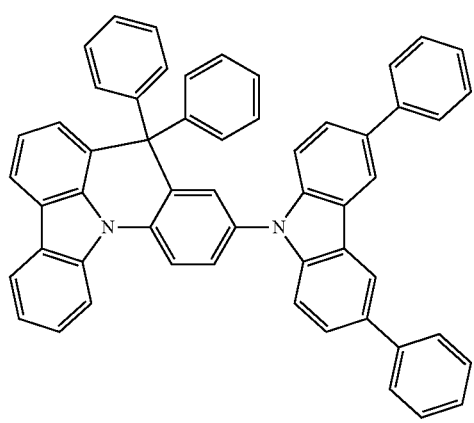 [SMILES: c1ccc(-c2ccc3c(c2)c2cc(-c4ccccc4)ccc2n3-c2ccc3c(c2)C(c2ccccc2)(c2ccccc2)c2cccc4c5ccccc5n-3c24)cc1]
140
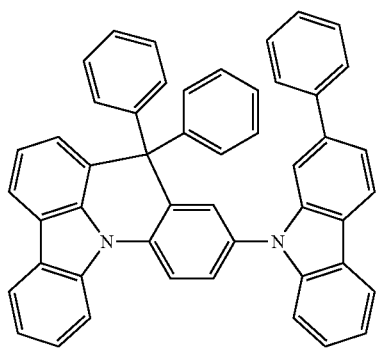 [SMILES: c1ccc(-c2ccc3c4ccccc4n(-c4ccc5c(c4)C(c4ccccc4)(c4ccccc4)c4cccc6c7ccccc7n-5c46)c3c2)cc1]

-continued
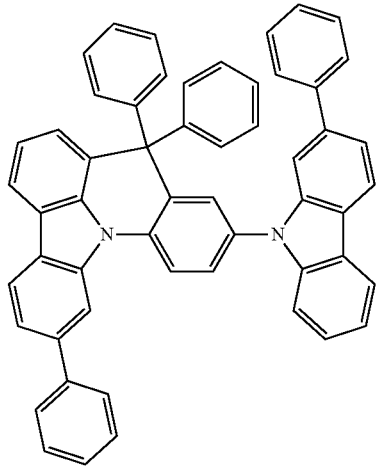 [SMILES: c1ccc(-c2ccc3c4ccccc4n(-c4ccc5c(c4)C(c4ccccc4)(c4ccccc4)c4cccc6c7ccc(-c8ccccc8)cc7n-5c46)c3c2)cc1]
141
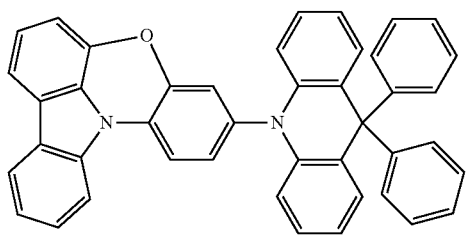 [SMILES: c1ccc(C2(c3ccccc3)c3ccccc3N(c3ccc4c(c3)Oc3cccc5c6ccccc6n-4c35)c3ccccc32)cc1]
142
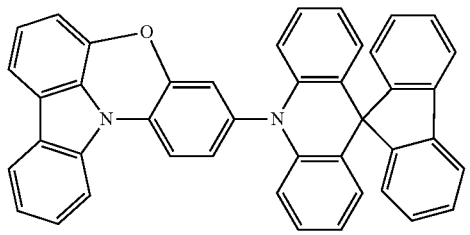 [SMILES: c1ccc2c(c1)-c1ccccc1C21c2ccccc2N(c2ccc3c(c2)Oc2cccc4c5ccccc5n-3c24)c2ccccc21]
143
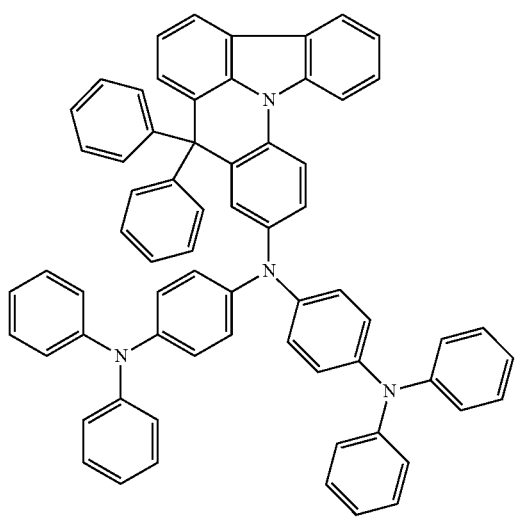 [SMILES: c1ccc(N(c2ccccc2)c2ccc(N(c3ccc(N(c4ccccc4)c4ccccc4)cc3)c3ccc4c(c3)C(c3ccccc3)(c3ccccc3)c3cccc5c6ccccc6n-4c35)cc2)cc1]
144

-continued
145
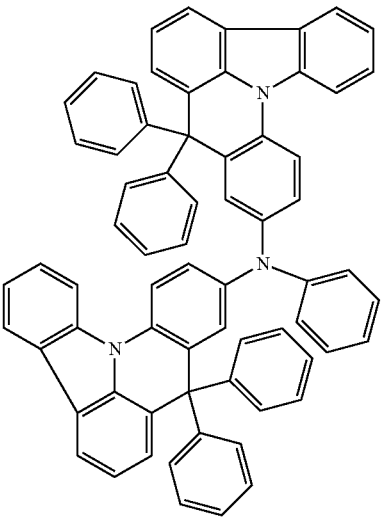 [SMILES: c1ccc(N(c2ccc3c(c2)C(c2ccccc2)(c2ccccc2)c2cccc4c5ccccc5n-3c24)c2ccc3c(c2)C(c2ccccc2)(c2ccccc2)c2cccc4c5ccccc5n-3c24)cc1]
146
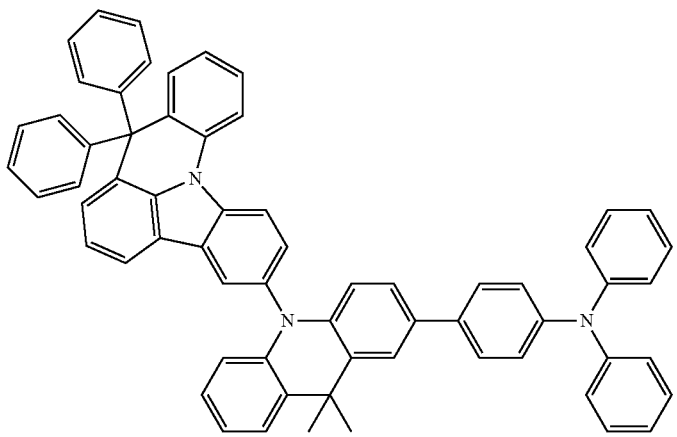 [SMILES: CC1(C)c2ccccc2N(c2ccc3c(c2)c2cccc4c2n3-c2ccccc2C4(c2ccccc2)c2ccccc2)c2ccc(-c3ccc(N(c4ccccc4)c4ccccc4)cc3)cc21]
147
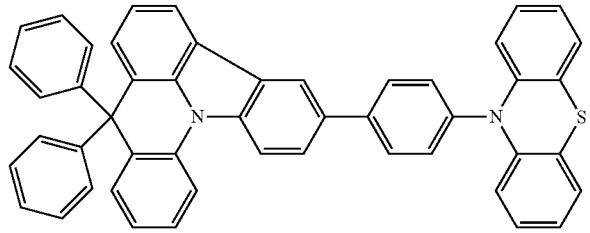 [SMILES: c1ccc(C2(c3ccccc3)c3ccccc3-n3c4ccc(-c5ccc(N6c7ccccc7Sc7ccccc76)cc5)cc4c4cccc2c43)cc1]
148
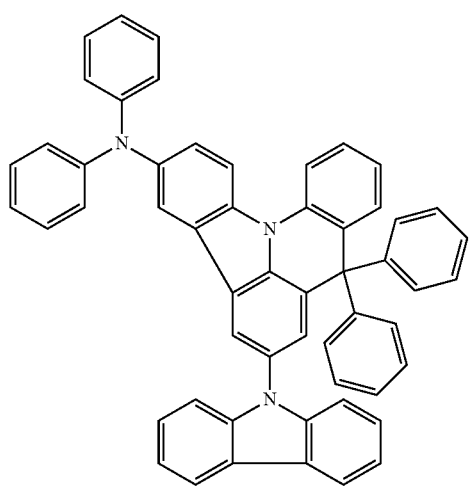 [SMILES: c1ccc(N(c2ccccc2)c2ccc3c(c2)c2cc(-n4c5ccccc5c5ccccc54)cc4c2n3-c2ccccc2C4(c2ccccc2)c2ccccc2)cc1]

149
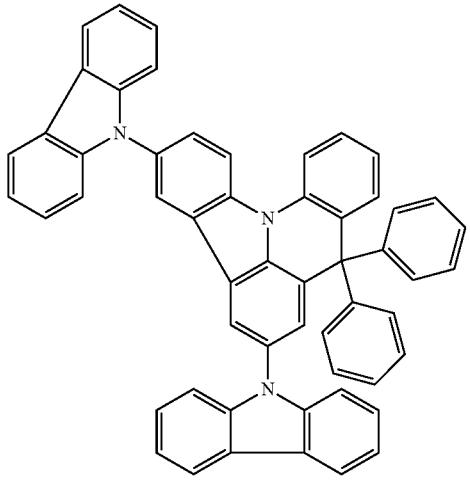 [SMILES: c1ccc(C2(c3ccccc3)c3ccccc3-n3c4ccc(-n5c6ccccc6c6ccccc65)cc4c4cc(-n5c6ccccc6c6ccccc65)cc2c43)cc1]
150
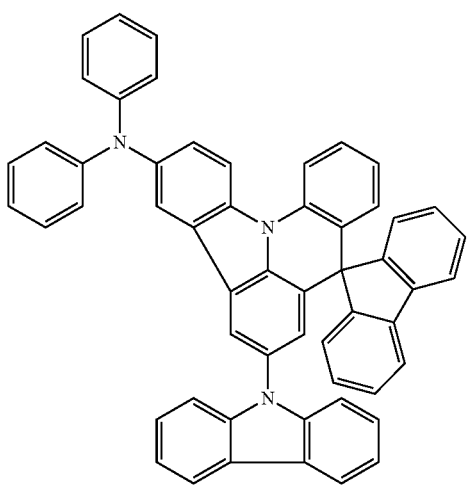 [SMILES: c1ccc(N(c2ccccc2)c2ccc3c(c2)c2cc(-n4c5ccccc5c5ccccc54)cc4c2n3-c2ccccc2C42c3ccccc3-c3ccccc32)cc1]
151
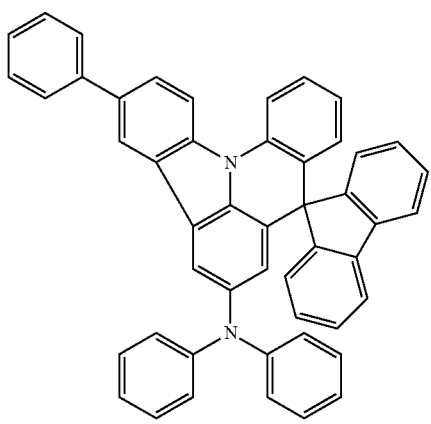 [SMILES: c1ccc(-c2ccc3c(c2)c2cc(N(c4ccccc4)c4ccccc4)cc4c2n3-c2ccccc2C42c3ccccc3-c3ccccc32)cc1]

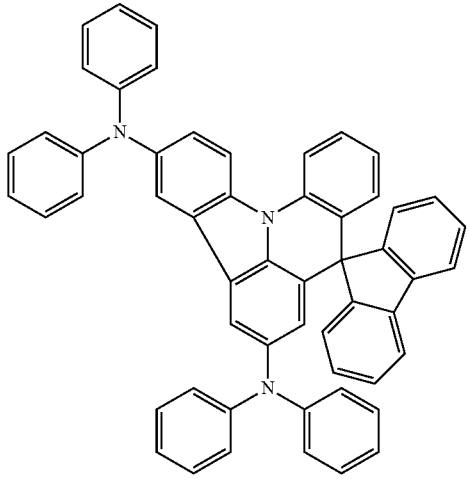 [SMILES: c1ccc(N(c2ccccc2)c2ccc3c(c2)c2cc(N(c4ccccc4)c4ccccc4)cc4c2n3-c2ccccc2C42c3ccccc3-c3ccccc32)cc1]
152
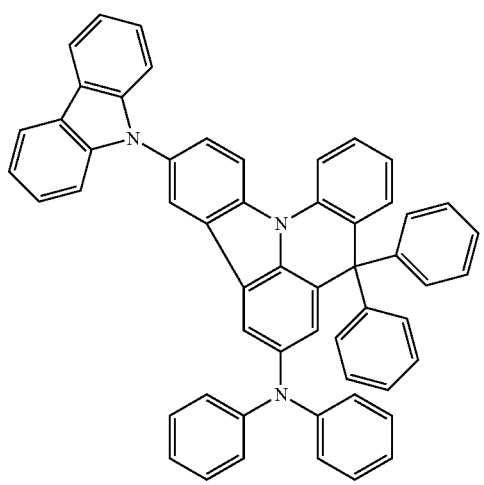 [SMILES: c1ccc(N(c2ccccc2)c2cc3c4c(c2)c2cc(-n5c6ccccc6c6ccccc65)ccc2n4-c2ccccc2C3(c2ccccc2)c2ccccc2)cc1]
153
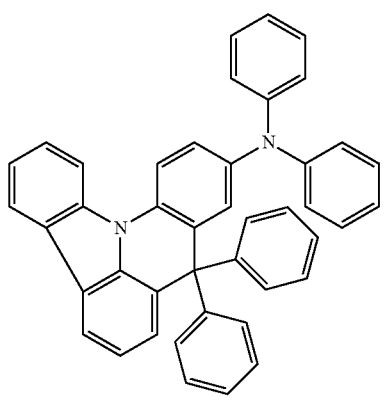 [SMILES: c1ccc(N(c2ccccc2)c2ccc3c(c2)C(c2ccccc2)(c2ccccc2)c2cccc4c5ccccc5n-3c24)cc1]
154

155
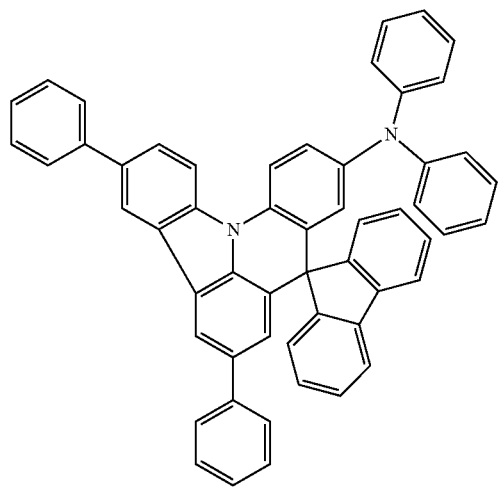 [SMILES: c1ccc(-c2ccc3c(c2)c2cc(-c4ccccc4)cc4c2n3-c2ccc(N(c3ccccc3)c3ccccc3)cc2C42c3ccccc3-c3ccccc32)cc1]
156
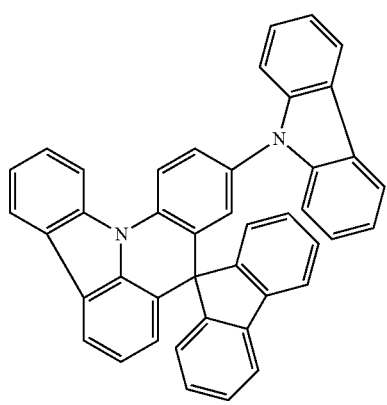 [SMILES: c1ccc2c(c1)-c1ccccc1C21c2cc(-n3c4ccccc4c4ccccc43)ccc2-n2c3ccccc3c3cccc1c32]
157
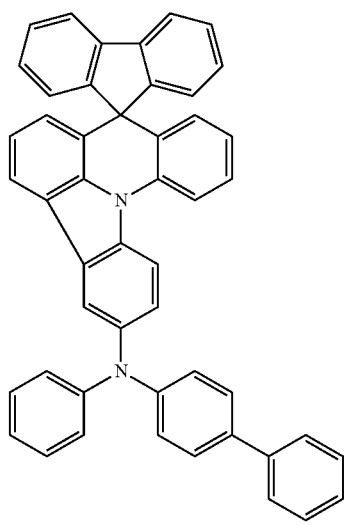 [SMILES: c1ccc(-c2ccc(N(c3ccccc3)c3ccc4c(c3)c3cccc5c3n4-c3ccccc3C53c4ccccc4-c4ccccc43)cc2)cc1]

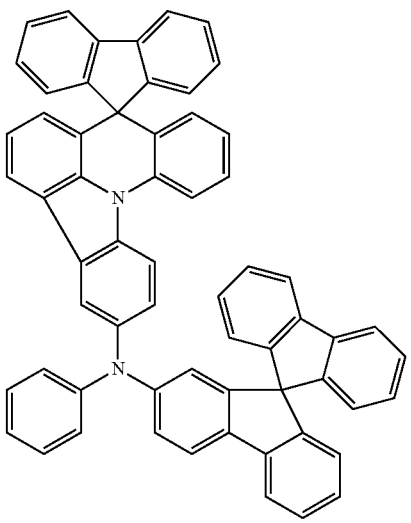 [SMILES: c1ccc(N(c2ccc3c(c2)C2(c4ccccc4-c4ccccc42)c2ccccc2-3)c2ccc3c(c2)c2cccc4c2n3-c2ccccc2C42c3ccccc3-c3ccccc32)cc1]
158
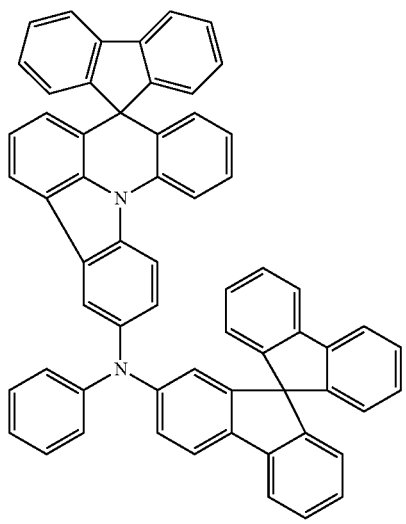 [SMILES: c1ccc(N(c2ccc3c(c2)C2(c4ccccc4-c4ccccc42)c2ccccc2-3)c2ccc3c(c2)c2cccc4c2n3-c2ccccc2C42c3ccccc3-c3ccccc32)cc1]
159
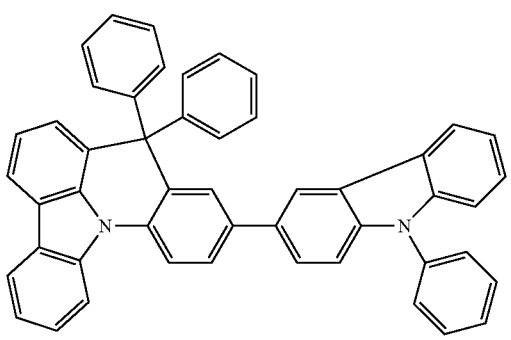 [SMILES: c1ccc(-n2c3ccccc3c3cc(-c4ccc5c(c4)C(c4ccccc4)(c4ccccc4)c4cccc6c7ccccc7n-5c46)ccc32)cc1]
160

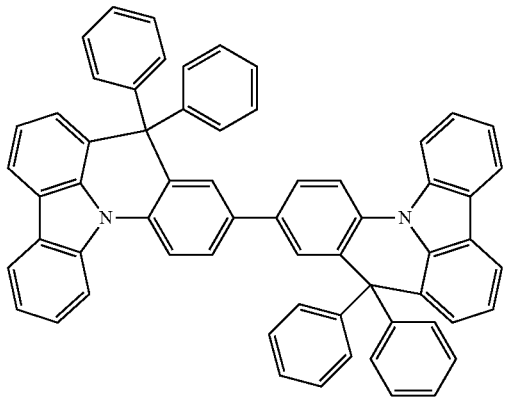 [SMILES: c1ccc(C2(c3ccccc3)c3cc(-c4ccc5c(c4)C(c4ccccc4)(c4ccccc4)c4cccc6c7ccccc7n-5c46)ccc3-n3c4ccccc4c4cccc2c43)cc1]
161
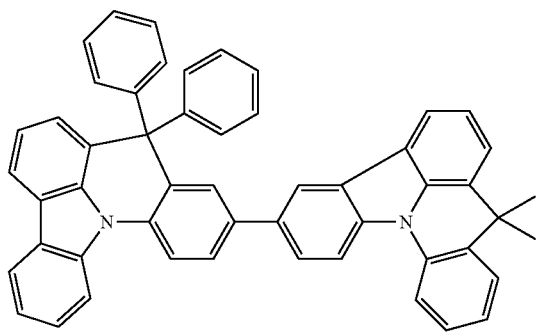 [SMILES: CC1(C)c2ccccc2-n2c3ccc(-c4ccc5c(c4)C(c4ccccc4)(c4ccccc4)c4cccc6c7ccccc7n-5c46)cc3c3cccc1c32]
162
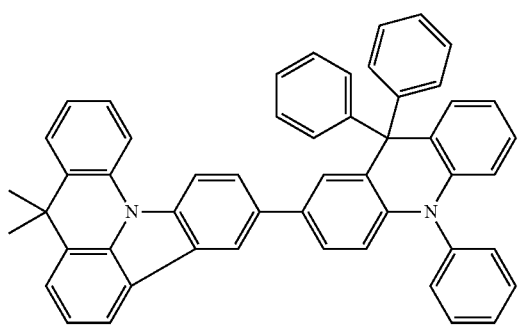 [SMILES: CC1(C)c2ccccc2-n2c3ccc(-c4ccc5c(c4)C(c4ccccc4)(c4ccccc4)c4ccccc4N5c4ccccc4)cc3c3cccc1c32]
163
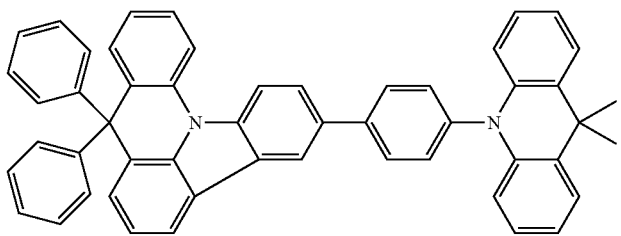 [SMILES: CC1(C)c2ccccc2N(c2ccc(-c3ccc4c(c3)c3cccc5c3n4-c3ccccc3C5(c3ccccc3)c3ccccc3)cc2)c2ccccc21]
164
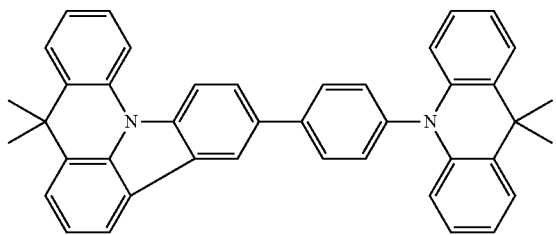
165

-continued

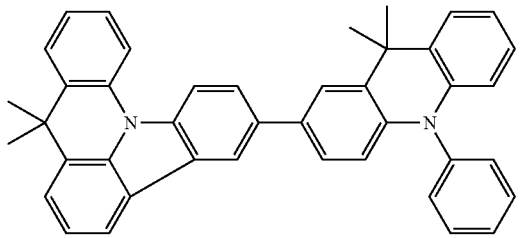 [SMILES: CC1(C)c2ccccc2N(c2ccccc2)c2ccc(-c3ccc4c(c3)c3cccc5c3n4-c3ccccc3C5(C)C)cc21]

166

The compounds according to the invention can be obtained by synthetic steps known to the person skilled in the art, such as, for example, transition metal-catalysed coupling reactions and acid-catalysed ring-closure reactions.

Thus, for example, a diarylamino group can be introduced by Hartwig-Buchwald coupling if a halogen-substituted group $Ar^1$ is present in a precursor molecule of the compounds according to the invention.

Scheme 1 below shows the synthesis of various bridged triarylamine units (A-E) which are important intermediates in the synthesis of the compounds according to the invention.

In general, R and R' in the following schemes stand for a radical as defined by $R^1$ and $R^2$ above.

Scheme 1

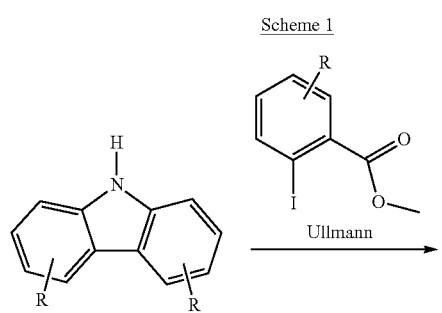

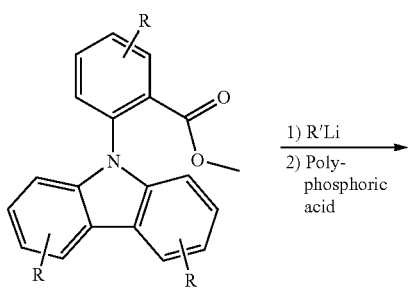

-continued

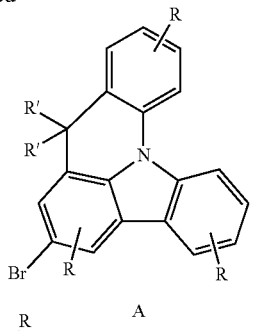

A

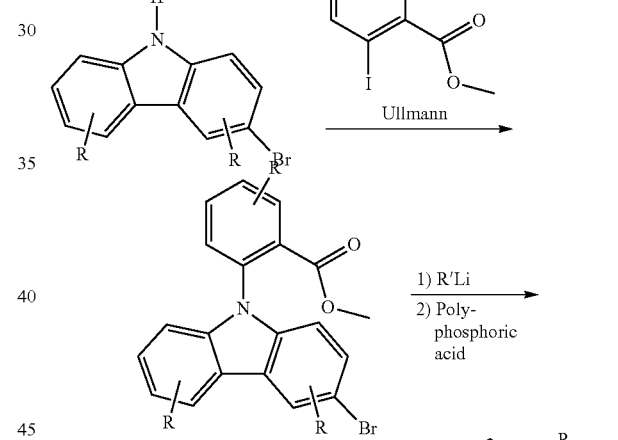

B

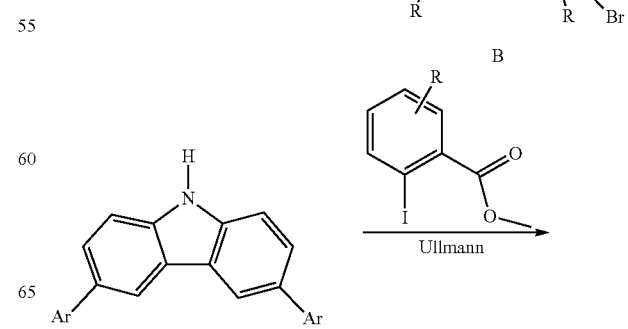

139
-continued
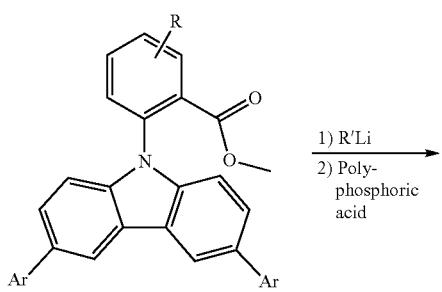
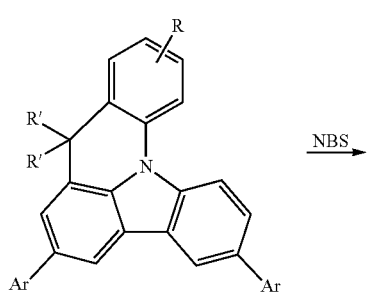
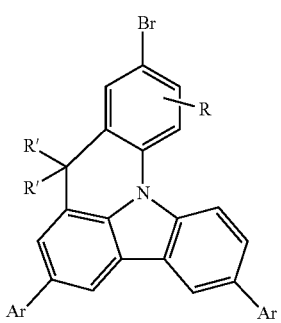
C
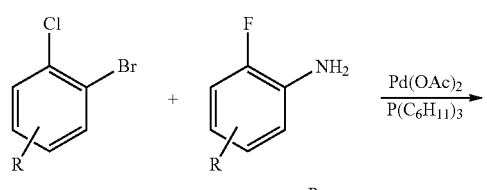
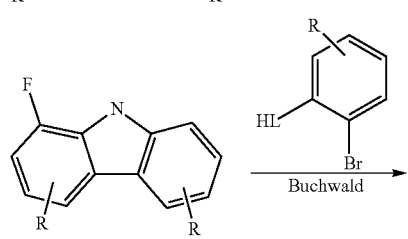
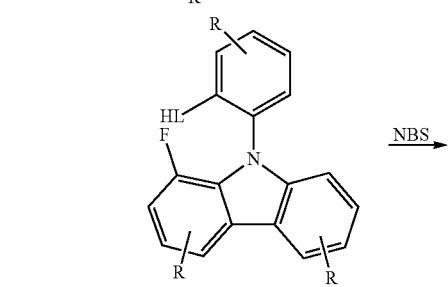
140
-continued
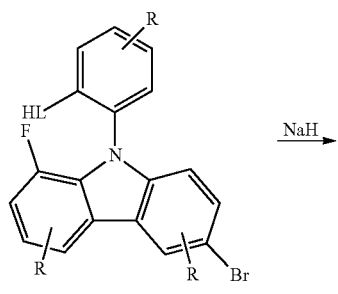
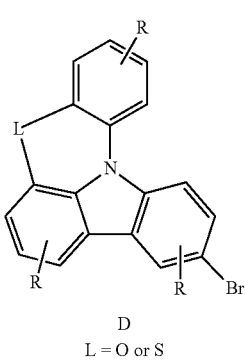
D
L = O or S
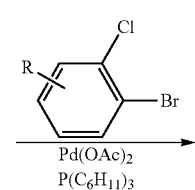
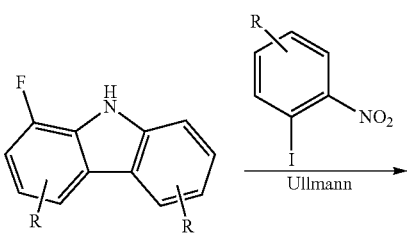
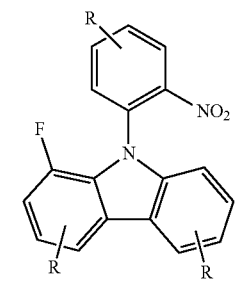
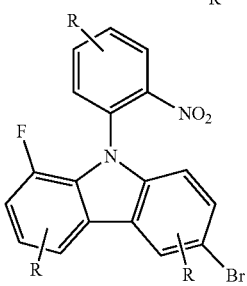

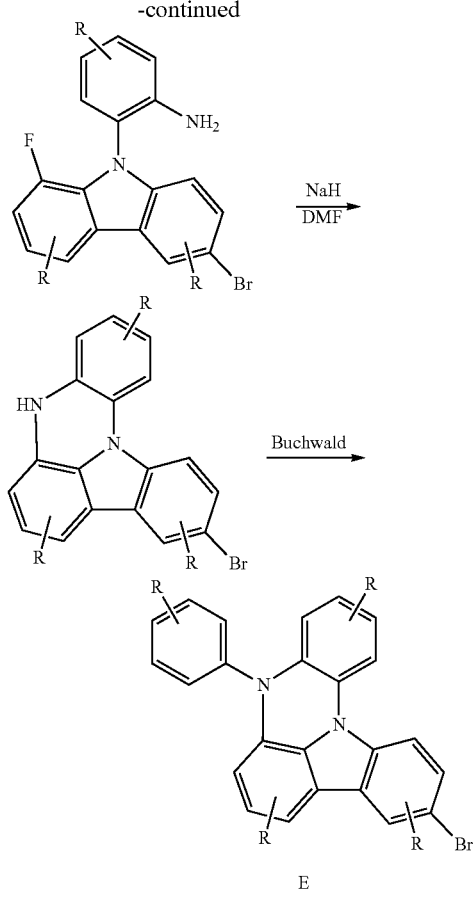

Depending on the desired bromine substitution (A-C, Scheme 1), cyclisation can take place via the intermediate of a tertiary alcohol before or after the bromination of the aromatic parent structure. Ring closure gives a divalent $C(R')_2$ bridge (A-C, Scheme 1).

Suitable starting compounds for the formation of the $C(R')_2$ bridge are, for example, a carboxylate group or an acetyl group, which can then be converted into a carbon bridge in the ring-closure reaction. Also suitable is a phenol group or thiophenol group, which can then be converted into an oxygen or sulfur bridge in the ring-closure reaction (D). Likewise suitable is a nitro group or amino group, which can then be converted into a nitrogen bridge in the ring-closure reaction (E). The divalent bridge may subsequently be substituted by further radicals, for example by alkyl or aryl groups. The bridged carbazole compound prepared in this way can then be functionalised, for example halogenated, preferably brominated, in a further step.

The functionalised, in particular brominated compounds from Scheme 1 represent a central unit for further functionalisation, as depicted in Scheme 2.

Hartwig-Buchwald coupling to diarylamines leads directly to the compounds according to the invention or to precursor compounds, which can be functionalised further. In this way, arylamino and carbazole groups can be introduced (Scheme 2).

Alternatively, the compounds A to E can be converted into aryl-substituted compounds by Suzuki coupling to corresponding arylboronic acids. In this way, relatively large aromatic systems can be achieved as embodiments of the groups $Ar^1$ in the compounds of the formula (I). This may be followed by halogenation and coupling to arylamino or carbazole groups, again giving compounds according to the invention.

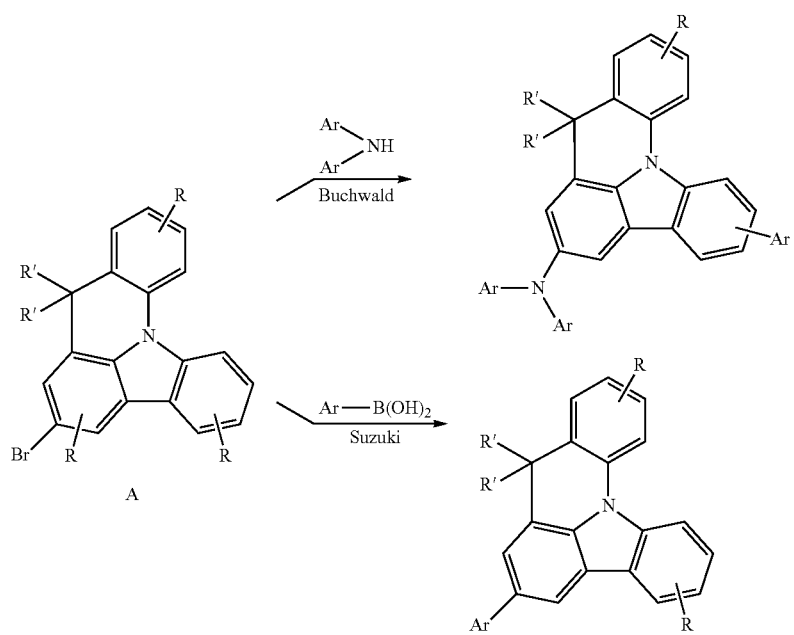

Scheme 2

-continued
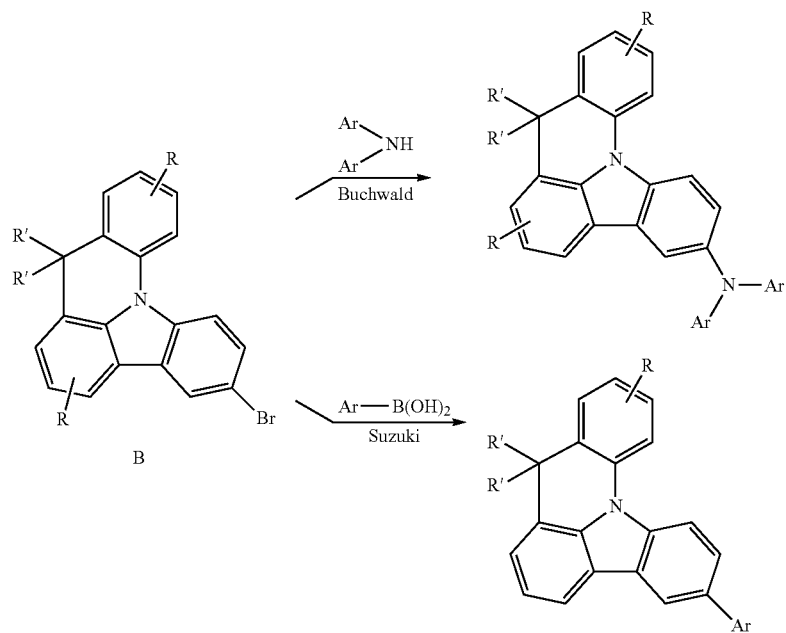
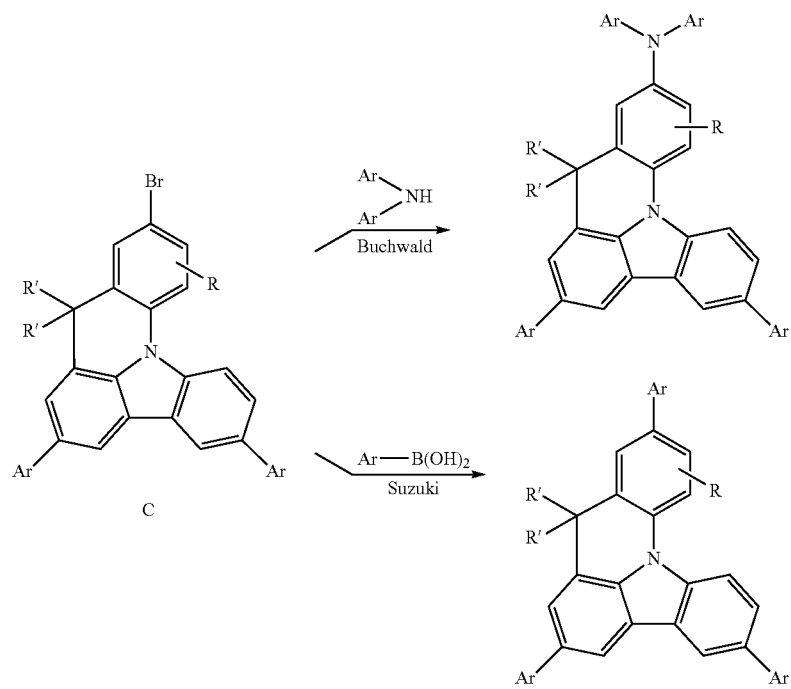

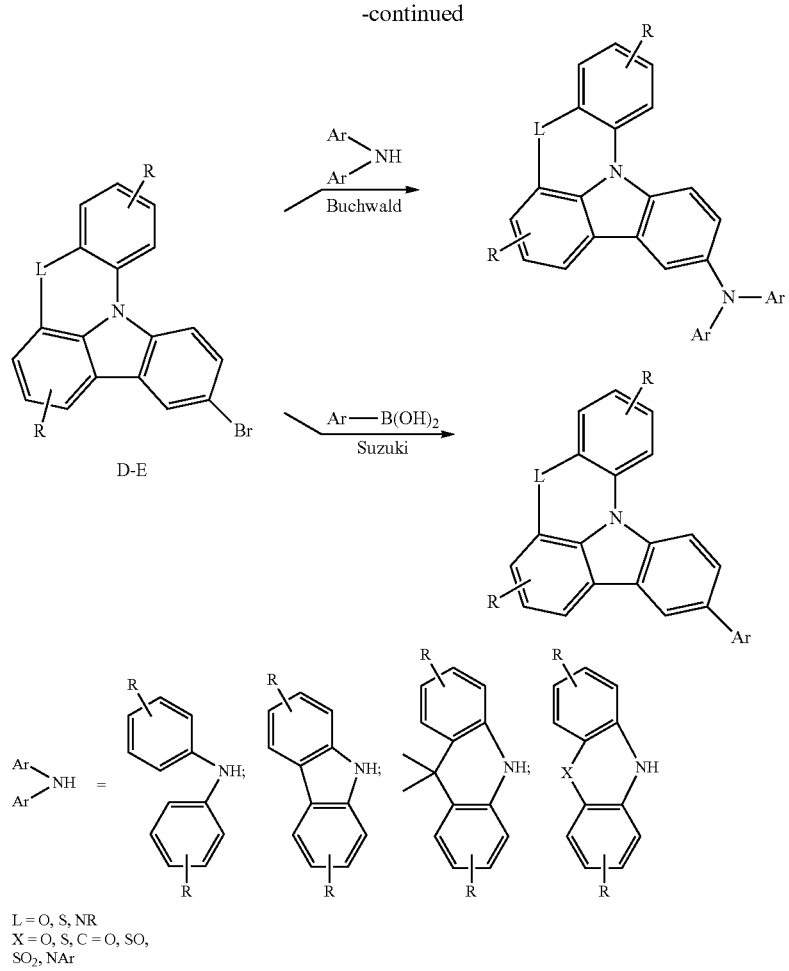

L = O, S, NR
X = O, S, C = O, SO, SO$_2$, NAr

The present invention furthermore relates to a process for the preparation of a compound of the formula (I), characterised in that at least one ring-closure reaction for the introduction of a bridging group Y, T$^1$, T$^2$, T$^3$ or L is carried out.

The ring-closure reaction can optionally be followed by a coupling reaction for the introduction of the diarylamino group. Alternatively, the said diarylamino group may already be present in the molecule before the introduction of the bridging groups.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oilgomerisation or polymerisation here is preferably carried out via the halogen functionality or the boronic acid functionality.

The invention therefore furthermore relates to oligomers, polymers or dendrimers comprising one or more compounds of the formula (I), where the bond(s) to the polymer, oligomer or dendrimer may be localised at any desired positions substituted by R$^1$ or R$^2$ in formula (I). Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a diva-group, for example via a substituted or unsubstituted alkylene group, via a heteroatom or via a divalent aromatic or heteroaromatic group. In and dendritic structures, three or more units of the formula (I) may, for example, be linked via a trivalent or polyvalent group, for example via a trivalent or polyvalent aromatic or heteroaromatic group, to give a or dendritic oligomer or polymer.

For the recurring units of the formula (I) in oligomers, dendrimers and polymers, the same preferences apply as described above for compounds of the formula (I).

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 03/048225, WO 04/037887 and WO 04/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyper-branched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The compounds of the formula (I) according to the invention are suitable for use in electronic devices, in particular in organic electroluminescent devices (OLEDs). Depending on the substitution, the compounds are employed in different functions and layers.

The invention therefore furthermore relates to the use of the compounds of the formula (I) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

The invention also relates to formulations comprising at least one compound of the formula (I) or at least one polymer, oligomer or dendrimer containing at least one unit of the formula (I) and at least one solvent, preferably an organic solvent.

The invention still furthermore relates to electronic devices comprising at least one compound of the formula (I). The electronic devices here are preferably selected from the devices mentioned above. Particular preference is given to organic electroluminescent devices comprising an anode, a cathode and at least one emitting layer, characterised in that at least one organic layer, which may be an emitting layer, a hole-transport layer or another layer, comprises at least one compound of the formula (I).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formula (I) and where the three layers exhibit blue, green and orange or red emission (for the basic structure see, for example, WO 05/011013). Alternatively and/or additionally, the compounds according to the invention may also be present in the hole-transport layer. Emitters which have broad-band emission bands and thus exhibit white emission are likewise suitable for white emission.

In a preferred embodiment of the invention, the compounds of the formula (I) are employed as hole-transport material. The compounds are then preferably employed in a hole-transport layer and/or in a hole-injection layer. A hole-injection layer in the sense of this invention is a layer which is directly adjacent to the anode. For the purposes of this invention, a hole-transport layer is a layer which is located between the hole-injection layer and the emission layer. The hole-transport layer can be directly adjacent to the emission layer. If the compounds of the formula (I) are used as hole-transport material, it may be preferred for them to be doped with electron-acceptor compounds, for example by $F_4$-TCNQ or with compounds as described in EP 1476881 or EP 1596445. If the compound of the formula (I) is employed as hole-transport material in a hole-transport layer, the compound can be employed as the pure material, i.e. in a proportion of 100%, in the hole-transport layer or it can be employed in combination with further compounds in the hole-transport layer.

It is preferred in accordance with the invention for the compound of the formula (I) to be employed in an electronic device comprising one or more phosphorescent emitters. The compound here can be used in a hole-transport layer, a hole-injection layer or in the emitting layer, particularly preferably in a hole-transport layer.

In a further embodiment of the present invention, the compounds of the formula (I) are employed as matrix material for emitting materials, preferably phosphorescent dopants. In this case, it is particularly preferred for the compounds of the formula (I) to be employed as matrix material for emitting materials in an organic electroluminescent device.

In a further preferred embodiment of the invention, the organic electroluminescent device may also comprise a plurality of emitting layers, where at least one emitting layer comprises at least one compound of the formula (I) and at least one emitter, preferably phosphorescent.

The mixture comprising the compound of the formula (I) and the phosphorescent emitter which is employed in the emitting layer preferably comprises between 99 and 50% by vol., preferably between 98 and 50% by vol., particularly preferably between 97 and 60% by vol., in particular between 95 and 85% by vol., of the compound of the formula (I), based on the entire mixture comprising emitter and matrix material. Correspondingly, the mixture comprises between 1 and 50% by vol., preferably between 2 and 50% by vol., particularly preferably between 3 and 40% by vol., in particular between 5 and 15% by vol., of the phosphorescent emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 04/013080, WO 04/093207, WO 06/005627 or the application WO 10/006,680, triarylamines, carbazole derivatives, for example CBP (N,N-bis-carbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example accordance with EP 1617710, EP 1617711, EP 1731584, bipolar matrix materials, for example in accordance with WO 07/137,725, silanes, for example in accordance with WO 05/111172, azaboroles or boronic esters, for example in accordance with WO 06/117052, triazine derivatives, for example in accordance with the application WO 10/015,306, WO 07/063,754 or WO 08/056,746, zinc complexes, for example in accordance with EP 652273 or WO 09/062,578, diazasilole or tetraazasilole derivatives, for example in accordance with the application WO 10/054,729, diazaphosphole derivatives, for example in accordance with the application WO 10/054,730, or indenocarbazole derivatives, for example in accordance with the unpublished application DE 102009023155.2.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent emitter compounds are revealed by the following table:

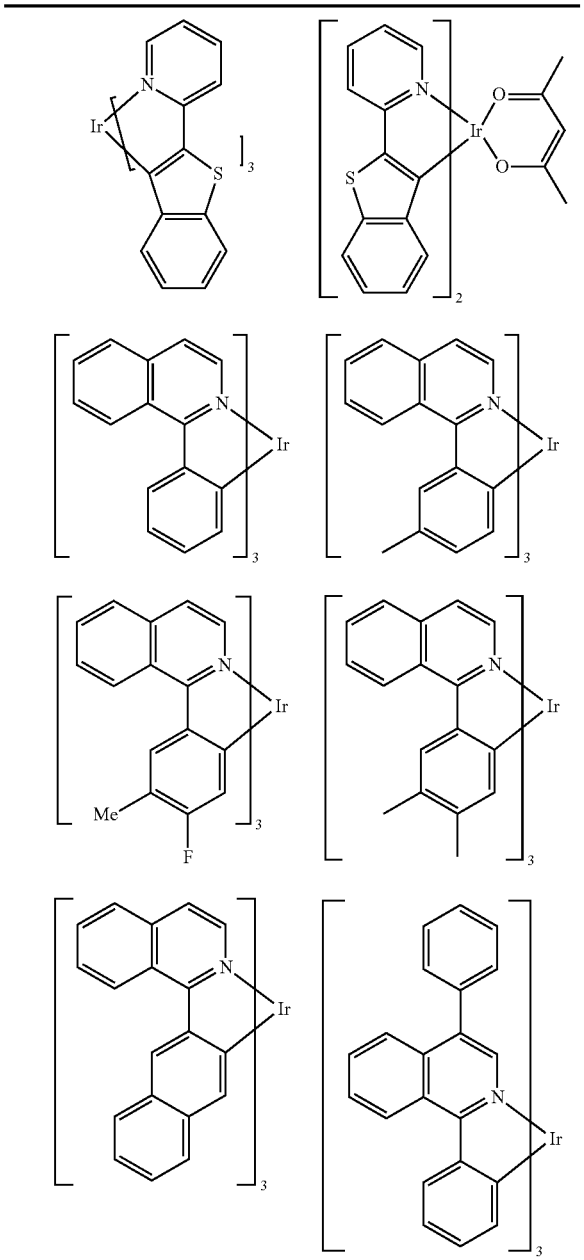

151
-continued
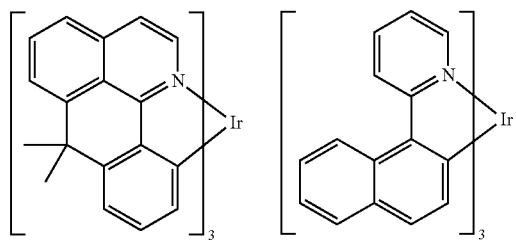
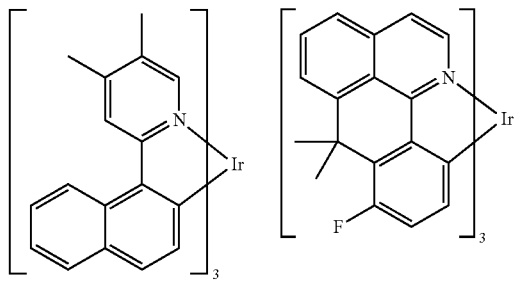
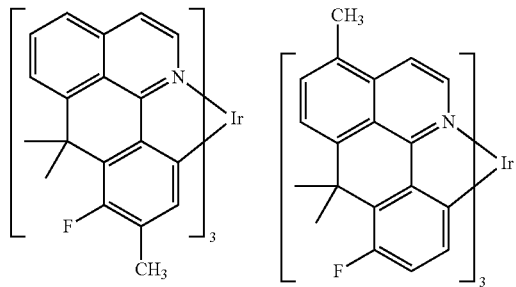
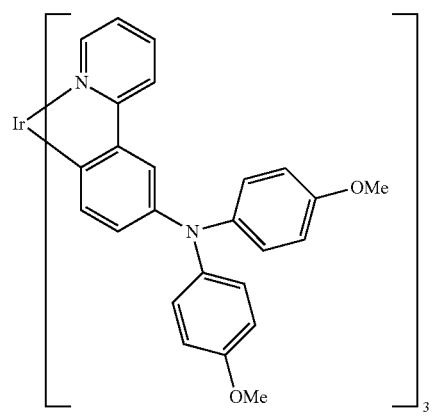
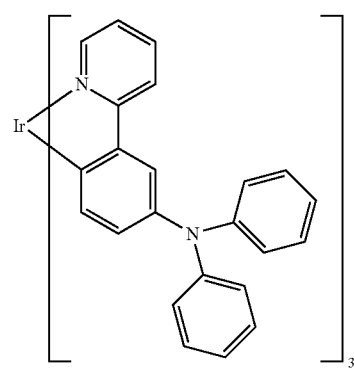
152
-continued
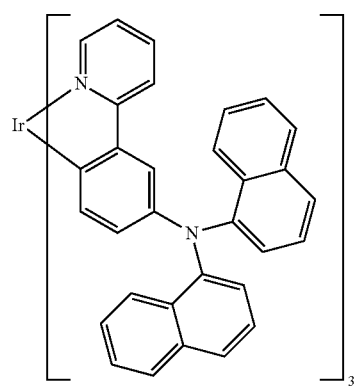
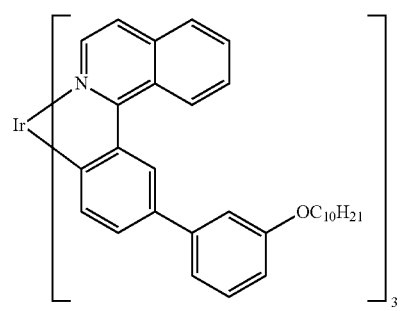
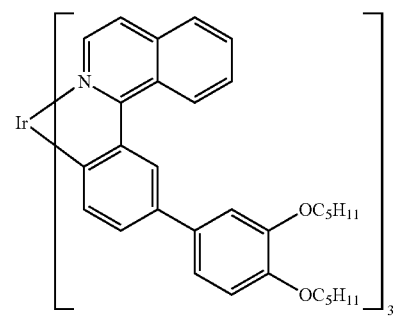
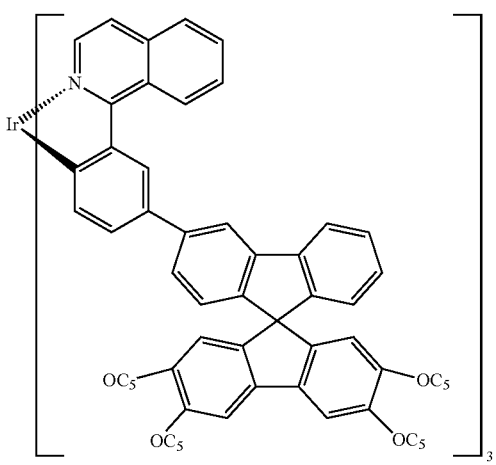

153
-continued
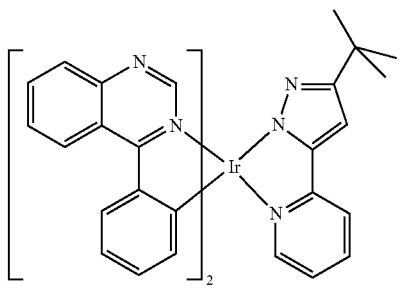
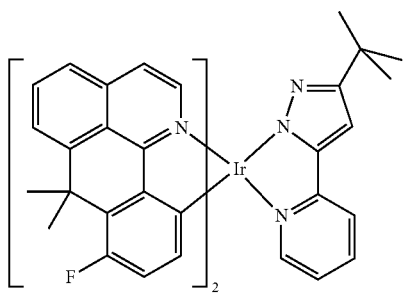
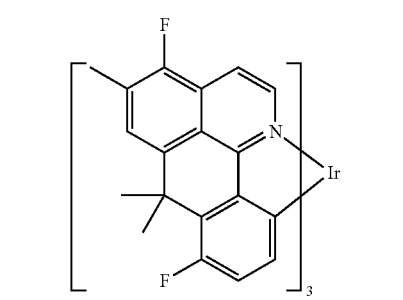
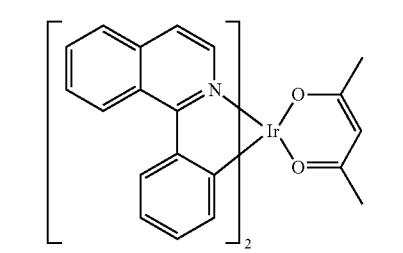
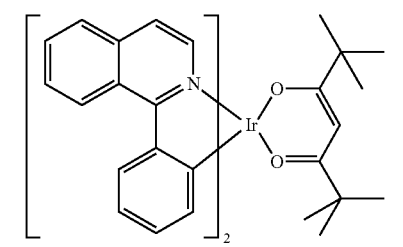
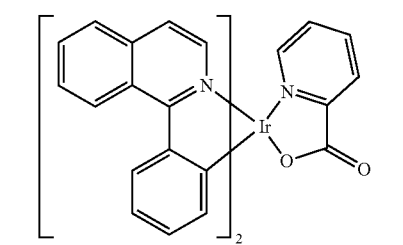
154
-continued
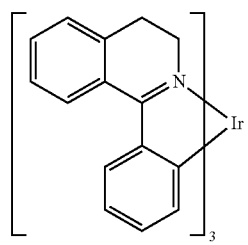
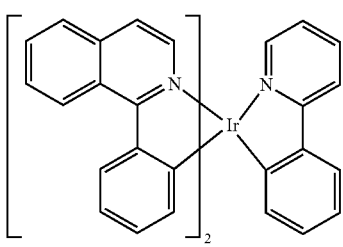
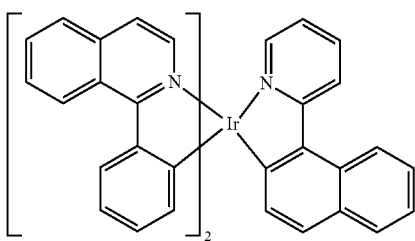
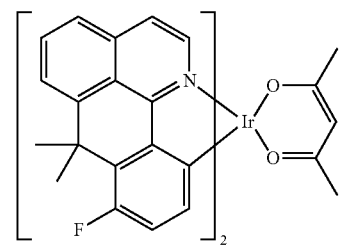
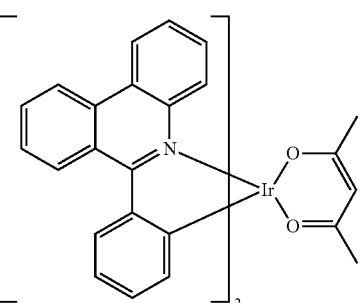
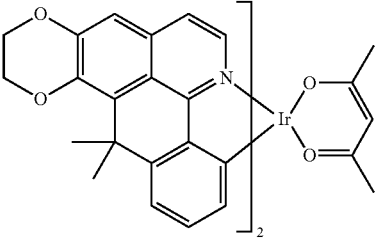

155
-continued
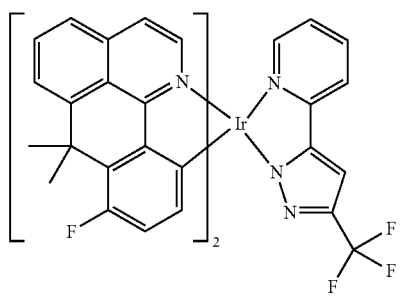
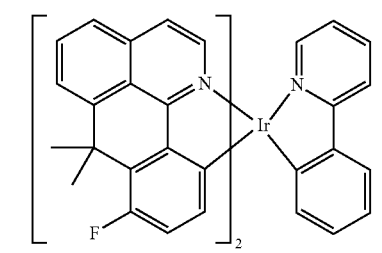
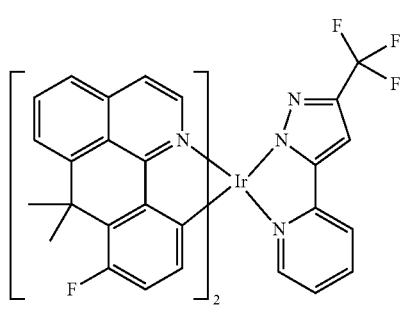
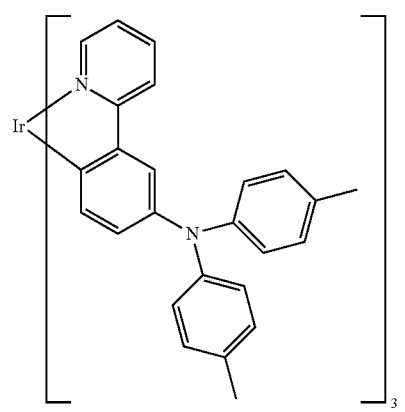
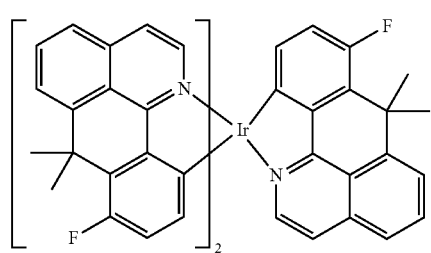
156
-continued
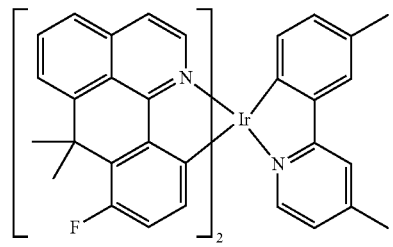
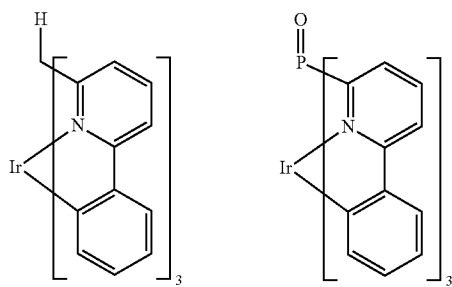
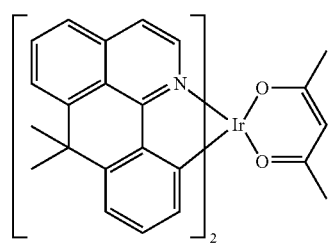
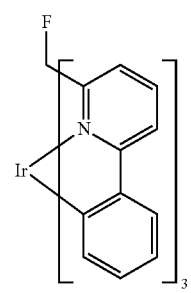
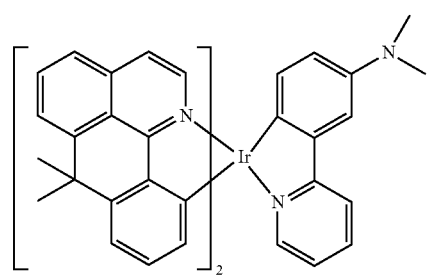
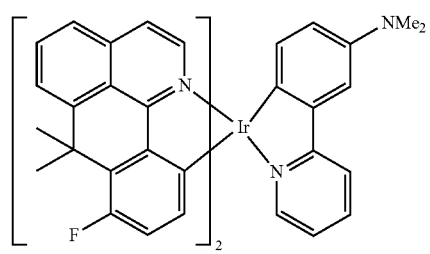

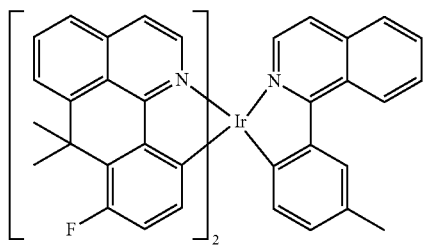
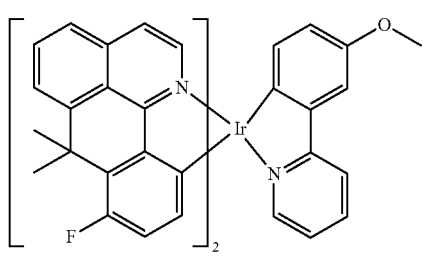
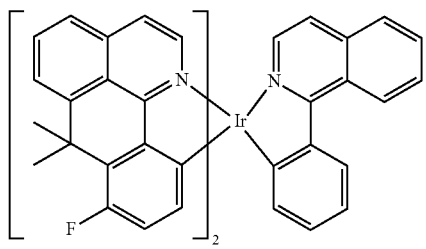
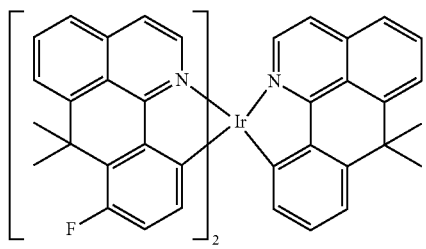
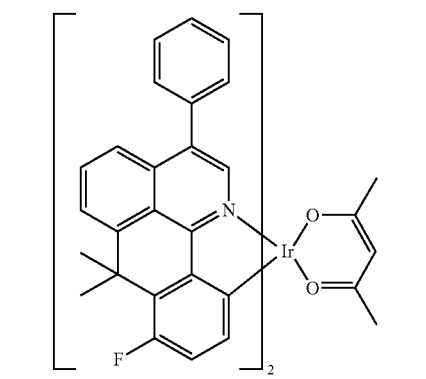
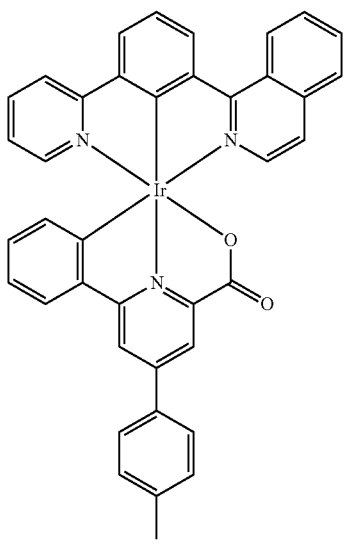
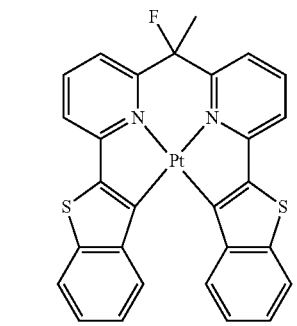
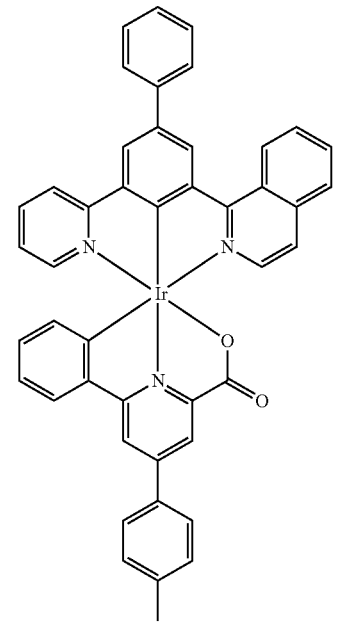

159
-continued
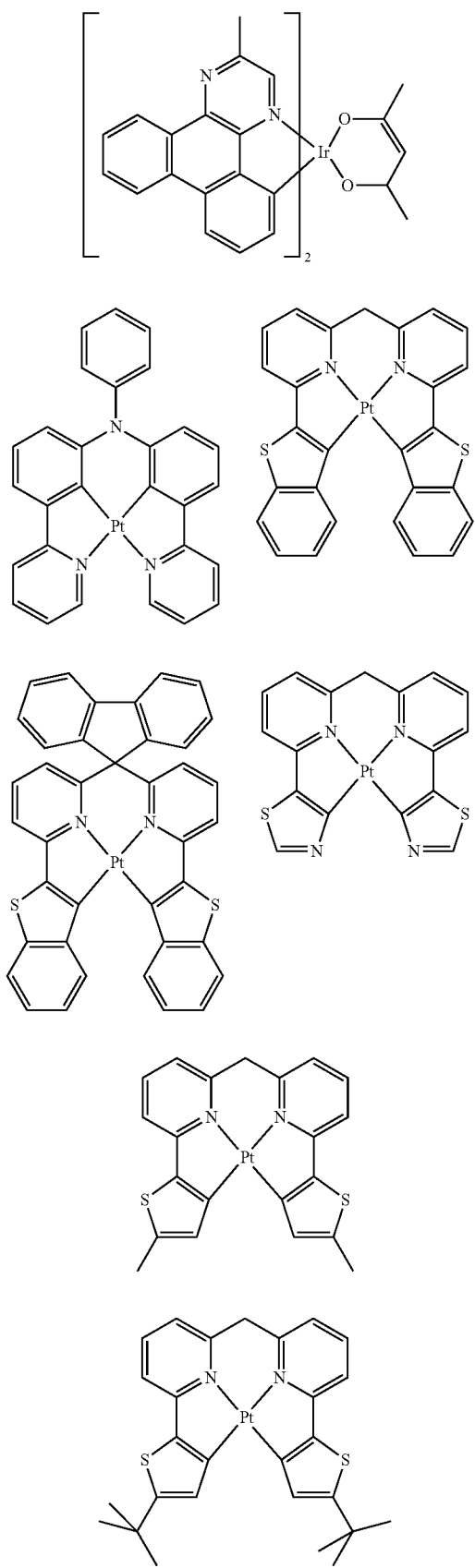
160
-continued
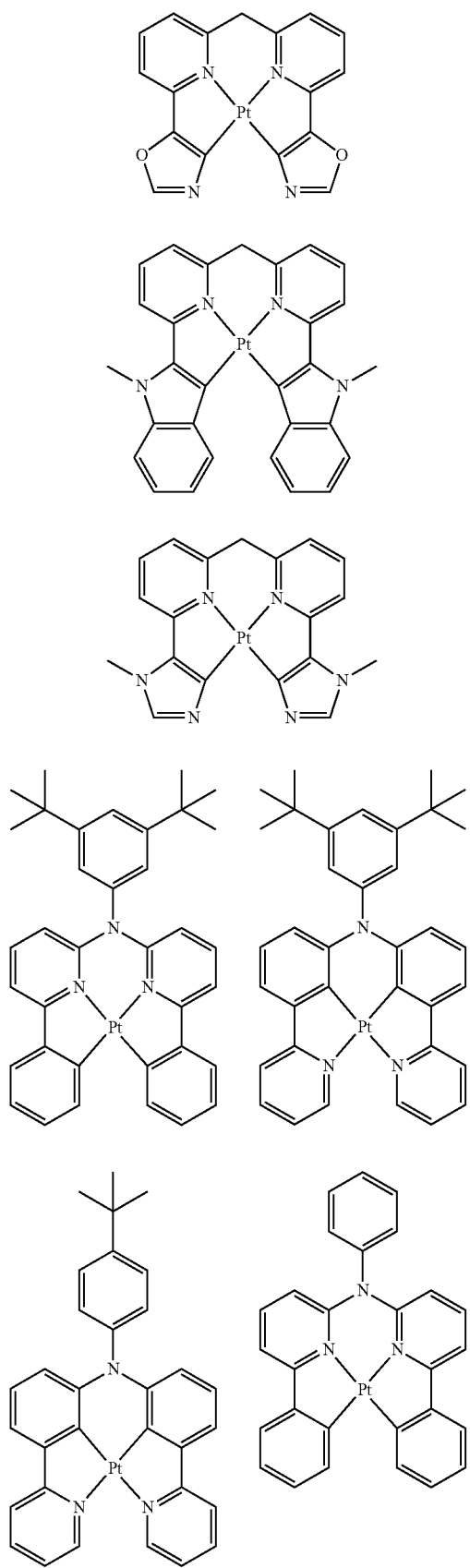

161
-continued
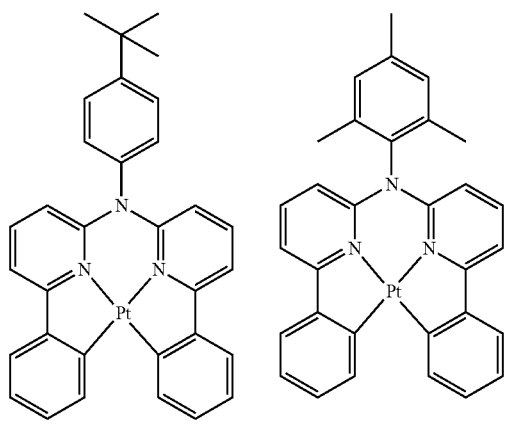
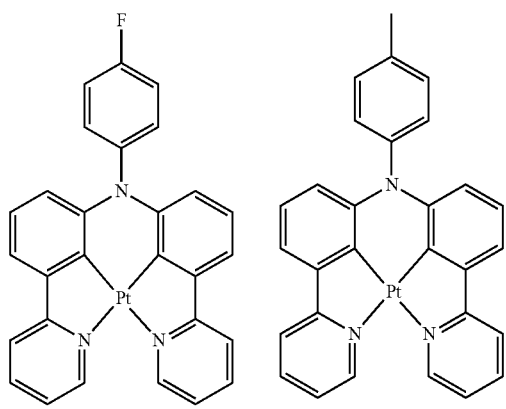
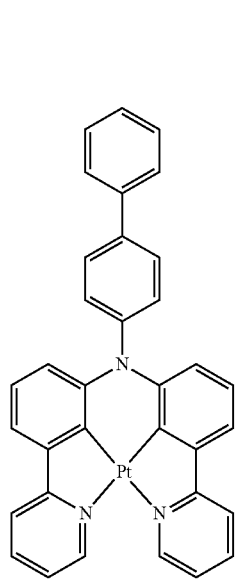
162
-continued
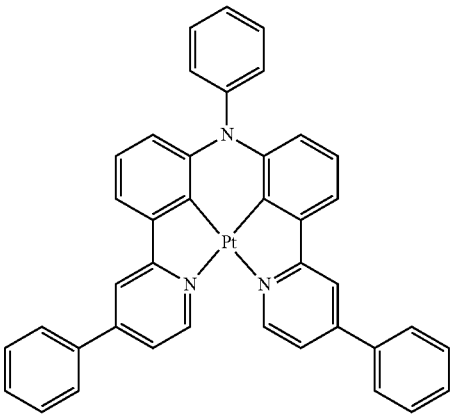
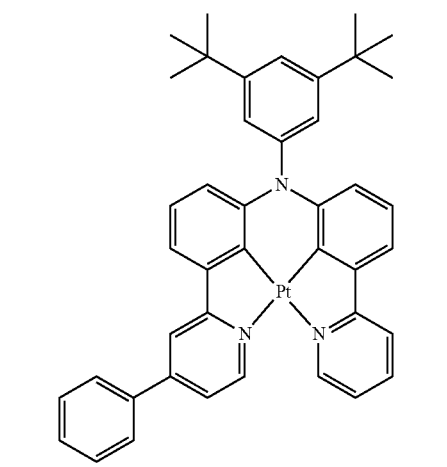
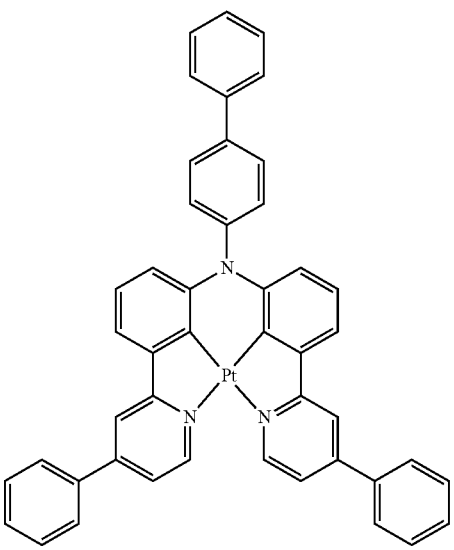

-continued
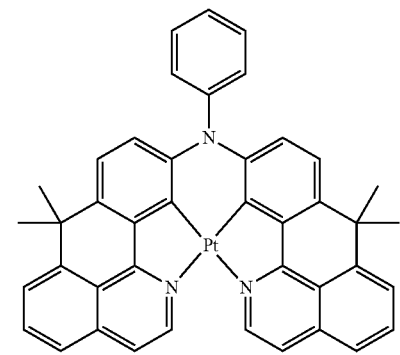
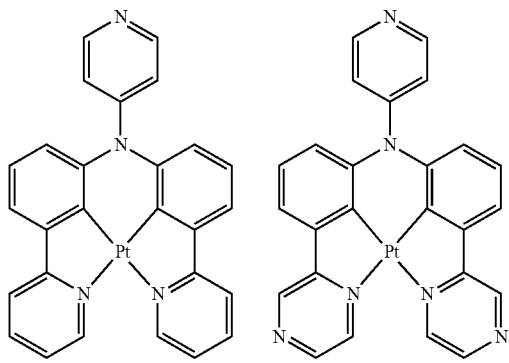
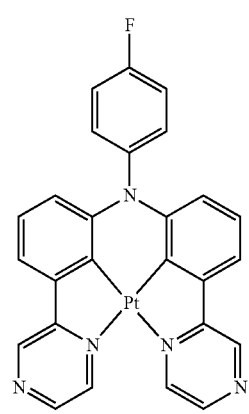
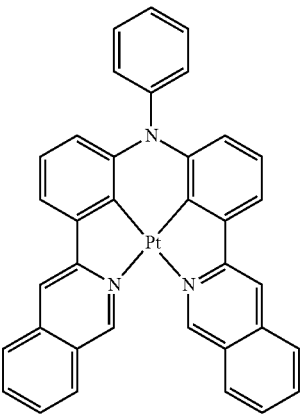
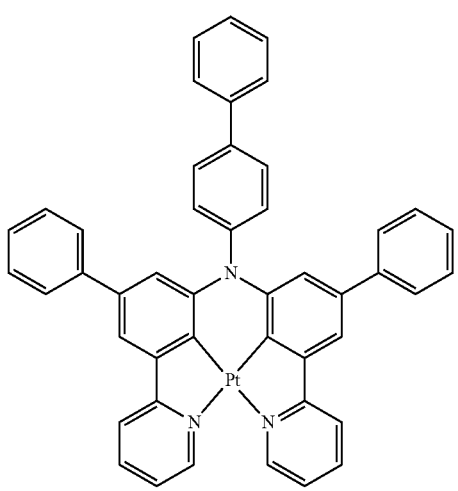
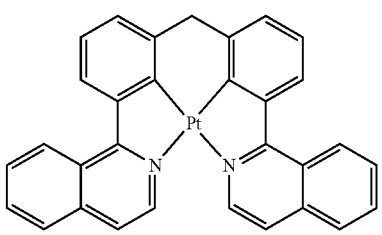

165
-continued
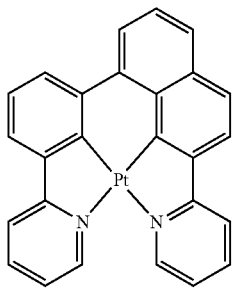
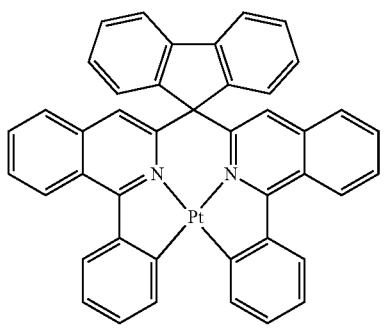
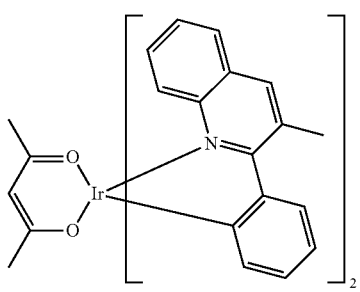
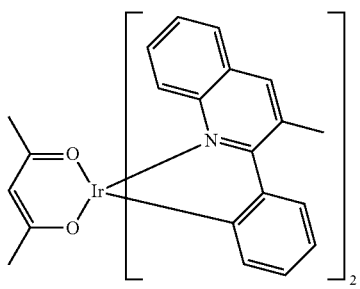
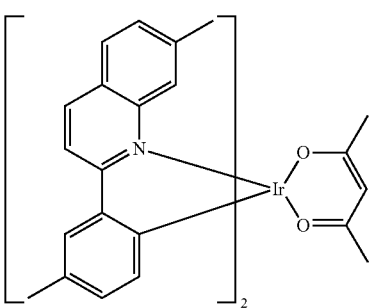
166
-continued
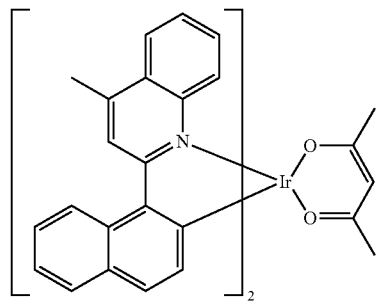
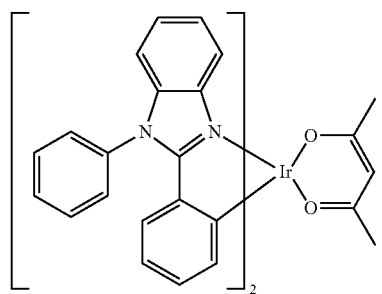
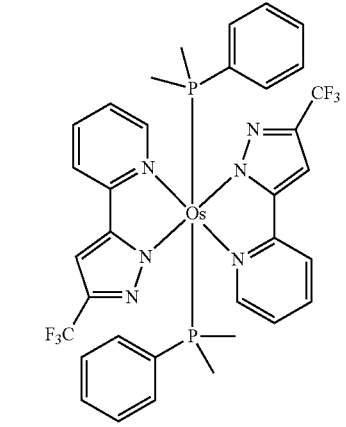
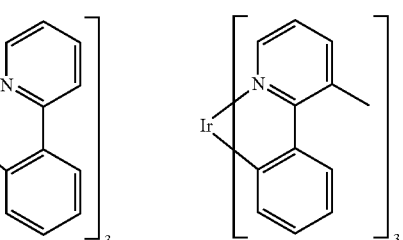
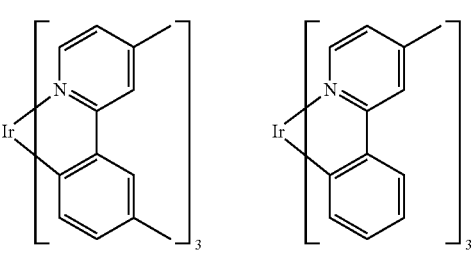

167
-continued
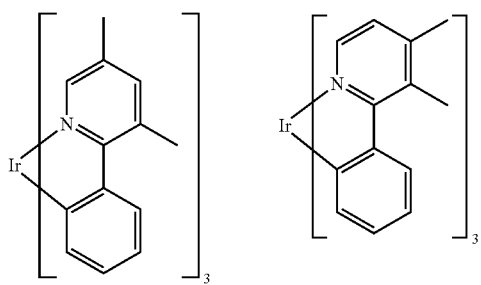
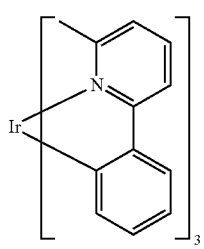
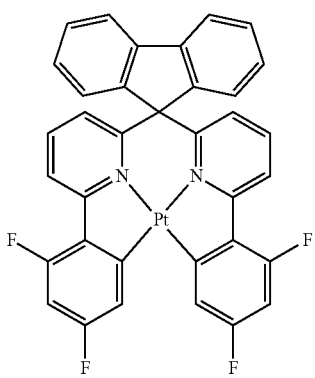
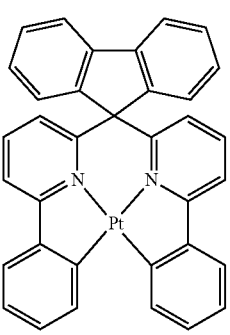
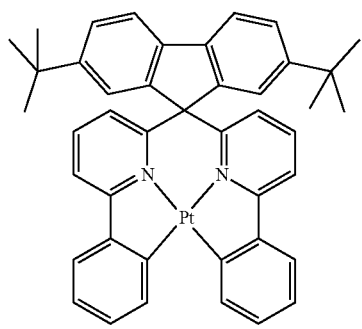
168
-continued
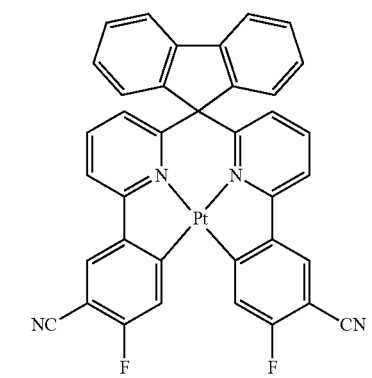
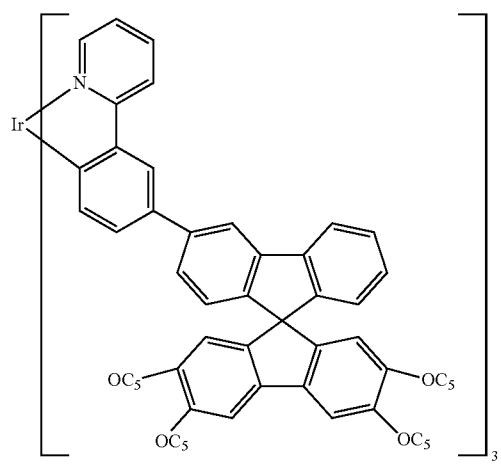
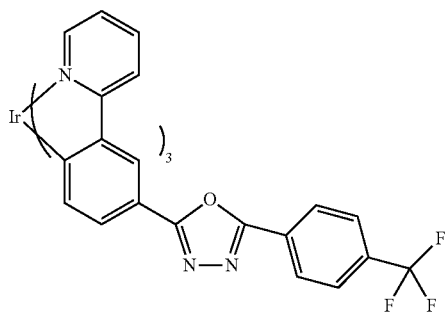
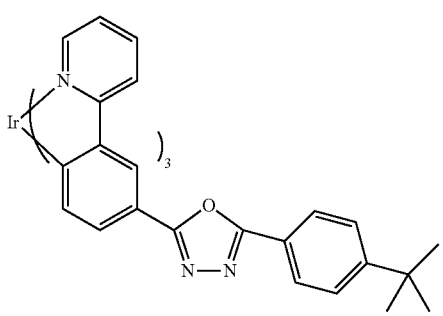

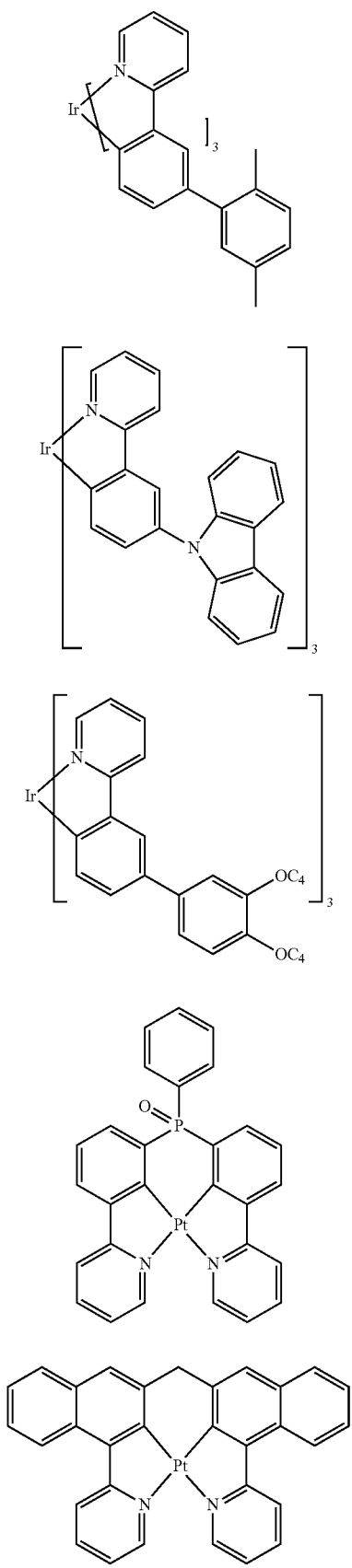
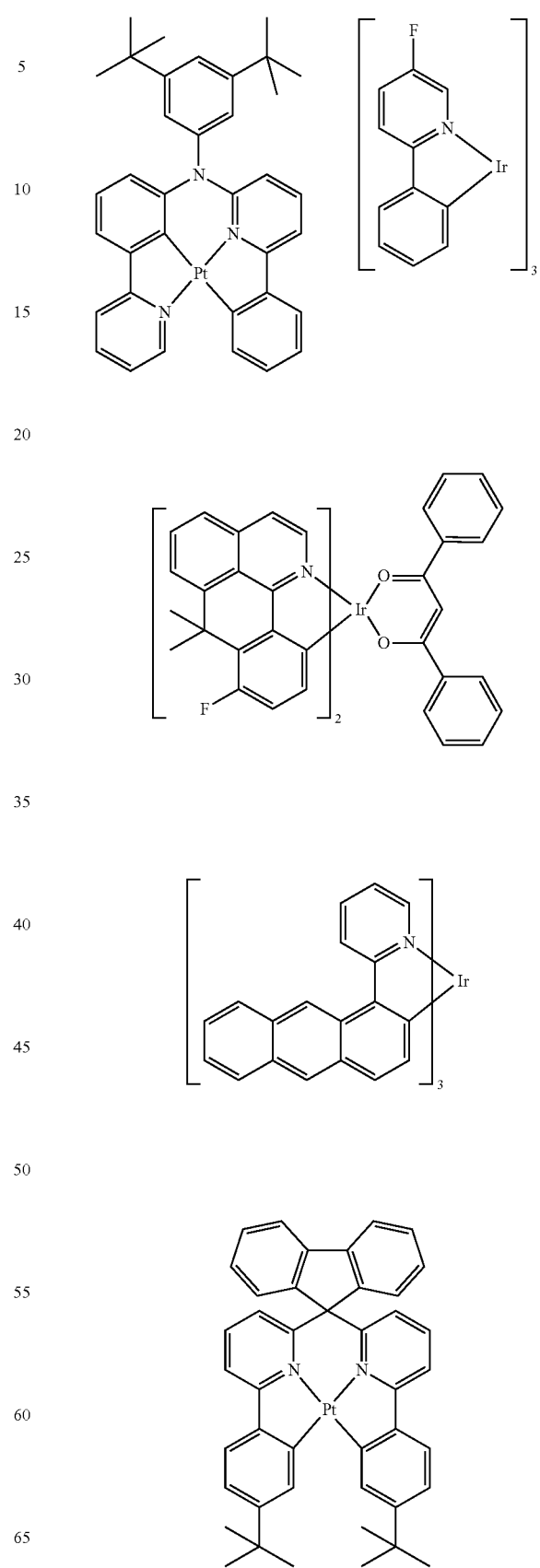

| 171 -continued | 172 -continued |
|---|---|
| 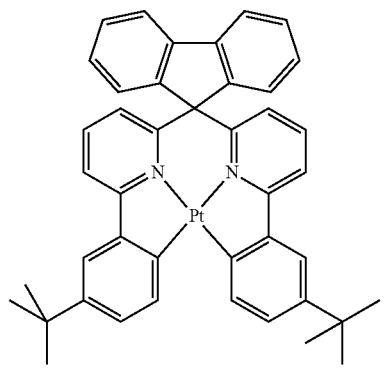<br>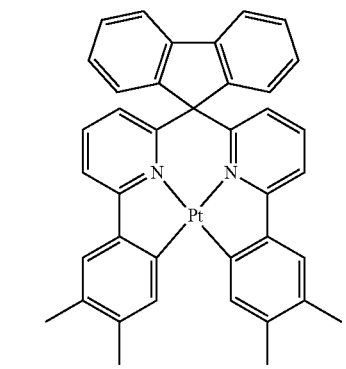<br>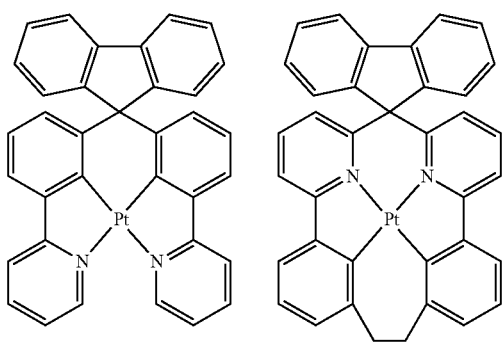<br>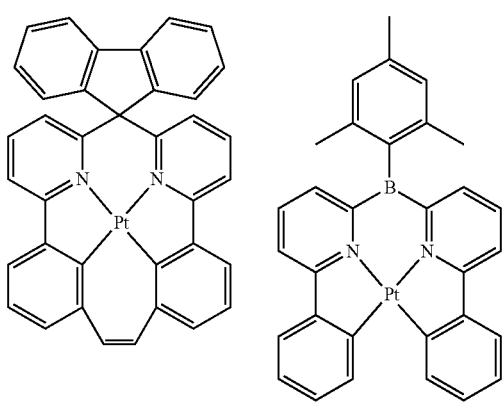 | 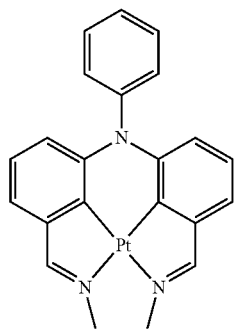<br>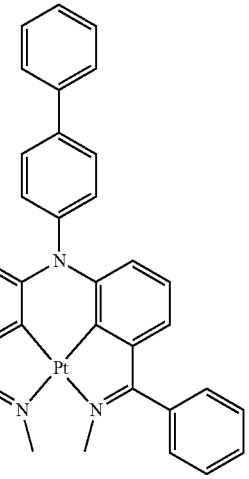<br>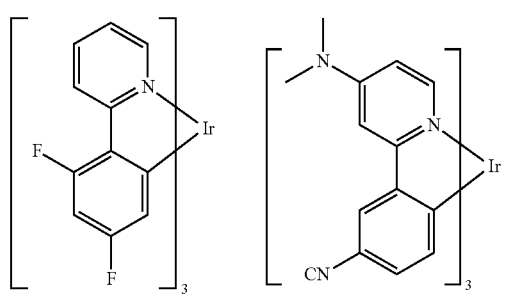<br>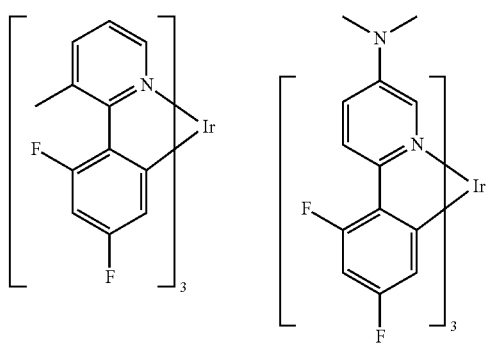 |

173
-continued
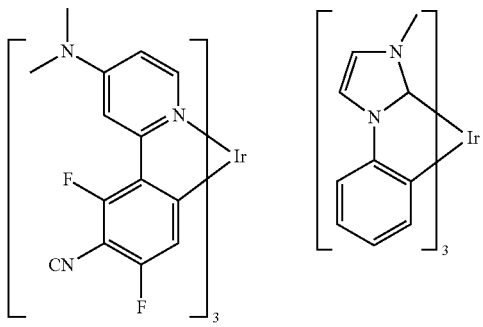
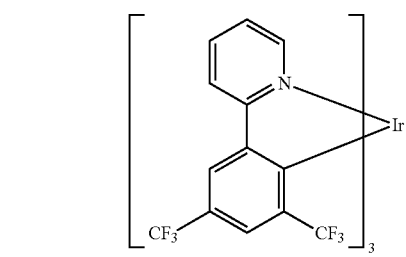
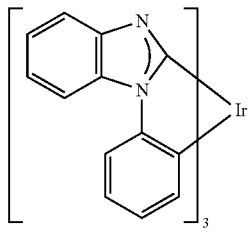
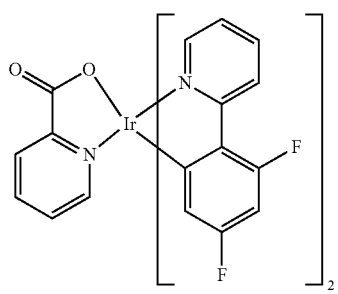
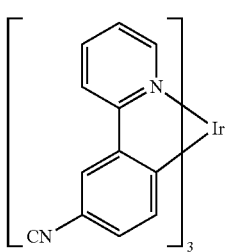
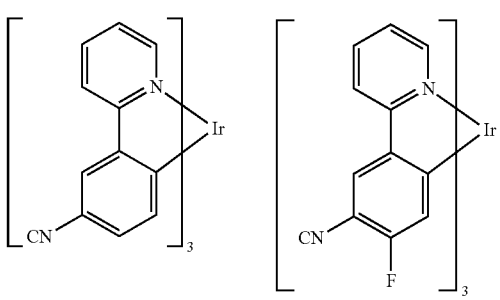
174
-continued
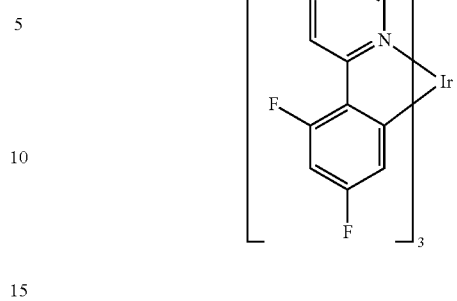
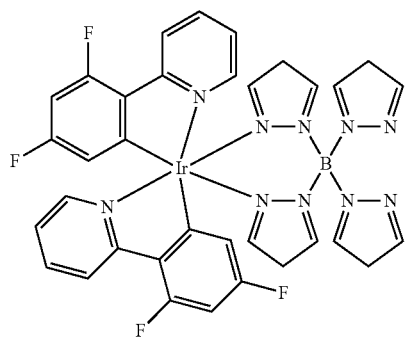
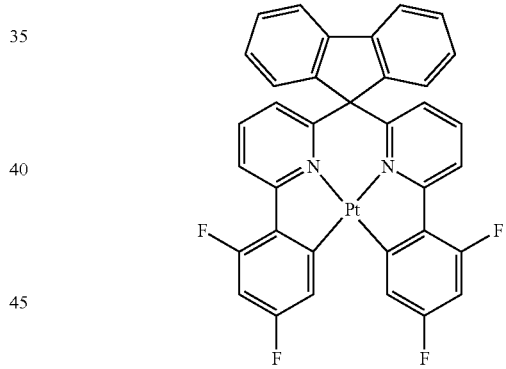
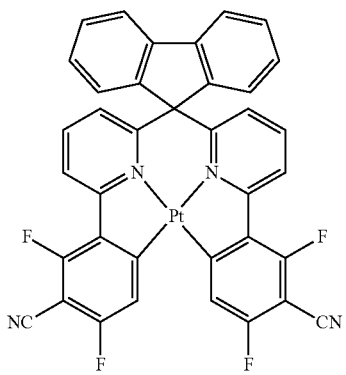

-continued

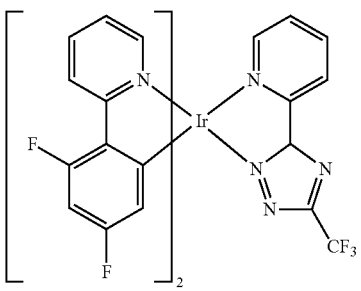

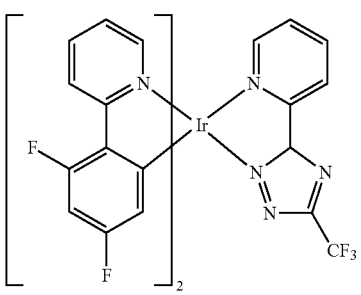

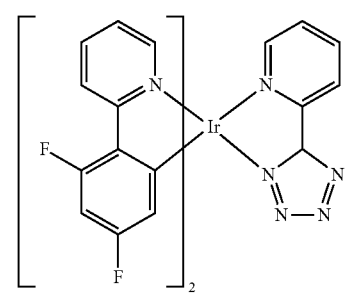

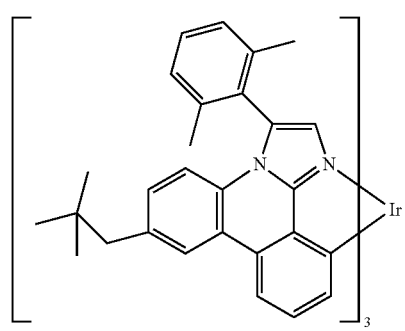

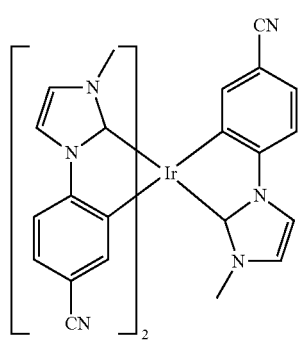

-continued

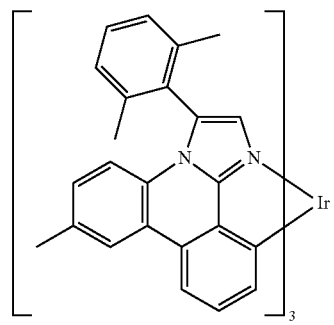

In a further embodiment of the invention, the compound of the formula (I) is employed in an interlayer between an emission layer comprising a singlet emitter compound and an emission layer comprising a triplet emitter compound. In this connection, reference is made to the application WO 10/115, 498. If the compounds according to the invention are used in an interlayer, it is preferred for this interlayer to be employed in an electronic device comprising three emitting layers between a green-emitting layer comprising a triplet emitter compound and a blue-emitting layer comprising a singlet emitter compound.

In a further preferred embodiment of the invention, the compound of the formula (I) is employed as emitting material in an emitting layer. The compounds of the formula (I) are particularly suitable as emitting material if at least one condensed aryl or heteroaryl group or a further diarylamino substituent is present in the molecule.

If the compound of the formula (I) is employed as emitting material in an emitting layer, it is preferably employed in combination with a matrix material. In a system comprising matrix and dopant, a matrix material is taken to mean the component which is present in the higher proportion in the system. In a system comprising a matrix and a plurality of dopants, the matrix is taken to mean the component whose proportion in the mixture is the highest.

The proportion of the compound of the formula (I) in the mixture of the emitting layer is between 0.1 and 50.0% by vol., preferably between 0.5 and 20.0% by vol., particularly preferably between 1.0 and 10.0% by vol. Correspondingly, the proportion of the matrix material is between 50.0 and 99.9% by vol., preferably between 80.0 and 99.5% by vol., particularly preferably between 90.0 and 99.0% by vol.

Matrix materials which are preferred in accordance with the invention are listed in a following section.

The materials preferably employed in the electronic devices according to the invention for the respective functions are mentioned below.

Preferred emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred exam-pies thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracene-diamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006, 449, and dibenzoindenoamines or dibenzoindenofluorenediamines, for example in accordance with WO 07/140,847. Examples of emitter materials from the class of the styrylamines are substituted or unsubstituted tristilbenamines or the emitter materials described in WO 06/000388, WO 06/058737, WO 06/000389, WO 07/065,549 and WO 07/115, 610. Preference is furthermore given to the condensed hydrocarbons disclosed in the application WO 10/012,328.

Preferred emitter materials are furthermore the compounds of the formula (I) according to the invention.

Suitable emitter materials are furthermore the structures depicted in the following table, and the derivatives of these structures disclosed in JP 06/001973, WO 04/047499, WO 06/098080, WO 07/065,678, US 2005/0260442 and WO 04/092111.

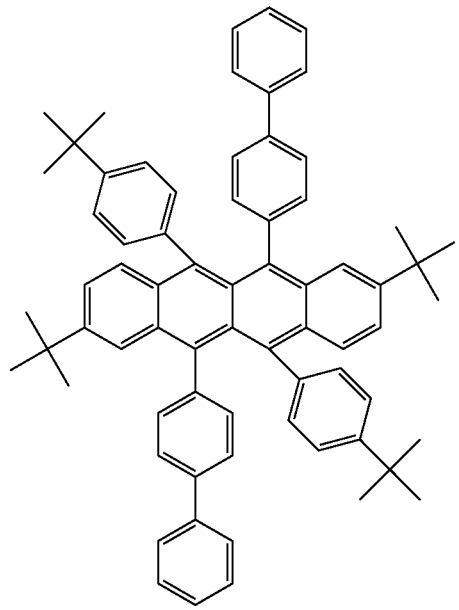 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

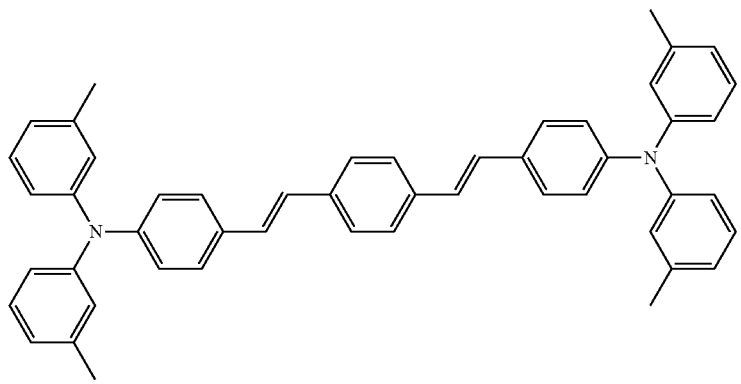 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]

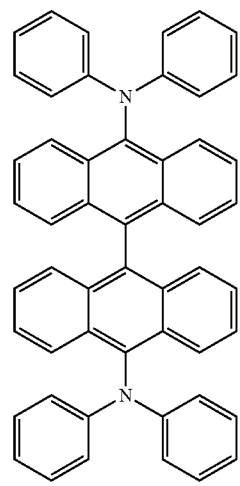 [SMILES: c1ccc(N(c2ccccc2)c2c3ccccc3c(-c3c4ccccc4c(N(c4ccccc4)c4ccccc4)c4ccccc34)c3ccccc23)cc1]
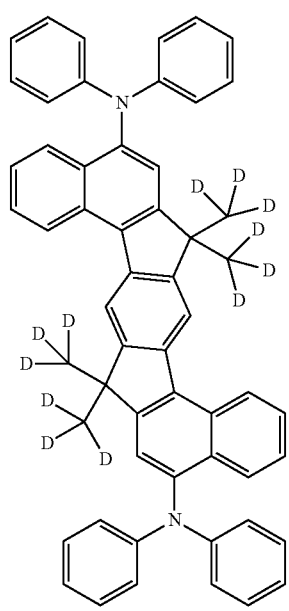 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

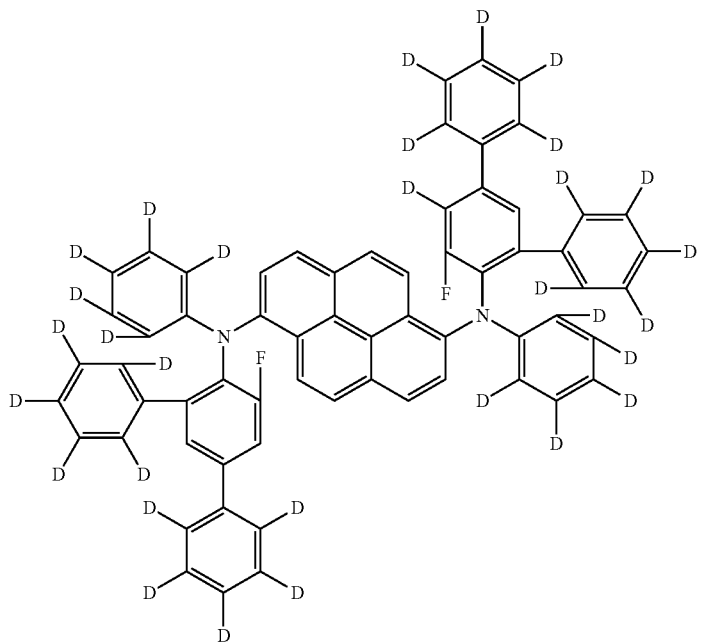 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
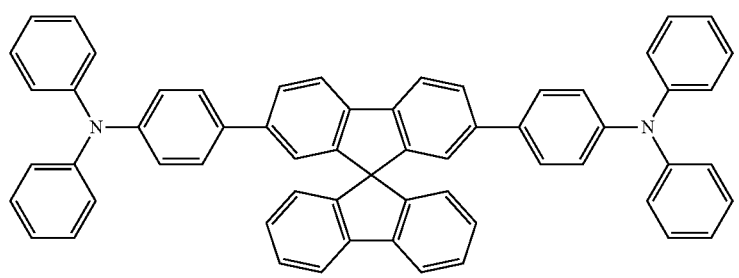 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]
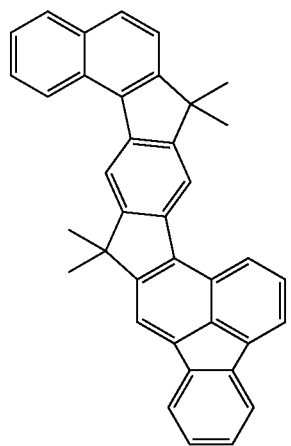 [SMILES: CC1(C)c2cc3c(cc2-c2c1ccc1ccccc21)C(C)(C)c1cc2c4c(cccc4c1-3)-c1ccccc1-2]

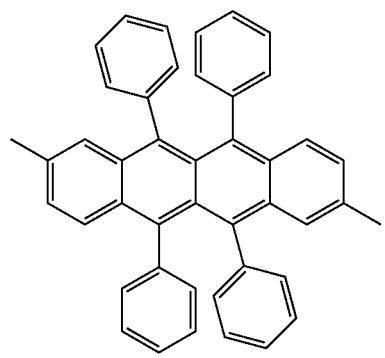
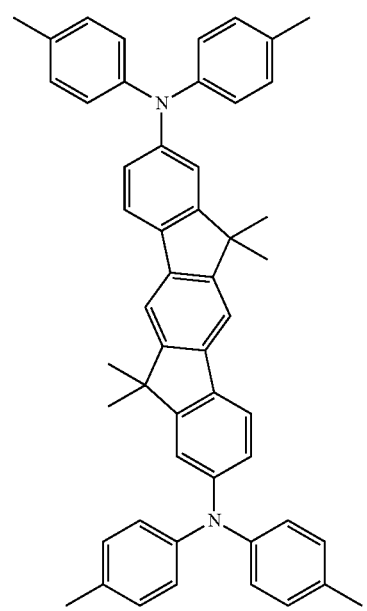
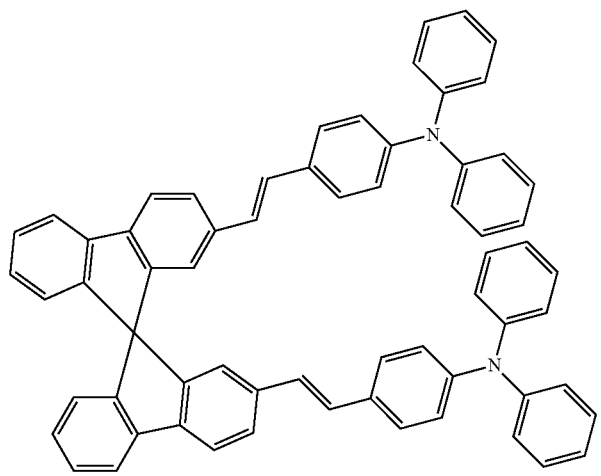 [SMILES: C(=C\c1ccc2c(c1)C1(c3ccccc3-2)c2ccccc2-c2ccc(/C=C/c3ccc(N(c4ccccc4)c4ccccc4)cc3)cc21)/c1ccc(N(c2ccccc2)c2ccccc2)cc1]

-continued
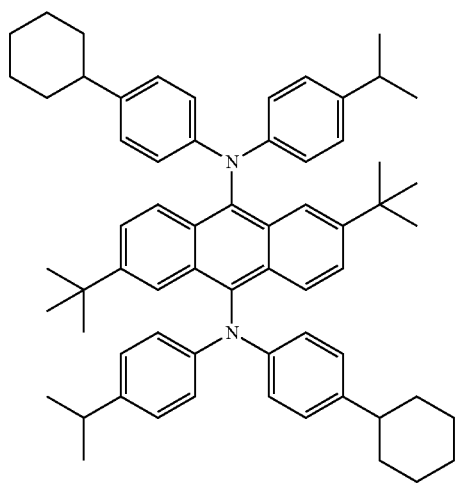 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
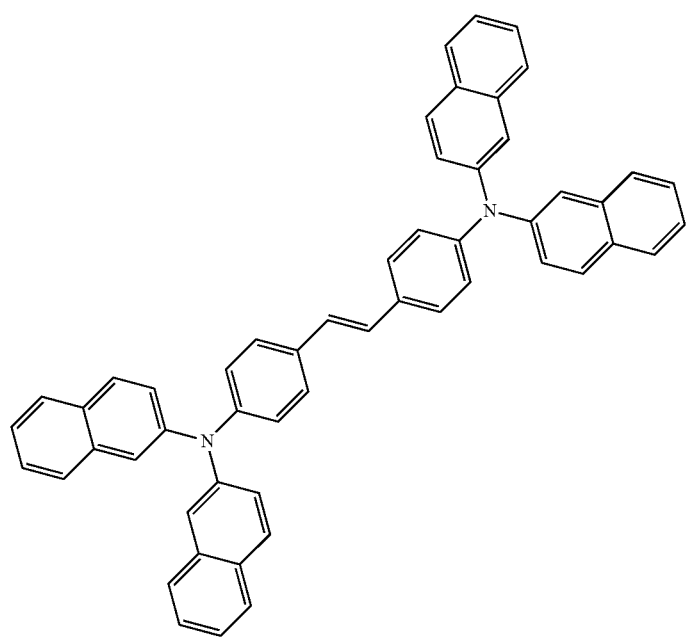 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

-continued
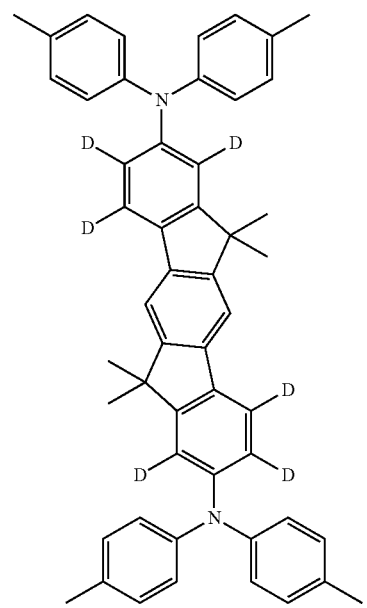
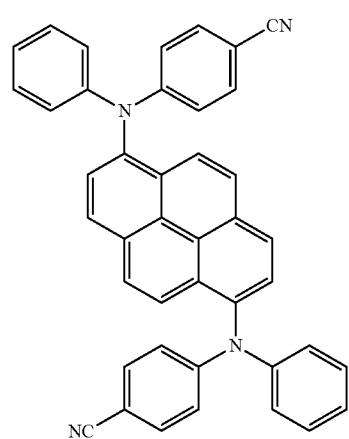 [SMILES: N#Cc1ccc(N(c2ccccc2)c2ccc3ccc4c(N(c5ccccc5)c5ccc(C#N)cc5)ccc5ccc2c3c54)cc1]

-continued
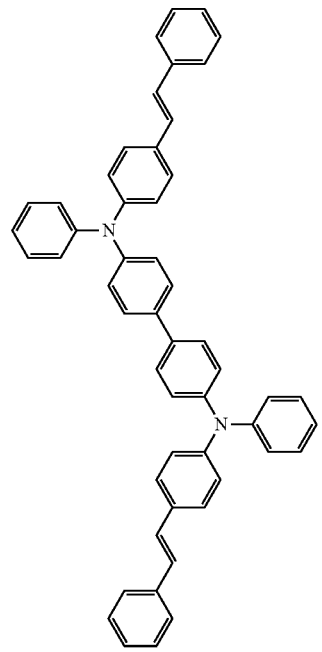 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
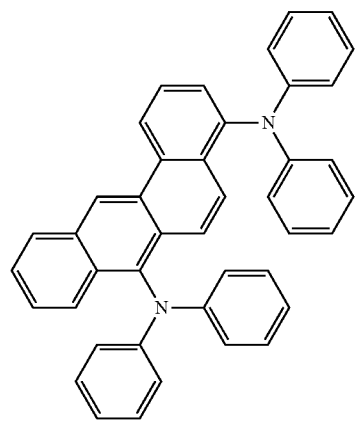 [SMILES: c1ccc(N(c2ccccc2)c2cccc3c2ccc2c(N(c4ccccc4)c4ccccc4)c4ccccc4cc23)cc1]
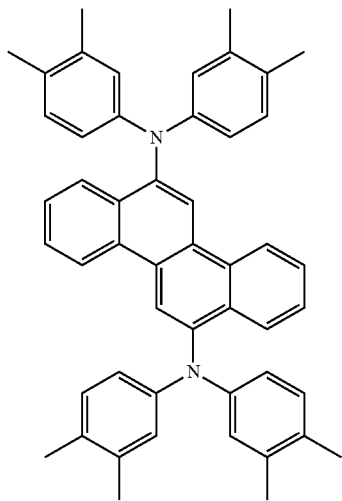

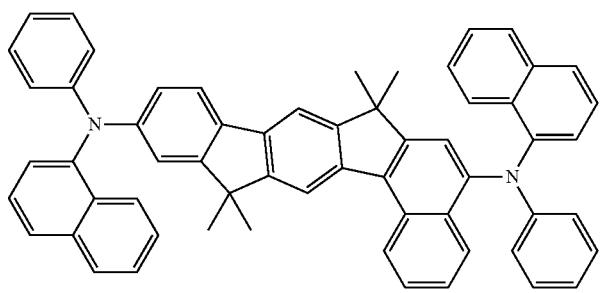 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
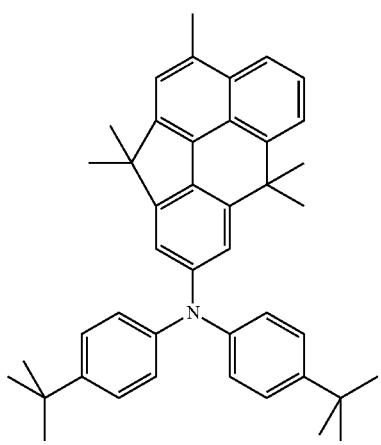 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
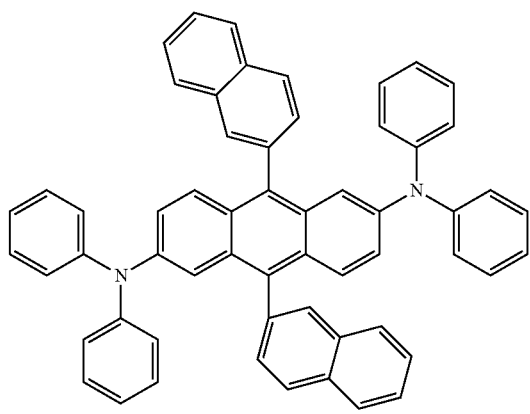 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
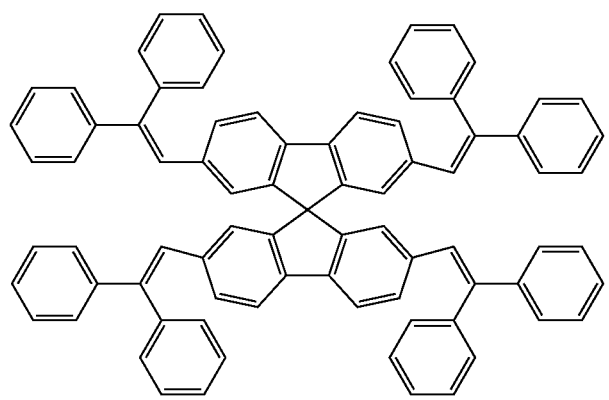 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

-continued
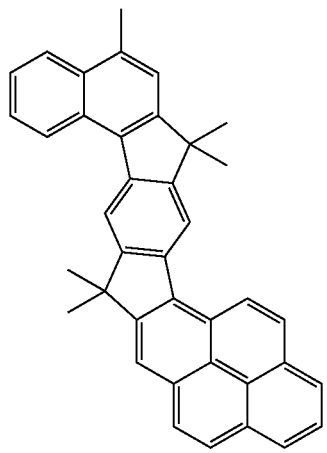 [SMILES: Cc1cc2c(c3ccccc13)-c1cc3c(cc1C2(C)C)-c1c(cc2ccc4cccc5ccc1c2c45)C3(C)C]
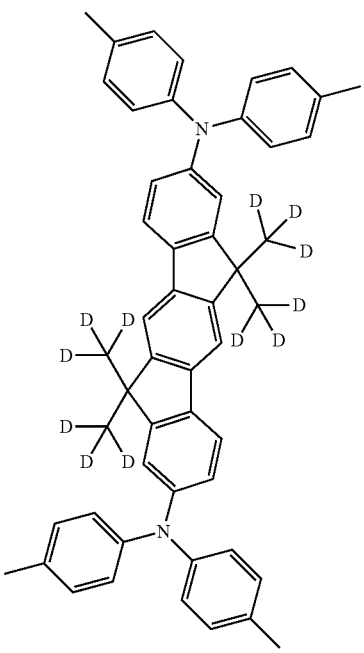
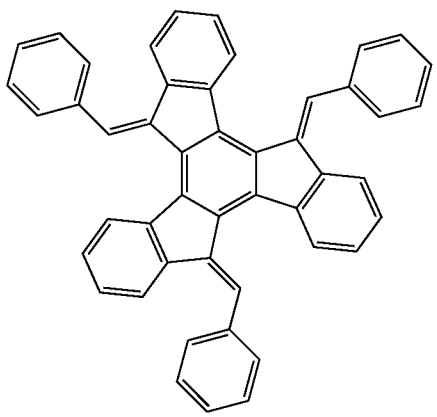 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]

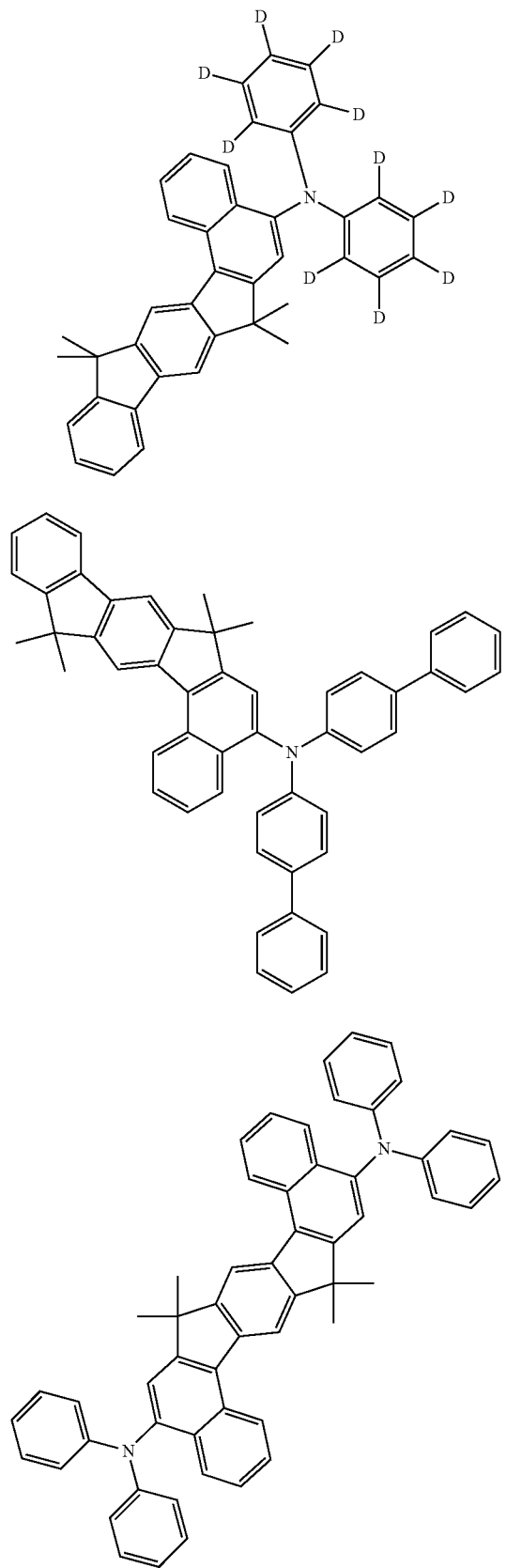

-continued
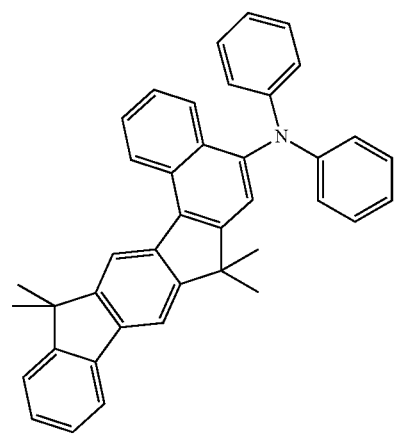 [SMILES: CC1(C)c2ccccc2-c2cc3c(cc21)-c1c(cc(N(c2ccccc2)c2ccccc2)c2ccccc12)C3(C)C]
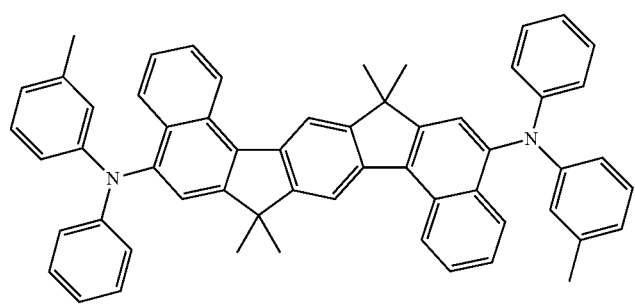 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
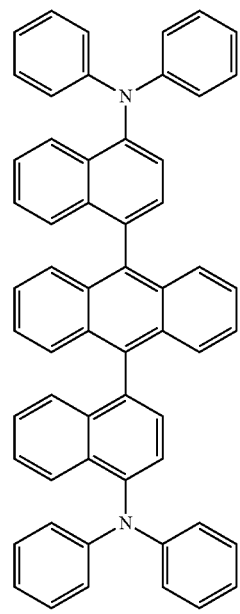 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]

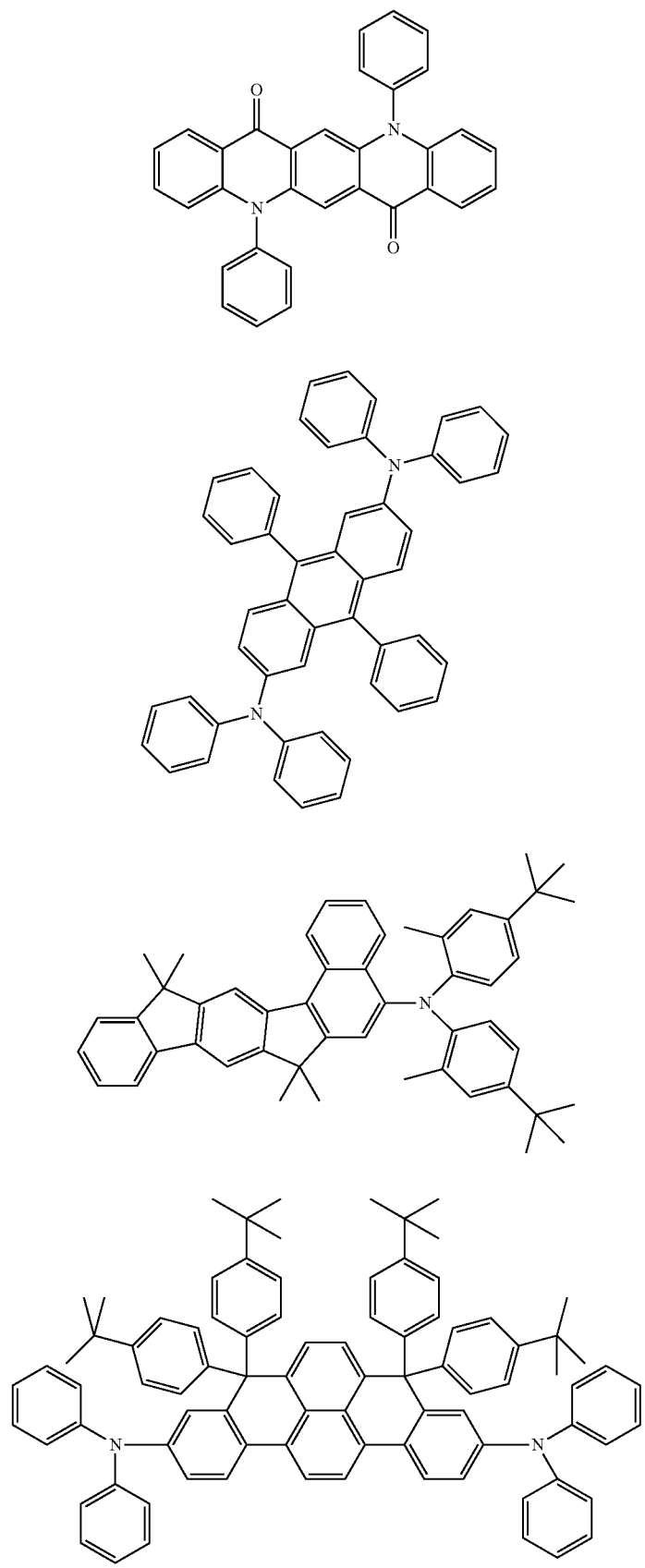

-continued
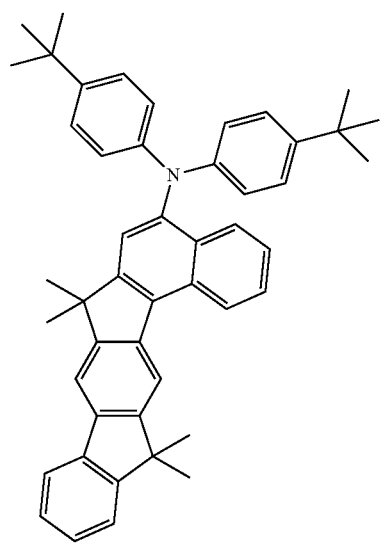 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
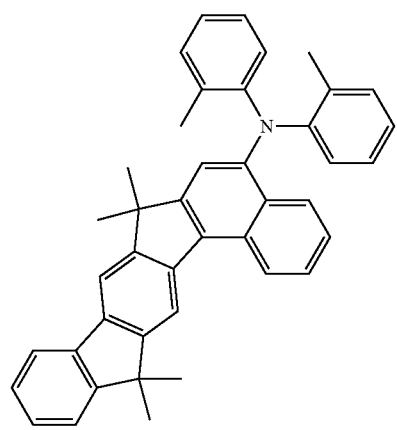 [SMILES: Cc1ccccc1N(c1ccccc1C)c1cc2c(c3ccccc13)-c1cc3c(cc1C2(C)C)-c1ccccc1C3(C)C]
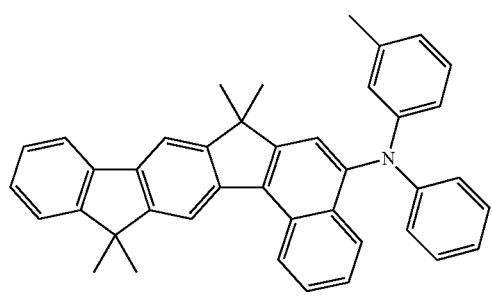 [SMILES: Cc1cccc(N(c2ccccc2)c2cc3c(c4ccccc24)-c2cc4c(cc2C3(C)C)-c2ccccc2C4(C)C)c1]
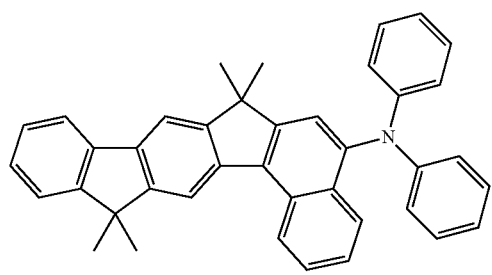 [SMILES: CC1(C)c2ccccc2-c2cc3c(cc21)-c1c(cc(N(c2ccccc2)c2ccccc2)c2ccccc12)C3(C)C]

-continued
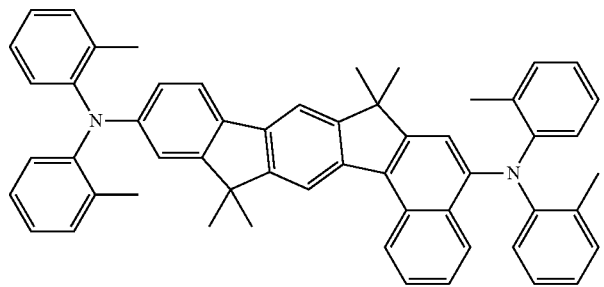 [SMILES: Cc1ccccc1N(c1ccc2c(c1)C(C)(C)c1cc3c(cc1-2)C(C)(C)c1cc(N(c2ccccc2C)c2ccccc2C)c2ccccc2c1-3)c1ccccc1C]
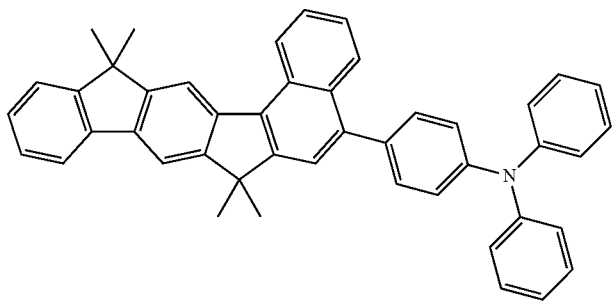 [SMILES: CC1(C)c2ccccc2-c2cc3c(cc21)-c1c(cc(-c2ccc(N(c4ccccc4)c4ccccc4)cc2)c2ccccc12)C3(C)C]
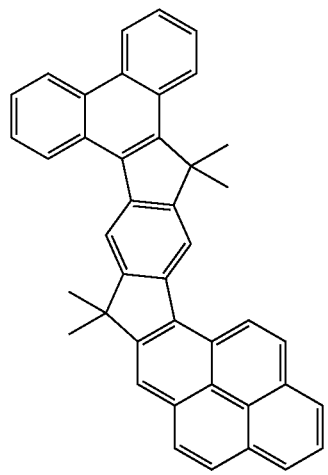 [SMILES: CC1(C)c2cc3c(cc2-c2c1cc1ccc4cccc5ccc2c1c45)C(C)(C)c1c-3c2ccccc2c2ccccc12]
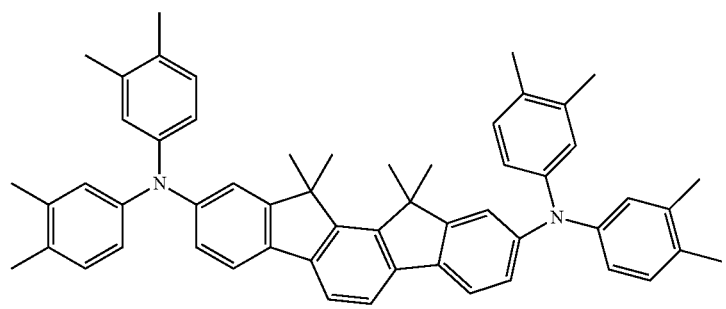
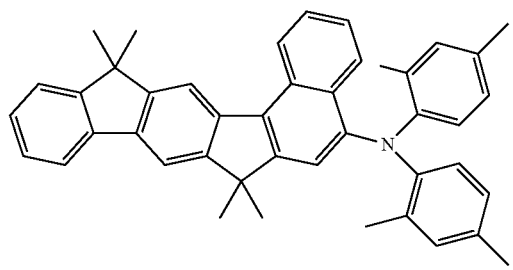 [SMILES: Cc1ccc(N(c2ccc(C)cc2C)c2cc3c(c4ccccc24)-c2cc4c(cc2C3(C)C)-c2ccccc2C4(C)C)c(C)c1]

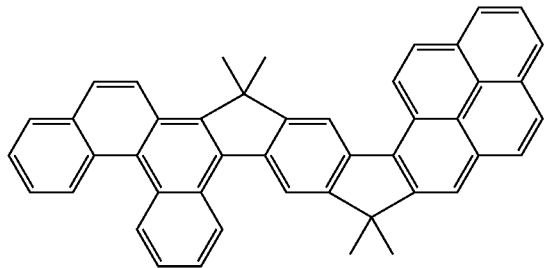 [SMILES: CC1(C)c2cc3c(cc2-c2c1cc1ccc4cccc5ccc2c1c45)C(C)(C)c1c-3c2ccccc2c2c1ccc1ccccc12]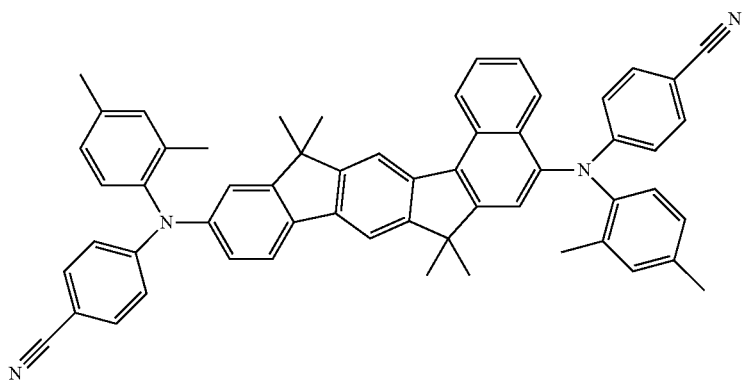 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]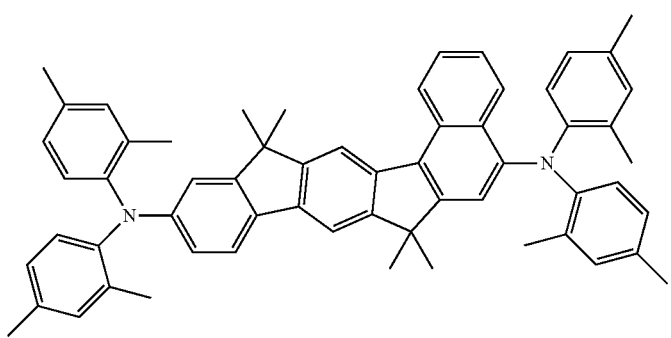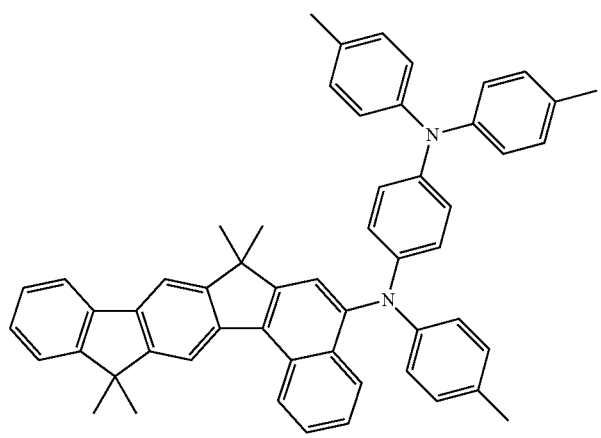 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

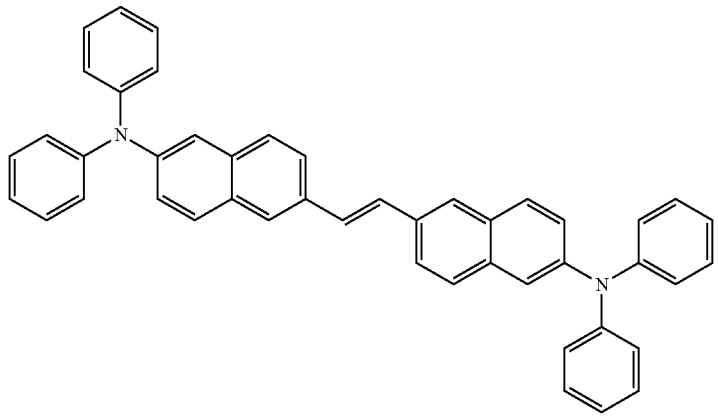 [SMILES: C(=C\c1ccc2cc(N(c3ccccc3)c3ccccc3)ccc2c1)/c1ccc2cc(N(c3ccccc3)c3ccccc3)ccc2c1]

Suitable matrix materials in the electronic devices according to the invention are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore also the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Apart from the compounds according to the invention, very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials are, for example, the materials depicted in the following table, and derivatives of these materials, as disclosed in WO 04/018587, WO 08/006,449, U.S. Pat. No. 5,935,721, US 2005/0181232, JP 2000/273056, EP 681019, US 2004/0247937 and US 2005/0211958.

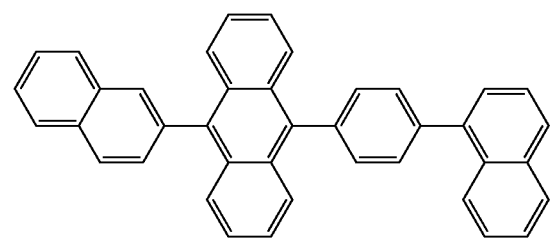 [SMILES: c1ccc2cc(-c3c4ccccc4c(-c4ccc(-c5cccc6ccccc56)cc4)c4ccccc34)ccc2c1]

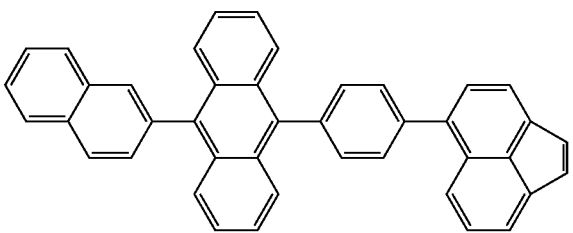 [SMILES: C1=Cc2ccc(-c3ccc(-c4c5ccccc5c(-c5ccc6ccccc6c5)c5ccccc45)cc3)c3cccc1c23]

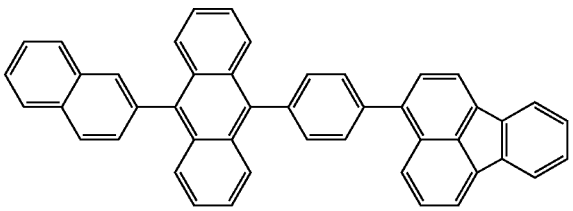 [SMILES: c1ccc2c(c1)-c1cccc3c(-c4ccc(-c5c6ccccc6c(-c6ccc7ccccc7c6)c6ccccc56)cc4)ccc-2c13]

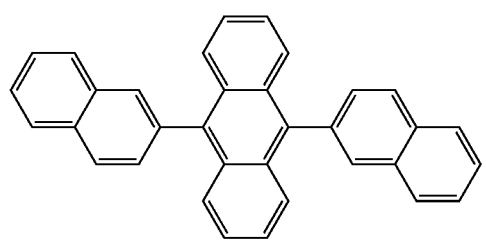 [SMILES: c1ccc2cc(-c3c4ccccc4c(-c4ccc5ccccc5c4)c4ccccc34)ccc2c1]

209
-continued
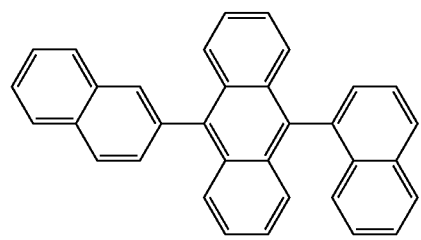 [SMILES: c1ccc2cc(-c3c4ccccc4c(-c4cccc5ccccc45)c4ccccc34)ccc2c1]
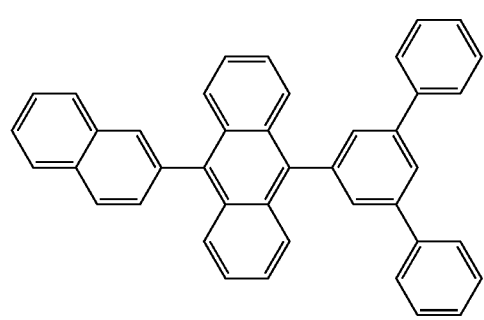 [SMILES: c1ccc(-c2cc(-c3ccccc3)cc(-c3c4ccccc4c(-c4ccc5ccccc5c4)c4ccccc34)c2)cc1]
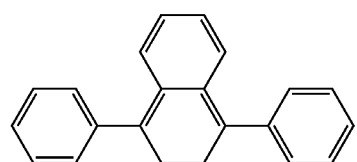
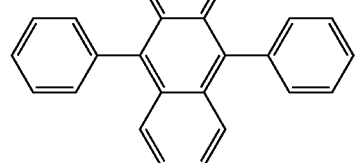
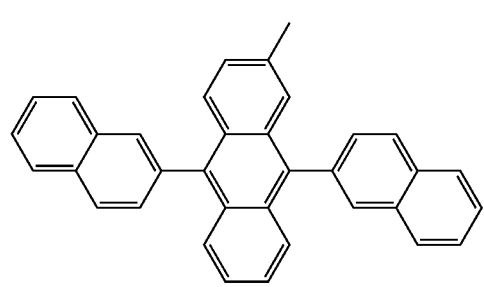 [SMILES: Cc1ccc2c(-c3ccc4ccccc4c3)c3ccccc3c(-c3ccc4ccccc4c3)c2c1]
210
-continued
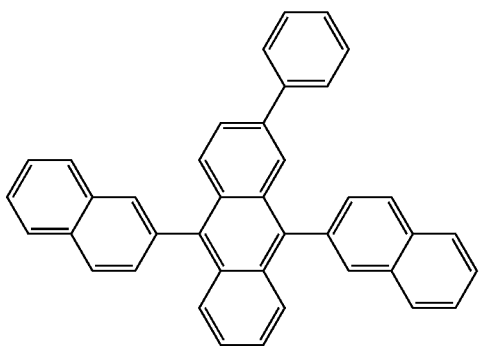 [SMILES: c1ccc(-c2ccc3c(-c4ccc5ccccc5c4)c4ccccc4c(-c4ccc5ccccc5c4)c3c2)cc1]
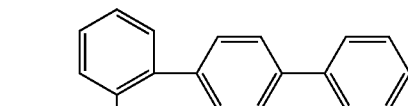
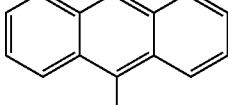
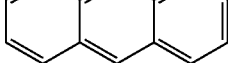
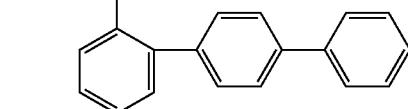
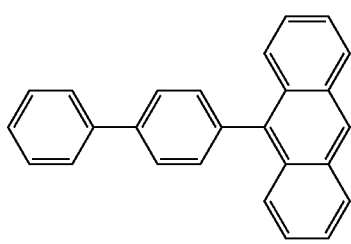
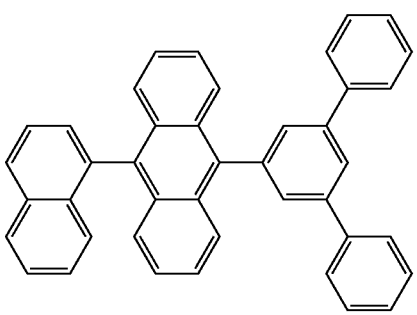 [SMILES: c1ccc(-c2cc(-c3ccccc3)cc(-c3c4ccccc4c(-c4cccc5ccccc45)c4ccccc34)c2)cc1]

| 211 -continued | 212 -continued |
|---|---|
| 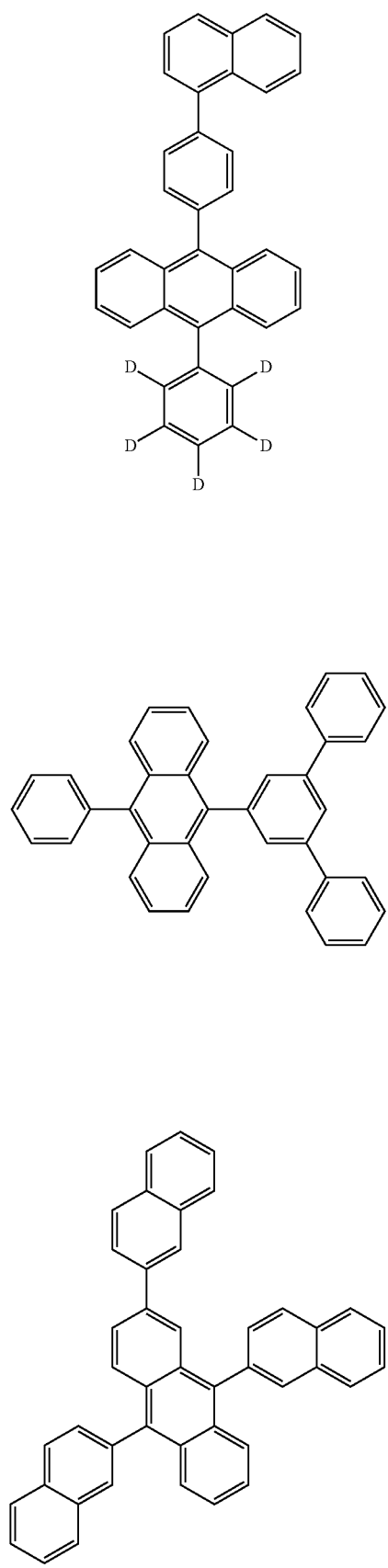 | 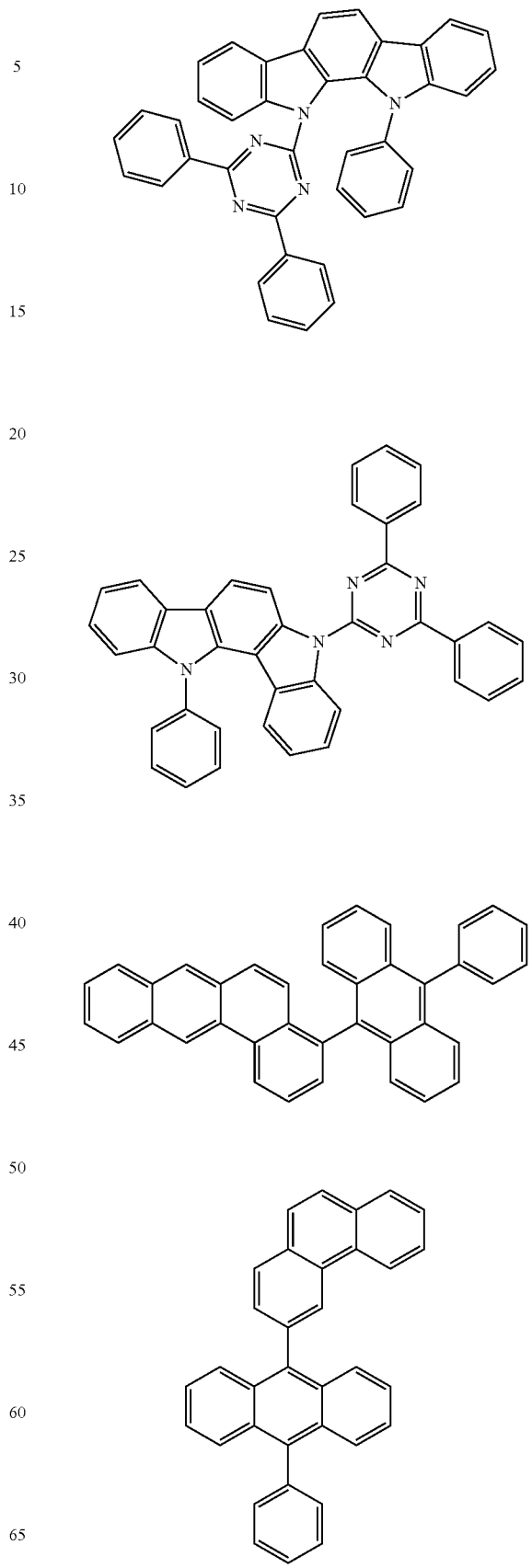 |

| 213 -continued | 214 -continued |
|---|---|
| 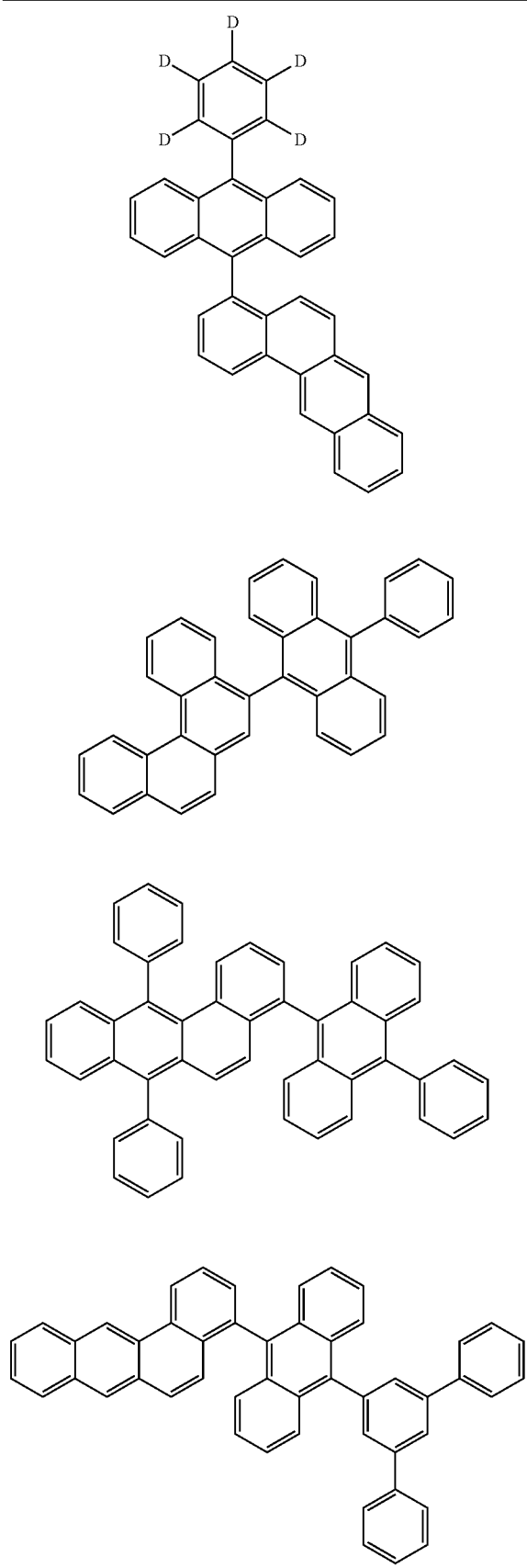 | 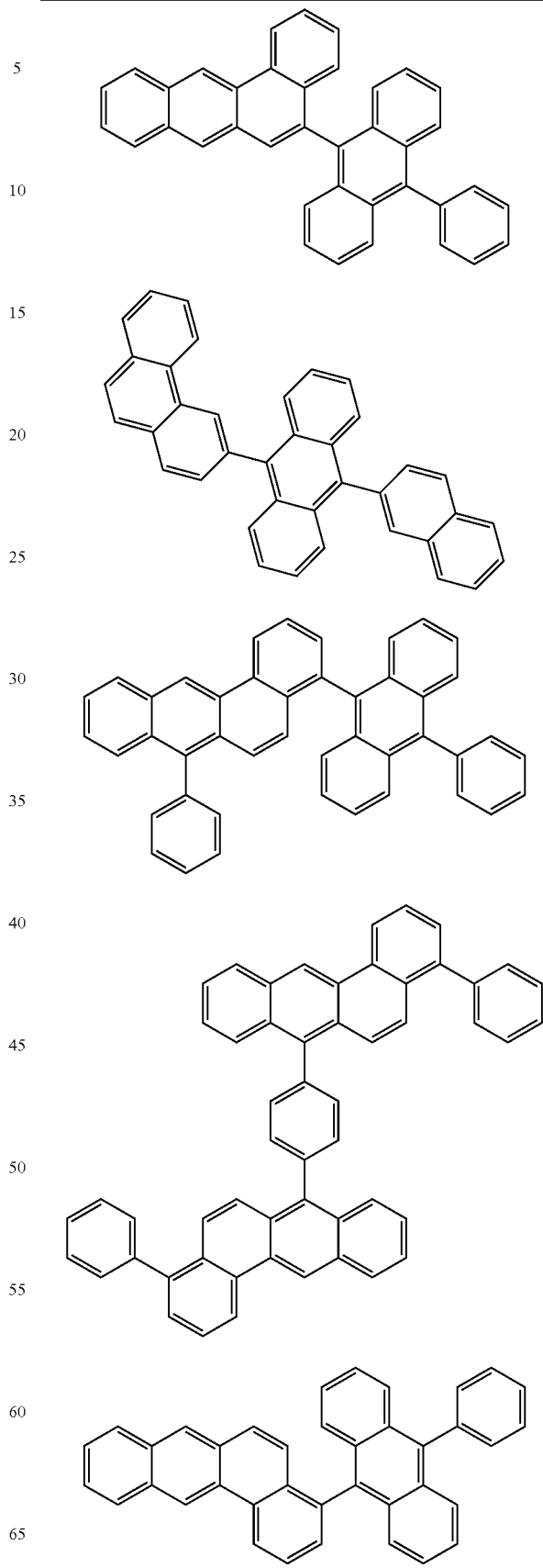 |

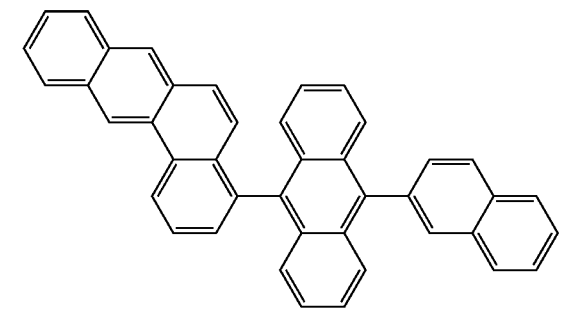 [SMILES: c1ccc2cc(-c3c4ccccc4c(-c4cccc5c4ccc4cc6ccccc6cc45)c4ccccc34)ccc2c1]
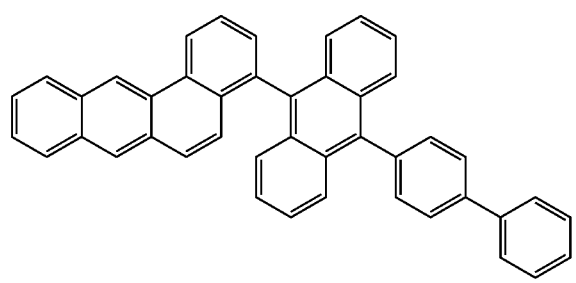 [SMILES: c1ccc(-c2ccc(-c3c4ccccc4c(-c4cccc5c4ccc4cc6ccccc6cc45)c4ccccc34)cc2)cc1]
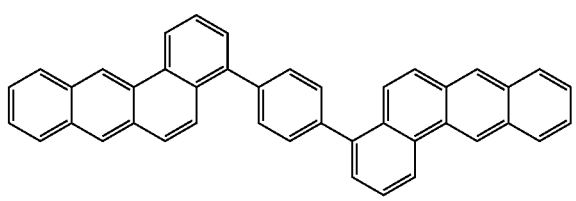 [SMILES: c1ccc2cc3c(ccc4c(-c5ccc(-c6cccc7c6ccc6cc8ccccc8cc67)cc5)cccc43)cc2c1]
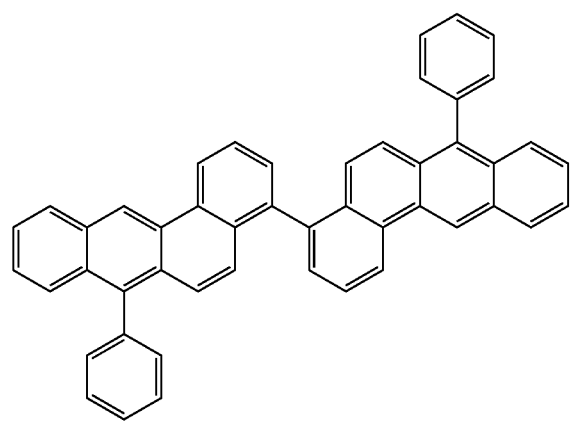 [SMILES: c1ccc(-c2c3ccccc3cc3c2ccc2c(-c4cccc5c4ccc4c(-c6ccccc6)c6ccccc6cc45)cccc23)cc1]
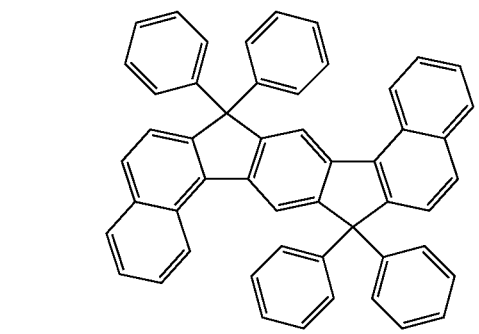 [SMILES: c1ccc(C2(c3ccccc3)c3cc4c(cc3-c3c2ccc2ccccc32)C(c2ccccc2)(c2ccccc2)c2ccc3ccccc3c2-4)cc1]
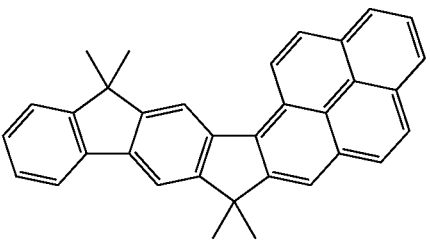 [SMILES: CC1(C)c2ccccc2-c2cc3c(cc21)-c1c(cc2ccc4cccc5ccc1c2c45)C3(C)C]
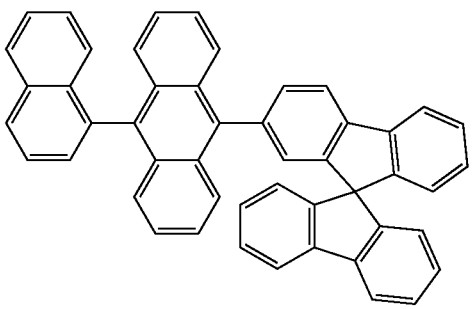 [SMILES: c1ccc2c(c1)-c1ccccc1C21c2ccccc2-c2ccc(-c3c4ccccc4c(-c4cccc5ccccc45)c4ccccc34)cc21]
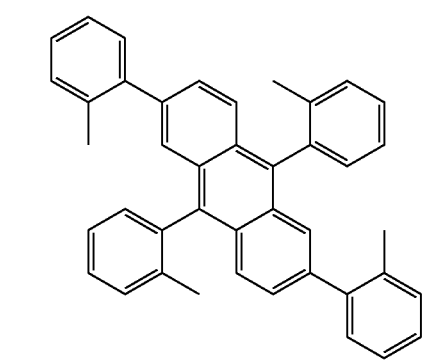 [SMILES: Cc1ccccc1-c1ccc2c(-c3ccccc3C)c3cc(-c4ccccc4C)ccc3c(-c3ccccc3C)c2c1]
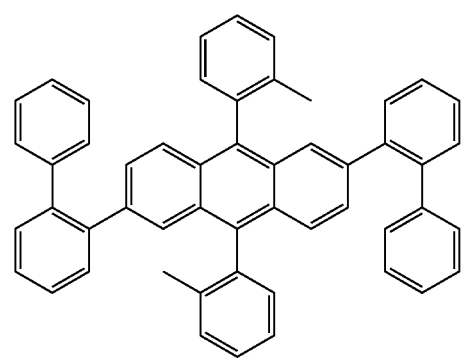 [SMILES: Cc1ccccc1-c1c2ccc(-c3ccccc3-c3ccccc3)cc2c(-c2ccccc2C)c2ccc(-c3ccccc3-c3ccccc3)cc12]
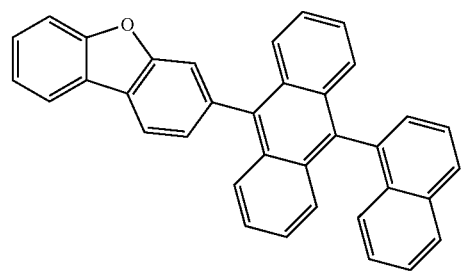 [SMILES: c1ccc2c(-c3c4ccccc4c(-c4ccc5c(c4)oc4ccccc45)c4ccccc34)cccc2c1]

-continued

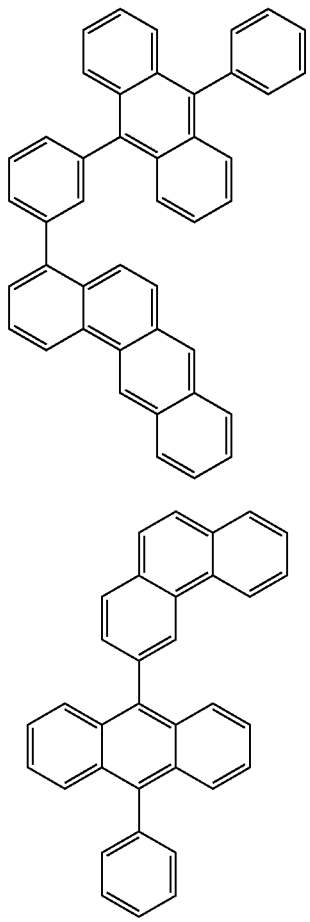

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably com-metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multi-layered structures, further which have a relatively high work function, such as, for example, Ag or Al, can also be used in addition to the said metals, in which case of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent in order to facilitate either irradiation of the organic material (organic solar cells) or the coupling-out of light (OLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

The compounds according to the invention have excellent hole mobility and are therefore very highly suitable as hole-transport materials. The high hole mobility enables a reduction in the operating voltage and an improvement in the operating lifetime of the electronic devices comprising the compounds according to the invention. Furthermore, the compounds according to the invention, on use in electronic devices, result in higher power efficiency of the devices.

Furthermore, the compounds of the formula (I) are distinguished by high oxidation stability in solution, which has an advantageous effect during purification and handling of the compounds and on use thereof in electronic devices.

The compounds are furthermore highly suitable for use as matrix materials in mixed-matrix systems, where they preferably result in a reduction in the operating voltage and an increase in the lifetime of the electronic devices.

Furthermore, the compounds of the formula (I) are temperature-stable and can thus be sublimed substantially without decomposition. Purification of the compounds is thus simplified, and the compounds can be obtained in higher purity, which has a positive effect on the performance data of the electronic devices comprising the materials. In particular, devices having longer operating lifetimes can thus be produced.

The invention is explained in greater detail by the following working examples, without wishing it to be restricted thereby.

WORKING EXAMPLES

A) Syntheses of Compounds According to the Invention in Accordance with Examples 1 to 30

The following syntheses are carried out, unless indicated otherwise, under a protective-gas atmosphere. The starting materials can be purchased from ALDRICH or ABCR (palladium(II) acetate, tri-o-tolylphosphine, inorganics, solvents). The synthesis of 8,8-dimethylindolo[3,2,1-de]acridine and 7,7,11,11-tetramethyl-7H,11H-benz[1,8]indolo[2,3,4,5,6-de]acridine can be carried out in accordance with the literature (Chemische Berichte 1980, 113 (1), 358-84). The syntheses of 8H-indolo[3,2,1-de]phenazine (Journal of the Chemical Society 1958, 4492-4) and B-[4-(1-phenyl-1H-benzimidazol-2-yl)phenyl]boronic acid (Advanced Functional Materials 2008, 18 (4), 584-590), 2-bromoindolo[3,2,1-jk]carbazole and indolo[3,2,1-jk]carbazoleboronic acid (Chemistry A European Journal, 2009, 15 (22), 5482-5490), N-[1,1'-biphenyl]-4-yl-9,9-dimethyl-9H-fluoren-2-amine (WO 2006073054) and 7-bromo-2,12-dimethyl-10-phenyl-10,12-dihydro-10-azaindeno[2,1-b]fluorene (see as yet unpublished application DE 102009023155.2) are likewise known from the literature.

Example 1

3-Bromo-8,8-dimethyl-8H-indolo[3,2,1-de]acridine

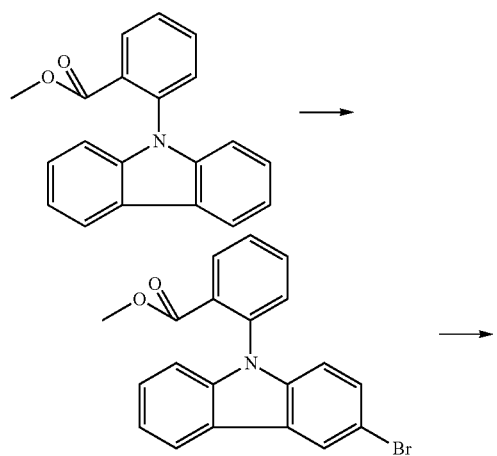

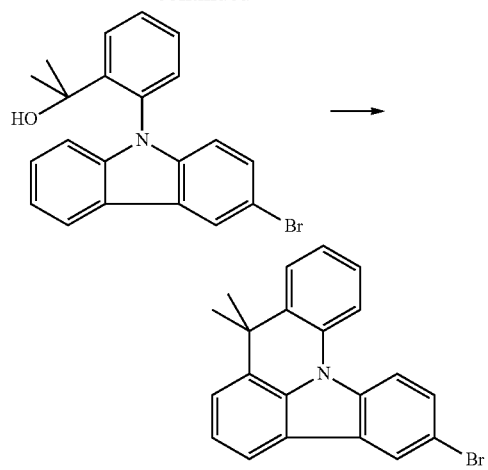

Methyl 2-(3-bromo-9H-carbazole)benzoate 62 g (207 mmol) of methyl 2-(9H-carbazole)benzoate are cooled to −10° C. in 2000 ml of DMF, 37.3 g (207 mmol) of NBS are added in portions, and the mixture is stirred at room temperature for 6 h. 500 ml of water are subsequently added to the mixture, which is then extracted with CH$_2$Cl$_2$. The organic phase is dried over MgSO$_4$, and the solvent is removed in vacuo. The product is washed by stirring with hot toluene and filtered off with suction.

Yield: 72 g (190 mmol), 92% of theory, purity according to $^1$H-NMR about 98%.

2-[2-(3-Bromocarbazol-9-yl)phenyl]propan-2-ol 81 g (213 mmol) of methyl 2-(3-bromo-9H-carbazole)benzoate are dissolved in 1500 ml of dried THF and degassed. The mixture is cooled to −78° C., and 569 ml (854 mmol) of methyllithium are added over the course of 40 min. The mixture is allowed to warm to −40° C. over the course of 1 h, and the reaction is monitored by TLC. When the reaction is complete, it is carefully quenched at −30° C. using MeOH. The reaction solution is evaporated to ⅓, and 1 l of CH$_2$Cl$_2$ is added, the mixture is washed, and the organic phase is dried over MgSO$_4$ and evaporated.

Yield: 73 g (193 mmol), 91% of theory, purity according to $^1$H-NMR about 94%.

6-Bromo-8,8-dimethyl-8H-indolo[3,2,1-de]acridine 16.3 g (44 mmol) of 2-[2-(3-bromocarbazol-9-yl)phenyl]propan-2-ol are dissolved in 1200 ml of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in CH$_2$Cl$_2$/THF (1:1). The solution is carefully rendered alkaline using 20% NaOH, and the phases are separated and dried over MgSO$_4$. The solid obtained is washed by stirring with heptane. Yield: 13.5 g (37 mmol), 87% of theory, purity according to $^1$H-NMR about 95%.

Example 2

6-Bromo-8,8-dimethyl-3-phenyl-8H-indolo[3,2,1-de]-acridine

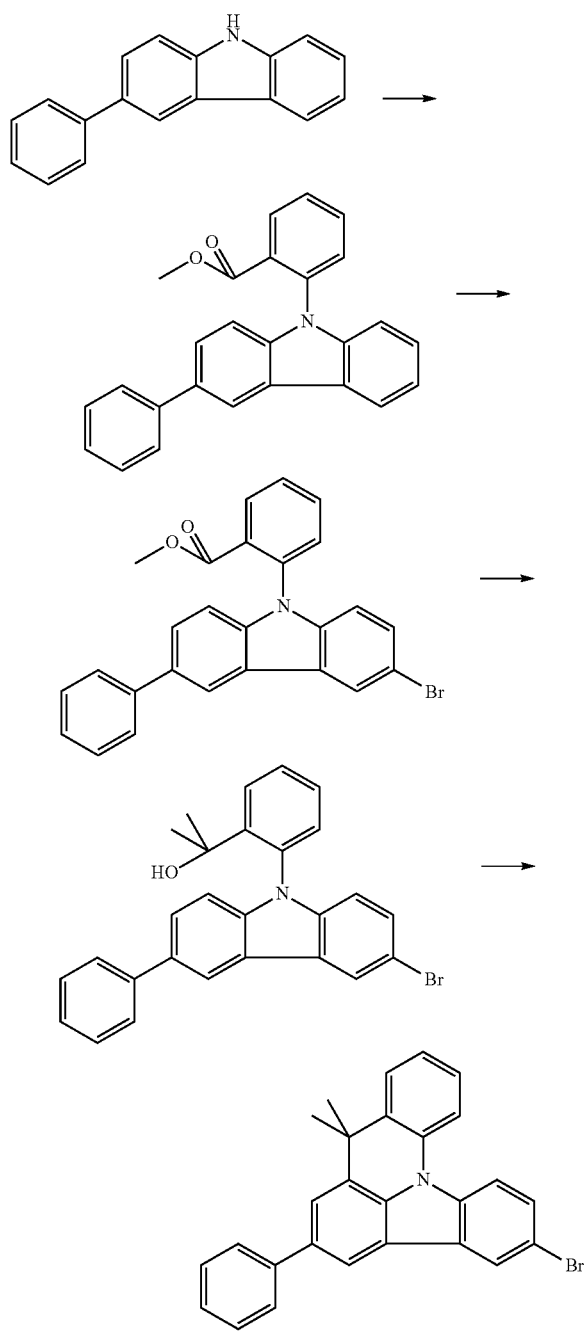

Methyl 2-(3-phenyl-9H-carbazole)benzoate 85 g (350 mmol) of 3-phenyl-9H-carbazole, 63 ml (262 mmol) of methyl 2-iodobenzoate, 87 g (631 mmol) of potassium carbonate and 9.3 g (35 mmol) of 18-crown-6 are initially introduced in 1200 ml of DMF under a protective gas and heated at 130° C. for 86 h. The mixture is subsequently evaporated, washed by stirring with hot heptane and purified by chromatography (heptane/CH₂Cl₂ 1:1). The product is washed by stirring with hot hexane and filtered off with suction.

Yield: 82 g (219 mmol), 62% of theory, purity according to ¹H-NMR about 97%.

Methyl 2-(3-bromo-6-phenyl-9H-carbazole)benzoate 78.4 g (207 mmol) of methyl 2-(3-phenyl-9H-carbazole)benzoate are cooled to −10° C. in 2000 ml of DMF, 37.3 g (207 mmol) of NBS are added in portions, and the mixture is stirred at room temperature for 6 h. 500 ml of water are subsequently added to the mixture, which is then extracted with CH₂Cl₂. The organic phase is dried over MgSO₄, and the solvent is removed in vacuo. The product is washed by stirring with hot toluene and filtered off with suction.

Yield: 91.4 g (200 mmol), 95% of theory, purity according to ¹H-NMR about 98%.

2-[2-(3-Bromo-6-phenylcarbazol-9-yl)phenyl]propan-2-ol 97 g (213 mmol) of methyl 2-(3-bromo-6-phenyl-9H-carbazole)benzoate are dissolved in 1500 ml of dried THF and degassed. The mixture is cooled to −78° C., and 569 ml (854 mmol) of methyllithium are added over the course of 40 min. The mixture is allowed to warm to −40° C. over the course of 1 h, and the reaction is monitored by TLC. When the reaction is complete, it is carefully quenched at −30° C. using MeOH. The reaction solution is evaporated to ⅓, and 1 l of CH₂Cl₂ is added, the mixture is washed, and the organic phase is dried over MgSO₄ and evaporated.

Yield: 93.4 g (204 mmol), 96% of theory, purity according to ¹H-NMR about 96%.

6-Bromo-8,8-dimethyl-3-phenyl-8H-indolo[3,2,1-de]acridine 20 g (43.6 mmol) of 2-[2-(3-bromo-6-phenylcarbazol-9-yl)phenyl]propan-2-ol are dissolved in 1200 ml of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in CH₂Cl₂/THF (1:1). The solution is carefully rendered alkaline using 20% NaOH, and the phases are separated and dried over MgSO₄. The solid obtained is washed by stirring with heptane. Yield: 16.3 g (37 mmol), 84% of theory, purity according to ¹H-NMR about 95%.

Example 3

3-Bromo-8,8-dimethyl-8H-indolo[3,2,1-de]acridine

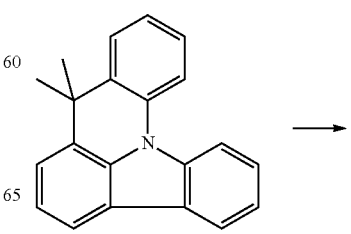

-continued

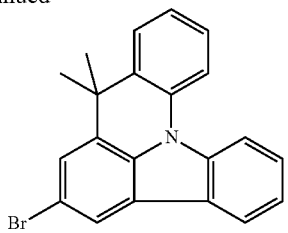

6.3 g (22.2 mmol) of 8,8-dimethylindolo[3,2,1-de]acridine are initially introduced in 150 ml of CH$_2$Cl$_2$. A solution of 3.9 g (22.3 mmol) of NBS in 100 ml of acetonitrile is subsequently added dropwise at −15° C. with exclusion of light, and the mixture is stirred at room temperature for a further 4 h. For work-up, 150 ml of water are added to the mixture, which is then extracted with CH$_2$Cl$_2$. The organic phase is dried over MgSO$_4$, and the solvent is removed in vacuo. The product is washed by stirring with hot hexane and filtered off with suction.

Yield: 4.5 g (12 mmol), 57% of theory, purity according to $^1$H-NMR about 97%.

Example 4

3,6-Dibromo-8,8-dimethyl-8H-indolo[3,2,1-de]acridine

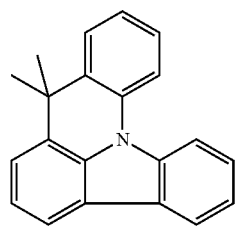 

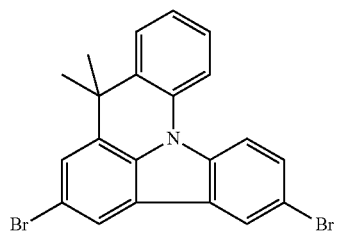

6.3 g (22.2 mmol) of 8,8-dimethylindolo[3,2,1-de]acridine are initially introduced in 150 ml of CH$_2$Cl$_2$. A solution of 8 g (45.1 mmol) of NBS in 100 ml of acetonitrile is subsequently added dropwise at −15° C. with exclusion of light, and the mixture is stirred at room temperature for a further 4 h. For work-up, 150 ml of water are added to the mixture, which is then extracted with CH$_2$Cl$_2$. The organic phase is dried over MgSO$_4$, and the solvents are removed in vacuo. The product is washed by stirring with hot hexane and filtered off with suction.

Yield: 7.3 g (16 mmol), 75% of theory, purity according to $^1$H-NMR about 97%.

Example 5

10-Bromo-8,8-dimethyl-3,6-diphenyl-8H-indolo[3,2,1-de]-acridine

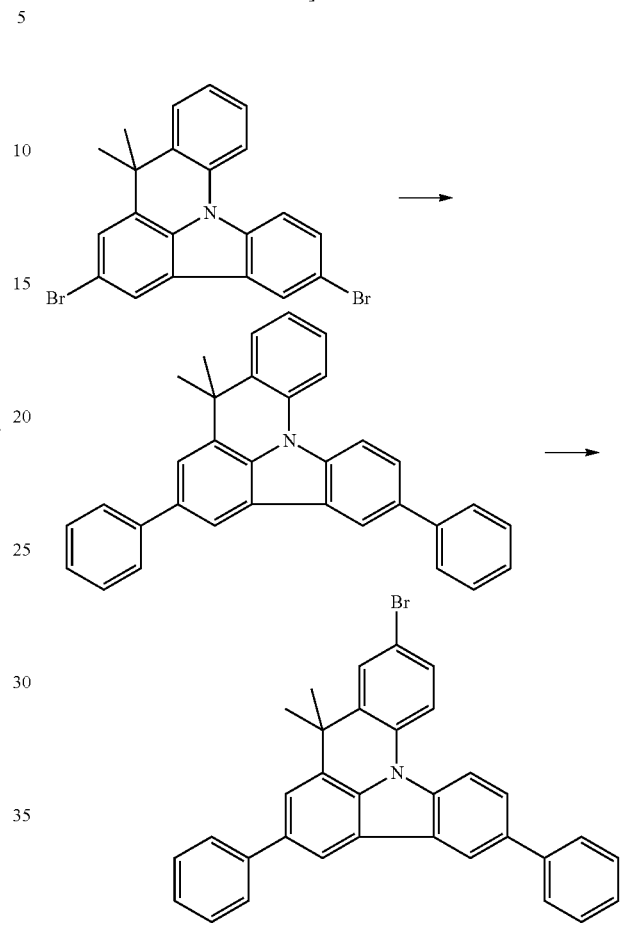

8,8-Dimethyl-3,6-diphenyl-8H-indolo[3,2,1-de]acridine 19.8 g (45 mmol) of 3,6-dibromo-8,8-dimethyl-8H-indolo[3,2,1-de]acridine, 11.4 g (94 mmol) of phenylboronic acid and 164 ml of saturated NaHCO$_3$ solution are suspended in 1500 ml of toluene and 150 ml of ethanol. 1.9 g (1.6 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness.

Yield: 18.5 g (42 mmol), 95% of theory, purity according to $^1$H-NMR about 98%.

10-Bromo-8,8-dimethyl-3,6-diphenyl-8H-indolo[3,2,1-de]acridine 9.6 g (22.2 mmol) of 8,8-dimethyl-3,6-diphenyl-8H-indolo[3,2,1-de]acridine are initially introduced in 150 ml of CH$_2$Cl$_2$. A solution of 3.9 g (22.3 mmol) of NBS in 100 ml of acetonitrile is subsequently added dropwise at −15° C. with exclusion of light, and the mixture is stirred at room temperature for a further 4 h. For work-up, 150 ml of water are added to the mixture, which is then extracted with CH$_2$Cl$_2$. The organic phase is dried over MgSO$_4$, and the solvent is removed in vacuo. The product is washed by stirring with hot hexane and filtered off with suction.

Yield: 10.7 g (20.8 mmol), 94% of theory, purity according to ¹H-NMR about 97%.

Example 6

3-Bromo-8H-8,12b-diazabenzo[a]aceanthrylene

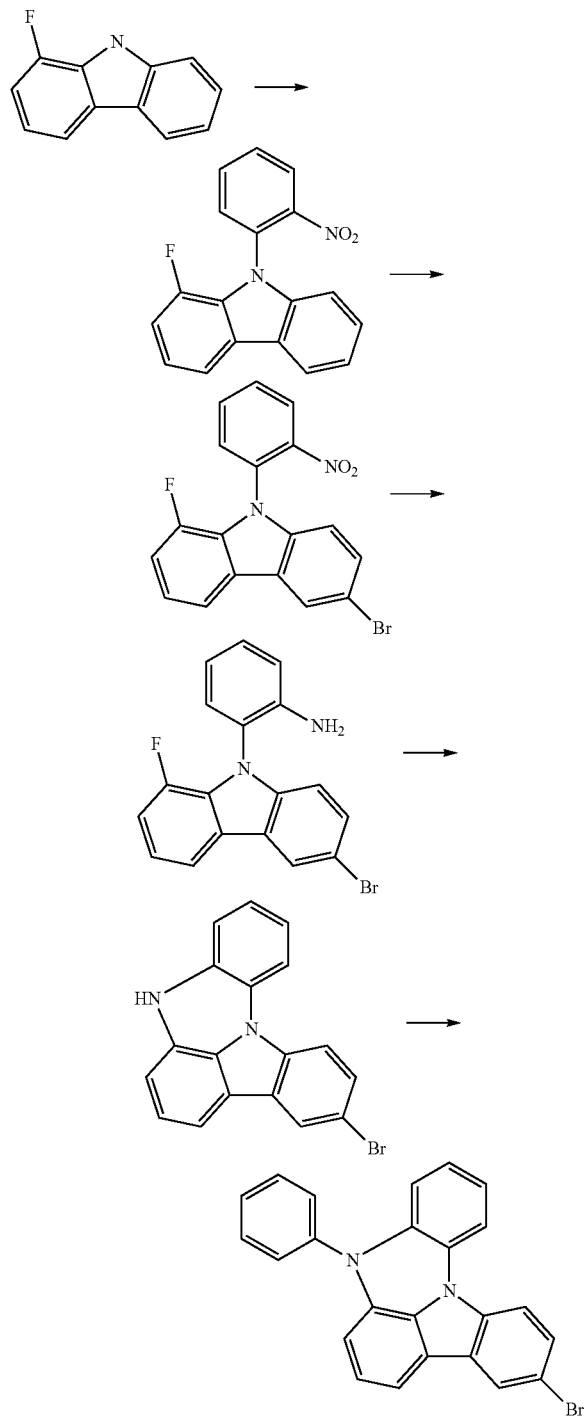

Fluoro-9-(2-nitrophenyl)-9H-carbazole

A degassed solution of 97 ml (990 mmol) of 2-fluoroaniline and 165 g (862 mmol) of 2-bromochlorobenzene in 1000 ml of NMP is saturated with $N_2$ for 1 h. Then firstly 28.9 g (100 mmol) of trichlorohexylphosphine, then 11.2 g (50 mmol) of palladium(II) acetate are added to the solution, and 549 g (2.5 mol) of potassium carbonate in the solid state are subsequently added. The reaction mixture is heated under reflux for 18 h. After cooling to room temperature, 1000 ml of water are carefully added. The organic phase is washed with 4×50 ml of water and dried over $MgSO_4$, and the solvent is removed in vacuo. The pure product is obtained by recrystallisation.

Yield: 111 g (760 mmol), 70% of theory, purity according to ¹H-NMR about 98%.

6-Bromo-1-fluoro-9-(2-nitrophenyl)-9H-carbazole 6.7 g (22.2 mmol) of fluoro-9-(2-nitrophenyl)-9H-carbazole are initially duced in 150 ml of $CH_2Cl_2$. A solution of 3.9 g (22.3 mmol) of NBS in 100 ml of acetonitrile is subsequently added dropwise at −15° C. with exclusion of light, and the mixture is stirred at room temperature for a further 4 h. For work-up, 150 ml of water are added to the mixture, which is then extracted with $CH_2Cl_2$. The organic phase is dried over $MgSO_4$, and the solvent is removed in vacuo. The product is washed by stirring with hot hexane and filtered off with suction.

Yield: 8 g (20 mmol), 97% of theory, purity according to ¹H-NMR about 97%.

2-(6-Bromo-1-fluorocarbazol-9-311)phenylamine 67 g (219 mmol) of 6-bromo-1-fluoro-9-(2-nitrophenyl)-9H-carbazole are dissolved in 820 ml of EtOH, 143 g (755 mmol) of $ZnCl_2$ are added at room temperature, and the mixture is heated under reflux for 6 h. The mixture is subsequently warmed to room temperature over the course of 1 h, 20% NaOH is added, and, after phase separation, the solvent is removed, and the residue is purified by chromatography.

Yield: 44 g (125 mmol), 72% of theory, purity according to ¹H-NMR about 97%.

3-Bromo-8H-8,12b-diazabenzo[a]aceanthrylene 25 g (72 mmol) of 2-(6-bromo-1-fluorocarbazol-9-yl)phenylamine are dissolved in 200 ml of DMF under a protective gas, 2.8 g (72 mmol) of NaH (60% in oil) are added at room temperature, and the mixture is boiled under reflux for 6 h. The mixture is subsequently warmed to room temperature over the course of 1 h, the solvent is removed, and the residue is purified by chromatography.

Yield: 19 g (54 mmol), 78% of theory, purity according to ¹H-NMR about 98%.

Bromo-8-phenyl-8H-8,12b-diazabenzo[a]aceanthrylene

A degassed solution of 30 g (86.6 mmol) of 3-bromo-8H-8,12b-diazabenzo[a]aceanthrylene and 8.8 g (95.9 mmol) of phenylamine in 1000 ml dioxane is saturated with $N_2$ for 1 h. Then firstly 0.9 ml (4.3 mmol) of $P(tBu)_3$, then 0.48 g (2.1 mmol) of palladium(II) acetate are added to the solution, and 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of water and dried over MgSO$_4$, and the solvent is removed in vacuo. The pure product is obtained by recrystallisation.

Yield: 27 g (64 mmol), 76% of theory, purity according to $^1$H-NMR about 98%.

Example 7

8,8-Dimethyl-8H-indolo[3,2,1-de]acridine-3-boronic acid

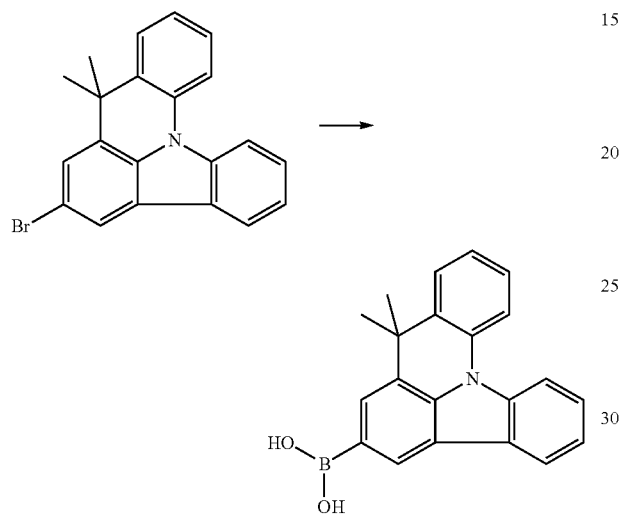

93.9 g (259 mmol) of 3-bromo-8,8-dimethyl-8H-indolo[3,2,1-de]acridine are dissolved in 1500 ml of dry THF, 135 ml (337 mmol) of a 2.5 M solution of n-butyllithium in cyclohexane are added dropwise at –70° C., after 1 h 37 ml of trimethyl borate (336 mmol) are added dropwise, the mixture is warmed to room temperature over the course of 1 h, the solvent is removed, and the residue, which is uniform according to $^1$H-NMR, is employed in the subsequent reaction without further purification.

Yield: 77 g (235 mmol), 91% of theory, purity according to $^1$H-NMR about 98%.

Example 8

8,8-Dimethyl-8H-indolo[3,2,1-de]acridine-6-boronic acid

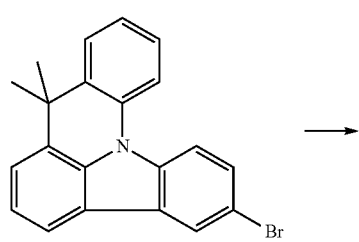

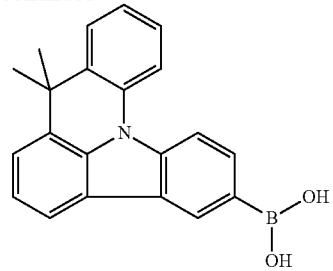

93.7 g (259 mmol) of 6-bromo-8,8-dimethyl-8H-indolo[3,2,1-de]acridine are dissolved in 1500 ml of dry THF, 135 ml (337 mmol) of a 2.5 M solution of n-butyllithium in cyclohexane are added dropwise at –70° C., after 1 h 37 ml of trimethyl borate (336 mmol) are added dropwise, the mixture is warmed to room temperature over the course of 1 h, the solvent is removed, and the residue, which is uniform according to $^1$H-NMR, is employed in the subsequent reaction without further purification.

Yield: 67 g (204 mmol), 80% of theory, purity according to $^1$H-NMR about 96%.

Example 9

8,8-Dimethyl-6-phenyl-8H-indolo[3,2,1-de]acridine-3-boronic acid

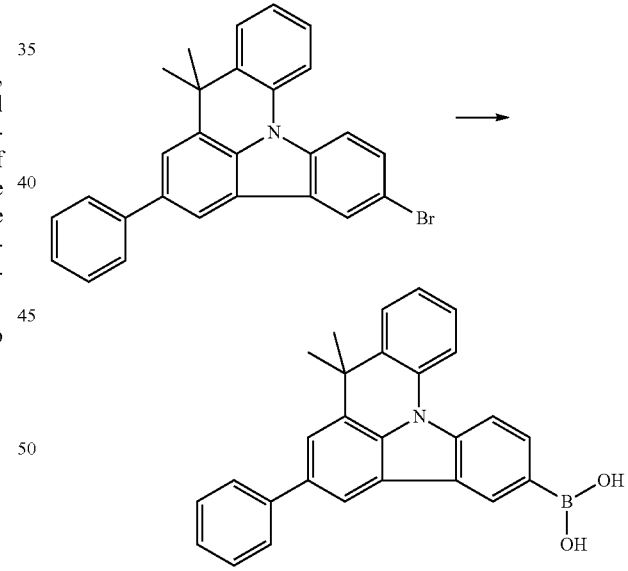

113.4 g (259 mmol) of 6-bromo-8,8-dimethyl-3-phenyl-8H-indolo[3,2,1-de]-acridine are dissolved in 1500 ml of dry THF, 135 ml (337 mmol) of a 2.5 M solution of n-butyllithium in cyclohexane are added dropwise at –70° C., after 1 h 37 ml of trimethyl borate (336 mmol) are added dropwise, the mixture is warmed to room temperature over the course of 1 h, the solvent is removed, and the residue, which is uniform according to $^1$H-NMR, is employed in the subsequent reaction without further purification.

Yield: 92 g (229 mmol), 89% of theory, purity according to $^1$H-NMR about 98%.

Example 10

8,8-Dimethyl-3,6-diphenyl-8H-indolo[3,2,1-de]acridine-10-boronic acid

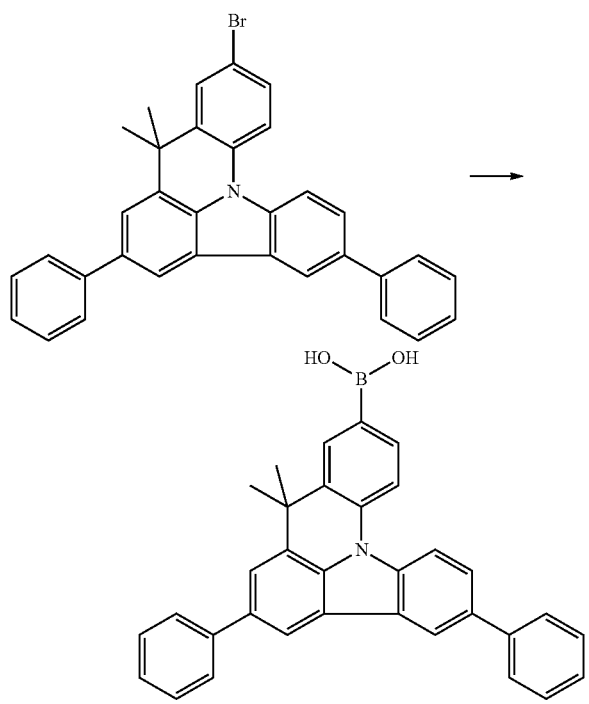

133 g (259 mmol) of 10-bromo-8,8-dimethyl-3,6-diphenyl-8H-indolo-[3,2,1-de]acridine are dissolved in 1500 ml of dry THF, 135 ml (337 mmol) of a 2.5 M solution of n-butyllithium in cyclohexane are added dropwise at −70° C., after 1 h 37 ml of trimethyl borate (336 mmol) are added dropwise, the mixture is warmed to room temperature over the course of 1 h, the solvent is removed, and the residue, which is uniform according to $^1$H-NMR, is employed in the subsequent reaction without further purification.

Yield: 111 g (233 mmol), 90% of theory, purity according to $^1$H-NMR about 98%.

Example 11

8,8-Dimethyl-3-(9-phenyl-9H-carbazol-3-yl)-8H-indolo-[3,2,1-de]acridine (compound H5)

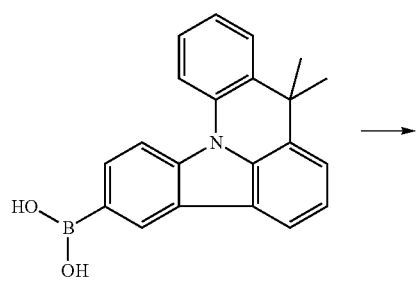

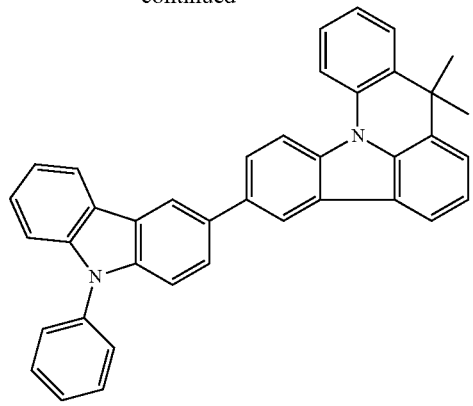

H5

36 g (110 mmol) of 8,8-dimethyl-8H-indolo[3,2,1-de]acridine-3-boronic acid, 35 g (110 mmol) of 3-bromo-9-phenyl-9H-carbazole and 9.7 g (92 mmol) of sodium carbonate are suspended in 350 ml of toluene, of dioxane and 500 ml of water. 913 mg (3.0 mmol) of tri-o-tolylphosphine and 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from CH$_2$Cl$_2$/isopanol and finally sublimed in a high vacuum.

Yield: 52 g (100 mmol), 91% of theory, purity according to HPLC 99.9%.

Example 12

4-(8,8-Dimethyl-8H-indolo[3,2,1-de]acridin-3-yl)phenyl]-diphenylamine (compound HTM2)

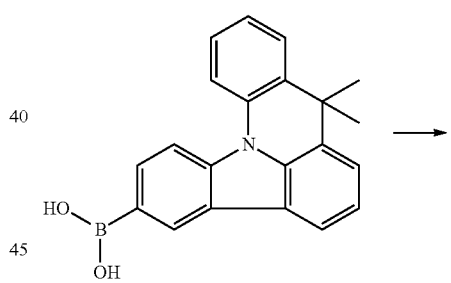

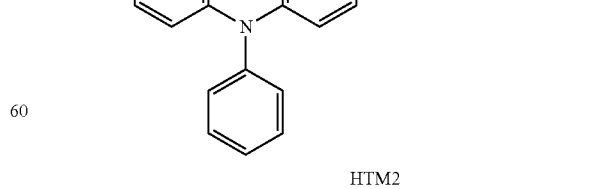

HTM2

The compound is synthesised by the same procedure as Example 13 by reaction of the corresponding indolo[3,2,1-de]acridineboronic acid with 35.6 g (110 mmol) of 4-bromophenyldiphenylamine.

The residue is recrystallised from toluene and from CH₂Cl₂/isopropanol and finally sublimed in a high vacuum.
Yield: 51 g (97 mmol), 89% of theory, purity according to HPLC 99.9%.

Example 13

8,8,8',8'-Tetramethyl-8H,8'H-[3,3']bi(indolo[3,2,1-de]-acridinyl) (compound H7)

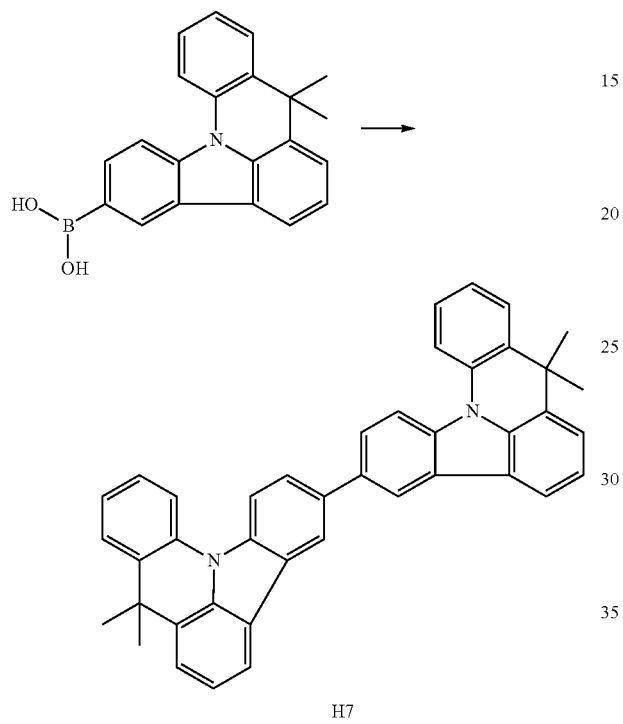

H7

The compound is synthesised by the same procedure as Example 13 by reaction of the corresponding indolo[3,2,1-de]acridineboronic acid with 39 g (110 mmol) of 3-bromo-8,8-dimethyl-8H-indolo[3,2,1-de]acridine.
The residue is recrystallised from toluene and from CH₂Cl₂/isopropanol and finally sublimed in a high vacuum.
Yield: 55 g (100 mmol), 92% of theory, purity according to HPLC 99.9%.

Example 14

8,8,8',8'-Tetramethyl-8H,8'H-[3,6']bi(indolo[3,2,1-de]-acridinyl) (compound H8)

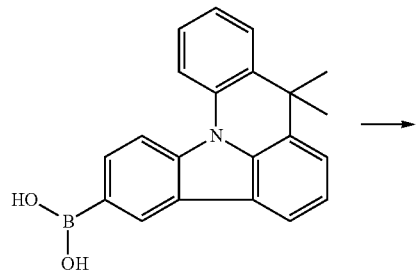

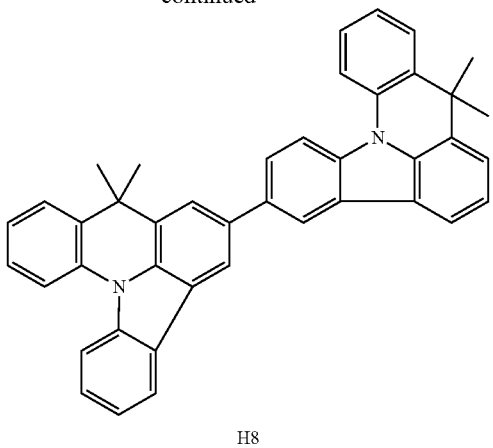

H8

The compound is synthesised by the same procedure as Example 13 by reaction of the corresponding indolo[3,2,1-de]acridineboronic acid with 39 g (110 mmol) of 6-bromo-8,8-dimethyl-8H-indolo[3,2,1-de]acridine. The residue is recrystallised from toluene and from CH₂Cl₂/isopropanol and finally sublimed in a high vacuum.
Yield: 49.5 g (90 mmol), 82% of theory, purity according to HPLC 99.9%.

Example 15

(8,8-Dimethyl-8H-indolo[3,2,1-de]acridin-3-yl)diphenylamine (compound HTM4)

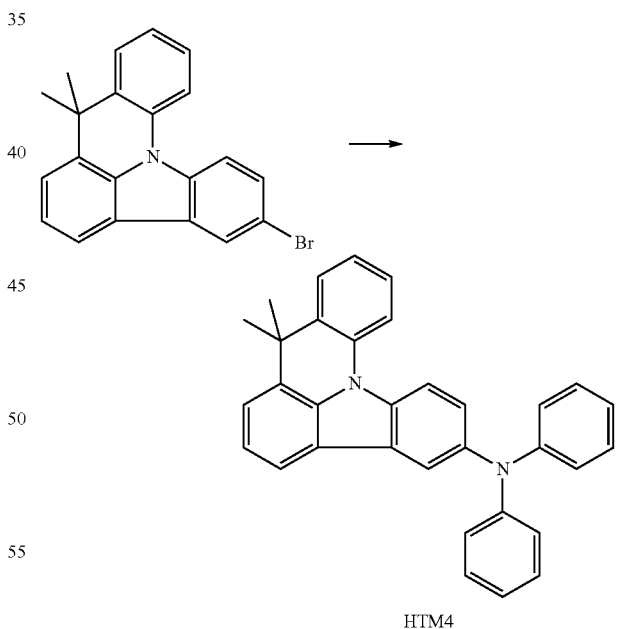

HTM4

A degassed solution of 31 g (86.6 mmol) of 3-bromo-8,8-dimethyl-8H-indolo[3,2,1-de]acridine and 16 g (95.9 mmol) of diphenylamine in 1000 ml of dioxane is saturated with N₂ for 1 h. Then firstly 0.9 ml (4.3 mmol) of P(tBu)₃, then 0.48 g (2.1 mmol) of palladium(II) acetate are added to the solution, and 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of water and dried over MgSO₄, and the solvent is removed in vacuo. The pure product is obtained by recrystallisation and final sublimation.

Yield: 34 g (76 mmol), 89% of theory, purity according to HPLC 99.9%.

Example 16

3-(9,9-Dimethyl-9H-acridin-10-yl)-8,8-dimethyl-8H-indolo[3,2,1-de]acridine (compound HTM5)

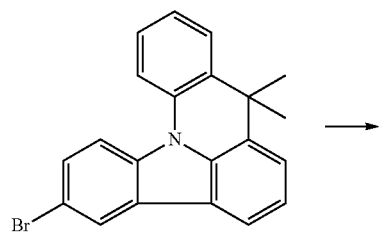

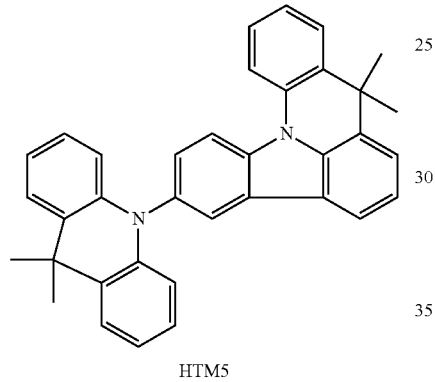

HTM5

The compound is synthesised by the same procedure as Example 18 by reaction of 31 g (86.6 mmol) of 3-bromo-8,8-dimethyl-8H-indolo[3,2,1-de]-acridine and 20 g (95.9 mmol) of 9,9'-dimethyl-9,10-dihydroacridine. The residue is recrystallised from toluene and finally sublimed in a high vacuum.

Yield: 37 g (76 mmol), 80% of theory, purity according to HPLC 99.9%.

Example 17

(8,8-Dimethyl-6-phenyl-8H-indolo[3,2,1-de]acridin-3-yl)-diphenylamine (compound HTM6)

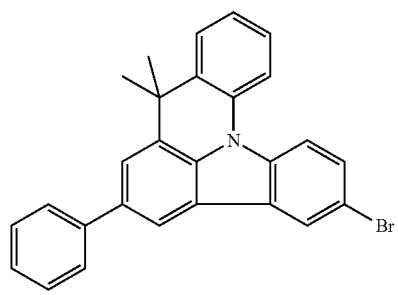

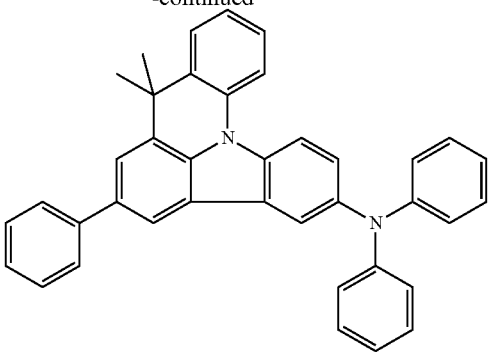

HTM6

The compound is synthesised by the same procedure as Example 18 by reaction of 37.6 g (86.6 mmol) of 6-bromo-8,8-dimethyl-3-phenyl-8H-indolo[3,2,1-de]acridine with the corresponding amine.

The residue is recrystallised from toluene and finally sublimed in a high vacuum.

Yield: 39 g (79 mmol), 87% of theory, purity according to HPLC 99.9%.

Example 18

8,8-Dimethyl-3,6-diphenyl-8H-indolo[3,2,1-de]acridin-10-yl)diphenylamine (compound HTM7

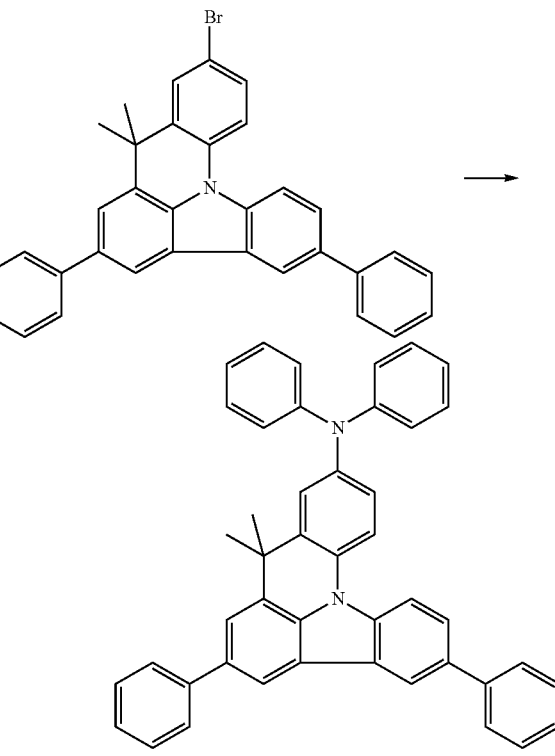

HTM7

The compound is synthesised by the same procedure as Example 18 by reaction of 44 g (86.6 mmol) of 10-bromo-8,8-dimethyl-3,6-diphenyl-8H-indolo[3,2,1-de]acridine with the corresponding amine.

The residue is recrystallised from toluene and finally sublimed in a high vacuum.

Yield: 39 g (64 mmol), 75% of theory, purity according to HPLC 99.9%.

Example 19

3-Carbazol-9-yl-8,8-dimethyl-8H-indolo[3,2,1-de]acridine (compound H9)

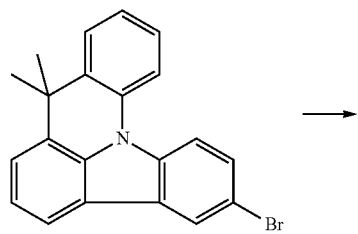

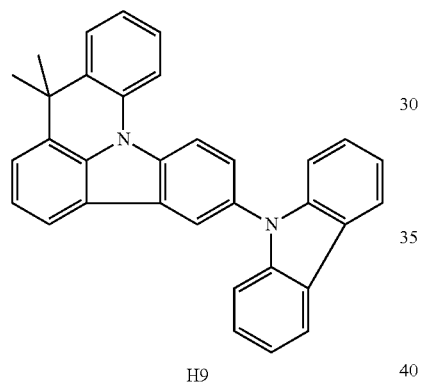

H9

The compound is synthesised by the same procedure as Example 18 by reaction of 31 g (86.0 mmol) of 3-bromo-8,8-dimethyl-8H-indolo[3,2,1-de]-acridine with 16 g (95.9 mmol) of carbazole.

The residue is recrystallised from toluene and finally sublimed in a high vacuum.

Yield: 38 g (64 mmol), 85% of theory, purity according to HPLC 99.9%.

Example 20

8-Carbazol-9-yl-2-eth-(E)-ylidene-3-phenyl-1-prop-2-en-(E)-ylidene-2,3-dihydro-1H-pyrazino[3,2,1-jk]carbazole (compound HTM9)

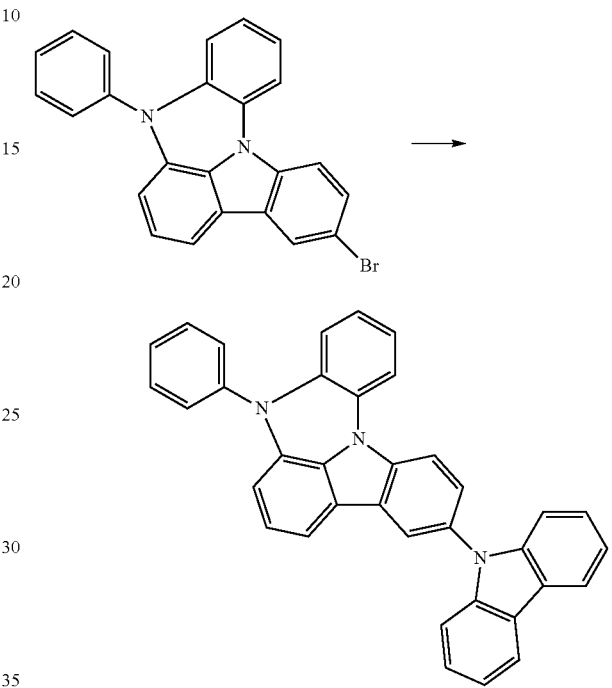

HTM9

The compound is synthesised by the same procedure as Example 18 by reaction of 37 g (86.6 mmol) of 3-bromo-8H-8,12b-diazabenzo[a]aceanthrylene with 16 g (95.9 mmol) of carbazole.

The residue is recrystallised from toluene and finally sublimed in a high vacuum.

Yield: 31 g (60 mmol), 70% of theory, purity according to HPLC 99.9%.

Example 21

N4,N4'-Bis-(8,8-dimethyl-8H-indolo[3,2,1-de]acridin-3-yl)-N4,N4'-diphenylbiphenyl-4,4'-diamine (compound HTM8)

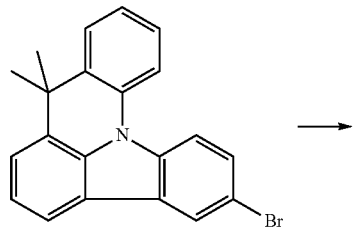

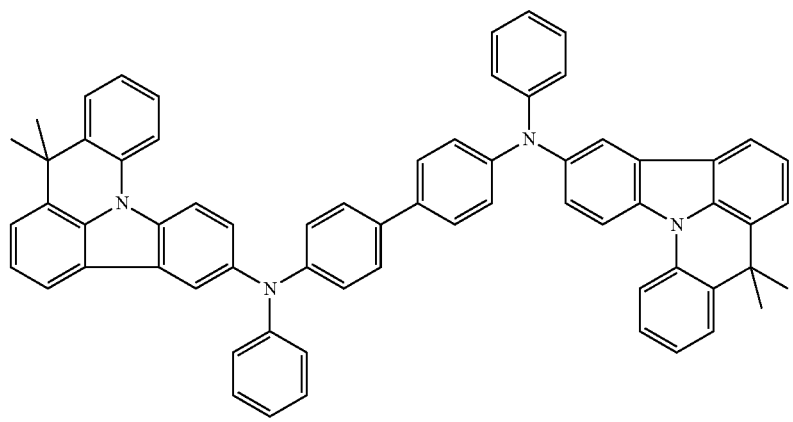

HTM8

A degassed solution of 31 g (86.6 mmol) of 3-bromo-8,8-dimethyl-8H-indolo[3,2,1-de]acridine and 13.4 g (40 mmol) of N,N'-diphenylbenzidine in 1000 ml of dioxane is saturated with $N_2$ for 1 h. Then firstly 0.9 ml (4.3 mmol) of P(tBu)$_3$, then 0.48 g (2.1 mmol) of palladium(II) acetate are added to the solution, and 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of $H_2O$ and dried over $MgSO_4$, and the solvent is removed in vacuo. The pure product is obtained by recrystallisation.

Yield: 29 g (32 mmol), 81% of theory, purity according to HPLC 99.9%.

Example 22

Biphenyl-4-yl-(9,9-dimethyl-9H-fluoren-2-yl)-[4-(8,8-dimethyl-8H-indolo[3,2,1-de]acridin-3-yl)phenyl]amine (compound HTM3)

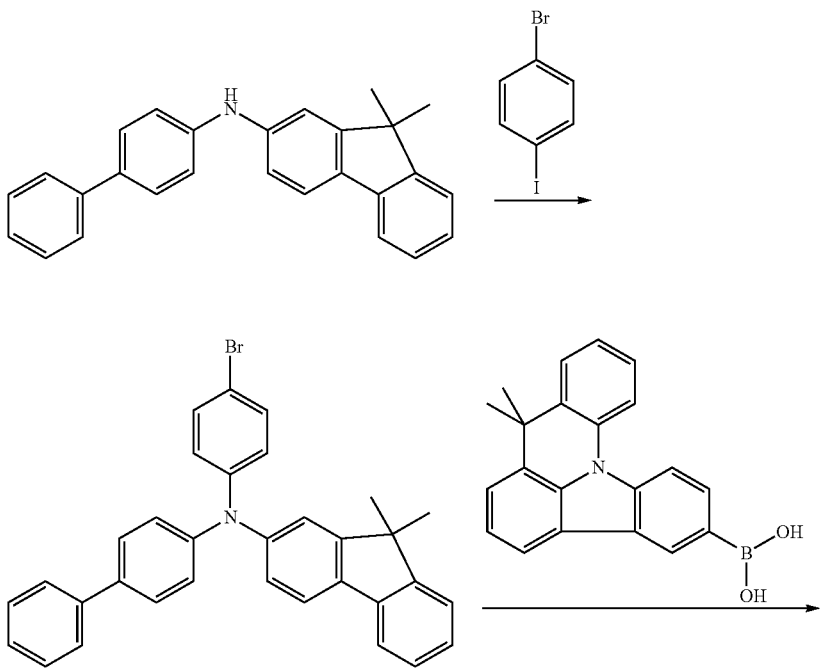

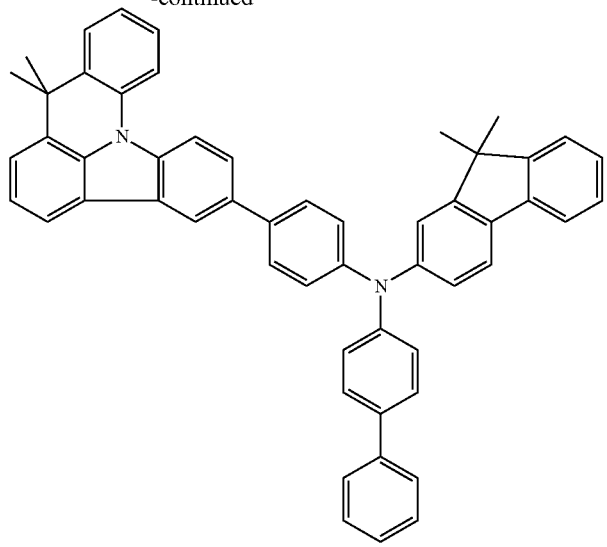

HTM3

Biphenyl-4-yl-(4-bromophenyl)-(9,9-dimethyl-9H-fluoren-2-yl)amine

A degassed solution of 490 mg (0.16 mmol) of copper(I) chloride and 906 mg (5 mmol) of 1,10-phenanthroline in 100 ml of toluene is saturated with $N_2$ for 1 h and heated to 130° C. 18 g (50 mmol) of N-[1,1-biphenyl]-4-yl-9,9-dimethyl-9H-fluoren-2-amine and 14 g (50 mmol) of 1-bromo-4-iodobenzene are subsequently added to the solution, which is then heated at 180° C. for 2 h. After cooling, 180 ml of water are added to the mixture, the organic phase is separated off, and the solvent is removed in vacuo. The product is recrystallised from n-hexane.

Yield: 15 g (29 mmol), 58% of theory, purity according to $^1$H-NMR about 98%.

Biphenyl-4-yl-(9,9-dimethyl-9H-fluoren-2-yl)-[4-(8,8-dimethyl-8H-indolo-[3,2,1-de]acridin-3-yl)phenyl]amine The compound is synthesised by the same procedure as Example 13 by reaction of the corresponding indolo[3,2,1-de]acridineboronic acid with 15 g (29 mmol) of biphenyl-4-yl-(4-bromophenyl)-(9,9-dimethyl-9H-fluoren-2-yl)amine.

The residue is recrystallised from ethyl acetate/heptane and finally sublimed in a high vacuum.

Yield: 14.4 g (20 mmol), 69% of theory, purity according to HPLC 99.9%.

Example 23

3-(12,12-Dimethyl-10-phenyl-10,12-dihydro-10-azaindeno[2,1-b]fluoren-7-yl)-8,8-dimethyl-8H-indolo[3,2,1-de]acridine (compound H10)

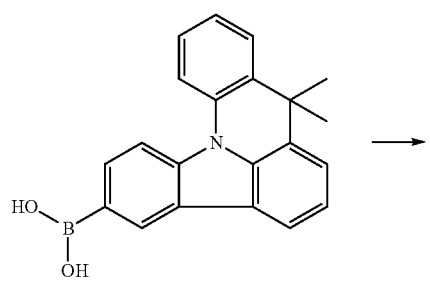

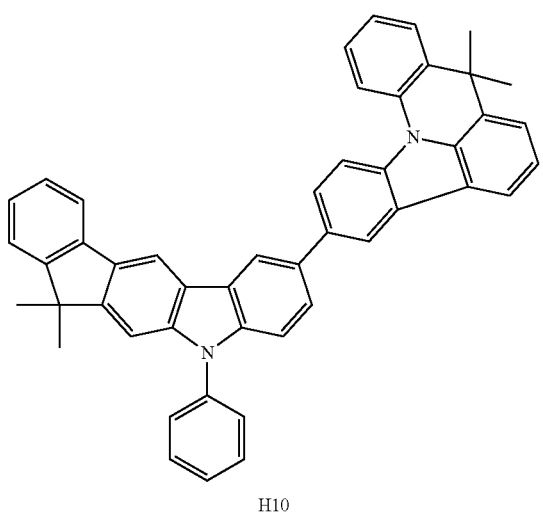

H10

The compound is synthesised by the same procedure as Example 13 by reaction of the corresponding indolo[3,2,1-de]acridineboronic acid with 48 g (110 mmol) of 7-bromo-2,12-dimethyl-10-phenyl-10,12-dihydro-10-azaindeno[2,1-b]fluorene.

The residue is recrystallised from toluene and from $CH_2Cl_2$/isopropanol and finally sublimed in a high vacuum.

Yield: 54.5 g (85 mmol), 78% of theory, purity according to HPLC 99.9%.

Example 24

[4'-(8,12b-Diazabenzo[a]aceanthrylen-8-yl)biphenyl-4-yl]-diphenylamine (compound HTM10)

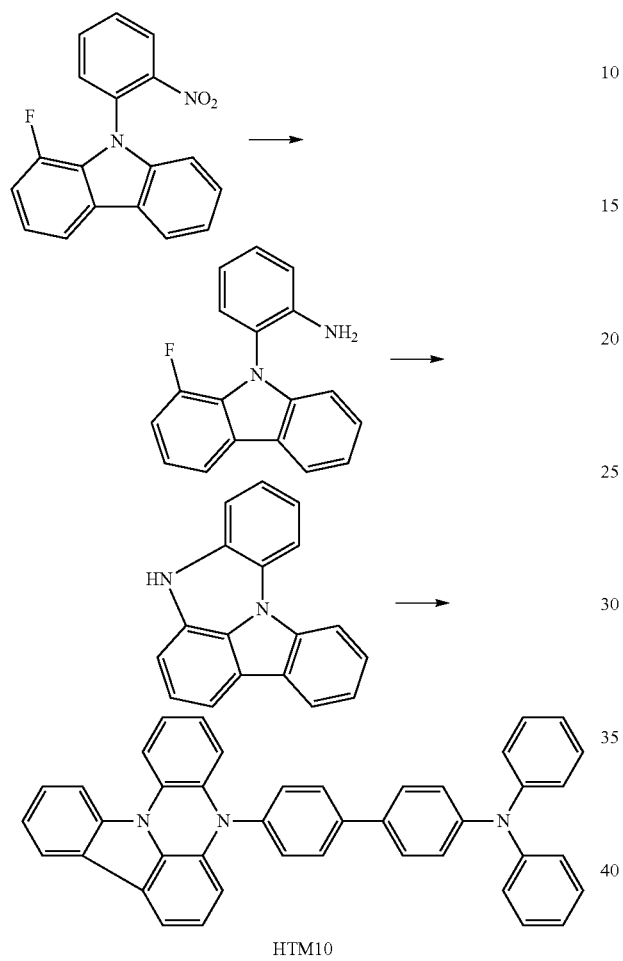

HTM10

1-Fluoro-9-(2-aminophenyl)-9H-carbazole 50 g (163 mmol) of 1-fluoro-9-(2-nitrophenyl)-9H-carbazole are dissolved in 600 ml of EtOH, 67 g (489 mmol) of $ZnCl_2$ are added at room temperature, and the mixture is heated under reflux for 6 h. The mixture is subsequently warmed to room temperature over the course of 1 h, 20% NaOH is added, and, after phase separation, the solvent is removed, and the residue is purified by chromatography.

Yield: 33 g (119 mmol), 73% of theory, purity according to $^1$H-NMR about 98%.

8H-8,12b-Diazabenzo[a]aceanthrylene 30 g (109 mmol) of 1-fluoro-9-(2-aminophenyl)-9H-carbazole are dissolved in 200 ml of DMF under a protective gas, 4.4 g (109 mmol) of NaH (60% in oil) are added at room temperature, and the mixture is boiled under reflux for 6 h. The mixture is subsequently warmed to room temperature over the course of 1 h, the solvent is removed, and the residue is purified by chromatography.

Yield: 23.4 g (86 mmol), 79% of theory, purity according to $^1$H-NMR about 98%.

[4'-(8,12b-Diazabenzo[a]aceanthrylen-8-yl)biphenyl-4-yl]diphenylamine

A degassed solution of 35.6 g (89 mmol) of (4'-bromobiphenyl-4-yl)-diphenylamine and 22.0 g (81 mmol) of 8H-8,12b-diazabenzo[a]aceanthrylene in 1000 ml of dioxane is saturated with $N_2$ for 1 h. Then firstly 1.0 ml (4 mmol) of $P(tBu)_3$, then 0.4 g (2 mmol) of palladium(II) acetate are added to the solution, and 11.7 g (122 mmol) of NaOtBu in the solid state are subsequently added. The reaction mixture is heated under reflux for 18 h. After cooling to room temperature, 1000 ml of water are carefully added. The organic phase is separated off, washed with 4×50 ml of water and dried over $MgSO_4$, and the solvent is removed in vacuo. The pure product is obtained by recrystallisation and final sublimation in a high vacuum.

Yield: 33.4 g (58 mmol), 72% of theory, purity according to HPLC 99.9%.

Example 25

3-Bromo-8,8-diphenyl-8H-indolo[3,2,1-de]acridine

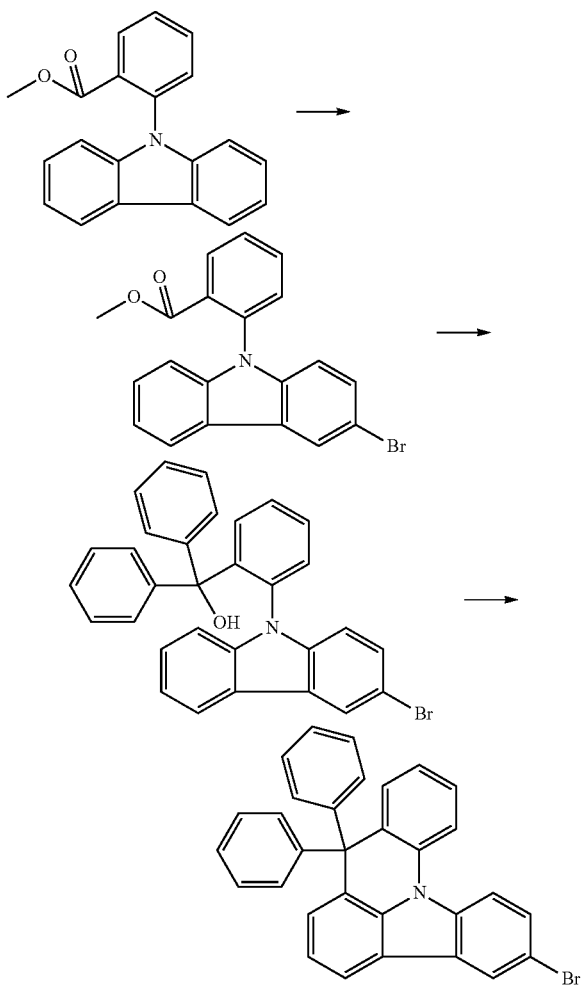

Methyl 2-(3-bromo-9H-carbazole)benzoate 62 g (207 mmol) of methyl 2-(9H-carbazole)benzoate are cooled to −10° C. in 2000 ml of DMF, 37.3 g (207 mmol) of NBS are added in portions, and the mixture is stirred at room temperature for 6 h. 500 ml of water are subsequently added to the mixture, which is then extracted with $CH_2Cl_2$. The organic phase is dried over $MgSO_4$, and the solvent is removed in vacuo. The product is washed by stirring with hot toluene and filtered off with suction.

Yield: 72 g (190 mmol), 92% of theory, purity according to $^1$H-NMR about 98%.

[2-(3-Bromocarbazol-9-yl)phenyl]diphenylmethanol 21.3 g (86.7 mmol) of Ce(III) chloride are initially introduced in 250 ml of THF. 30 g (78.9 mmol) of methyl 2-(3-bromo-9H-carbazole)benzoate (dissolved in 600 ml of dried THF) are added dropwise to this solution at room temperature, and the mixture is stirred for 2.5 hours. The mixture is cooled to 0° C., and 118.3 ml (236 mmol) of 2 M phenylmagnesium bromide in THF are added, and the mixture is stirred overnight. When the reaction is complete, it is carefully quenched at −30° C. using MeOH. The reaction solution is evaporated to ⅓, 1 l of $CH_2Cl_2$ is added, and the mixture is washed. The organic phase is subsequently dried over $MgSO_4$ and evaporated.

Yield: 38.7 g (76.7 mmol), 97% of theory, purity according to $^1$H-NMR about 94%.

Bromo-8,8-diphenyl-8H-indolo[3,2,1-de]acridine 38.7 g (76.7 mmol) of 2-[2-(3-bromocarbazol-9-yl)phenyl]propan-2-ol are dissolved in 750 ml of degassed dichloromethane, a suspension of 49.6 g of polyphosphoric acid and 33 ml of methanesulfonic acid is added, and the mixture is heated at 60° C. for 1 h. The batch is cooled, and water is added. A solid precipitates out and is dissolved in $CH_2Cl_2$/THF (1:1). The solution is carefully rendered alkaline using 20% NaOH, and the phases are separated and dried over $MgSO_4$. The solid obtained is washed by stirring with heptane. Yield: 22 g (45 mmol), 59% of theory, purity according to $^1$H-NMR about 95%.

The following compounds are obtained analogously:

| Ex. | Starting material 1 | Starting material 2 | Product | Yield |
|---|---|---|---|---|
| 25a | ![structure] | ![structure] | ![structure] | 63% |
| 25b | ![structure] | ![structure] | ![structure] | 74% |
| 25c | ![structure] | ![structure] | ![structure] | 59% |

Example 26

8,8-Diphenyl-8H-indolo[3,2,1-de]acridine-6-boronic acid

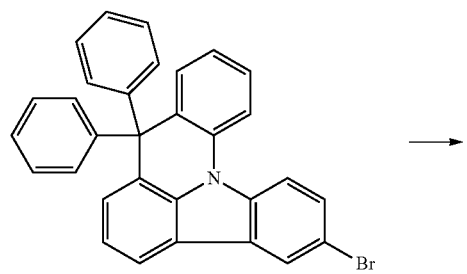 → 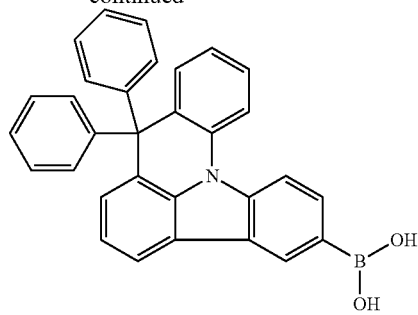

125.9 g (259 mmol) of bromo-8,8-diphenyl-8H-indolo[3,2,1-de]acridine are dissolved in 1500 ml of dry THF. 135 ml (337 mmol) of a 2.5 M solution of n-butyllithium in cyclohexane are added dropwise at −70° C., and, after 1 h, 37 ml of trimethyl borate (336 mmol) are added dropwise. The mixture is warmed to room temperature over the course of 1 h, the solvent is removed, and the residue, which is uniform according to $^1$H-NMR, is employed in the subsequent reaction without further purification.

Yield: 87.6 g (194 mmol), 75% of theory, purity according to $^1$H-NMR about 96%.

The following compounds are obtained analogously:

| Ex. | Starting material | Product | Yield |
|---|---|---|---|
| 26a | 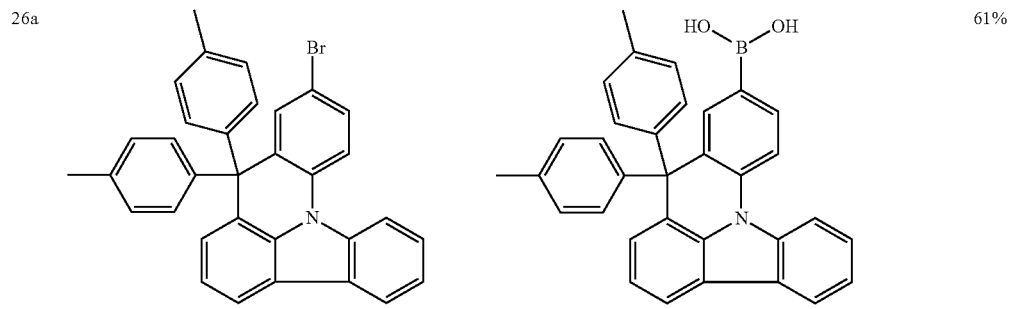 [J. Mater. Chem. 2009, 19, 7661-7665] | | 61% |
| 26b | 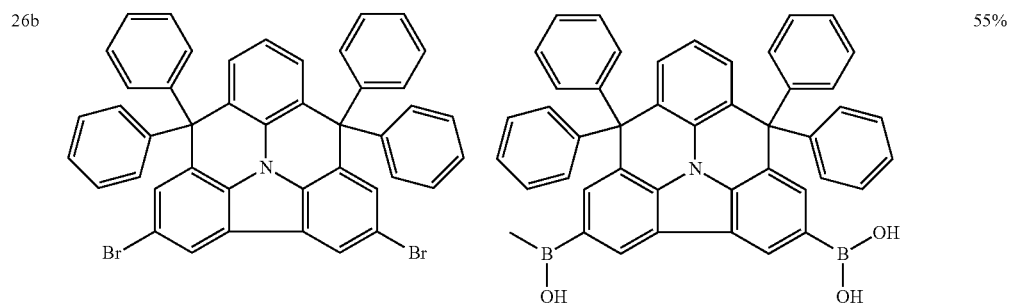 | | 55% |

| Ex. | Starting material | Product | Yield |
|---|---|---|---|
| 26c | | | 56% |
| 26d | | | 51% |

Example 27

Biphenyl-4-yl-(4-bromophenyl)-(9,9-dimethyl-9H-fluoren-2-yl)amine

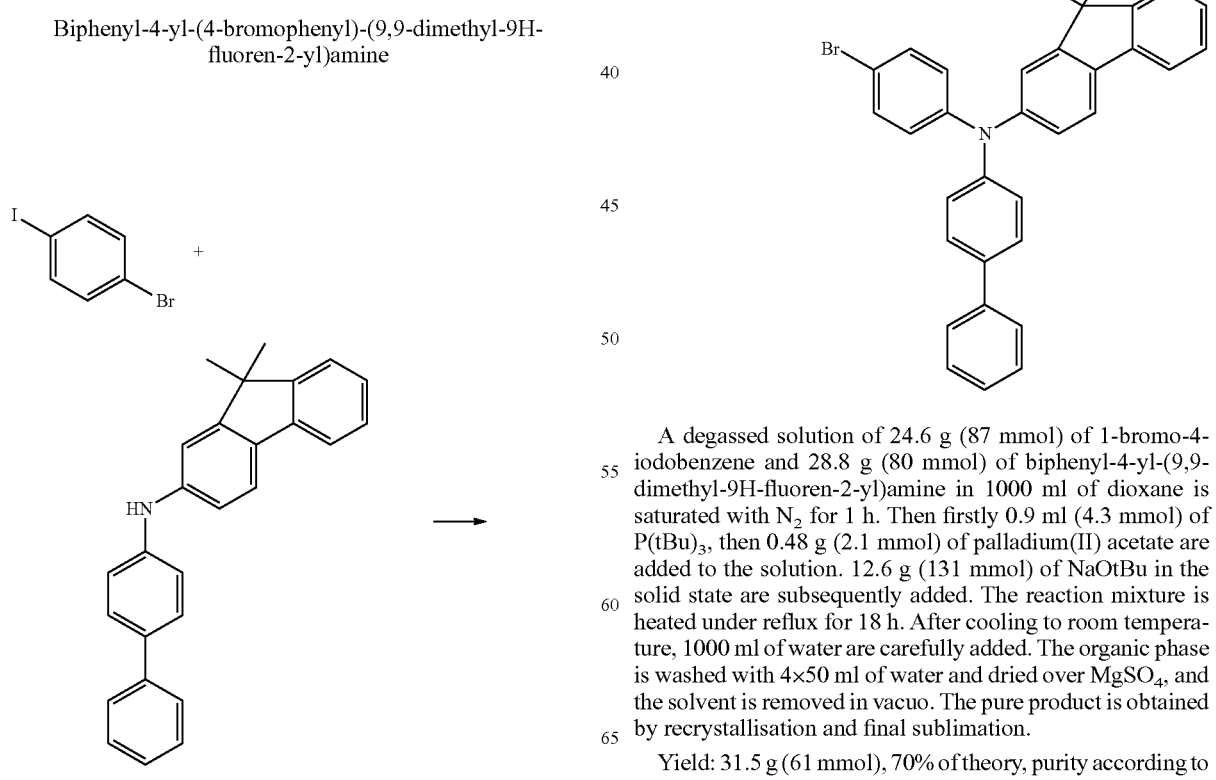

A degassed solution of 24.6 g (87 mmol) of 1-bromo-4-iodobenzene and 28.8 g (80 mmol) of biphenyl-4-yl-(9,9-dimethyl-9H-fluoren-2-yl)amine in 1000 ml of dioxane is saturated with $N_2$ for 1 h. Then firstly 0.9 ml (4.3 mmol) of $P(tBu)_3$, then 0.48 g (2.1 mmol) of palladium(II) acetate are added to the solution. 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of water and dried over $MgSO_4$, and the solvent is removed in vacuo. The pure product is obtained by recrystallisation and final sublimation.

Yield: 31.5 g (61 mmol), 70% of theory, purity according to HPLC 98%.

Example 28

Biphenyl-4-yl-(9,9-dimethyl-9H-fluoren-2-yl)-[4-(8,8-diphenyl-8H-indolo[3,2,1-de]acridin-3-yl)phenyl]amine (HTM14)

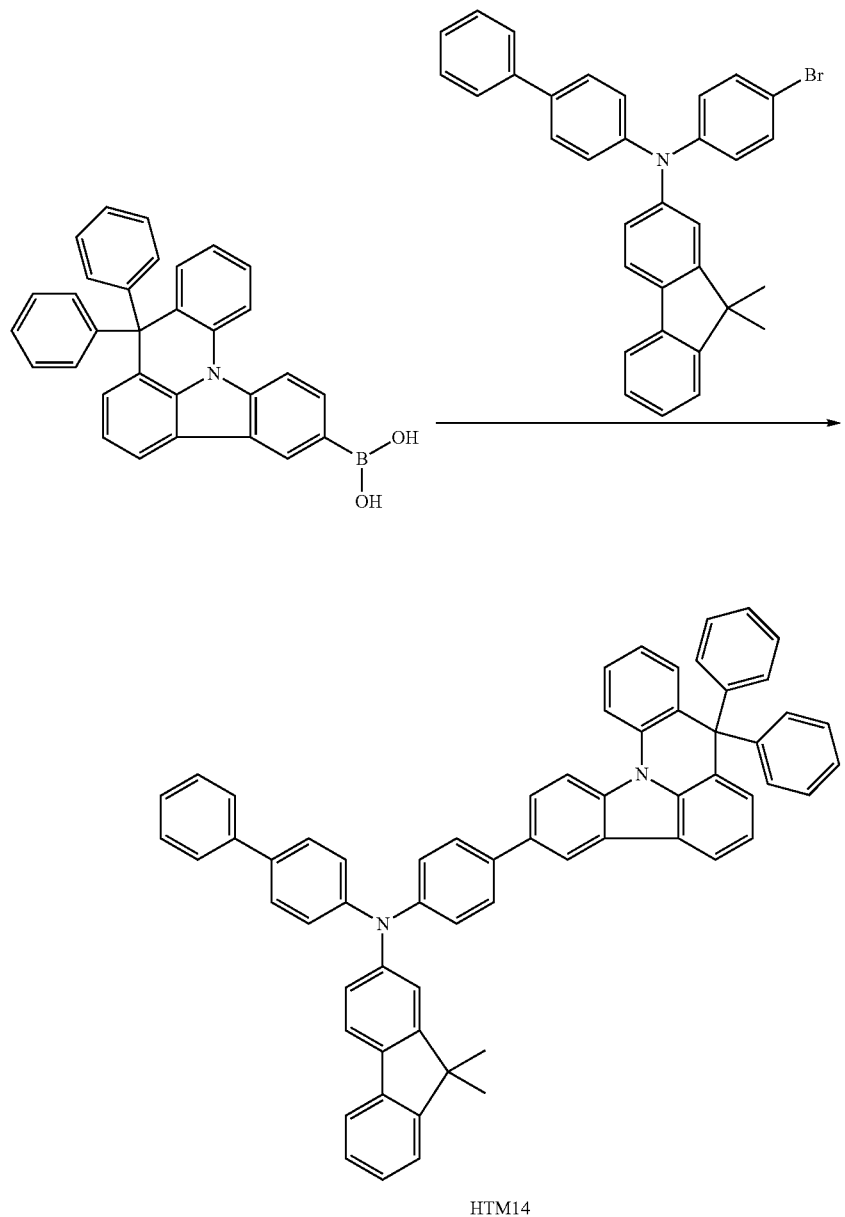

HTM14

85 g (190 mmol) of 8,8-diphenyl-8H-indolo[3,2,1-de]acridine-3-boronic acid, 98 g (190 mmol) of biphenyl-4-yl-(4-bromophenyl)-(9,9-dimethyl-9H-fluoren-2-yl)amine and 13 g (123 mmol) of sodium carbonate are suspended in 180 ml of toluene, 180 ml of dioxane and 60 ml of water. 3.0 mg mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum. The purity is 99.9%. The yield is 124 g (147 mmol), corresponding to 78% of theory.

The following compounds are obtained analogously:

| Ex. | Starting material | |
|---|---|---|
| 28a | 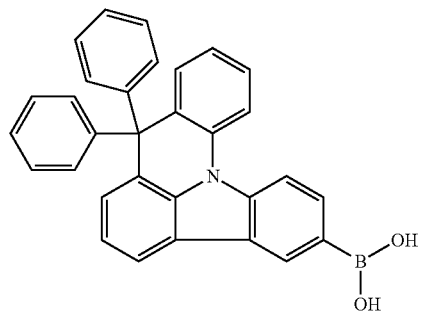 [SMILES: OB(O)c1ccc2c(c1)c1cccc3c1n2-c1ccccc1C3(c1ccccc1)c1ccccc1] | 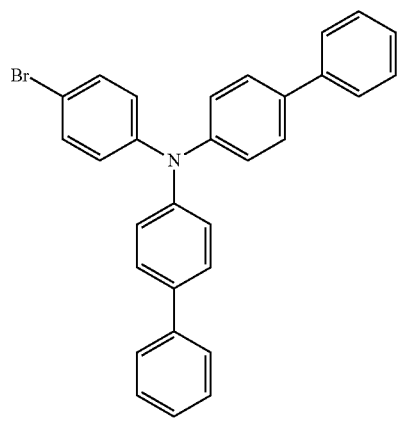
[499128-71-1] |
| 28b | 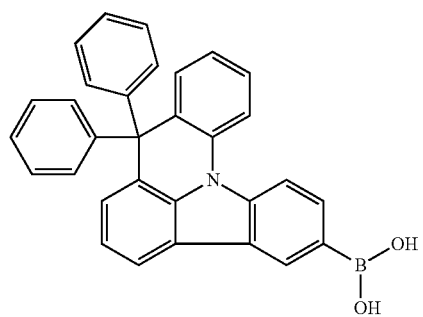 [SMILES: OB(O)c1ccc2c(c1)c1cccc3c1n2-c1ccccc1C3(c1ccccc1)c1ccccc1] | 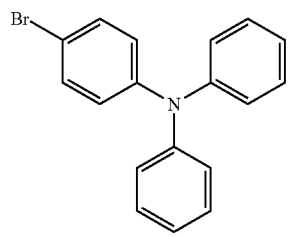
[36809-26-4] |
| 28c | 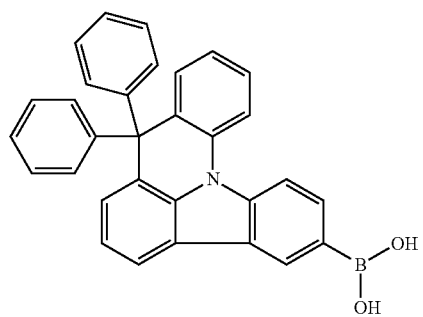 [SMILES: OB(O)c1ccc2c(c1)c1cccc3c1n2-c1ccccc1C3(c1ccccc1)c1ccccc1] | 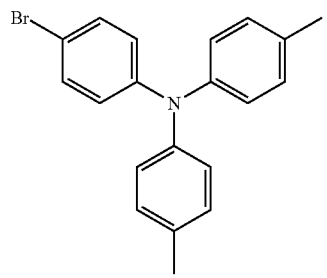
[58047-42-0] |
| 28d | 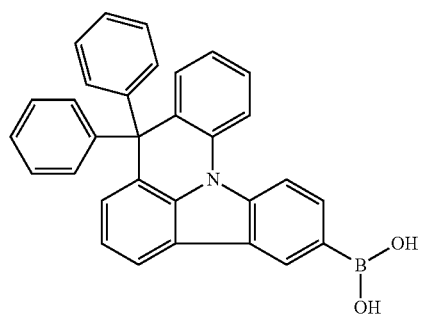 [SMILES: OB(O)c1ccc2c(c1)c1cccc3c1n2-c1ccccc1C3(c1ccccc1)c1ccccc1] | 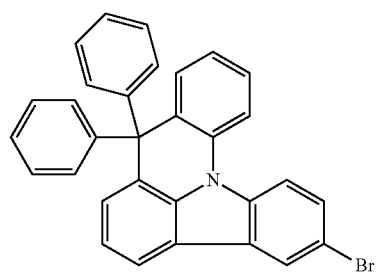 [SMILES: Brc1ccc2c(c1)c1cccc3c1n2-c1ccccc1C3(c1ccccc1)c1ccccc1] |

| | |
|---|---|
| 28e 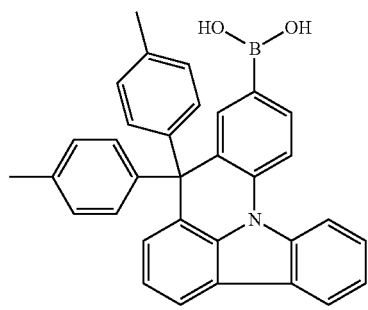 [SMILES: Cc1ccc(C2(c3ccc(C)cc3)c3cc(B(O)O)ccc3-n3c4ccccc4c4cccc2c43)cc1] | 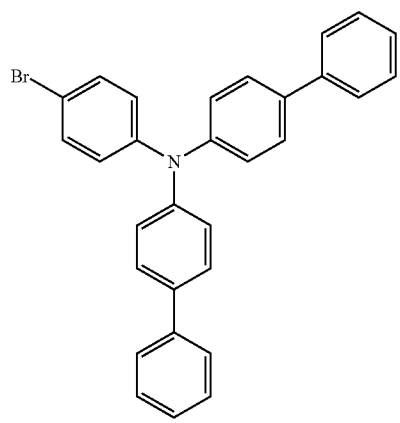 [499128-71-1] |
| 28f 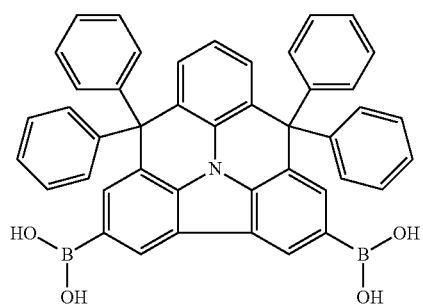 [SMILES: OB(O)c1cc2c3c(c1)c1cc(B(O)O)cc4c1n3-c1c(cccc1C4(c1ccccc1)c1ccccc1)C2(c1ccccc1)c1ccccc1] | 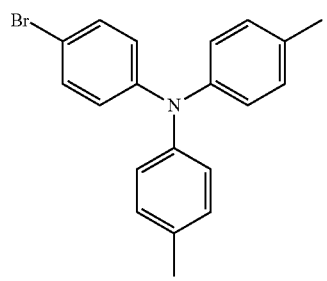 [SMILES: Cc1ccc(N(c2ccc(C)cc2)c2ccc(Br)cc2)cc1] |
| 28g 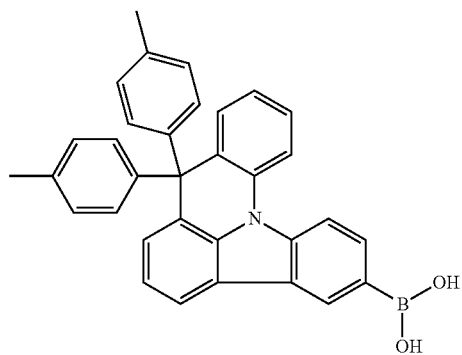 [SMILES: Cc1ccc(C2(c3ccc(C)cc3)c3ccccc3-n3c4ccc(B(O)O)cc4c4cccc2c43)cc1] | 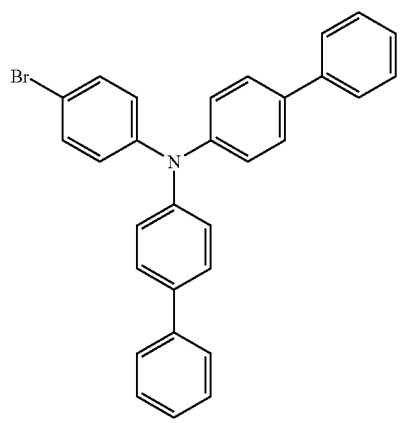 [SMILES: Brc1ccc(N(c2ccc(-c3ccccc3)cc2)c2ccc(-c3ccccc3)cc2)cc1] |
| 28h 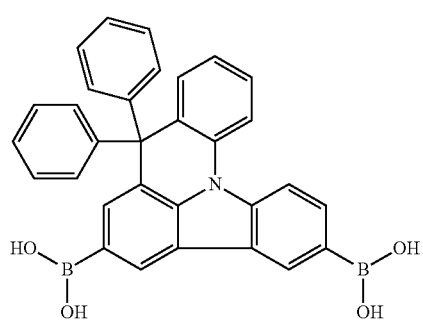 [SMILES: OB(O)c1ccc2c(c1)c1cc(B(O)O)cc3c1n2-c1ccccc1C3(c1ccccc1)c1ccccc1] | 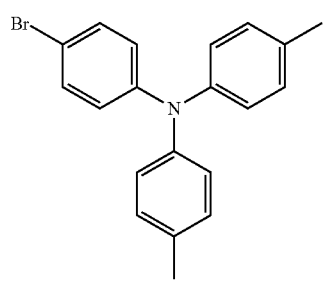 [SMILES: Cc1ccc(N(c2ccc(C)cc2)c2ccc(Br)cc2)cc1] |

| | | |
|---|---|---|
| 28i | 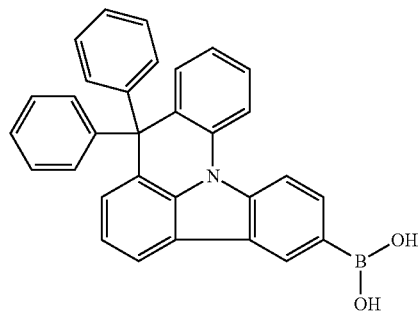 [SMILES: OB(O)c1ccc2c(c1)c1cccc3c1n2-c1ccccc1C3(c1ccccc1)c1ccccc1] | 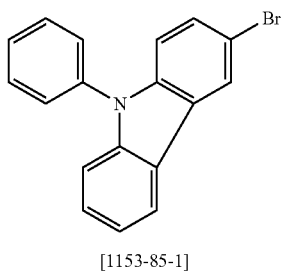 [SMILES: Brc1ccc2c(c1)c1ccccc1n2-c1ccccc1]
[1153-85-1] |
| 28j | 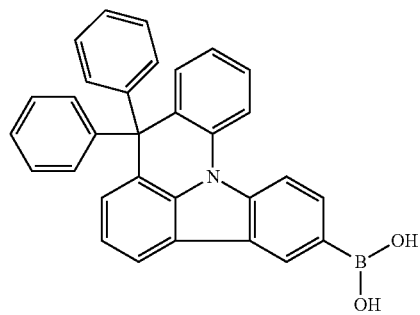 [SMILES: OB(O)c1ccc2c(c1)c1cccc3c1n2-c1ccccc1C3(c1ccccc1)c1ccccc1] | 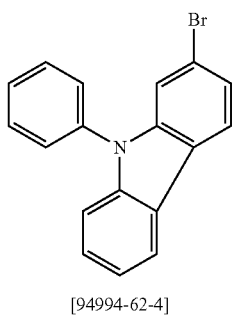 [SMILES: Brc1ccc2c3ccccc3n(-c3ccccc3)c2c1]
[94994-62-4] |
| 28k | 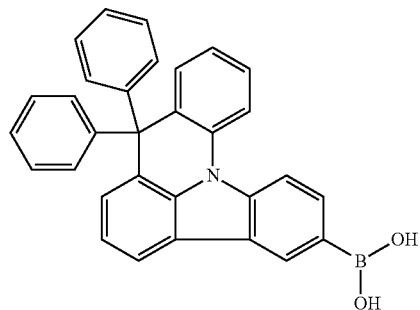 [SMILES: OB(O)c1ccc2c(c1)c1cccc3c1n2-c1ccccc1C3(c1ccccc1)c1ccccc1] | 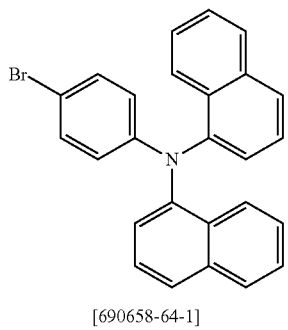 [SMILES: Brc1ccc(N(c2cccc3ccccc23)c2cccc3ccccc23)cc1]
[690658-64-1] |
| Ex. | Product | Yield |
|---|---|---|
| 28a | 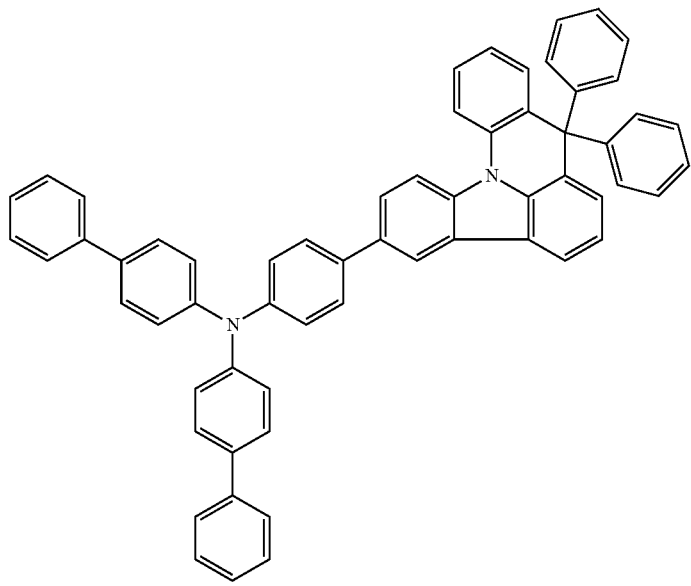
HTM13 | 64% |

28b 62%
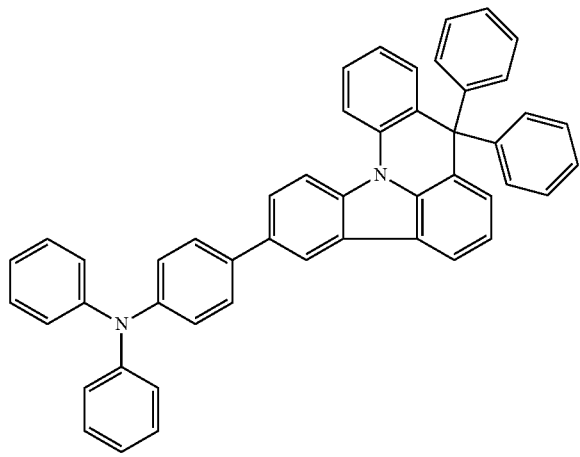 [SMILES: c1ccc(N(c2ccccc2)c2ccc(-c3ccc4c(c3)c3cccc5c3n4-c3ccccc3C5(c3ccccc3)c3ccccc3)cc2)cc1]
28c 73%
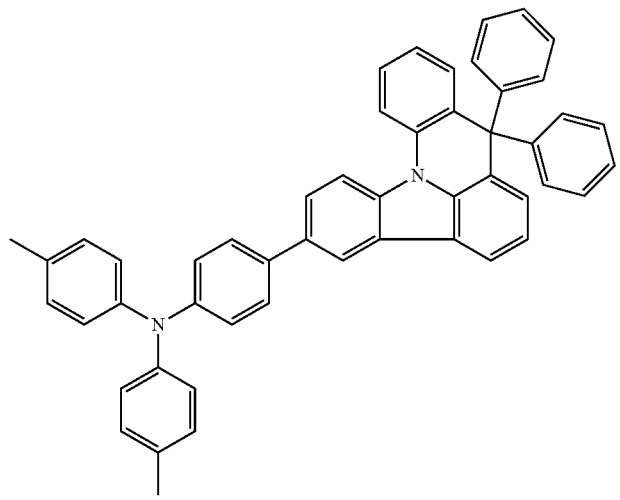
HTM15
28d 68%
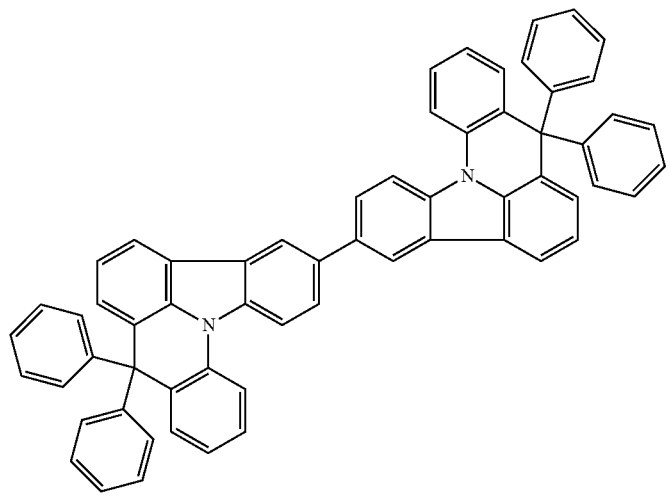
H12

28e 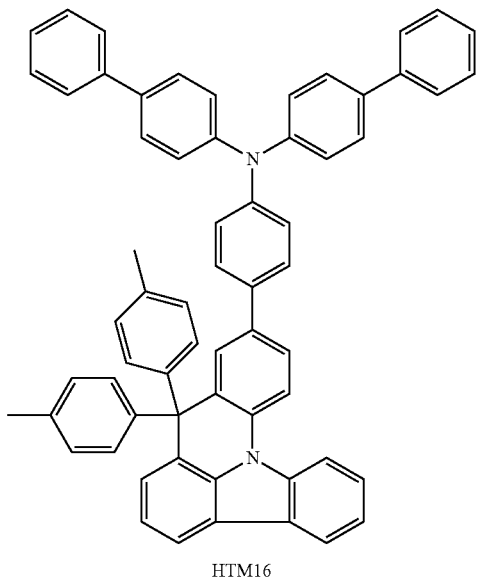 59%
HTM16
28f 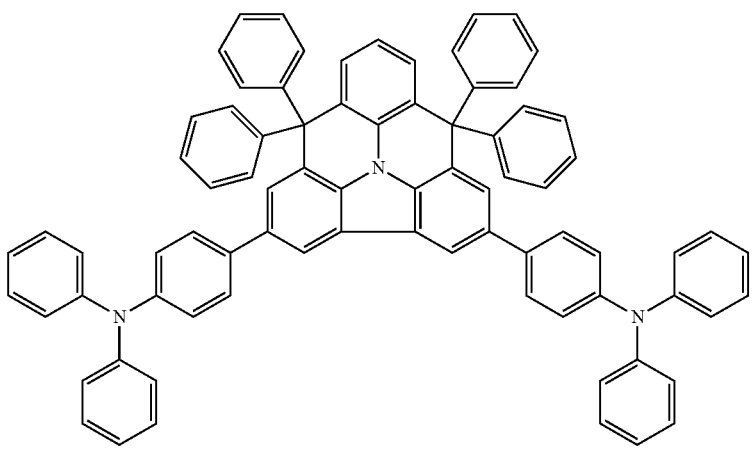 57%
HTM17

| | | |
|---|---|---|
| 28g | 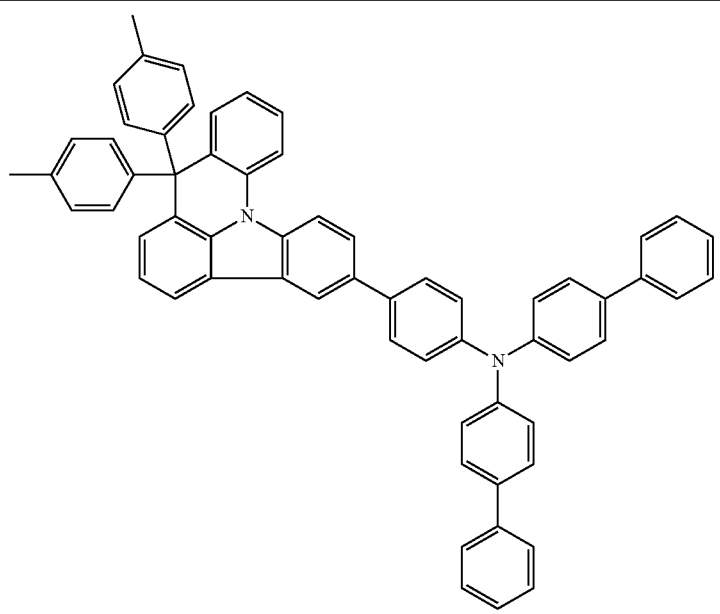
HTM18 | 52% |
| 28h | 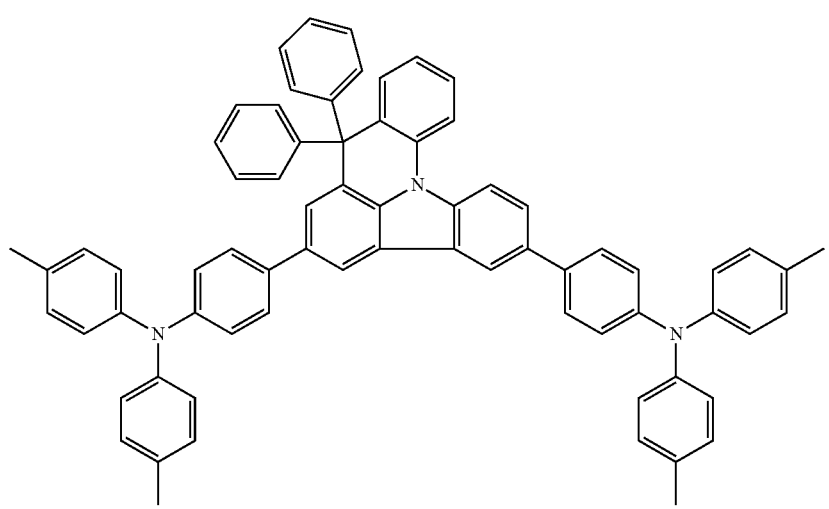
HTM19 | 55% |
| 28i | 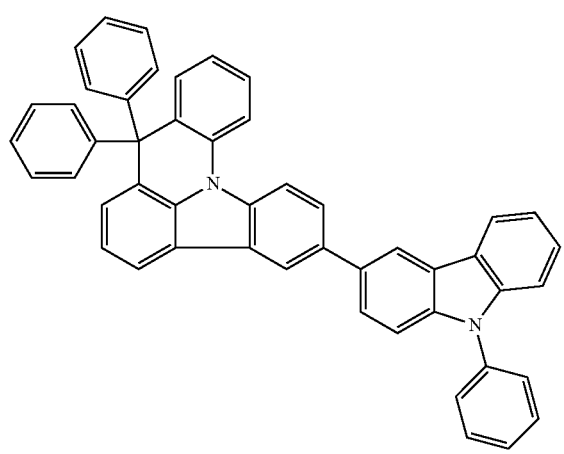
H14 | 75% |

| | |
|---|---|
| 28j 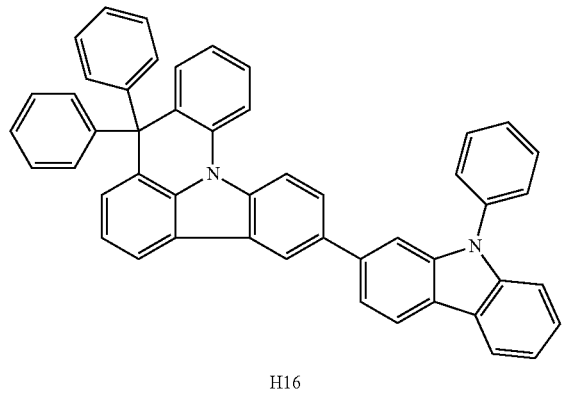 [SMILES: c1ccc(-n2c3ccccc3c3ccc(-c4ccc5c(c4)c4cccc6c4n5-c4ccccc4C6(c4ccccc4)c4ccccc4)cc32)cc1 ; "H16"] H16 | 66% |
| 28k 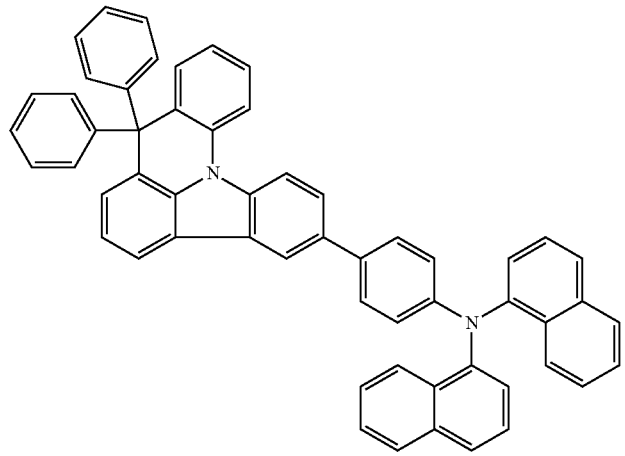 HTM20 | 64% |

Example 29

(8,8-Diphenyl-8H-indolo[3,2,1-de]acridin-3-yl)diphenylamine (HTM21)

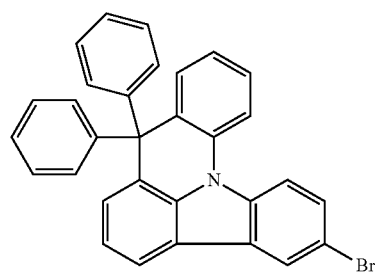 [SMILES: Brc1ccc2c(c1)c1cccc3c1n2-c1ccccc1C3(c1ccccc1)c1ccccc1]

→

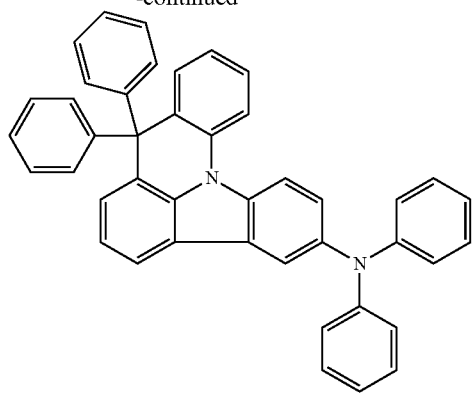

HTM21

A degassed solution of 42 g (86.6 mmol) of 3-bromo-8,8-diphenyl-8H-indolo[3,2,1-de]acridine and 16 g (95.9 mmol) of diphenylamine in 1000 ml of dioxane is saturated with $N_2$ for 1 h. Then firstly 0.9 ml (4.3 mmol) of $P(tBu)_3$, then 0.48 g (2.1 mmol) of palladium(II) acetate are added, and 12.6 g (131 mmol) of NaOtBu in the solid state are subsequently added to the solution. The reaction mixture is heated under reflux for 18 h. After cooling to room temperature, 1000 ml of water are carefully added. The organic phase is washed with 4×50 ml of water and dried over MgSO₄, and the solvent is removed in vacuo. The pure product is obtained by recrystallisation and final sublimation.

Yield: 39 g (69 mmol), 80% of theory, purity according to HPLC 99.9%.

The following compounds are obtained analogously:

| Ex. | Starting material | | |
|---|---|---|---|
| 29a | 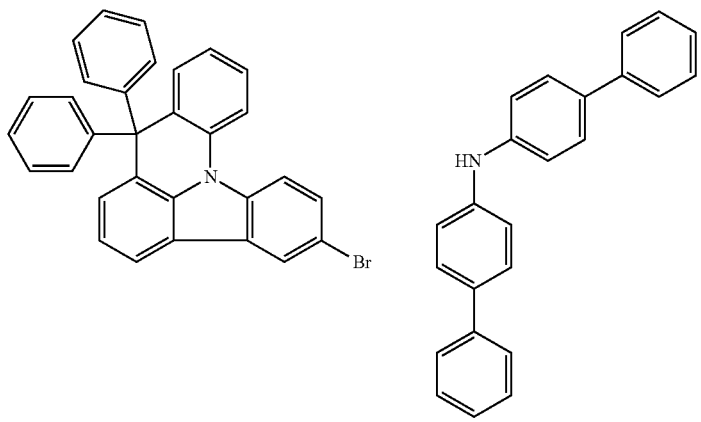 | | [102113-98-4] |
| 29b | 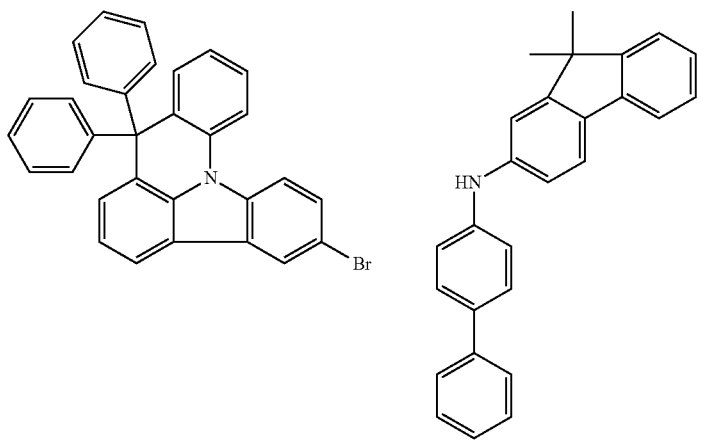 | | [897671-69-1] |
| 29c | 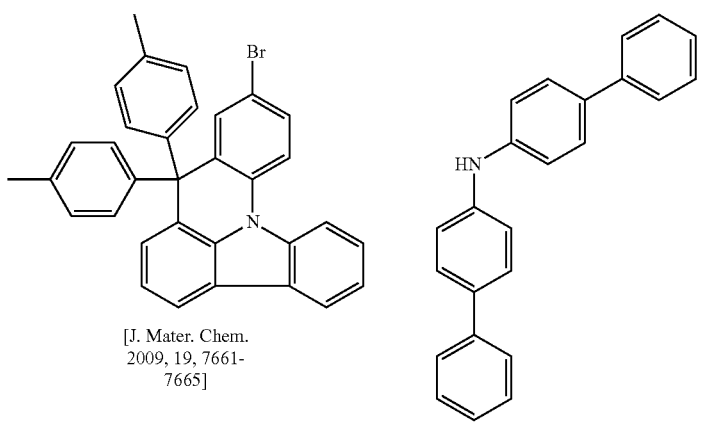 | [J. Mater. Chem. 2009, 19, 7661-7665] | |

-continued
| | | |
|---|---|---|
| 29d | 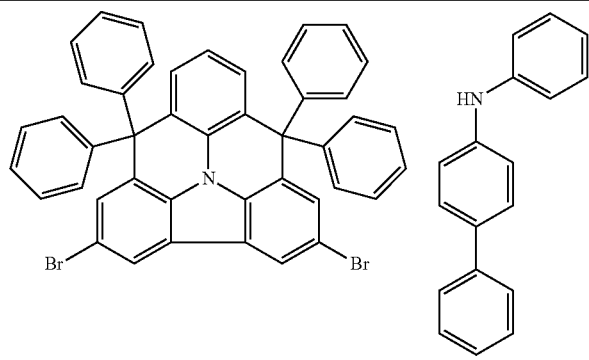 | [32228-99-2] |
| 29e | 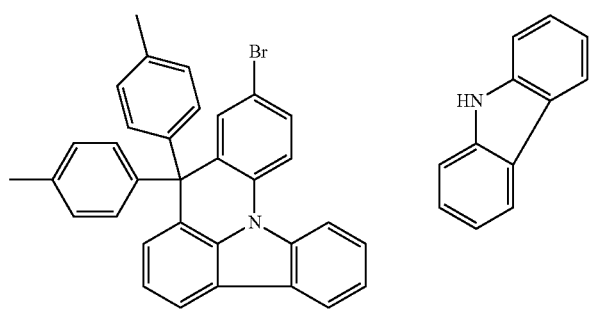 | |
| 29f | 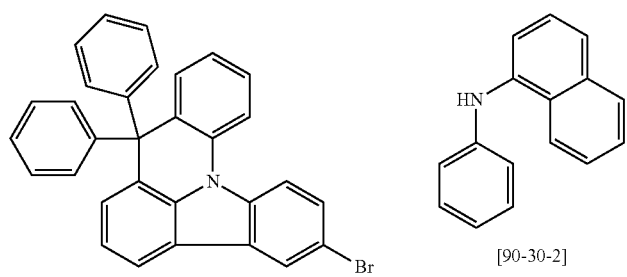 | [90-30-2] |
| 29g | 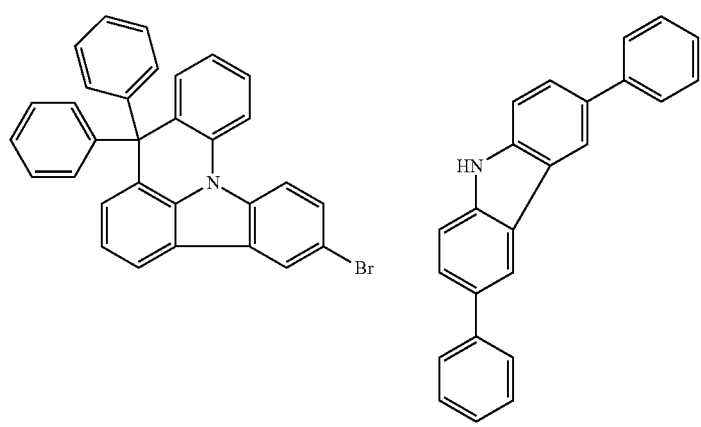 | [56525-79-2] |

-continued
| Ex. | Product | Yield |
|---|---|---|
| 29a | 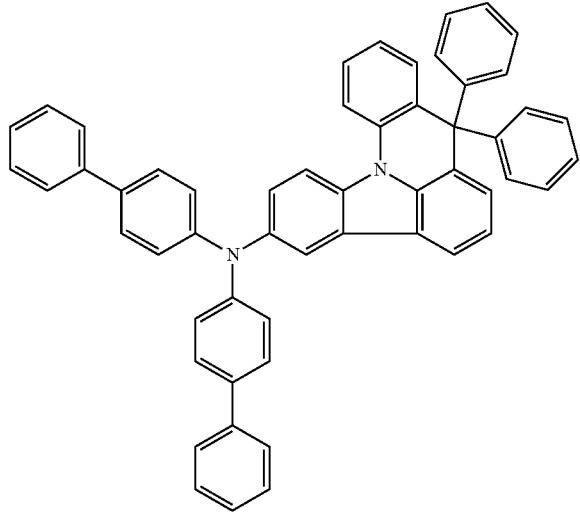
HTM22 | 64% |
| 29b | 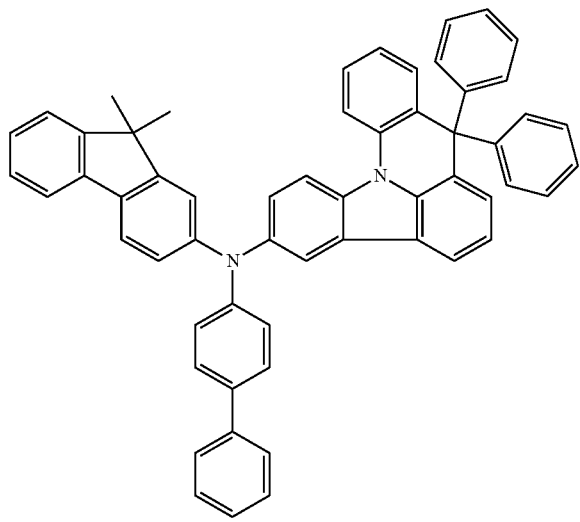
HTM23 | 72% |
| 29c | 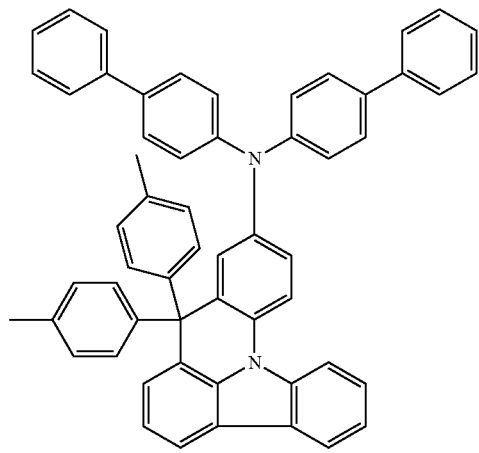
HTM24 | 61% |

| 29d | 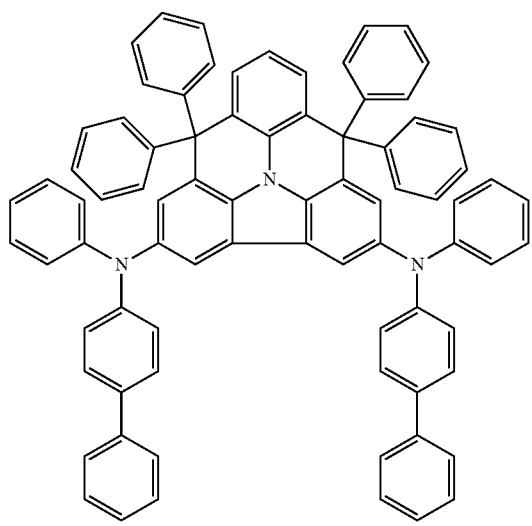 HTM25 | 66% |
| 29e | 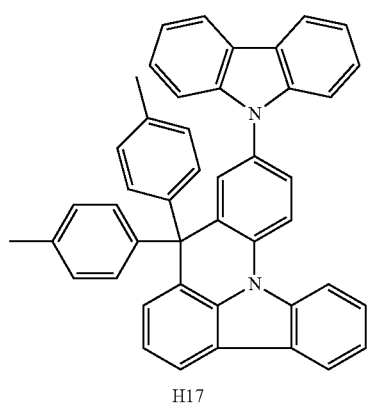 H17 | 72% |
| 29f | 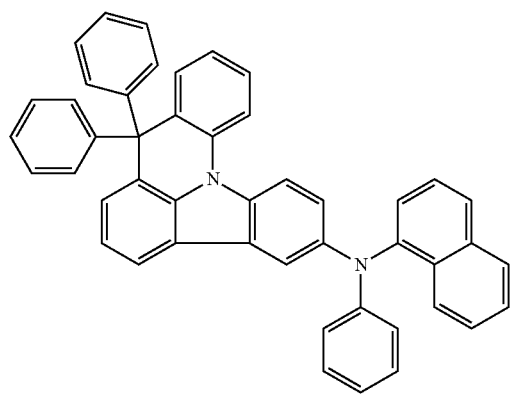 HTM26 | 67% |

29g

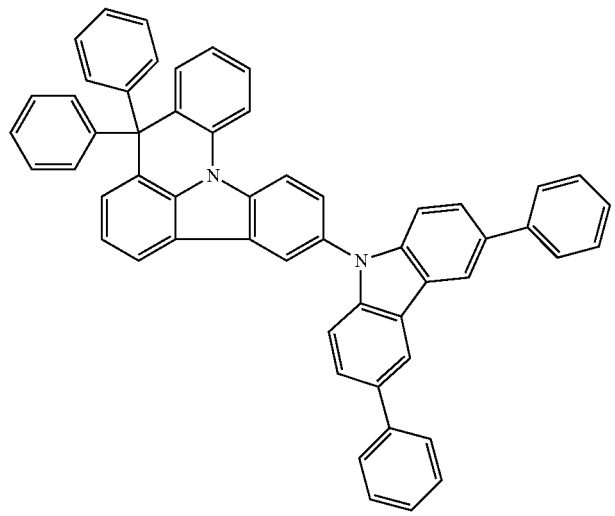

H11

58%

Example 30

3-(9,9-Dimethyl-10-phenyl-9,10-dihydroacridin-2-yl)-8,8-dimethyl-8H-indolo[3,2,1-de]acridine

2-Chloro-9,9-dimethyl-9,10-dihydroacridine

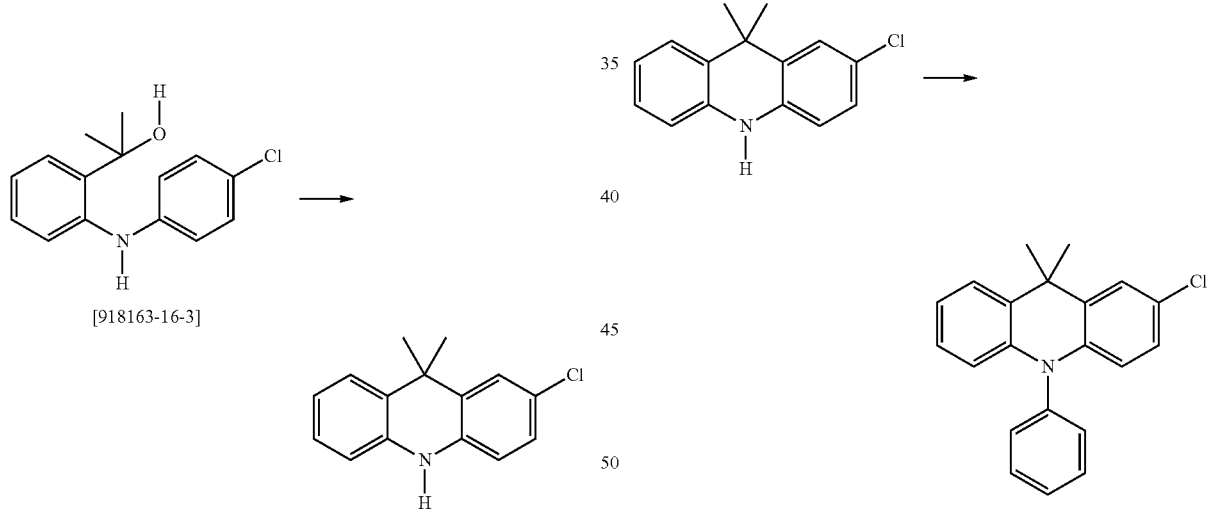

[918163-16-3]

2-Chloro-9,9-dimethyl-10-phenyl-9,10-dihydroacridine 30.3 g (116 mmol) of 2-[2-(4-chlorophenylamino)phenyl]propan-2-ol are dissolved in 700 ml of degassed toluene, a suspension of 93 g of polyphosphoric acid and 61.7 g of methanesulfonic acid is added, and the mixture is stirred at room temperature for 1 h and heated at 50° C. for 1 h. The batch is cooled and poured onto ice and extracted three times with ethyl acetate. The combined organic phases are washed with saturated sodium chloride solution, dried over magnesium sulfate and evaporated. Filtration of the crude product through silica gel with heptane/ethyl acetate (20:1) gives 25.1 g (89%) of 2-chloro-9,9-dimethyl-9,10-dihydroacridine as pale-yellow crystals.

A degassed solution of 16.6 ml (147 mmol) of 4-iodobenzene and 30 g (123 mmol) of 2-chloro-9,9-dimethyl-9,10-dihydroacridine in 600 ml of toluene is saturated with $N_2$ for 1 h. Then firstly 2.09 ml (8.6 mmol) of $P(tBu)_3$ and then 1.38 g (6.1 mmol) of palladium(II) acetate are added to the solution. 17.7 g (185 mmol) of NaOtBu as solid are subsequently added. The reaction mixture is heated under reflux for 1 h. After cooling to room temperature, 500 ml of water are carefully added. The aqueous phase is washed with 3×50 ml of toluene and dried over $MgSO_4$, and the solvent is removed in vacuo. Filtration of the crude product through silica gel with heptane/ethyl acetate (20:1) gives 32.2 g (81%) of 2-chloro-9,9-dimethyl-10-phenyl-9,10-dihydroacridine as pale-yellow crystals.

3-(9,9-Dimethyl-10-phenyl-9,10-dihydroacridin-2-yl)-8,8-dimethyl-8H-indolo[3,2,1-de]acridine

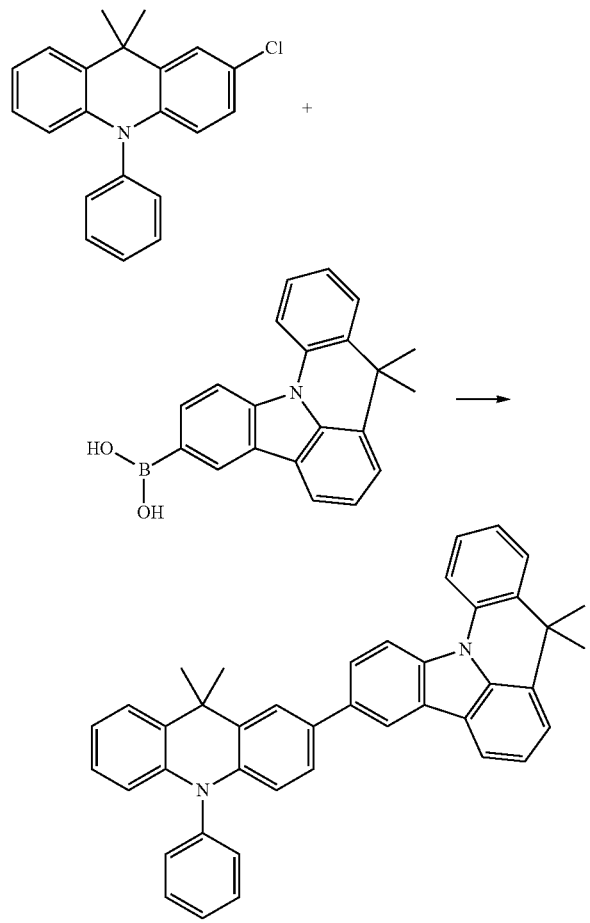

36 g (110 mmol) of 8,8-dimethyl-8H-indolo[3,2,1-de]acridine-3-boronic acid, 35.2 g (110 mmol) of 2-chloro-9,9-dimethyl-10-phenyl-9,10-dihydroacridine and 9.7 g (92 mmol) of sodium carbonate are suspended in 350 ml of toluene, 350 ml of dioxane and 500 ml of water. 913 mg (3.0 mmol) of tri-o-tolylphosphine and 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from $CH_2Cl_2$/isopropanol and finally sublimed in a high vacuum.

Yield: 52 g (100 mmol), 91% of theory, purity according to HPLC 99.9%.

B) Device Examples C1-I63

Production of OLEDs

OLEDs according to the invention and OLEDs in accordance with the prior art are produced by a general process in accordance with WO 04/058911, which is adapted to the circumstances described here (layer-thickness variation, materials used).

Data for various OLEDs are presented in the examples C1 to I63 below (see Tables 1-3). Glass plates coated with structured ITO (indium tin oxide) in a thickness of 150 nm are coated with 20 nm of PEDOT (poly(3,4-ethylenedioxy-2,5-thiophene, applied by spin coating from water; purchased from H. C. Starck, Goslar, Germany) for improved processing. These coated glass plates form the substrates, to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 4.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as H3:CBP:TER1 (55%:35%:10%) here means that material H3 is present in the layer in a proportion by volume of 55%, CBP is present in the layer in a proportion of 35% and TER1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current-voltage-luminance characteristic lines (IUL characteristic lines), and the lifetime are determined. The lifetime is defined as the time after which the luminous density has dropped to a certain proportion from a particular initial luminous density. The designation LD80 means that the said lifetime is the time at which the luminous density has dropped to 80% of the initial luminous density, i.e. from, for example, 4000 cd/m² to 3200 cd/m². Analogously, LD50 denotes the time after which the initial luminance has dropped to half. The values for the lifetime can be converted to a figure for other initial luminous densities with the aid of conversion formulae known to the person skilled in the art. The lifetime for an initial luminous density of 1000 cd/m² is a usual expression here.

OLEDs which comprise the blue-fluorescent emitter D1 are started at an initial luminous density of 6000 cd/m² for determination of the lifetime. OLEDs which comprise the green-fluorescent emitter D2 are started at a luminous density of 25,000 cd/m². OLEDs comprising the phosphorescent emitters TER1 and TEG1 are started at 4000 cd/m².

The data for the various OLEDs are summarised in Tables 2 and 3. Examples C1-C22 are comparative examples in accordance with the prior art, Examples I1-I63 show data for OLEDs in which materials according to the invention are employed.

Some of the examples are explained in greater detail below in order to illustrate the advantages of the compounds according to the invention. However, it should be pointed out that this only represents a selection of the data shown in Tables 2 and 3. As can be seen from the table, significant improvements over the prior art are also achieved on use of the compounds according to the invention that are not described in greater detail in all parameters, but in some cases only an improvement in the efficiency or voltage or lifetime is observed. However, even the improvement in one of the said parameters represents a significant advance.

Use of Compounds According to the Invention as Hole-Transport or Electron-Blocking Materials The materials according to the invention can be employed in accordance with the invention, inter alia, on the hole-transport side of OLEDs, more precisely as hole-transport or electron-blocking materials. This is shown with reference to Examples I1-I26, I40-I55, I57. Comparative Examples C1-C9, C11, C12 and C19-C22 in accordance with the prior art comprise materials HTM1 and HTM12 as hole-transport materials and NPB, EBM1, HTM11 and HTM12 as electron-blocking materials.

If Example I1 is compared with Example C3, it can be seen that the operating voltage can be reduced by 0.2 V through the use of material HTM8 according to the invention in the hole-transport layer, which, in combination with slightly improved quantum efficiency, results in an improvement in the power efficiency from 10.7 lm/W to 12.1 lm/W, i.e. by about 15%. A similar improvement is also observed in the case of a hole-transport layer with a thickness of 200 nm (Examples C5 and I2). Furthermore, it is evident that the difference between the voltage for a thick HTL (200 nm) and a thinner HTL (110 nm) reduces from 0.5 V (Examples C3 and C5) to 0.3 V (Examples I1 and I2). This is an important aspect, since thicker hole-transport layers are often desirable for optimisation of the optical coupling-out. It is desirable here for the operating voltage to remain as low as possible. A further advantage of material HTM8 is the increase in the lifetime. In the case of a layer with a thickness of 110 nm, although the improvement is only 10%, material HTM1 in accordance with the prior art exhibits a significant drop in the lifetime to 250,000 h in an OLED having an HTL with a thickness of 200 nm compared with an OLED having an HTL with a thickness of 110 nm, while an OLED comprising 200 nm of the material according to the invention even exhibits a slight improvement in the lifetime to 340,000 h (Examples C3, C5, I1 and I2). Compared with the triarylamine-substituted compound HTM12 in accordance with the prior art, material HTM8 exhibits an even more significant improvement in the performance data (Examples C19, C20, I1 and I2).

If HTM3 is used as electron-blocking material together with fluorescent dopants D1 and D2, a significant improvement in the operating voltage and efficiency is obtained compared with NPB (Examples C1-3, C5, I3-I6). However, it is much more important that the lifetime can be increased through the use of HTM3 in the case of blue emission (Examples C1, C2, I3 and I4) to about 7700 h compared with 5200 h with NPB (with ETM1 as electron-transport material). This corresponds to a significant increase of 50%. In the case of green emission, the improvement in the lifetime is somewhat less, with an increase of about 25% being obtained (Examples C3, C5, I5 and I6). Similar improvements can be achieved through the use of compound HTM2 according to the invention (Examples I7-I9). In particular, a combination of the novel materials HTM8 as hole-transport material and HTM3 as electron-blocking material gives very good performance data: compared with the prior art, the lifetime is improved by about 50% and the power efficiency by about 25% (Examples C2 and I12).

Furthermore, the compounds according to the invention can also be employed as single layers, which represents a significant advantage over the combination of HTM1 and NPB with respect to the processing complexity. This is demonstrated with reference to materials HTM2 and HTM3 in combination with the blue-fluorescent dopant D1. Although the two-layer structure HTM1/HTM2 (Ex. 18) or HTM1/HTM3 (Ex. I4) exhibits a better voltage and efficiency than the single layer (Examples I10 and I11), the single layer is, however, still significantly superior to the prior art (Ex. C2) with respect to the lifetime. The voltage and efficiency are approximately the same.

In phosphorescent OLEDs, the compounds according to the invention exhibit, in particular, a significant improvement in the lifetime and an improvement in the quantum or current efficiency on use as electron-blocking layer (Examples C4, C6-C9, C11, C12 and I13-I26, I41, I43, I44, I46, I50-I53, I57). For example, if compound HTM3 according to the invention is used in an OLED comprising the green-phosphorescent emitter TEG1, the lifetime is increased by up to more than 60% compared with material EBM1 in accordance with the prior art (Examples C12 and I17). The quantum efficiency is increased by about 10%, which, owing to the virtually unchanged operating voltage, has the consequence that the power efficiency is also increased by about 10%. The increase in efficiency can be explained by the greater triplet gap of the compounds according to the invention. Compared with materials HTM11 and HTM12 in accordance with the prior art, significant improvements likewise arise on use of HTM3 as electron-blocking material (Examples C21, C22 and I15). The other materials according to the invention exhibit similar improvements compared with the prior art. In the case of red emission, the compounds according to the invention exhibit, in particular, a significant improvement in the lifetime compared with NPB in accordance with the prior art (Examples C4, C6, I25 and I26).

Thus, the use of compounds according to the invention on the hole-transport side of OLEDs produces significant improvements, in particular with respect to the lifetime and the operating voltage, power efficiency, lifetime and processing complexity.

Use of Compounds According to the Invention as Component in Mixed-Matrix Systems Mixed-matrix systems, i.e. OLEDs having an emission layer consisting of three or more components, in some cases exhibit significant advantages over systems comprising single-matrix materials. The said systems are described in detail, inter alia, in the application WO 10/108,579. The compounds can also be employed in such systems in accordance with the present invention. Compared with mixed-matrix components in accordance with the prior art, significant improvements arise with respect to the efficiency, voltage and lifetime. The compounds in accordance with the prior art used are the materials CBP, TCTA and FTPh (see Table 4). The corresponding OLEDs are denoted by C6, C10 and C14-C18. The materials according to the invention employed are compounds H5-H17 in combination with matrix materials H3, Ket1 and DAP1. The corresponding OLEDs are denoted by I27-I39, I56, I58-I63.

Firstly, mixed-matrix systems comprising the green-emitting dopant TEG1 are compared. On replacement of CBP or TCTA with the compounds according to the invention, a significant improvement is observed in the operating voltage, power efficiency and especially also the lifetime. On use of compound H10 according to the invention in combination with H3, for example, the power efficiency is increased by 60% compared with the use of CBP and by about 70% compared with TCTA (Examples C10, C18 and I27). The lifetime is increased by almost 60% compared with CBP, and virtually a quadrupling of the lifetime is observed compared with TCTA. Similar improvements are also obtained on combination of H10 with the ketone matrix Ket1 and diazaphosphole matrix DAP1 (Examples C14-C17, I28 and I29). Very good lifetimes can also be achieved with compounds H12 and H14, in which the bridge atoms are substituted by phenyl rings (Examples I58, I60). Other compounds according to the invention also exhibit significant improvements with respect to the voltage, power efficiency and lifetime.

In red-emitting mixed-matrix systems, significant improvements are likewise obtained on use of the compounds according to the invention (cf. Example C6 with I37-I39, I62, I63). On replacement of CBP with H10, for example, an improvement in the voltage of 1.1V, an increase in the power efficiency by about 50% and a virtually doubled lifetime are obtained (Examples C6 and I37). Similarly good performance data can be achieved with compounds H7 and H9 according to the invention. Furthermore, significant improvements compared with the prior art are also obtained with compounds H16 and H17, which are substituted by phenyl rings on the bridge atoms (I62, I63).

The use of materials according to the invention in mixed-matrix systems thus produces significant improvements with respect to the voltage, efficiency and especially also the lifetime of the OLEDs. These improvements can be achieved in combination with very different classes of matrix materials (ketones: Ket1, spirotriazines: H3, diazaphospholes: DAP1). It can thus be assumed that similar improvements are also achievable through combination of the compounds according to the invention with other classes of material.

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| C1 | HIL1 5 nm | HTM1 140 nm | — | NPB 20 nm | H1:D1 (95%:5%) 30 nm | — | Alq$_3$ 20 nm | LiF 1 nm |
| C2 | HIL1 5 nm | HTM1 140 nm | — | NPB 20 nm | H1:D1 (95%:5%) 30 nm | — | ETM1:LiQ (50%:50%) 20 nm | — |
| C3 | HIL1 5 nm | HTM1 110 nm | — | NPB 20 nm | H2:D2 (90%:10%) 30 nm | — | Alq$_3$ 20 nm | LiF 1 nm |
| C4 | — | HTM1 20 nm | — | NPB 20 nm | H3:TER1 (85%:15%) 30 nm | — | Alq$_3$ 20 nm | LiF 1 nm |
| C5 | HIL1 5 nm | HTM1 200 nm | — | NPB 20 nm | H2:D2 (90%:10%) 30 nm | — | Alq$_3$ 20 nm | LiF 1 nm |
| C6 | — | HTM1 20 nm | — | NPB 20 nm | H3:CBP:TER1 (45%:45%:10%) 30 nm | H3 10 nm | Alq$_3$ 20 nm | LiF 1 nm |
| C7 | — | HTM1 160 nm | — | EBM1 20 nm | H3:TEG1 (90%:10%) 30 nm | H3 10 nm | ETM1:LiQ (50%:50%) 30 nm | — |
| C8 | — | HTM1 160 nm | — | EBM1 20 nm | H3:TEG1 (90%:10%) 30 nm | — | ETM1:LiQ (50%:50%) 40 nm | — |
| C9 | — | HTM1 70 nm | HIL1 5 nm | EBM1 90 nm | H4:TEG1 (85%:15%) 30 nm | — | H3:LiQ (50%:50%) 40 nm | — |
| C10 | — | HTM1 70 nm | HIL1 5 nm | EBM1 90 nm | H3:CBP:TEG1 (30%:60%:10%) 30 nm | H3 10 nm | H3:LiQ (50%:50%) 30 nm | — |
| C11 | — | HTM1 70 nm | HIL1 5 nm | EBM1 90 nm | H3:TEG1 (90%:10%) 30 nm | H3 10 nm | H3:LiQ (50%:50%) 30 nm | — |
| C12 | — | HTM1 70 nm | HIL1 5 nm | EBM1 90 nm | H3:TEG1 (90%:10%) 30 nm | — | H3:LiQ (50%:50%) 40 nm | — |
| C14 | HIL1 20 nm | — | — | EBM1 20 nm | Ket1:FTPh:TEG1 (60%:30%:10%) 30 nm | Ket1 10 nm | ETM2 20 nm | LiF 1 nm |
| C15 | HIL1 20 nm | — | — | EBM1 20 nm | Ket1:TCTA:TEG1 (60%:30%:10%) 30 nm | Ket1 10 nm | ETM2 20 nm | LiF 1 nm |
| C16 | HIL1 20 nm | — | — | EBM1 20 nm | Ket1:CBP:TEG1 (60%:30%:10%) 30 nm | Ket1 10 nm | ETM2 20 nm | LiF 1 nm |
| C17 | — | HTM1 70 nm | HIL1 5 nm | EBM1 90 nm | DAP1:CBP:TEG1 (30%:60%:10%) 30 nm | — | H3:LiQ (50%:50%) 30 nm | — |
| C18 | — | HTM1 70 nm | HIL1 5 nm | EBM1 90 nm | H3:TCTA:TEG1 (30%:60%:10%) 30 nm | — | H3:LiQ (50%:50%) 30 nm | — |
| C19 | HIL1 5 nm | HTM12 110 nm | — | NPB 20 nm | H2:D2 (90%:10%) 30 nm | — | Alq$_3$ 20 nm | LiF 1 nm |
| C20 | HIL1 5 nm | HTM12 200 nm | — | NPB 20 nm | H2:D2 (90%:10%) 30 nm | — | Alq$_3$ 20 nm | LiF 1 nm |
| C21 | — | HTM1 70 nm | HIL1 5 nm | HTM11 90 nm | H4:TEG1 (85%:15%) 30 nm | — | H3:LiQ (50%:50%) 40 nm | — |
| C22 | — | HTM1 70 nm | HIL1 5 nm | HTM12 90 nm | H4:TEG1 (85%:15%) 30 nm | — | H3:LiQ (50%:50%) 40 nm | — |
| I1 | HIL1 5 nm | HTM8 110 nm | — | NPB 20 nm | H2:D2 (90%:10%) 30 nm | — | Alq$_3$ 20 nm | LiF 1 nm |
| I2 | HIL1 5 nm | HTM8 200 nm | — | NPB 20 nm | H2:D2 (90%:10%) 30 nm | — | Alq$_3$ 20 nm | LiF 1 nm |
| I3 | HIL1 5 nm | HTM1 140 nm | — | HTM3 20 nm | H1:D1 (95%:5%) 30 nm | — | Alq$_3$ 20 nm | LiF 1 nm |
| I4 | HIL1 5 nm | HTM1 140 nm | — | HTM3 20 nm | H1:D1 (95%:5%) 30 nm | — | ETM1:LiQ (50%:50%) 20 nm | — |
| I5 | HIL1 5 nm | HTM1 110 nm | — | HTM3 20 nm | H2:D2 (90%:10%) 30 nm | — | Alq$_3$ 20 nm | LiF 1 nm |
| I6 | HIL1 5 nm | HTM1 200 nm | — | HTM3 20 nm | H2:D2 (90%:10%) 30 nm | — | Alq$_3$ 20 nm | LiF 1 nm |
| I7 | HIL1 5 nm | HTM1 140 nm | — | HTM2 20 nm | H1:D1 (95%:5%) 30 nm | — | Alq$_3$ 20 nm | LiF 1 nm |
| I8 | HIL1 5 nm | HTM1 140 nm | — | HTM2 20 nm | H1:D1 (95%:5%) 30 nm | — | ETM1:LiQ (50%:50%) 20 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| I9 | HIL1 5 nm | HTM1 110 nm | — | HTM2 20 nm | H2:D2 (90%:10%) 30 nm | — | Alq₃ 20 nm | LiF 1 nm |
| I10 | HIL1 5 nm | — | — | HTM2 160 nm | H1:D1 (95%:5%) 30 nm | — | ETM1:LiQ (50%:50%) 20 nm | — |
| I11 | HIL1 5 nm | — | — | HTM3 160 nm | H1:D1 (95%:5%) 30 nm | — | ETM1:LiQ (50%:50%) 20 nm | — |
| I12 | HIL1 5 nm | HTM8 140 nm | — | HTM3 20 nm | H1:D1 (95%:5%) 30 nm | — | ETM1:LiQ (50%:50%) 20 nm | — |
| I13 | — | HTM1 160 nm | — | HTM3 20 nm | H3:TEG1 (90%:10%) 30 nm | H3 10 nm | ETM1:LiQ (50%:50%) 30 nm | — |
| I14 | — | HTM1 160 nm | — | HTM3 20 nm | H3:TEG1 (90%:10%) 30 nm | — | ETM1:LiQ (50%:50%) 40 nm | — |
| I15 | — | HTM1 70 nm | HIL1 5 nm | HTM3 90 nm | H4:TEG1 (85%:15%) 30 nm | — | H3:LiQ (50%:50%) 40 nm | — |
| I16 | — | HTM1 70 nm | HIL1 5 nm | HTM3 90 nm | H3:TEG1 (90%:10%) 30 nm | H3 10 nm | H3:LiQ (50%:50%) 40 nm | — |
| I17 | — | HTM1 70 nm | HIL1 5 nm | HTM3 90 nm | H3:TEG1 (90%:10%) 30 nm | — | H3:LiQ (50%:50%) 40 nm | — |
| I18 | — | HTM1 70 nm | HIL1 5 nm | HTM2 90 nm | H4:TEG1 (85%:15%) 30 nm | — | H3:LiQ (50%:50%) 40 nm | — |
| I19 | — | HTM1 70 nm | HIL1 5 nm | HTM4 90 nm | H4:TEG1 (85%:15%) 30 nm | — | H3:LiQ (50%:50%) 40 nm | — |
| I20 | — | HTM1 70 nm | HIL1 5 nm | HTM5 90 nm | H4:TEG1 (85%:15%) 30 nm | — | H3:LiQ (50%:50%) 40 nm | — |
| I21 | — | HTM1 70 nm | HIL1 5 nm | HTM6 90 nm | H4:TEG1 (85%:15%) 30 nm | — | H3:LiQ (50%:50%) 40 nm | — |
| I22 | — | HTM1 70 nm | HIL1 5 nm | HTM7 90 nm | H4:TEG1 (85%:15%) 30 nm | — | H3:LiQ (50%:50%) 40 nm | — |
| I23 | — | HTM1 70 nm | HIL1 5 nm | HTM9 90 nm | H4:TEG1 (85%:15%) 30 nm | — | H3:LiQ (50%:50%) 40 nm | — |
| I24 | — | HTM1 70 nm | HIL1 5 nm | HTM10 90 nm | H4:TEG1 (85%:15%) 30 nm | — | H3:LiQ (50%:50%) 40 nm | — |
| I25 | — | HTM1 20 nm | — | HTM3 20 nm | H3:TER1 (85%:15%) 30 nm | — | Alq₃ 20 nm | LiF 1 nm |
| I26 | — | HTM1 20 nm | — | HTM3 20 nm | H3:CBP:TER1 (45%:45%:10%) 30 nm | H3 10 nm | Alq₃ 20 nm | LiF 1 nm |
| I27 | — | HTM1 70 nm | HIL1 5 nm | EBM1 90 nm | H3:H10:TEG1 (30%:60%:10%) 30 nm | H3 10 nm | H3:LiQ (50%:50%) 30 nm | — |
| I28 | HIL1 20 nm | — | — | EBM1 20 nm | Ket1:H10:TEG1 (60%:30%:10%) 30 nm | Ket1 10 nm | ETM2 20 nm | LiF 1 nm |
| I29 | — | HTM1 70 nm | HIL1 5 nm | EBM1 90 nm | DAP1:H10:TEG1 (30%:60%:10%) 30 nm | — | H3:LiQ (50%:50%) 30 nm | — |
| I30 | — | HTM1 70 nm | HIL1 5 nm | EBM1 90 nm | H3:H7:TEG1 (30%:60%:10%) 30 nm | H3 10 nm | H3:LiQ (50%:50%) 30 nm | — |
| I31 | HIL1 20 nm | — | — | EBM1 20 nm | Ket1:H7:TEG1 (60%:30%:10%) 30 nm | Ket1 10 nm | ETM2 20 nm | LiF 1 nm |
| I32 | — | HTM1 70 nm | HIL1 5 nm | EBM1 90 nm | DAP1:H7:TEG1 (30%:60%:10%) 30 nm | — | H3:LiQ (50%:50%) 30 nm | — |
| I33 | — | HTM1 70 nm | HIL1 5 nm | EBM1 90 nm | H3:H5:TEG1 (30%:60%:10%) 30 nm | H3 10 nm | H3:LiQ (50%:50%) 30 nm | — |
| I35 | — | HTM1 70 nm | HIL1 5 nm | EBM1 90 nm | H3:H8:TEG1 (30%:60%:10%) 30 nm | H3 10 nm | H3:LiQ (50%:50%) 30 nm | — |
| I36 | — | HTM1 70 nm | HIL1 5 nm | EBM1 90 nm | H3:H9:TEG1 (30%:60%:10%) 30 nm | H3 10 nm | H3:LiQ (50%:50%) 30 nm | — |
| I37 | — | HTM1 20 nm | — | NPB 20 nm | H3:H10:TER1 (45%:45%:10%) 30 nm | H3 10 nm | Alq₃ 20 nm | LiF 1 nm |
| I38 | — | HTM1 20 nm | — | NPB 20 nm | H3:H7:TER1 (45%:45%:10%) 30 nm | H3 10 nm | Alq₃ 20 nm | LiF 1 nm |
| I39 | — | HTM1 20 nm | — | NPB 20 nm | H3:H9:TER1 (45%:45%:10%) 30 nm | H3 10 nm | Alq₃ 20 nm | LiF 1 nm |
| I40 | HIL1 5 nm | HTM1 140 nm | — | HTM13 20 nm | H1:D1 (95%:5%) 30 nm | — | ETM1:LiQ (50%:50%) 20 nm | — |
| I41 | — | HTM1 70 nm | HIL1 5 nm | HTM13 90 nm | H4:TEG1 (85%:15%) 30 nm | — | H3:LiQ (50%:50%) 40 nm | — |
| I42 | HIL1 5 nm | HTM1 140 nm | — | HTM14 20 nm | H1:D1 (95%:5%) 30 nm | — | ETM1:LiQ (50%:50%) 20 nm | — |
| I43 | — | HTM1 70 nm | HIL1 5 nm | HTM14 90 nm | H4:TEG1 (85%:15%) 30 nm | — | H3:LiQ (50%:50%) 40 nm | — |
| I44 | — | HTM1 70 nm | HIL1 5 nm | HTM15 90 nm | H4:TEG1 (85%:15%) 30 nm | — | H3:LiQ (50%:50%) 40 nm | — |
| I45 | HIL1 5 nm | HTM17 110 nm | — | NPB 20 nm | H2:D2 (90%:10%) 30 nm | — | Alq₃ 20 nm | LiF 1 nm |
| I46 | — | HTM1 70 nm | HIL1 5 nm | HTM18 90 nm | H4:TEG1 (85%:15%) 30 nm | — | H3:LiQ (50%:50%) 40 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| I47 | HIL1 5 nm | HTM19 110 nm | — | NPB 20 nm | H2:D2 (90%:10%) 30 nm | — | Alq$_3$ 20 nm | LiF 1 nm |
| I48 | HIL1 5 nm | HTM1 140 nm | — | HTM20 20 nm | H1:D1 (95%:5%) 30 nm | — | ETM1:LiQ (50%:50%) 20 nm | — |
| I49 | HIL1 5 nm | HTM1 110 nm | — | HTM20 20 nm | H2:D2 (90%:10%) 30 nm | — | Alq$_3$ 20 nm | LiF 1 nm |
| I50 | — | HTM1 70 nm | HIL1 5 nm | HTM21 90 nm | H4:TEG1 (85%:15%) 30 nm | — | H3:LiQ (50%:50%) 40 nm | — |
| I51 | — | HTM1 70 nm | HIL1 5 nm | HTM22 90 nm | H4:TEG1 (85%:15%) 30 nm | — | H3:LiQ (50%:50%) 40 nm | — |
| I52 | — | HTM1 70 nm | HIL1 5 nm | HTM23 90 nm | H4:TEG1 (85%:15%) 30 nm | — | H3:LiQ (50%:50%) 40 nm | — |
| I53 | — | HTM1 70 nm | HIL1 5 nm | HTM24 90 nm | H4:TEG1 (85%:15%) 30 nm | — | H3:LiQ (50%:50%) 40 nm | — |
| I54 | HIL1 5 nm | HTM25 110 nm | — | NPB 20 nm | H2:D2 (90%:10%) 30 nm | — | Alq$_3$ 20 nm | LiF 1 nm |
| I55 | HIL1 5 nm | HTM1 110 nm | — | HTM26 20 nm | H2:D2 (90%:10%) 30 nm | — | Alq$_3$ 20 nm | LiF 1 nm |
| I56 | — | HTM1 70 nm | HIL1 5 nm | EBM1 90 nm | H3:H11:TEG1 (30%:60%:10%) 30 nm | H3 10 nm | H3:LiQ (50%:50%) 30 nm | — |
| I57 | — | HTM1 70 nm | HIL1 5 nm | HTM16 90 nm | H4:TEG1 (85%:15%) 30 nm | — | H3:LiQ (50%:50%) 40 nm | — |
| I58 | — | HTM1 70 nm | HIL1 5 nm | EBM1 90 nm | H3:H12:TEG1 (30%:60%:10%) 30 nm | H3 10 nm | H3:LiQ (50%:50%) 30 nm | — |
| I60 | — | HTM1 70 nm | HIL1 5 nm | EBM1 90 nm | H3:H14:TEG1 (30%:60%:10%) 30 nm | H3 10 nm | H3:LiQ (50%:50%) 30 nm | — |
| I62 | — | HTM1 20 nm | — | NPB 20 nm | H3:H16:TER1 (45%:45%:10%) 30 nm | H3 10 nm | Alq$_3$ 20 nm | LiF 1 nm |
| I63 | — | HTM1 20 nm | — | NPB 20 nm | H3:H17:TER1 (45%:45%:10%) 30 nm | H3 10 nm | Alq$_3$ 20 nm | LiF 1 nm |

TABLE 2

Data of the OLEDs

| Ex. | Voltage for 1000 cd/m$^2$ | Efficiency at 1000 cd/m$^2$ | Efficiency at 1000 cd/m$^2$ | EQE at 1000 cd/m$^2$ | CIE x/y at 1000 cd/m$^2$ | LD80 from 4000 cd/m$^2$ |
|---|---|---|---|---|---|---|
| C1 | 6.4 V | 5.1 cd/A | 2.5 lm/W | 4.2% | 0.14/0.15 | 5500 h |
| C2 | 4.7 V | 8.1 cd/A | 5.4 lm/W | 6.3% | 0.14/0.16 | 5200 h |
| C3 | 5.0 V | 17.1 cd/A | 10.7 lm/W | 5.0% | 0.28/0.61 | 300000 h |
| C4 | 5.0 V | 7.2 cd/A | 4.5 lm/W | 12.0% | 0.69/0.31 | 14000 h |
| C5 | 5.5 V | 15.9 cd/A | 9.1 lm/W | 4.8% | 0.31/0.58 | 250000 h |
| C6 | 5.2 V | 8.1 cd/A | 4.9 lm/W | 11.4% | 0.68/0.32 | 15000 h |
| C19 | 5.2 V | 16.8 cd/A | 10.1 lm/W | 4.9% | 0.28/0.61 | 280000 h |
| C20 | 5.7 V | 15.5 cd/A | 8.5 lm/W | 4.7% | 0.31/0.58 | 220000 h |
| I1 | 4.8 V | 18.5 cd/A | 12.1 lm/W | 5.4% | 0.28/0.61 | 330000 h |
| I2 | 5.1 V | 17.2 cd/A | 10.6 lm/W | 5.2% | 0.30/0.59 | 340000 h |
| I3 | 5.8 V | 5.8 cd/A | 3.2 lm/W | 4.8% | 0.14/0.15 | 7800 h |
| I4 | 4.4 V | 8.8 cd/A | 6.3 lm/W | 6.8% | 0.14/0.15 | 7700 h |
| I5 | 4.7 V | 19.5 cd/A | 13.0 lm/W | 5.7% | 0.28/0.61 | 380000 h |
| I6 | 5.2 V | 18.2 cd/A | 11.0 lm/W | 5.5% | 0.31/0.58 | 350000 h |
| I7 | 6.0 V | 5.7 cd/A | 3.0 lm/W | 4.7% | 0.14/0.15 | 7100 h |
| I8 | 4.7 V | 8.5 cd/A | 5.7 lm/W | 6.6% | 0.14/0.15 | 6700 h |
| I9 | 4.8 V | 19.1 cd/A | 12.5 lm/W | 5.6% | 0.28/0.61 | 340000 h |
| I10 | 4.7 V | 8.0 cd/A | 5.3 lm/W | 6.2% | 0.14/0.16 | 6700 h |
| I11 | 4.6 V | 8.3 cd/A | 5.7 lm/W | 6.5% | 0.14/0.16 | 6300 h |
| I12 | 4.2 V | 9.1 cd/A | 6.8 lm/W | 7.0% | 0.14/0.15 | 7900 h |
| I25 | 4.9 V | 7.5 cd/A | 4.8 lm/W | 12.5% | 0.69/0.31 | 21000 h |
| I26 | 5.1 V | 8.3 cd/A | 5.1 lm/W | 11.6% | 0.68/0.32 | 21000 h |
| I37 | 4.1 V | 9.6 cd/A | 7.4 lm/W | 13.3% | 0.68/0.32 | 29000 h |
| I38 | 4.0 V | 9.2 cd/A | 7.2 lm/W | 12.8% | 0.68/0.32 | 27000 h |
| I39 | 4.0 V | 9.3 cd/A | 7.3 lm/W | 13.0% | 0.68/0.32 | 24000 h |
| I40 | 4.6 V | 9.0 cd/A | 6.1 lm/W | 7.0% | 0.14/0.15 | 6500 h |
| I42 | 4.6 V | 8.7 cd/A | 6.0 lm/W | 6.7% | 0.14/0.16 | 7200 h |
| I45 | 5.1 V | 18.5 cd/A | 11.3 lm/W | 5.4% | 0.28/0.61 | 280000 h |
| I47 | 4.9 V | 17.5 cd/A | 11.1 lm/W | 5.1% | 0.28/0.61 | 310000 h |
| I48 | 4.8 V | 8.5 cd/A | 5.6 lm/W | 6.6% | 0.14/0.16 | 6700 h |
| I49 | 5.0 V | 17.8 cd/A | 11.2 lm/W | 5.2% | 0.28/0.61 | 340000 h |
| I54 | 5.0 V | 18.0 cd/A | 11.3 lm/W | 5.3% | 0.28/0.61 | 320000 h |
| I55 | 4.9 V | 18.8 cd/A | 11.9 lm/W | 5.5% | 0.28/0.61 | 340000 h |

TABLE 2-continued

Data of the OLEDs

| Ex. | Voltage for 1000 cd/m² | Efficiency at 1000 cd/m² | Efficiency at 1000 cd/m² | EQE at 1000 cd/m² | CIE x/y at 1000 cd/m² | LD80 from 4000 cd/m² |
| --- | --- | --- | --- | --- | --- | --- |
| I62 | 4.2 V | 8.7 cd/A | 6.5 lm/W | 12.2% | 0.68/0.32 | 19000 h |
| I63 | 4.4 V | 7.7 cd/A | 5.5 lm/W | 10.8% | 0.68/0.32 | 16000 h |

TABLE 3

Data of the OLEDs

| Ex. | Voltage for 1000 cd/m² | Efficiency at 1000 cd/m² | Efficiency at 1000 cd/m² | EQE at 1000 cd/m² | CIE x/y at 1000 cd/m² | LD50 from 1000 cd/m² |
| --- | --- | --- | --- | --- | --- | --- |
| C7 | 4.7 V | 55 cd/A | 37 lm/W | 15.4% | 0.36/0.61 | 350 h |
| C8 | 4.6 V | 54 cd/A | 37 lm/W | 15.0% | 0.37/0.60 | 320 h |
| C9 | 3.6 V | 52 cd/A | 45 lm/W | 14.6% | 0.37/0.60 | 430 h |
| C10 | 4.4 V | 48 cd/A | 34 lm/W | 13.3% | 0.37/0.60 | 450 h |
| C11 | 4.4 V | 54 cd/A | 39 lm/W | 15.0% | 0.36/0.60 | 320 h |
| C12 | 4.3 V | 55 cd/A | 40 m/W | 15.3% | 0.37/0.61 | 300 h |
| C14 | 4.0 V | 46 cd/A | 36 lm/W | 12.8% | 0.36/0.61 | 430 h |
| C15 | 3.9 V | 42 cd/A | 34 lm/W | 11.6% | 0.35/0.60 | 160 h |
| C16 | 4.1 V | 44 cd/A | 34 lm/W | 12.3% | 0.36/0.61 | 320 h |
| C17 | 4.6 V | 47 cd/A | 32 lm/W | 13.2% | 0.36/0.60 | 480 h |
| C18 | 4.2 V | 43 cd/A | 32 lm/W | 12.0% | 0.35/0.60 | 190 h |
| C21 | 3.6 V | 55 cd/A | 48 lm/W | 15.5% | 0.37/0.60 | 450 h |
| C22 | 3.9 V | 46 cd/A | 38 lm/W | 12.9% | 0.36/0.60 | 360 h |
| I13 | 4.7 V | 61 cd/A | 41 lm/W | 17.0% | 0.36/0.61 | 460 h |
| I14 | 4.5 V | 59 cd/A | 41 lm/W | 16.4% | 0.37/0.60 | 440 h |
| I15 | 3.7 V | 56 cd/A | 48 lm/W | 15.7% | 0.37/0.60 | 670 h |
| I16 | 4.4 V | 63 cd/A | 45 lm/W | 17.5% | 0.36/0.61 | 510 h |
| I17 | 4.5 V | 61 cd/A | 43 lm/W | 16.9% | 0.37/0.61 | 500 h |
| I18 | 3.9 V | 62 cd/A | 50 lm/W | 17.4% | 0.37/0.60 | 570 h |
| I19 | 3.7 V | 64 cd/A | 54 lm/W | 17.9% | 0.36/0.60 | 520 h |
| I20 | 4.0 V | 60 cd/A | 47 lm/W | 16.7% | 0.37/0.60 | 540 h |
| I21 | 3.7 V | 65 cd/A | 52 lm/W | 18.2% | 0.37/0.60 | 550 h |
| I22 | 3.7 V | 58 cd/A | 49 lm/W | 16.3% | 0.36/0.60 | 490 h |
| I23 | 3.8 V | 56 cd/A | 46 lm/W | 15.7% | 0.36/0.61 | 470 h |
| I24 | 3.5 V | 57 cd/A | 51 lm/W | 16.0% | 0.36/0.60 | 510 h |
| I27 | 3.2 V | 56 cd/A | 55 lm/W | 15.8% | 0.36/0.61 | 710 h |
| I28 | 3.1 V | 49 cd/A | 50 lm/W | 13.8% | 0.36/0.61 | 630 h |
| I29 | 4.0 V | 46 cd/A | 36 lm/W | 12.9% | 0.36/0.60 | 640 h |
| I30 | 3.3 V | 54 cd/A | 52 lm/W | 15.2% | 0.36/0.61 | 680 h |
| I31 | 3.1 V | 50 cd/A | 51 lm/W | 13.9% | 0.36/0.61 | 590 h |
| I32 | 4.1 V | 48 cd/A | 37 lm/W | 13.5% | 0.36/0.60 | 620 h |
| I33 | 3.3 V | 56 cd/A | 53 lm/W | 15.7% | 0.36/0.61 | 640 h |
| I35 | 3.3 V | 54 cd/A | 52 lm/W | 15.3% | 0.36/0.61 | 660 h |
| I36 | 3.5 V | 50 cd/A | 45 lm/W | 14.0% | 0.36/0.61 | 620 h |
| I41 | 3.9 V | 60 cd/A | 49 lm/W | 16.7% | 0.36/0.60 | 640 h |
| I43 | 3.8 V | 56 cd/A | 46 lm/W | 15.5% | 0.36/0.60 | 610 h |
| I44 | 3.6 V | 61 cd/A | 53 lm/W | 16.8% | 0.36/0.60 | 520 h |
| I46 | 3.8 V | 60 cd/A | 49 lm/W | 16.5% | 0.36/0.60 | 650 h |
| I50 | 3.8 V | 62 cd/A | 51 lm/W | 17.2% | 0.36/0.60 | 500 h |
| I51 | 3.8 V | 63 cd/A | 52 lm/W | 17.4% | 0.36/0.60 | 560 h |
| I52 | 3.7 V | 60 cd/A | 50 lm/W | 16.6% | 0.36/0.60 | 510 h |
| I53 | 3.9 V | 55 cd/A | 45 lm/W | 15.3% | 0.36/0.60 | 450 h |
| I56 | 3.7 V | 49 cd/A | 42 lm/W | 13.7% | 0.37/0.61 | 540 h |
| I57 | 4.0 V | 57 cd/A | 45 lm/W | 15.8% | 0.37/0.60 | 420 h |
| I58 | 3.4 V | 54 cd/A | 49 lm/W | 14.8% | 0.36/0.61 | 710 h |
| I60 | 3.8 V | 51 cd/A | 42 lm/W | 14.0% | 0.37/0.61 | 660 h |

TABLE 4
Structural formulae of the materials used
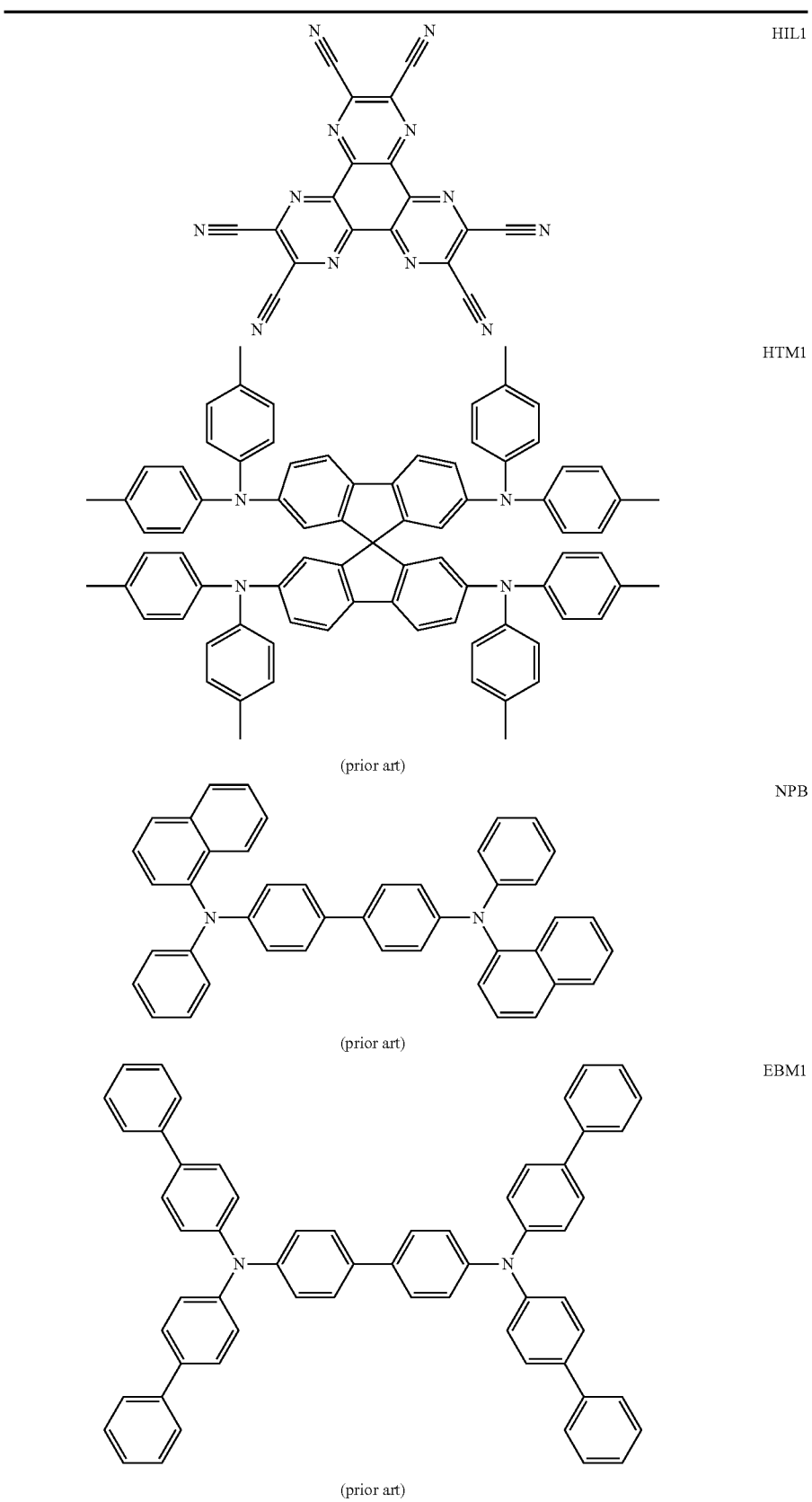
HIL1
HTM1
(prior art)
NPB
(prior art)
EBM1
(prior art)

TABLE 4-continued
Structural formulae of the materials used
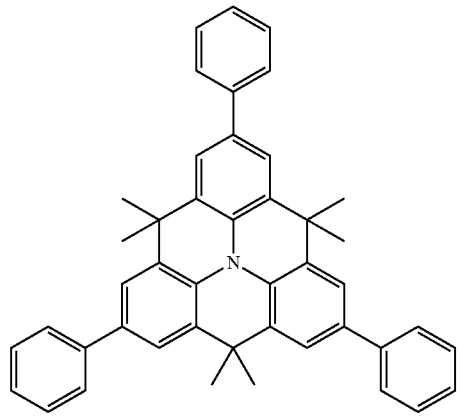
HTM11
(prior art)
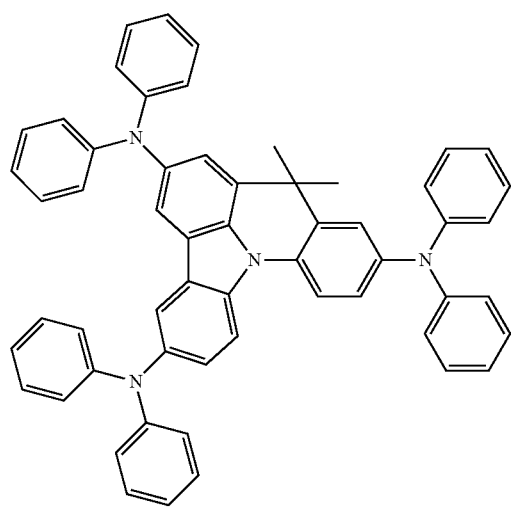
HTM12
(prior art)
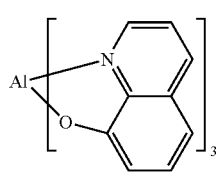
Alq₃
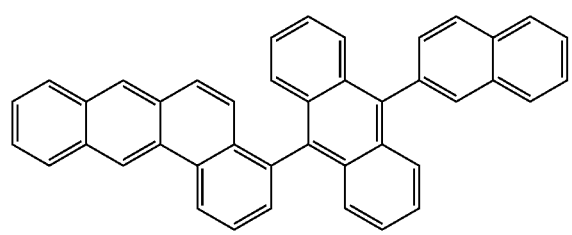 [SMILES: c1ccc2cc(-c3c4ccccc4c(-c4cccc5c4ccc4cc6ccccc6cc45)c4ccccc34)ccc2c1]
H1

TABLE 4-continued
Structural formulae of the materials used
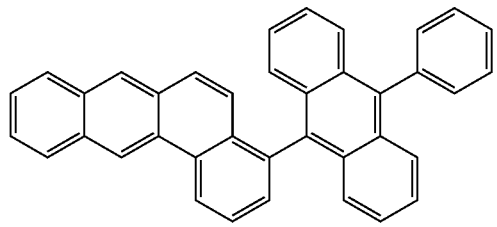 [SMILES: c1ccc(-c2c3ccccc3c(-c3cccc4c3ccc3cc5ccccc5cc34)c3ccccc23)cc1]
H2
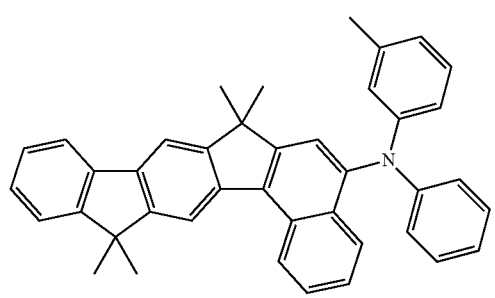 [SMILES: Cc1cccc(N(c2ccccc2)c2cc3c(c4ccccc24)-c2cc4c(cc2C3(C)C)-c2ccccc2C4(C)C)c1]
D1
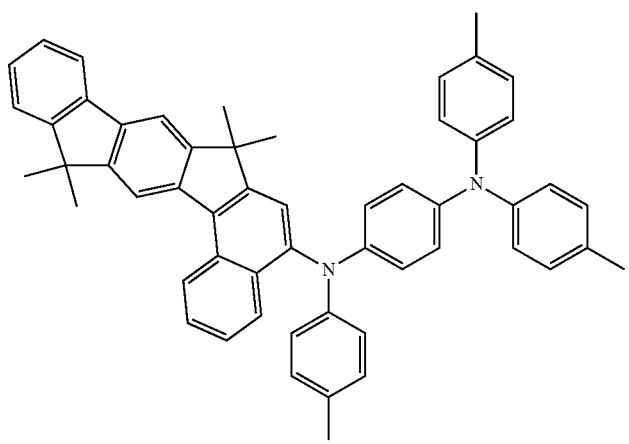 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
D2
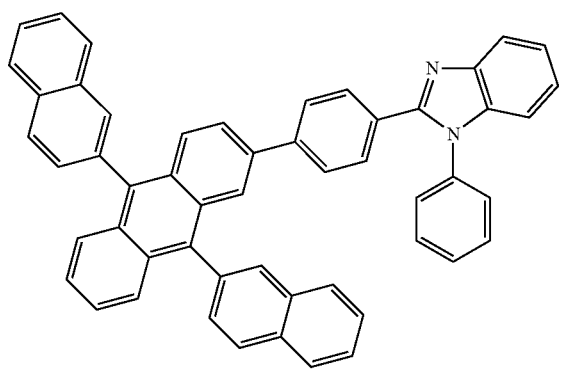 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1

TABLE 4-continued
Structural formulae of the materials used
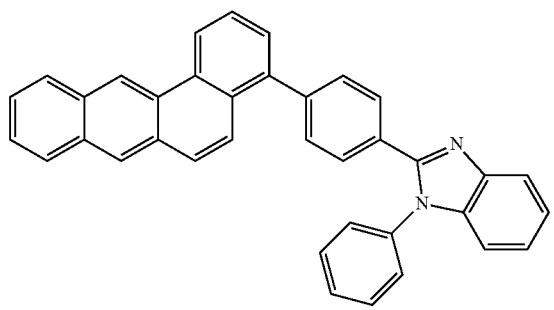 [SMILES: c1ccc(-n2c(-c3ccc(-c4cccc5c4ccc4cc6ccccc6cc45)cc3)nc3ccccc32)cc1]
ETM2
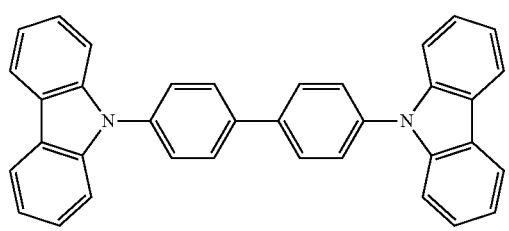
CBP
(prior art)
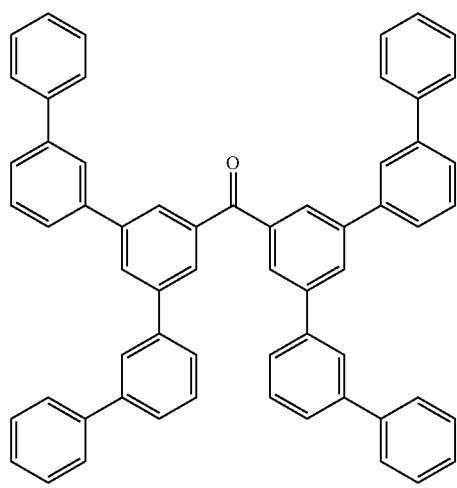 [SMILES: O=C(c1cc(-c2cccc(-c3ccccc3)c2)cc(-c2cccc(-c3ccccc3)c2)c1)c1cc(-c2cccc(-c3ccccc3)c2)cc(-c2cccc(-c3ccccc3)c2)c1]
Ket1
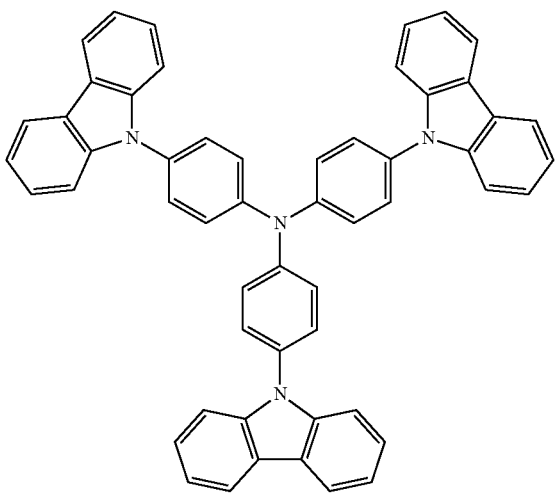
TCTA
(prior art)

TABLE 4-continued
Structural formulae of the materials used
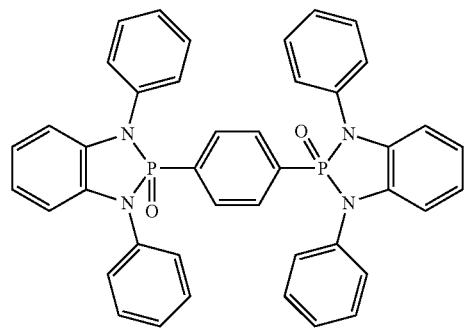 [SMILES: O=P1(c2ccc(P3(=O)N(c4ccccc4)c4ccccc4N3c3ccccc3)cc2)N(c2ccccc2)c2ccccc2N1c1ccccc1]
DAP1
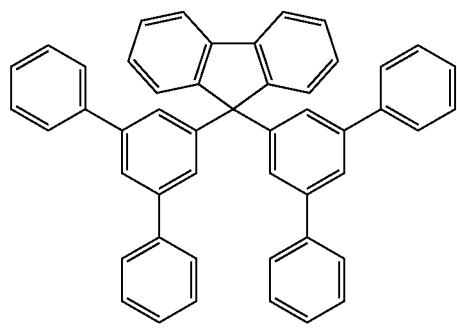
FTPh
(prior art)
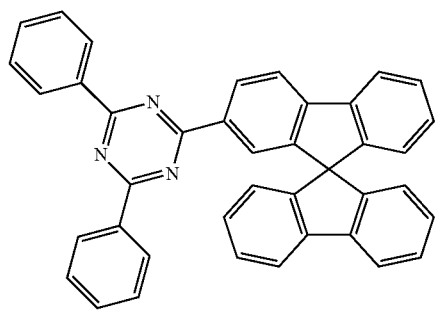 [SMILES: c1ccc(-c2nc(-c3ccccc3)nc(-c3ccc4c(c3)C3(c5ccccc5-c5ccccc53)c3ccccc3-4)n2)cc1]
H3
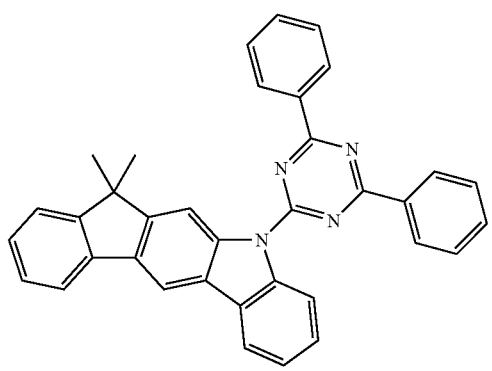 [SMILES: CC1(C)c2ccccc2-c2cc3c4ccccc4n(-c4nc(-c5ccccc5)nc(-c5ccccc5)n4)c3cc21]
H4
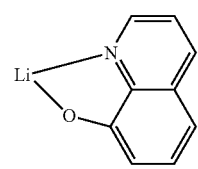
LiQ TABLE 4-continued
Structural formulae of the materials used
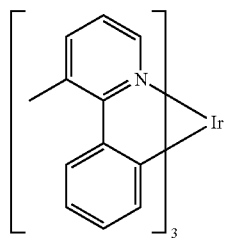
TEG1
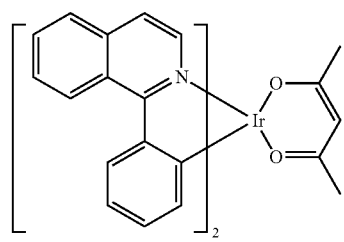
TER1
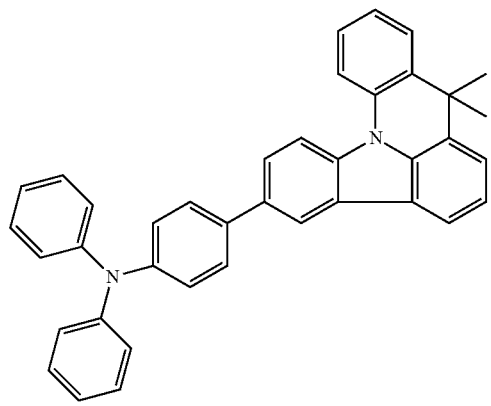 [SMILES: CC1(C)c2ccccc2-n2c3ccc(-c4ccc(N(c5ccccc5)c5ccccc5)cc4)cc3c3cccc1c32]
HTM2
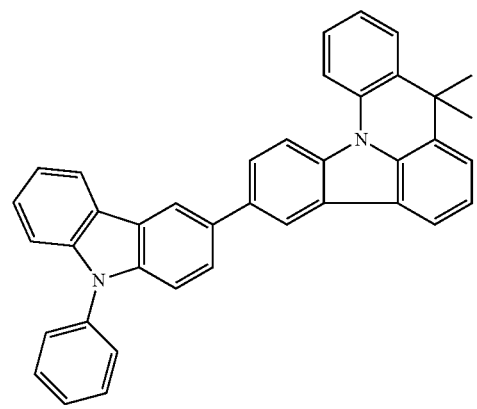 [SMILES: CC1(C)c2ccccc2-n2c3ccc(-c4ccc5c(c4)c4ccccc4n5-c4ccccc4)cc3c3cccc1c32]
H5

TABLE 4-continued
Structural formulae of the materials used
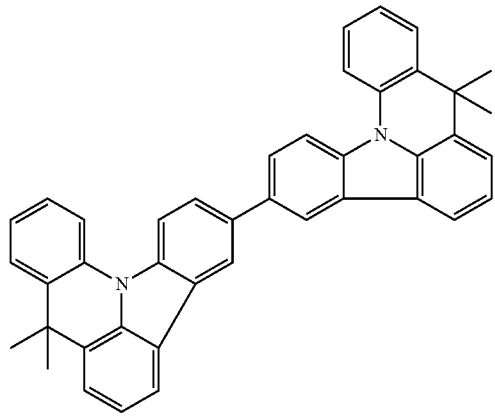 [SMILES: CC1(C)c2ccccc2-n2c3ccc(-c4ccc5c(c4)c4cccc6c4n5-c4ccccc4C6(C)C)cc3c3cccc1c32]
H7
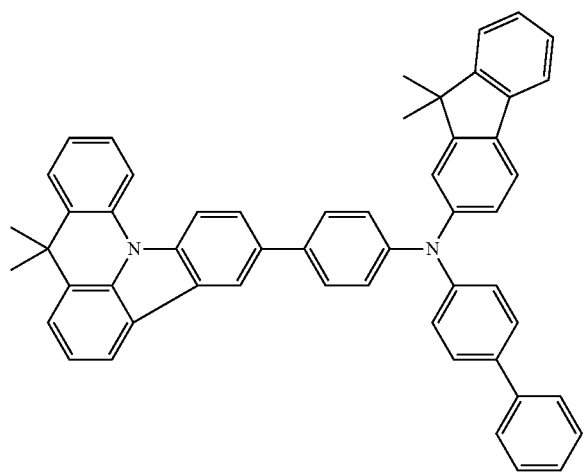 [SMILES: CC1(C)c2ccccc2-c2ccc(N(c3ccc(-c4ccccc4)cc3)c3ccc(-c4ccc5c(c4)c4cccc6c4n5-c4ccccc4C6(C)C)cc3)cc21]
HTM3
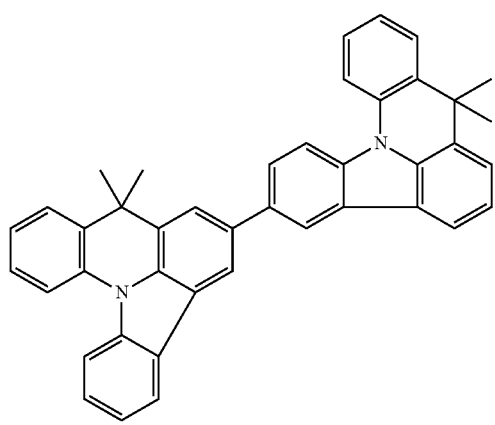 [SMILES: CC1(C)c2ccccc2-n2c3ccc(-c4cc5c6c(c4)c4ccccc4n6-c4ccccc4C5(C)C)cc3c3cccc1c32]
H8

TABLE 4-continued
Structural formulae of the materials used
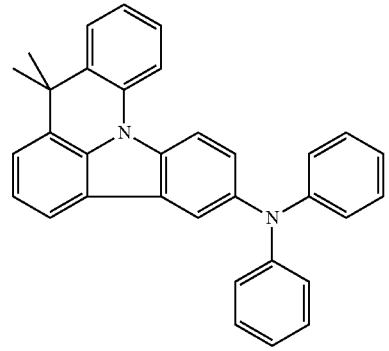 [SMILES: CC1(C)c2ccccc2-n2c3ccc(N(c4ccccc4)c4ccccc4)cc3c3cccc1c32]
HTM4
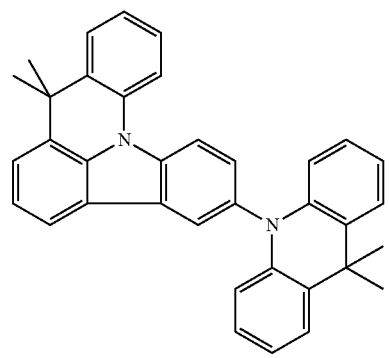 [SMILES: CC1(C)c2ccccc2N(c2ccc3c(c2)c2cccc4c2n3-c2ccccc2C4(C)C)c2ccccc21]
HTM5
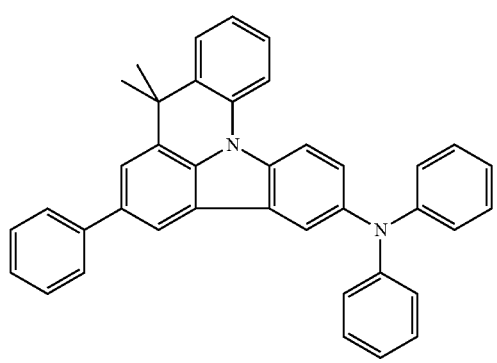 [SMILES: CC1(C)c2ccccc2-n2c3ccc(N(c4ccccc4)c4ccccc4)cc3c3cc(-c4ccccc4)cc1c32]
HTM6
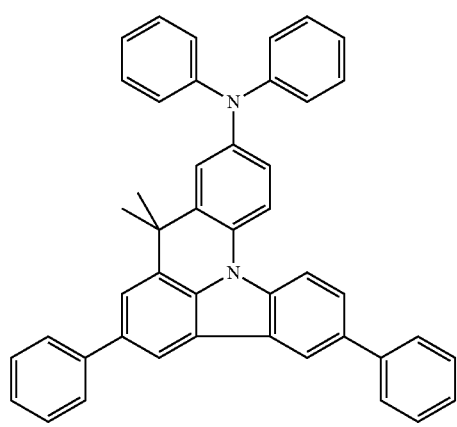 [SMILES: CC1(C)c2cc(N(c3ccccc3)c3ccccc3)ccc2-n2c3ccc(-c4ccccc4)cc3c3cc(-c4ccccc4)cc1c32]
HTM7

TABLE 4-continued
Structural formulae of the materials used
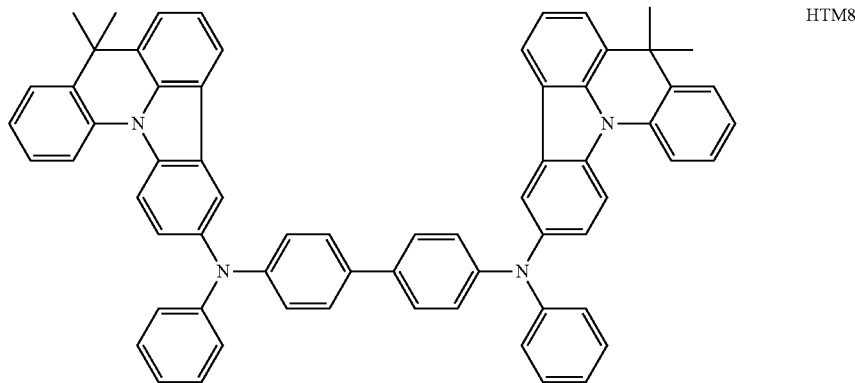
HTM8
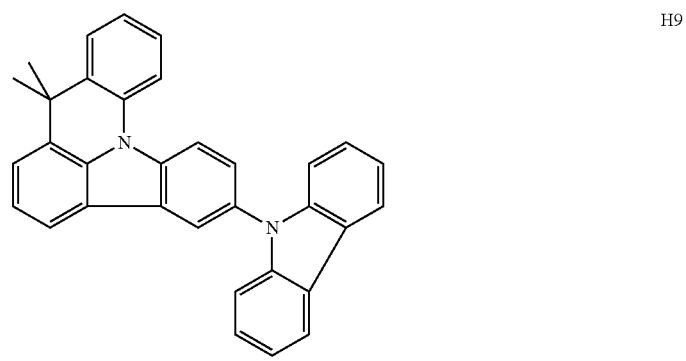
H9
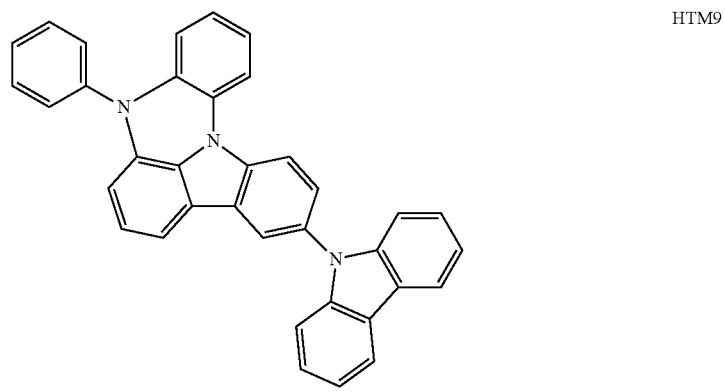
HTM9
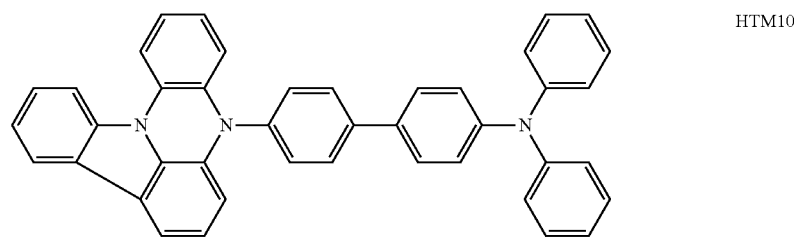
HTM10

TABLE 4-continued
Structural formulae of the materials used
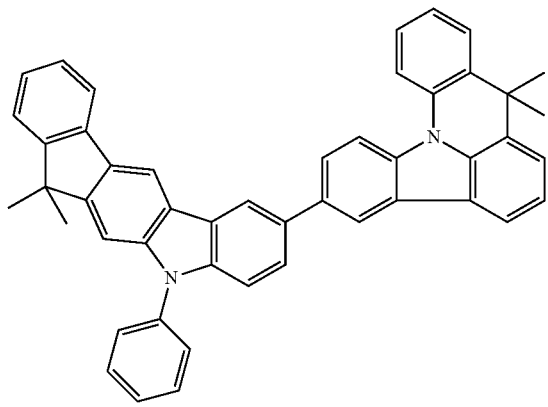
H10
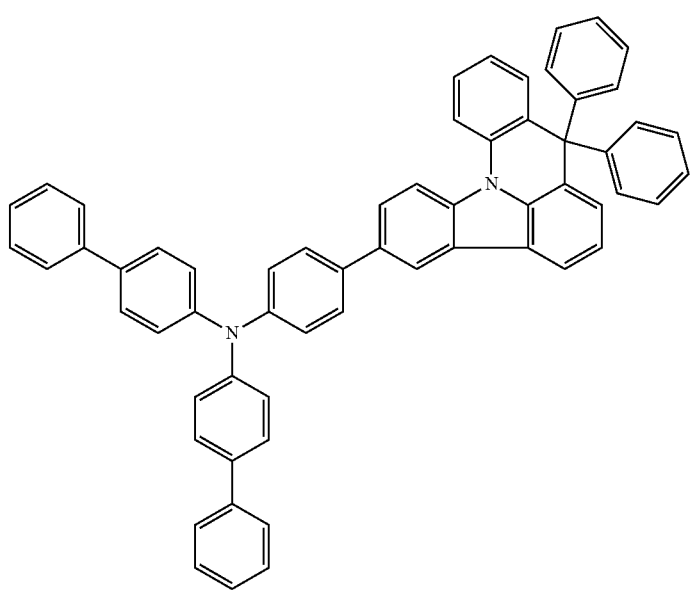 [SMILES: c1ccc(-c2ccc(N(c3ccc(-c4ccccc4)cc3)c3ccc(-c4ccc5c(c4)c4cccc6c4n5-c4ccccc4C6(c4ccccc4)c4ccccc4)cc3)cc2)cc1]
HTM13
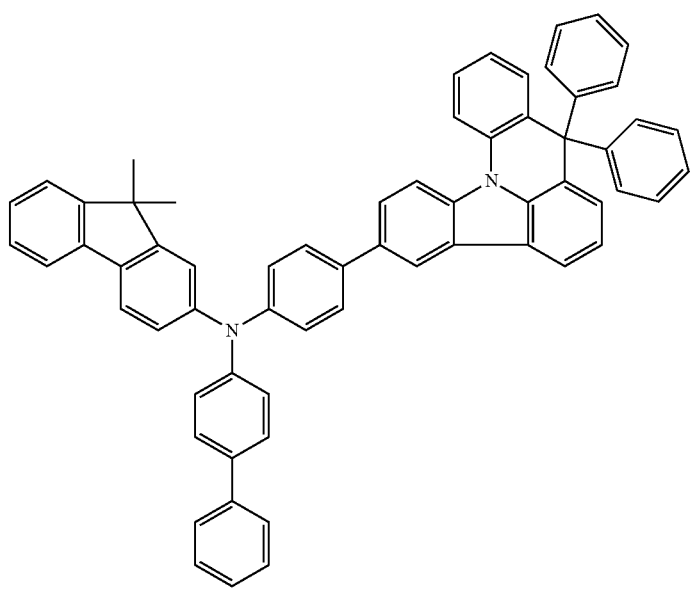 [SMILES: CC1(C)c2ccccc2-c2ccc(N(c3ccc(-c4ccccc4)cc3)c3ccc(-c4ccc5c(c4)c4cccc6c4n5-c4ccccc4C6(c4ccccc4)c4ccccc4)cc3)cc21]
HTM14

TABLE 4-continued
Structural formulae of the materials used
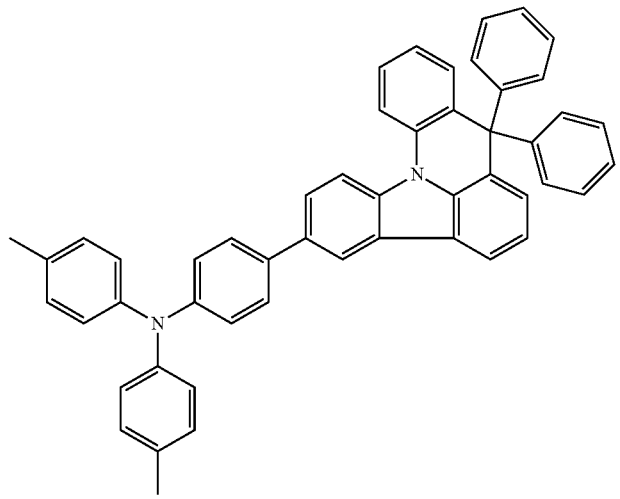 [SMILES: Cc1ccc(N(c2ccc(C)cc2)c2ccc(-c3ccc4c(c3)c3cccc5c3n4-c3ccccc3C5(c3ccccc3)c3ccccc3)cc2)cc1]
HTM15
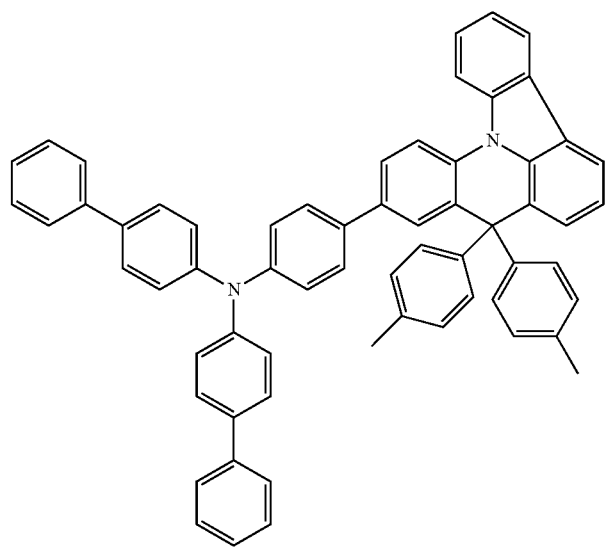 [SMILES: Cc1ccc(C2(c3ccc(C)cc3)c3cc(-c4ccc(N(c5ccc(-c6ccccc6)cc5)c5ccc(-c6ccccc6)cc5)cc4)ccc3-n3c4ccccc4c4cccc2c43)cc1]
HTM16
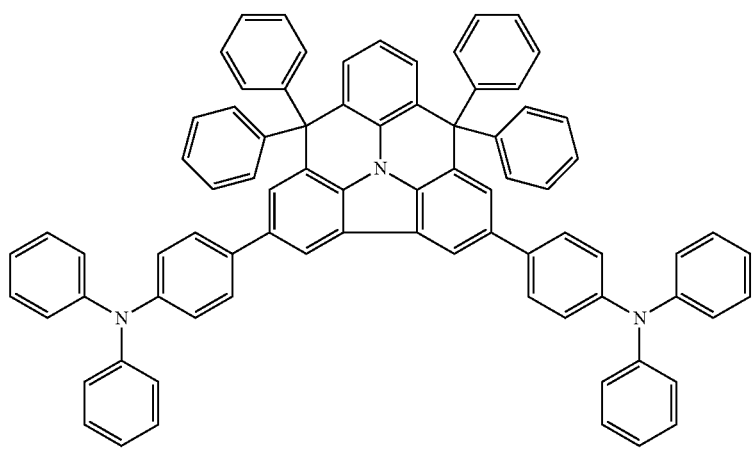 [SMILES: c1ccc(N(c2ccccc2)c2ccc(-c3cc4c5c(c3)c3cc(-c6ccc(N(c7ccccc7)c7ccccc7)cc6)cc6c3n5-c3c(cccc3C6(c3ccccc3)c3ccccc3)C4(c3ccccc3)c3ccccc3)cc2)cc1]
HTM17

TABLE 4-continued
Structural formulae of the materials used
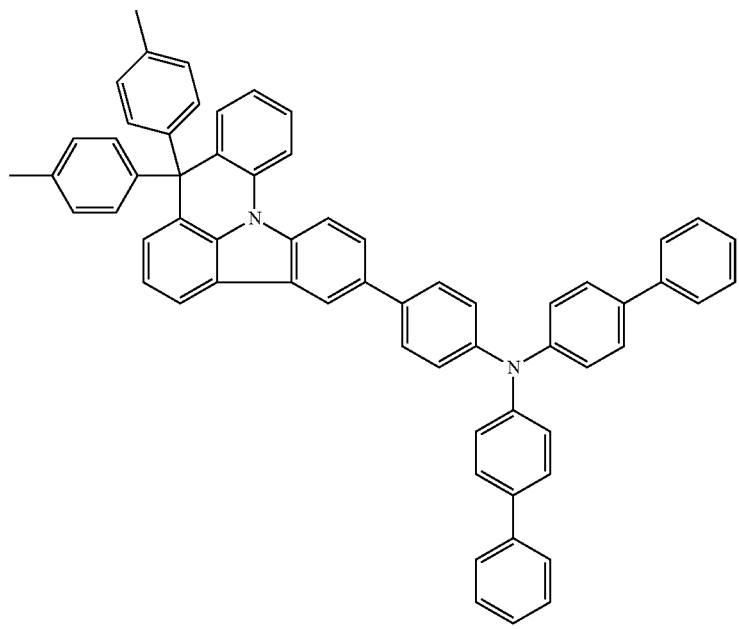 [SMILES: Cc1ccc(C2(c3ccc(C)cc3)c3ccccc3-n3c4ccc(-c5ccc(N(c6ccc(-c7ccccc7)cc6)c6ccc(-c7ccccc7)cc6)cc5)cc4c4cccc2c43)cc1]
HTM18
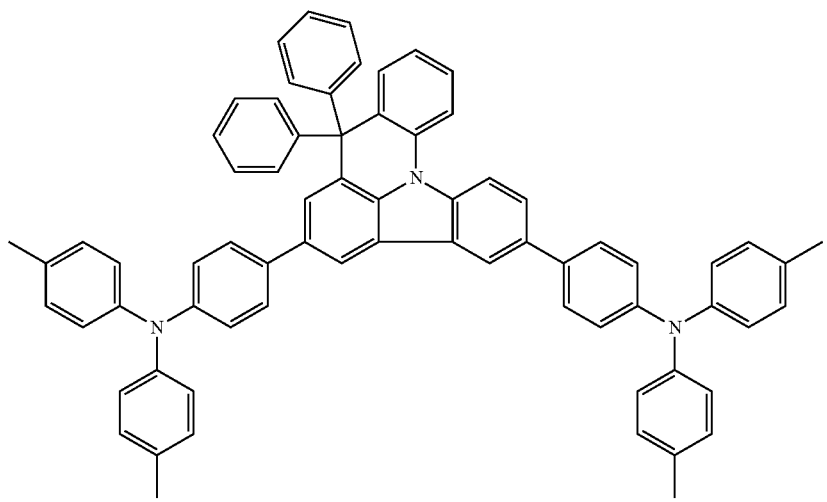
HTM19
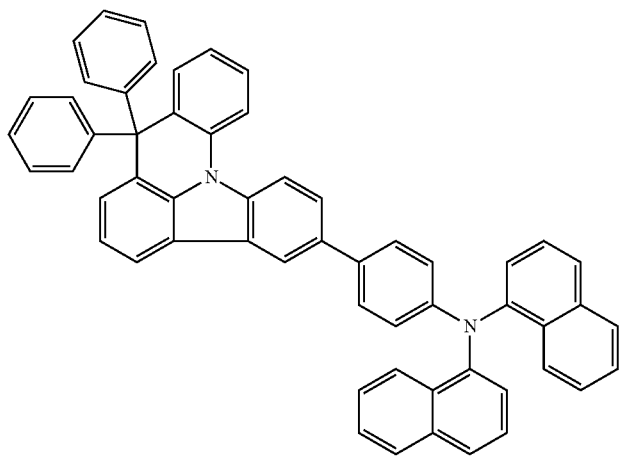 [SMILES: c1ccc(C2(c3ccccc3)c3ccccc3-n3c4ccc(-c5ccc(N(c6cccc7ccccc67)c6cccc7ccccc67)cc5)cc4c4cccc2c43)cc1]
HTM20

TABLE 4-continued
Structural formulae of the materials used
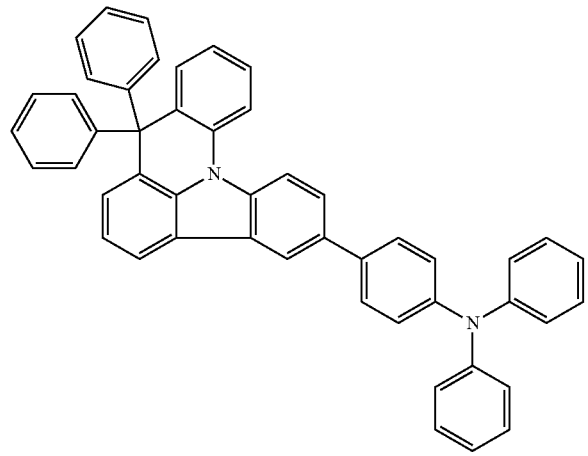 [SMILES: c1ccc(N(c2ccccc2)c2ccc(-c3ccc4c(c3)c3cccc5c3n4-c3ccccc3C5(c3ccccc3)c3ccccc3)cc2)cc1]
HTM21
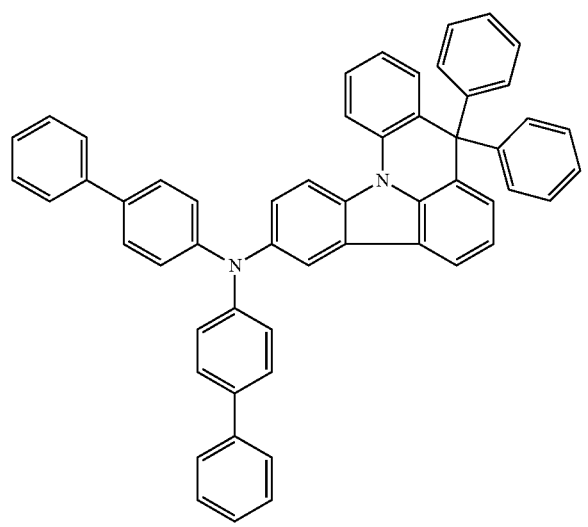 [SMILES: c1ccc(-c2ccc(N(c3ccc(-c4ccccc4)cc3)c3ccc4c(c3)c3cccc5c3n4-c3ccccc3C5(c3ccccc3)c3ccccc3)cc2)cc1]
HTM22
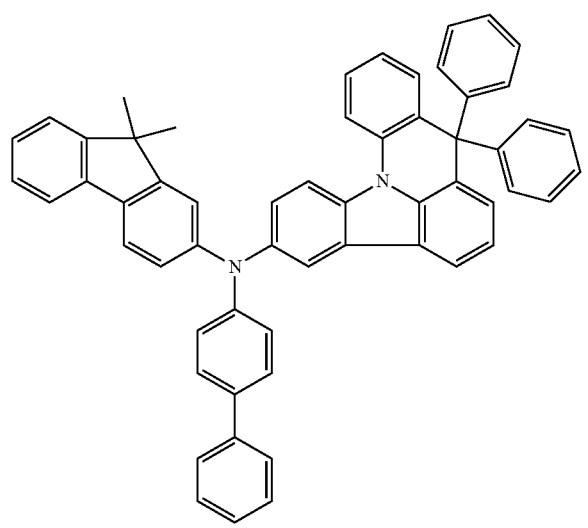 [SMILES: CC1(C)c2ccccc2-c2ccc(N(c3ccc(-c4ccccc4)cc3)c3ccc4c(c3)c3cccc5c3n4-c3ccccc3C5(c3ccccc3)c3ccccc3)cc21]
HTM23

TABLE 4-continued
Structural formulae of the materials used
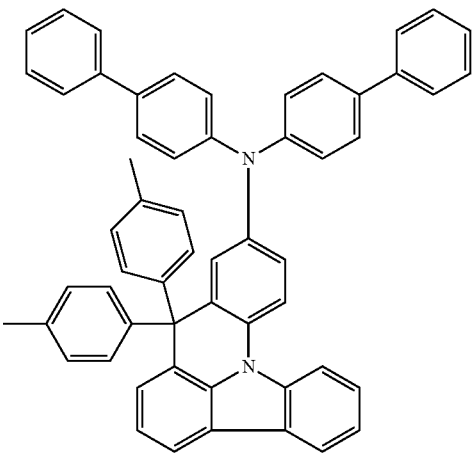 [SMILES: Cc1ccc(C2(c3ccc(C)cc3)c3cc(N(c4ccc(-c5ccccc5)cc4)c4ccc(-c5ccccc5)cc4)ccc3-n3c4ccccc4c4cccc2c43)cc1]
HTM24
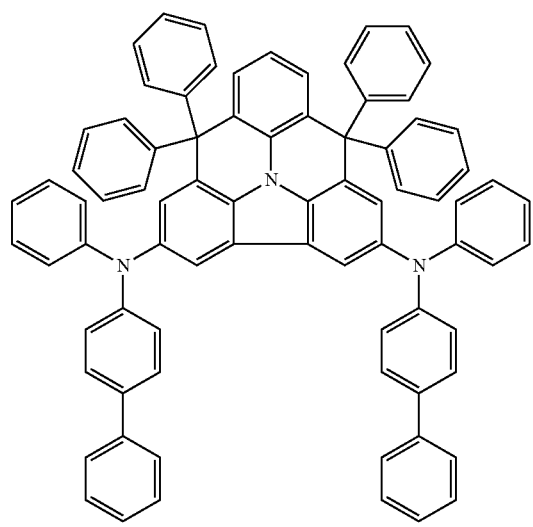 [SMILES: c1ccc(-c2ccc(N(c3ccccc3)c3cc4c5c(c3)c3cc(N(c6ccccc6)c6ccc(-c7ccccc7)cc6)cc6c3n5-c3c(cccc3C6(c3ccccc3)c3ccccc3)C4(c3ccccc3)c3ccccc3)cc2)cc1]
HTM25
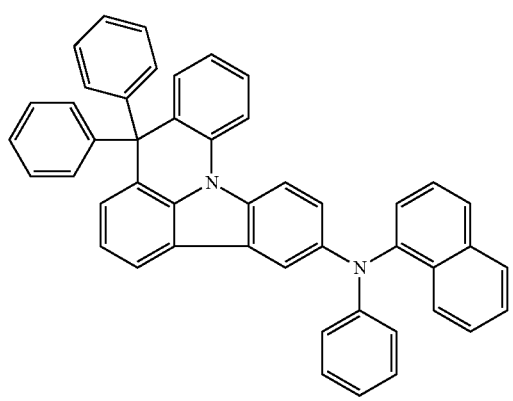 [SMILES: c1ccc(N(c2ccc3c(c2)c2cccc4c2n3-c2ccccc2C4(c2ccccc2)c2ccccc2)c2cccc3ccccc23)cc1]
HTM26

TABLE 4-continued
Structural formulae of the materials used
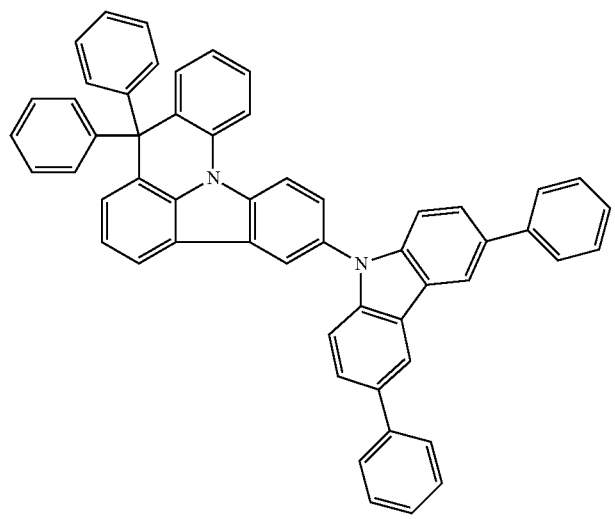 [SMILES: c1ccc(-c2ccc3c(c2)c2cc(-c4ccccc4)ccc2n3-c2ccc3c(c2)c2cccc4c2n3-c2ccccc2C4(c2ccccc2)c2ccccc2)cc1]
H11
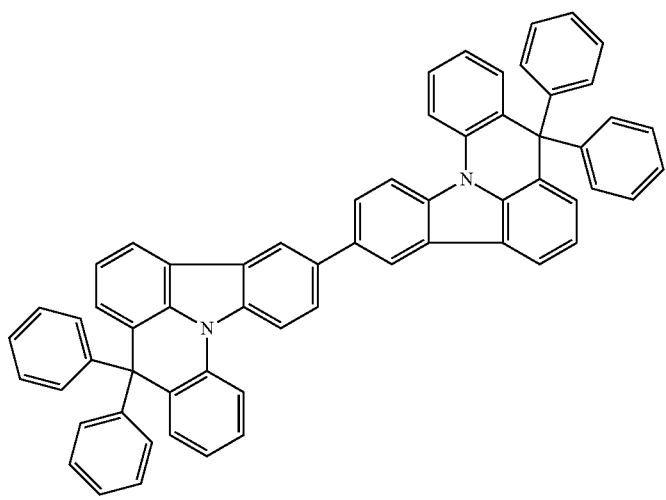 [SMILES: c1ccc(C2(c3ccccc3)c3ccccc3-n3c4ccc(-c5ccc6c(c5)c5cccc7c5n6-c5ccccc5C7(c5ccccc5)c5ccccc5)cc4c4cccc2c43)cc1]
H12
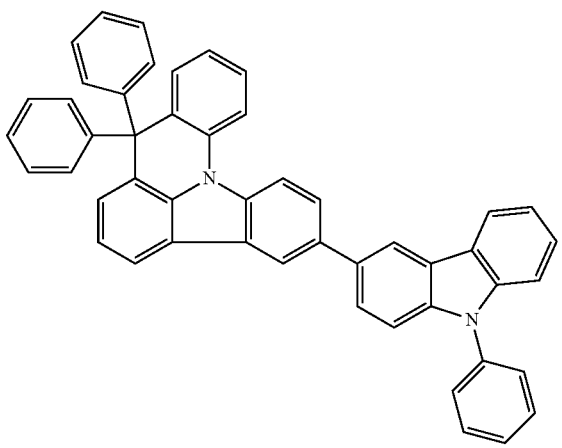 [SMILES: c1ccc(-n2c3ccccc3c3cc(-c4ccc5c(c4)c4cccc6c4n5-c4ccccc4C6(c4ccccc4)c4ccccc4)ccc32)cc1]
H14

TABLE 4-continued

Structural formulae of the materials used

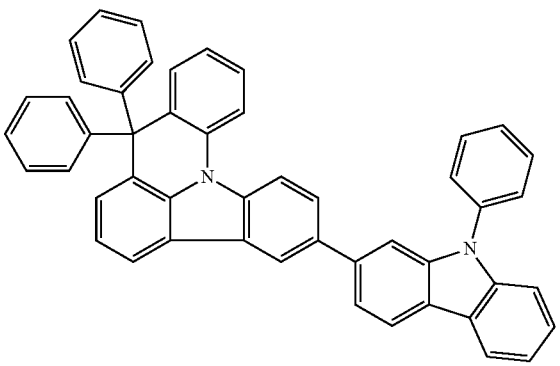 [SMILES: c1ccc(-n2c3ccccc3c3ccc(-c4ccc5c(c4)c4cccc6c4n5-c4ccccc4C6(c4ccccc4)c4ccccc4)cc32)cc1]

H16

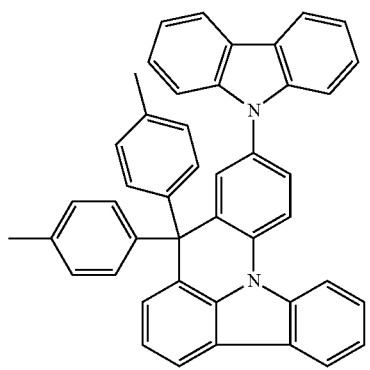 [SMILES: Cc1ccc(C2(c3ccc(C)cc3)c3cc(-n4c5ccccc5c5ccccc54)ccc3-n3c4ccccc4c4cccc2c43)cc1]

H17

The invention claimed is:

1. A compound of the formula (II)

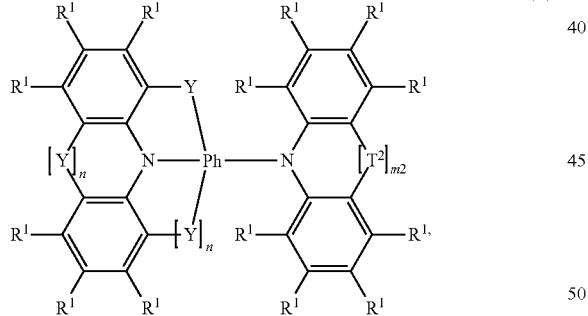

formula (II)

where the following applies to the symbols and indices occurring:

Y is on each occurrence, identically or differently, a single bond or $C(R_2)$ and precisely one group Y represents a single bond and precisely one further group Y is $C(R_2)_2$;

$T^2$ is a single bond;

Ph is a phenyl group, which is optionally substituted by one or more radicals $R^1$;

$R^1$ is on each occurrence, identically or differently, H, D, F, Cl, Br, I, CHO, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OSO_2R^3$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or a mono- or polycyclic aromatic or ring system having 5 to 60 aromatic ring atoms, which may in each case be substituted by one or more non-aromatic radicals $R^3$, or an aryloxy or heteroaryloxy group having 5 to 60 aromatic ring atoms, which is optionally substituted by one or more non-aromatic radicals $R^3$, or a combination of these systems, where two or more radicals $R^1$ and/or $R^2$ is optionally linked to one another and may form a mono- or polycyclic, aliphatic or aromatic ring system;

$R^2$ is on each occurrence, identically or differently, H, D, F, Cl, Br, I, CHO, $N(R^3)_2$, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OSO_2R^3$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals $R^3$, or an aryloxy or heteroaryloxy group having 5 to 60 aromatic ring atoms, which is optionally substituted by one or more non-aromatic radicals R³, or a combination of these systems, where two or more radicals R¹ and/or R² is optionally linked to one another and may form a mono- or polycyclic, aliphatic or aromatic ring system;

R³ is on each occurrence, identically or differently, H, D, F, Cl, Br, I, CHO, N(R⁴)₂, C(=O)R⁴, P(=O)(R⁴)₂, S(=O)R⁴, S(=O)₂R⁴, CR⁴=C(R⁴)₂, CN, NO₂, Si(R⁴)₃, B(OR⁴)₂, OSO₂R⁴, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R⁴, where one or more non-adjacent CH₂ groups is optionally replaced by R⁴C=CR⁴, C≡C, Si(R⁴)₂, Ge(R⁴)₂, Sn(R⁴)₂, C=O, C=S, C=Se, C=NR⁴, P(=O)(R⁴), SO, SO₂, NR⁴, O, S or CONR⁴ and where one or more H atoms is optionally replaced by D, F, Cl, Br, I, CN or NO₂, or a mono- or polycyclic aromatic or heteroaromatic ring system having 5 to 60 aromatic ring atoms, which may in each case be substituted by one or more non-aromatic radicals R⁴, or an aryloxy or heteroaryloxy group having 5 to 60 aromatic ring atoms, which is optionally substituted by one or more non-aromatic radicals R⁴, or a combination of these systems, where two or more radicals R³ is optionally linked to one another and may form a mono- or polycyclic, aliphatic or aromatic ring system;

R⁴ is on each occurrence, identically or differently, H, D, F or an aliphatic, aromatic and/or heteroaromatic organic radical having 1 to 20 C atoms, in which, in addition, one or more H atoms is optionally replaced by D or F; two or more identical or different substituents R⁴ here may also be linked to one another and may form a mono- or polycyclic, aliphatic or aromatic ring system;

n is on each occurrence, identically or differently, 0 or 1, where the sum of the values of n is equal to 1 and where, for n=0, a group R' is bonded instead of a group Y;

m2 is 0 or 1, where, for m2=0, a group R¹ is bonded instead of a group T²;

where the following structures are excluded:

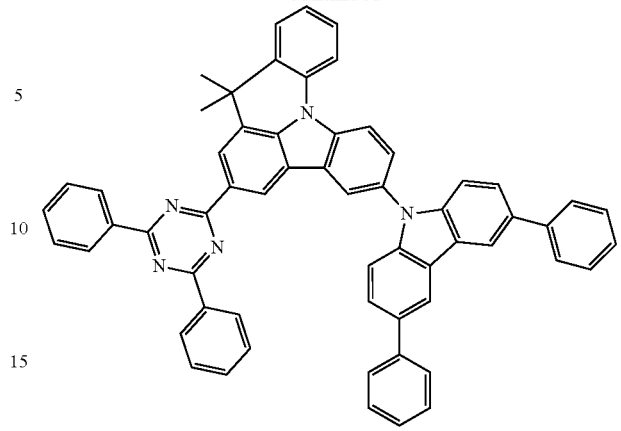

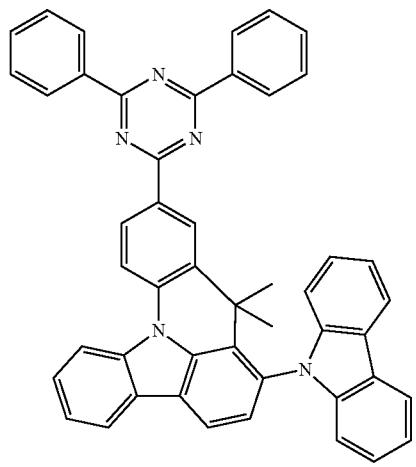

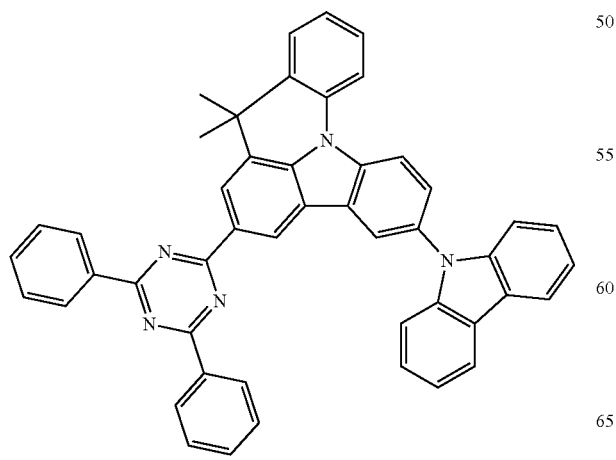

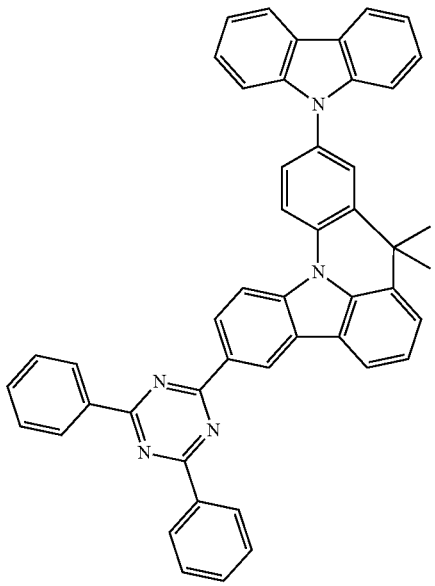

-continued

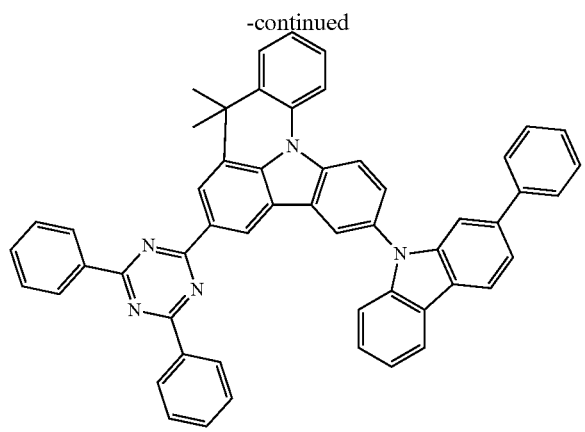

and where not more than one group $R^1$ which represents a group of the formula $-N(R^3)_2$, where $R^3$ is an aryl group, is optionally bonded to a single triarylamine group in formula (I).

2. The compound according to claim 1, wherein $R^1$ is selected on each occurrence, identically or differently, from H, D, F, CN, $Si(R^3)_3$ or a straight-chain alkyl or alkoxy group having 1 to 20 C atoms or a branched or cyclic alkyl or alkoxy group having 3 to 20 C atoms, each of which is optionally substituted by one or more radicals $R^3$, where one or more adjacent or non-adjacent $CH_2$ groups is optionally replaced by $-C\equiv C-$, $R^3C=CR^3$, $Si(R^3)_2$, $C=O$, $C=NR^3$, $NR^3$, O, S, COO or $CONR^3$, or an aryl or group having 5 to 30 aromatic ring atoms, which may in each case be substituted by one or more radicals $R^3$.

3. The compound according to claim 1, wherein $R^2$ is selected on each occurrence, identically or differently, from H, D, a straight-chain alkyl group having 1 to 8 carbon atoms, a branched alkyl group having 3 to 8 carbon atoms or an aryl group having 6 to 18 carbon atoms, where the said groups may each be substituted by one or more groups $R^3$.

4. The compound according to claim 1, wherein at least one group $R^2$ which represents an aryl group having 6 to 10 carbon atoms which is substituted by one or more radicals $R^3$ must be present.

5. The compound according to claim 1, wherein the group Ph conforms to one of the formulae (Ph-1) and (Ph-2):

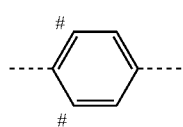

formula (Ph-1)

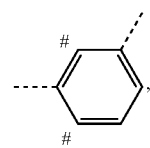

formula (Ph-2)

where the bonds to the two nitrogen atoms are represented by the dashed lines, and the symbols # mark the position of the bond to a group Y, if present, and where the structures is optionally substituted in all free positions by radicals $R^1$ as defined in claim 1.

6. A compound which conforms to one of the following (I-1), (I-2), (I-3), (I-11), (I-12) or (I-13):

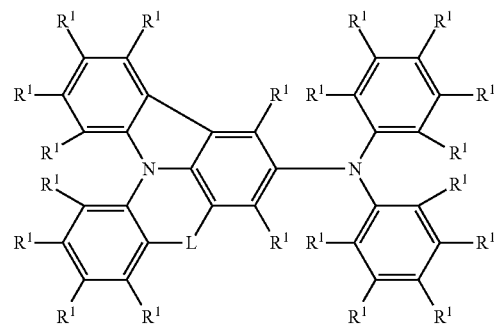

formula (I-1)

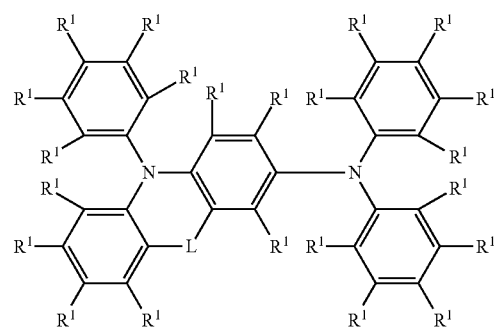

formula (I-2)

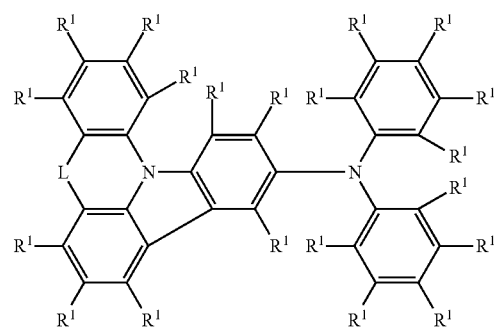

formula (I-3)

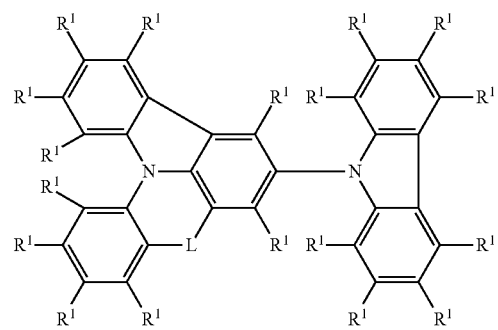

formula (I-11)

-continued

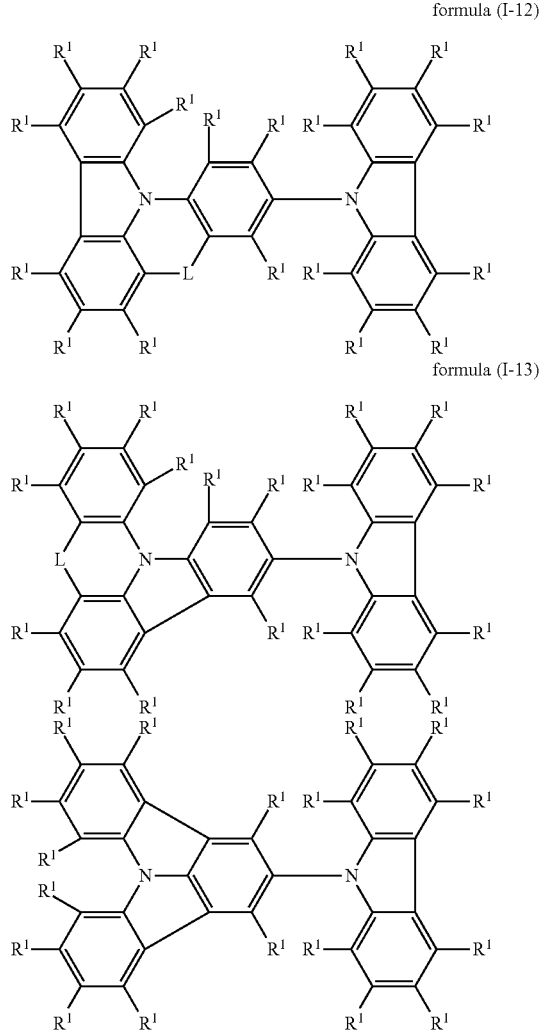

formula (I-12)

formula (I-13)

where
L is selected on each occurrence, identically or differently, from C(R²)₂ and
R¹ is on each occurrence, identically or differently, H, D, F, Cl, Br, I, CHO, C(=O)R³, P(=O)(R³)₂, S(=O)R³, S(=O)₂R³, CR³=C(R³)₂, CN, NO₂, Si(R³)₃, B(OR³)₂, OSO₂R³, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or a mono- or polycyclic aromatic or ring system having 5 to 60 aromatic ring atoms, which may in each case be substituted by one or more non-aromatic radicals R³, or an aryloxy or heteroaryloxy group having 5 to 60 aromatic ring atoms, which is optionally substituted by one or more non-aromatic radicals R³, or a combination of these systems, where two or more radicals R¹ and/or R² is optionally linked to one another and may form a mono- or polycyclic, aliphatic or aromatic ring system;

R² is on each occurrence, identically or differently, H, D, F, Cl, Br, I, CHO, N(R³)₂, C(=O)R³, P(=O)(R³)₂, S(=O)R³, S(=O)₂R³, CR³=C(R³)₂, CN, NO₂, Si(R³)₃, B(OR³)₂, OSO₂R³, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or a mono- or polycyclic aromatic or heteroaromatic ring system having 5 to 60 aromatic ring atoms, which may in each case be substituted by one or more non-aromatic radicals R³, or an aryloxy or heteroaryloxy group having 5 to 60 aromatic ring atoms, which is optionally substituted by one or more non-aromatic radicals R³, or a combination of these systems, where two or more radicals R¹ and/or R² is optionally linked to one another and may form a mono- or polycyclic, aliphatic or aromatic ring system;

R³ is on each occurrence, identically or differently, H, D, F, Cl, Br, I, CHO, N(R⁴)₂, C(=O)R⁴, P(=O)(R⁴)₂, S(=O)R⁴, S(=O)₂R⁴, CR⁴=C(R⁴)₂, CN, NO₂, Si(R⁴)₃, B(OR⁴)₂, OSO₂R⁴, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R⁴, where one or more non-adjacent CH₂ groups is optionally replaced by R⁴C=CR⁴, C≡C, Si(R⁴)₂, Ge(R⁴)₂, Sn(R⁴)₂, C=O, C=S, C=Se, C=NR⁴, P(=O)(R⁴), SO, SO₂, NR⁴, O, S or CONR⁴ and where one or more H atoms is optionally replaced by D, F, Cl, Br, I, CN or NO₂, or a mono- or polycyclic aromatic or heteroaromatic ring system having 5 to 60 aromatic ring atoms, which may in each case be substituted by one or more non-aromatic radicals R⁴, or an aryloxy or heteroaryloxy group having 5 to 60 aromatic ring atoms, which is optionally substituted by one or more non-aromatic radicals R⁴, or a combination of these systems, where two or more radicals R³ is optionally linked to one another and may form a mono- or polycyclic, aliphatic or aromatic ring system; and R⁴ is on each occurrence, identically or differently, H, D, F or an aliphatic, aromatic and/or heteroaromatic organic radical having 1 to 20 C atoms, in which, in addition, one or more H atoms is optionally replaced by D or F; two or more identical or different substituents R⁴ here may also be linked to one another and may form a mono- or polycyclic, aliphatic or aromatic ring system.

7. An oligomer, polymer or dendrimer comprising one or more compounds according to claim 1, where the bond(s) to the polymer, oligomer or dendrimer is optionally localised at any positions substituted by R¹ or R² in formula (I).

8. A formulation comprising at least one compound according to claim 1 and at least one solvent.

9. A formulation comprising at least polymer, oligomer or dendrimer according to claim 7 and at least one solvent.

10. A process for the preparation of a compound according to claim 1, which comprises carrying out at least one ring-closure reaction for the introduction of a bridging group Y, $T^2$ or L.

11. An electronic device comprising the compound according to claim 1.

12. An electronic device comprising the polymer, oligomer or dendrimer according to claim 7.

13. The Electronic device according to claim 11, wherein the device is an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), an organic laser diode (O-laser) or an organic electroluminescent devices (OLED).

14. An organic electroluminescent device which comprises the compound according to claim 1 as hole-transport material in a hole-transport layer or hole-injection layer and/or as matrix material in an emitting layer.

15. An organic electroluminescent device which comprises the compound according to claim 1 as hole-transport material in a hole-transport layer or hole-injection layer and/or as matrix material, in combination with one or more further matrix materials, in an emitting layer.

16. An organic electroluminescent device which comprises the polymer, oligomer or dendrimer according to claim 7 as hole-transport material in a hole-transport layer or hole-injection layer and/or as matrix material in an emitting layer.

17. An organic electroluminescent device which comprises the polymer, oligomer or dendrimer according to claim 7 as hole-transport material in a hole-transport layer or hole-injection layer and/or as matrix material, in combination with one or more further matrix materials, in an emitting layer.

* * * * *